US007863465B2

(12) United States Patent
Balkovec et al.

(10) Patent No.: US 7,863,465 B2
(45) Date of Patent: Jan. 4, 2011

(54) ANTIFUNGAL AGENTS

(75) Inventors: James M. Balkovec, Martinsville, NJ (US); Frances Aileen Bouffard, Scotch Plains, NJ (US); Bruno Tse, San Diego, CA (US); James Dropinski, Colts Neck, NJ (US); Dongfang Meng, Westfield, NJ (US); Mark L. Greenlee, Plainfield, NJ (US); Michael Peel, Chapel Hill, NC (US); Weiming Fan, Chapel Hill, NC (US); Ahmed Mamai, Raleigh, NC (US); Hao Liu, Raleigh, NC (US); Keqaing Li, Cary, NC (US)

(73) Assignees: Merck Sharp & Dohme Corp., Rahway, NJ (US); Scynexis, Inc., Research Triangle Park, NC (US)

( * ) Notice: Subject to any disclaimer, the term of this patent is extended or adjusted under 35 U.S.C. 154(b) by 693 days.

(21) Appl. No.: 11/727,927

(22) Filed: Mar. 29, 2007

(65) Prior Publication Data

US 2008/0009504 A1    Jan. 10, 2008

Related U.S. Application Data

(60) Provisional application No. 60/788,648, filed on Apr. 3, 2006, provisional application No. 60/872,201, filed on Dec. 1, 2006.

(51) Int. Cl.
*C07D 311/00* (2006.01)
*C07D 315/00* (2006.01)
(52) U.S. Cl. ..................................... 549/381; 417/432
(58) Field of Classification Search ................ 549/381, 549/432, 417
See application file for complete search history.

(56) References Cited

U.S. PATENT DOCUMENTS 5,756,472 A    5/1998    Liesch et al.

FOREIGN PATENT DOCUMENTS

WO    WO-97/27860    8/1997

OTHER PUBLICATIONS

J. Onishi et al., Discovery of Novel Antifungal (1,3)-beta-D-Glycan Synthase Inhibitors, 44(2) Antimicrobial Agents & Chemotherapy, pp. 368-377 (Feb. 2000).
Fernando Pelaez et al., The Discovery of Enfumafungin, A Novel Antifungal Compound Produced by an Endophytic Hormonema Species Biological Activity and Taxonomy of the Producing Organisms, 23(3) Systemic & Applied Microbiology, pp. 333-343 (2000).
Robert E. Schwartz, et al., Isolation and Structural Determination of Enfumafungin, a Triterpene Glycoside Antifungal Agent That Is a Specific Inhibitor of Glucan Synthesis, 122 J. Am. Chem. Soc., pp. 4882-4886 (2000).
Ali Shafiee et al., Enzymatic Deglycosylation of Enfumafungin, a Triterpene Glycoside Natural Product, and its Chemically Synthesized Analogues, Journal of Molecular Catalysis B: Enzymatic 16, pp. 27-32 (2001).
Robert E. Schwartz, Cell Wall Active Antifungal Agents, 11(11) Expert Opinion on Therapeutic Patents, pp. 1761-1772 (2001).

*Primary Examiner*—Janet L. Andres
*Assistant Examiner*—Raymond Covington
(74) *Attorney, Agent, or Firm*—Covington & Burling LLP; Paul J. Berman

(57) ABSTRACT

The present invention relates to novel enfumafungin derivatives of formula I and pharmaceutically acceptable salts thereof, their synthesis, and their use as inhibitors of (1,3)-β-D-glucan synthase. The present compounds and pharmaceutically acceptable salts thereof, as well as pharmaceutical compositions comprising the present compounds and pharmaceutically acceptable salts thereof, are useful for treating or preventing antifungal infections and associated diseases and conditions.

38 Claims, No Drawings

ANTIFUNGAL AGENTS

JOINT RESEARCH AGREEMENT

The claimed invention was made as a result of activities undertaken within the scope of a joint research agreement between Merck & Co., Inc. and Scynexis Chemistry & Automation, Inc (now known as Scynexis, Inc.). The field of the invention is described below.

FIELD OF THE INVENTION

The present invention relates to novel enfumafungin derivatives and pharmaceutically acceptable salts thereof, their synthesis, and their use as inhibitors of (1,3)-β-D-glucan synthase. The present compounds and pharmaceutically acceptable salts thereof, as well as pharmaceutical compositions comprising the present compounds and pharmaceutically acceptable salts thereof, are useful for treating or preventing fungal infections and associated diseases and conditions.

BACKGROUND OF THE INVENTION

Fungal infection remains to be a major healthcare problem. Incidence of hospital-acquired fungal diseases continues to rise. Severe systemic fungal infection in hospitals (such as candidiasis, aspergillosis, histoplasmosis, blastomycosis and coccidioidomycosis) is commonly seen in neutropaenic patients following chemotherapy and other oncology patients with immune suppression, patients immune compromised due to Acquired Immune Deficiency Syndrome (AIDS) caused by HIV infection, and patients in intensive care. Systemic fungal infections cause ~25% of infection-related deaths in leukaemics. Infections due to *Candida* species are the fourth most important cause of nosocomial bloodstream infection. Serious fungal infections may cause 5-10% of deaths in those undergoing lung, pancreas or liver transplantation. Thus, treatment failures are still very common with all systemic mycoses. Secondary resistance also arises. There remains an increasing need for effective new therapy against mycotic infections.

Enfumafungin is a hemiacetal triterpene glycoside that is produced in fermentations of a *Hormonema* sp. associated with living leaves of *Juniperus communis* (U.S. Pat. No. 5,756,472; Pelaez et al., *Systematic and Applied Microbiology*, 23:333-343, 2000; Schwartz et al., *JACS*, 122:4882-4886, 2000; Schwartz, R. E., *Expert Opinion on Therapeutic Patents*, 11(11):1761-1772, 2001). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase (Onishi et al., *Antimicrobial Agents and Chemotherapy*, 44:368-377, 2000; Pelaez et al., *Systematic and Applied Microbiology*, 23:333-343, 2000). 1,3-β-D-Glucan synthase remains an attractive target for antifungal drug action because it is present in many pathogenic fungi which affords broad antifungal spectrum and there is no mammalian counterpart and as such, these compounds have little or no mechanism-based toxicity.

SUMMARY OF THE INVENTION

The present invention relates to novel enfumafungin derivatives. These compounds or pharmaceutically acceptable salts are useful in the inhibition of (1,3)-β-D-glucan synthase inhibitors, and thus in the prevention or treatment of mycotic infections caused by various pathogens including, but are not limited to, *Aspergillus, Cryptococcus, Candida, Mucor, Actinomyces, Histoplasma, Dermatophyte, Malassezia, Fusarium, Pneumocystis carinii*. In particular, the present invention includes a compound of Formula I:

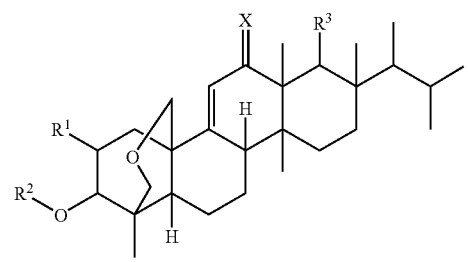

or a pharmaceutically acceptable salt thereof, wherein:

X is O or H,H;

$R^1$ is
  a) OH;
  b) $OC(O)C_1$-$C_{12}$-alkyl, unsubstituted or substituted with 1 or 2 substituents selected from $OR^0$, $N(R^0)_2$, and $CO_2R^0$;
  c) $OC(O)C_1$-$C_6$-haloalkyl;
  d) $OC(O)C_3$-$C_8$-cycloalkyl;
  e) $O$—$C_1$-$C_6$-alkyl, unsubstituted or substituted with 1 or 2 substituents selected from $OR^0$ and $N(R^0)_2$;
  f) $OC(O)NHC_1$-$C_6$-alkyl, unsubstituted or substituted with phenyl;
  g) $OC(O)OC_1$-$C_6$-alkyl;
  h) $NHC(O)C_1$-$C_6$-alkyl, unsubstituted or substituted with phenyl; or
  i) $(O)_nCH_2C(O)C_1$-$C_6$-alkyl;

n is 0 or 1;

$R^2$ is
  a) $CH_2R^4$,
  b) $CH_2CHR^5(CH_2)_mNR^6R^7$,
  c) $CH_2C(R^8)(R^9)(CH_2)_mNR^6R^7$,
  d) $CH_2C(R^{10})(R^{11})R^{12}$,
  e) $CH_2CH(OR^0)CH_2OR^0$,
  f) $CHR^{13}CHR^5(CH_2)_mNR^6R^7$,
  g) $(CH_2)_pC(R^8)(R^9)NR^6R^7$, or,
  h) $CH_2CHR^5C(R^8)(R^9)NR^6R^7$, m is 0, 1 or 2;

p is 2 to 6;

$R^1$ and $R^2$ are optionally taken together to form a methylenedioxy or ethylenedioxy, unsubstituted or substituted with 1 or 2 substituents selected from $C_1$-$C_6$-alkyl and $C_1$-$C_6$-alkoxy;

$R^3$ is
  a) $C(O)R^{14}$;
  b) $CH_2OH$; or
  c) $CH_2OC(O)C_1$-$C_6$-alkyl;

$R^{14}$ is OH, $OR^{15}$, H, $N(R^0)_2$, or $C_1$-$C_6$-alkyl;

$R^{15}$ is $C_1$-$C_6$-alkyl, unsubstituted or substituted with 1 or 2 substituents selected from phenyl, $OC(O)C_1$-$C_6$-alkyl, $C(O)OR^0$, $OR^0$, $C(O)N(R^0)_2$, and $C(O)NH_2(CH_2)_{2-4}NH_2$ and wherein said phenyl is optionally substituted with 1 to 3 halo groups;

$R^4$ is
  a) H;
  b) $(CH_2)_{1-6}$—$R^{16}$;

c) $OC_1$-$C_6$-alkyl;
d) aryl, wherein aryl is phenyl or naphthyl and aryl is unsubstituted or substituted with 1 to 3 substituents selected from halo, $N(R^o)_2$, $OR^o$, $C_1$-$C_6$-alkyl, $CF_3$, $OCF_3$, $CO_2R^o$, and $C(O)N(R^o)_2$;
e) heterocyclyl, wherein heterocyclyl is a 3- or 6-membered, saturated or unsaturated non-aromatic ring having 1, 2 or 3 heteroatoms selected from N, O or S, attached through a carbon or nitrogen on the ring, and optionally substituted on a ring carbon or nitrogen that is not the point of attachment, with 1 to 2 substituents selected from oxo, $N(R^o)_2$, $OR^o$, $CO_2R^o$, $CON(R^o)_2$, and $C_1$-$C_6$-alkyl unsubstituted or substituted with 1 or 2 substituents selected from $N(R^o)_2$, $NHC(=NH)NH_2$, $OC(O)C_1$-$C_6$-alkyl and $CO_2R^o$; or
f) heteroaryl, wherein heteroaryl is a 5- or 6-membered aromatic ring having 1, 2 or 3 heteroatoms selected from N, O or S, attached through a ring carbon or nitrogen, and optionally substituted on a ring carbon or nitrogen that is not the point of attachment, with 1 or 2 substituents selected from $N(R^o)_2$, $OR^o$, $CO_2R^o$, $CON(R^o)_2$, and $C_1$-$C_6$ alkyl unsubstituted or substituted with 1 or 2 substituents selected from $N(R^o)_2$, $NHC(=NH)NH_2$, $OC(O)C_1$-$C_6$ alkyl and $CO_2R^o$;

$R^{16}$ is
a) H;
b) OH;
c) $NH_2$;
d) $NHC(O)R^{17}$;
e) $NHSO_2R^{17}$;
f) $NHC(O)NHR^o$;
g) $NHC(O)CHR^{18}NH_2$;
h) heterocyclyl, wherein heterocyclyl is a 5- or 6-membered, saturated or unsaturated non-aromatic ring having 1, 2 or 3 heteroatoms selected from N, O or S, attached through a carbon or nitrogen on the ring, and optionally substituted on a ring carbon or nitrogen that is not the point of attachment, with 1 to 2 substituents selected from $N(R^o)_2$, imino, oxo, $OR^o$, $CO_2R^o$, $CON(R^o)_2$, and $C_1$-$C_6$-alkyl unsubstituted or substituted with 1 or 2 substituents selected from $N(R^o)_2$, $NHC(=NH)NH_2$, $OC(O)C_1$-$C_6$-alkyl, $OR^o$, and $CO_2R^o$;
i) NH—$N(C_1$-$C_6$-alkyl$)_2$;
j) $NHC(=NH)NHC(=NH)NH_2$;
k) $NR^a(CH_2)_pNHR^a$;
l) $NR^aR^b$;
m) $N(R^b)_2$;
n) $NHC(=NR^d)NH_2$;
o) $NHC(=NR^c)NH$—$C_1$-$C_6$-alkyl, wherein said alkyl is unsubstituted or substituted with phenyl, $CF_3$ or $NHC(O)C_1$-$C_6$-alkyl;
p) $NHC(=NR^d)NH$—$C_3$-$C_6$-cycloalkyl;
q) $NHC(=NR^d)NH$-phenyl, wherein said phenyl is unsubstituted or substituted with 1 or 2 substituents selected from halo and $CF_3$;
r) $CO_2C_1$-$C_6$-alkyl;
s) $OCOC_1$-$C_6$ alkyl;
t) heteroaryl, wherein heteroaryl is a 5- or 6-membered aromatic ring having 1, 2 or 3 heteroatoms selected from N, O or S, attached through a carbon or nitrogen on the ring, and optionally substituted on a ring carbon or nitrogen that is not the point of attachment, with 1 or 2 substituents selected from $N(R^o)_2$, $OR^o$, $CO_2R^o$, $CON(R^o)_2$, and $C_1$-$C_6$ alkyl unsubstituted or substituted with 1 or 2 substituents selected from $N(R^o)_2$, $NHC(=NH)NH_2$, $OC(O)C_1$-$C_6$ alkyl, $OR^o$, and $CO_2R^o$; or
u) CN;

p is 1, 2, 3 or 4;
$R^a$ is H or $C(=NH)NH_2$;
$R^b$ is $C_1$-$C_6$ alkyl, unsubstituted or substituted with 1 or 2 substituents selected from $N(R^o)_2$ and $OR^o$;
$R^c$ is H or CN;
$R^d$ is H or $C_3$-$C_6$-cycloalkyl;

$R^5$ is
a) $C_1$-$C_6$-alkyl, unsubstituted or substituted with 1 or 2 substituents selected from $N(R^o)_2$ and $OR^o$;
b) OH;
c) $OC_1$-$C_6$-alkyl, unsubstituted or substituted with phenyl;
d) $OC(O)C_1$-$C_6$-alkyl;
e) $C_3$-$C_6$-cycloalkyl;
f) aryl, wherein aryl is phenyl or naphthyl and aryl is unsubstituted or substituted with 1 to 3 substituents selected from halo, $OCF_3$, $CF_3$, $N(R^o)_2$ and $OR^o$;
g) heteroaryl, wherein heteroaryl is a 5- or 6-membered aromatic ring having 1, 2 or 3 heteroatoms selected from N, O or S, attached through a carbon or nitrogen on the ring, and optionally substituted on a ring carbon or nitrogen that is not the point of attachment, with 1 or 2 substituents selected from $N(R^o)_2$, $OR^o$, and $C_1$-$C_6$-alkyl; or
h) heterocyclyl, wherein heterocyclyl is a 5- or 6-membered, saturated or unsaturated non-aromatic ring having 1, 2 or 3 heteroatoms selected from N, O or S, attached through a ring carbon or nitrogen, and optionally substituted on a ring carbon or nitrogen that is not the point of attachment, with 1 to 2 substituents selected from $N(R^o)_2$, $OR^o$, and $C_1$-$C_6$-alkyl;

$R^6$ is H or $C_1$-$C_6$-alkyl, wherein said alkyl is unsubstituted or substituted with a 5- to 6-membered saturated, unsaturated or aromatic ring having 1, 2 or 3 heteroatoms selected from N, O or S, attached through a ring carbon or nitrogen, and optionally substituted on a ring carbon or nitrogen that is not the point of attachment, with 1 to 2 substituents selected from $N(R^o)_2$, $OR^o$, $CO_2R^o$, $CON(R^o)_2$ and $C_1$-$C_6$-alkyl unsubstituted or substituted with one or two substituents selected from $OR^o$, $N(R^o)_2$, $NHC(=NH)NH_2$, $OC(O)C_1$-$C_6$-alkyl, $CO_2R^o$, $C(O)N(R^o)_2$, and $NHC(O)R^o$;

$R^7$ is
a) H;
b) $C_1$-$C_6$-alkyl, unsubstituted or substituted with 1 or 2 substituents selected from $N(R^o)_2$, $OR^o$, $CO_2R^o$, $OC(O)C_1$-$C_6$-alkyl, $NHC(O)R^o$, $C(O)N(R^o)_2$, phenyl, heteroaryl, and heterocyclyl, wherein heteroaryl is as defined below in (j) and heterocyclyl is as defined below in (k);
c) C(O)H;
d) $C(O)C_1$-$C_6$-haloalkyl;
e) $C(O)C_1$-$C_6$-alkyl, unsubstituted or substituted with 1 or 2 substituents selected from $CO_2R^o$, $OR^o$, $OCH_2CO_2R^o$, $N(R^o)_2$, $C(O)C_1$-$C_6$-alkyl, $O(CH_2)_2OC_1$-$C_6$-alkyl, $C(O)N(R^o)_2$, $OC(O)C_1$-$C_6$ alkyl, and $NHC(O)R^o$;
f) $C(O)OC_1$-$C_6$-alkyl;
g) $C(O)NH$—$C_1$-$C_6$-alkyl;
h) $SO_2C_1$-$C_6$-alkyl;
i) $C_3$-$C_6$-cycloalkyl;
j) aryl, wherein aryl is phenyl or naphthyl and aryl is unsubstituted or substituted with 1 to 3 substituents selected from halo, $N(R^o)_2$, $OR^o$, $C_1$-$C_6$-alkyl, $CF_3$, $OCF_3$, $CO_2R^o$, and $C(O)N(R^o)_2$;
k) heteroaryl, wherein heteroaryl is a 5- or 6-membered aromatic ring having 1, 2 or 3 heteroatoms selected from N, O or S, attached through a carbon or nitrogen on the ring, and optionally substituted on a ring carbon or nitrogen that is not the point of attachment, with 1 or 2 substituents selected from N(R⁰)₂, OR⁰, CO₂R⁰, OC(O)C₁-C₆-alkyl, CON(R⁰)₂, NHC(O)R⁰, and C₁-C₆-alkyl unsubstituted or substituted with 1 or 2 substituents selected from N(R⁰)₂, NHC(=NH)NH₂, OC(O)C₁-C₆ alkyl, OR⁰, CO₂R⁰, C(O)N(R⁰)₂ and NHC(O)R⁰;

l) heterocyclyl, wherein heterocyclyl is a 5- or 6-membered, saturated or unsaturated non-aromatic ring having 1, 2 or 3 heteroatoms selected from N, O or S, attached through a carbon or nitrogen on the ring, and optionally substituted on a ring carbon or nitrogen that is not the point of attachment, with 1 to 2 substituents selected from N(R⁰)₂, imino, oxo, OR⁰, CO₂R⁰, OC(O)C₁-C₆-alkyl, CON(R⁰)₂, NHC(O)R⁰, and C₁-C₆-alkyl unsubstituted or substituted with 1 or 2 substituents selected from N(R⁰)₂, NHC(=NH)NH₂, OC(O)C₁-C₆-alkyl, OR⁰, CO₂R⁰, C(O)N(R⁰)₂ and NHC(O)R⁰;

m) C(=NH)C₁-C₆-alkyl, wherein said alkyl is unsubstituted or substituted with 1 or 2 substituents selected from halo, CF₃, N(R⁰)₂, OR⁰, and NHC(O)C₁-C₆-alkyl;

n) C(=NR$^d$)NH₂;

o) C(=NH)NH—C₁-C₆-alkyl, wherein said alkyl is unsubstituted or substituted with 1 to 3 substituents selected from halo, CF₃, N(R⁰)₂, OR⁰, and NHC(O)C₁-C₆-alkyl;

p) C(=NH)NH—C₃-C₆-cycloalkyl;

q) C(=NH)NH-phenyl, wherein phenyl is unsubstituted or substituted with 1 to 3 substituents selected from halo and CF₃; or r) C(=NH)NHC(=NH)NH₂;

R⁶ and R⁷ are optionally taken together with the attached nitrogen atom to form a 3- to 6-membered saturated, unsaturated or aromatic ring having 0-2 additional heteroatoms selected from N, O and S, wherein said ring is optionally substituted on a ring carbon or nitrogen that is not the point of attachment, with 1 to 2 substituents selected from halo, N(R⁰)₂, OR⁰, CO₂R⁰, CON(R⁰)₂, and C₁-C₆ alkyl unsubstituted or substituted with 1 or 2 substituents selected from OR⁰ and N(R⁰)₂, and wherein two adjacent substituents of said ring are optionally taken together to form a fused 5- or 6-membered saturated, unsaturated, or aromatic ring having 0-2 heteroatoms selected from N, O and S; or R⁶ and R⁹ are optionally taken together, with the nitrogen atom R⁶ is attached to, to form a pyrrolidinyl ring;

R⁸ is selected from the group consisting of
  a) hydrogen,
  b) C₁-C₆-alkyl, unsubstituted or substituted with OR⁰ or SO₂R⁰,
  c) C₃-C₆-cycloalkyl, and
  d) aryl, wherein aryl is phenyl or naphthyl and aryl is unsubstituted or substituted with 1 to 3 substituents selected from halo, OCF₃, CF₃, N(R⁰)₂ and OR⁰;

R⁹ is C₁-C₆-alkyl, unsubstituted or substituted with OR⁰ or SO₂R⁰;

R⁸ and R⁹ are optionally taken together to form a 3- to 6-membered saturated ring having 0-1 heteroatom selected from N, O or S;

R¹⁰ is independently selected from the group consisting of
  a) C₁-C₆-alkyl unsubstituted or substituted with OR⁰, N(R⁰)₂, OC(O)C₁-C₆ alkyl or CO₂R⁰, and
  b) CO₂R⁰;

R¹¹ is C₁-C₆ alkyl unsubstituted or substituted with OR⁰, OC(O)C₁-C₆ alkyl, OC(O)-phenyl, CO₂R⁰, or N(R⁰)₂;

R¹² is OH or C₁-C₆ alkyl, wherein said alkyl is unsubstituted or substituted with OC(O)C₁-C₆ alkyl or OR⁰;

R¹³ is C₁-C₄-alkyl;

R¹⁷ is
  a) C₁-C₆-alkyl, unsubstituted or substituted with 1 to 2 substituents selected from CO₂R⁰, OR⁰, N(R⁰)₂, and OC(O)C₁-C₆-alkyl;
  b) aryl, wherein aryl is phenyl or naphthyl and aryl is unsubstituted or substituted with 1 to 2 substituents selected from halo, OR⁰ and N(R⁰)₂; or
  c) C₁-C₆-haloalkyl;

R¹⁸ is H or C₁-C₆-alkyl, wherein said alkyl is unsubstituted or substituted with 1 to 2 substituents selected from OR⁰, N(R⁰)₂, heteroaryl, heterocyclyl, CO₂N(R⁰)₂, and CO₂R⁰, wherein heteroaryl is as defined in R¹⁶ (t) and heterocyclyl is as defined in R¹⁶ (h); and each R⁰ is independently H or C₁-C₆ alkyl.

In one embodiment (hereinafter referred to as "Embodiment P"), the present invention includes a compound of Formula I:

or a pharmaceutically acceptable salt thereof, wherein:

X is O or H,H;

R¹ is
  a) OH;
  b) OC(O)C₁-C₁₂-alkyl, unsubstituted or substituted with 1 or 2 substituents selected from OR⁰, N(R⁰)₂, and CO₂R⁰;
  c) OC(O)C₁-C₆-haloalkyl;
  d) OC(O)C₃-C₈-cycloalkyl;
  e) O—C₁-C₆-alkyl, unsubstituted or substituted with 1 or 2 substituents selected from OR⁰ and N(R⁰)₂;
  f) OC(O)NHC₁-C₆-alkyl, unsubstituted or substituted with phenyl;
  g) OC(O)OC₁-C₆-alkyl;
  h) NHC(O)C₁-C₆-alkyl, unsubstituted or substituted with phenyl; or
  i) (O)$_n$CH₂C(O)C₁-C₆-alkyl;

n is 0 or 1;

R² is
  a) CH₂R⁴;
  b) CH₂CHR⁵(CH₂)$_m$NR⁶R⁷;
  c) CH₂C(R⁸)(R⁹)(CH₂)$_m$NR⁶R⁷;
  d) CH₂C(R¹⁰)(R¹¹)R¹²;
  e) CH₂CH(OR⁹)CH₂OR⁰;
  f) CHR¹³CHR⁵(CH₂)$_m$NR⁶R⁷; or
  g) (CH₂)$_p$C(R⁸)(R⁹)NR⁶R⁷;

m is 0, 1 or 2;

p is 2 to 6;

R¹ and R² are optionally taken together to form a methylenedioxy or ethylenedioxy, unsubstituted or substituted with 1 or 2 substituents selected from C₁-C₆-alkyl and C₁-C₆-alkoxy;

R³ is
  a) C(O)R¹⁴;
  b) CH₂OH; or
  c) CH₂OC(O)C₁-C₆-alkyl;

$R^{14}$ is OH, $OR^{15}$, H, $N(R^o)_2$, or $C_1$-$C_6$-alkyl;

$R^{15}$ is $C_1$-$C_6$-alkyl, unsubstituted or substituted with 1 or 2 substituents selected from phenyl, $OC(O)C_1$-$C_6$-alkyl, $C(O)OR^o$, $OR^o$, $C(O)N(R^o)_2$, and $C(O)NH_2(CH_2)_{2-4}NH_2$ and wherein said phenyl is optionally substituted with 1 to 3 halo groups;

$R^4$ is
- a) H;
- b) $(CH_2)_{1-6}$—$R^{16}$;
- c) $OC_1$-$C_6$-alkyl;
- d) aryl, wherein aryl is phenyl or naphthyl and aryl is unsubstituted or substituted with 1 to 3 substituents selected from halo, $N(R^o)_2$, $OR^o$, $C_1$-$C_6$-alkyl, $CF_3$, $OCF_3$, $CO_2R^o$, and $C(O)N(R^o)_2$;
- e) heterocyclyl, wherein heterocyclyl is a 3- or 6-membered, saturated or unsaturated non-aromatic ring having 1, 2 or 3 heteroatoms selected from N, O or S, attached through a carbon or nitrogen on the ring, and optionally substituted on a ring carbon or nitrogen that is not the point of attachment, with 1 to 2 substituents selected from oxo, $N(R^o)_2$, $OR^o$, $CO_2R^o$, $CON(R^o)_2$, and $C_1$-$C_6$-alkyl unsubstituted or substituted with 1 or 2 substituents selected from $N(R^o)_2$, NHC(=NH)$NH_2$, $OC(O)C_1$-$C_6$-alkyl and $CO_2R^o$; or
- f) heteroaryl, wherein heteroaryl is a 5- or 6-membered aromatic ring having 1, 2 or 3 heteroatoms selected from N, O or S, attached through a ring carbon or nitrogen, and optionally substituted on a ring carbon or nitrogen that is not the point of attachment, with 1 or 2 substituents selected from $N(R^o)_2$, $OR^o$, $CO_2R^o$, $CON(R^o)_2$, and $C_1$-$C_6$ alkyl unsubstituted or substituted with 1 or 2 substituents selected from $N(R^o)_2$, NHC(=NH)$NH_2$, $OC(O)C_1$-$C_6$ alkyl and $CO_2R^o$;

$R^{16}$ is
- a) H;
- b) OH;
- c) $NH_2$;
- d) $NHC(O)R^{17}$;
- e) $NHSO_2R^{17}$;
- f) $NHC(O)NHR^o$;
- g) $NHC(O)CHR^{18}NH_2$;
- h) heterocyclyl, wherein heterocyclyl is a 5- or 6-membered, saturated or unsaturated non-aromatic ring having 1, 2 or 3 heteroatoms selected from N, O or S, attached through a carbon or nitrogen on the ring, and optionally substituted on a ring carbon or nitrogen that is not the point of attachment, with 1 to 2 substituents selected from $N(R^o)_2$, imino, oxo, $OR^o$, $CO_2R^o$, $CON(R^o)_2$, and $C_1$-$C_6$-alkyl unsubstituted or substituted with 1 or 2 substituents selected from $N(R^o)_2$, NHC(=NH)$NH_2$, $OC(O)C_1$-$C_6$-alkyl, $OR^o$, and $CO_2R^o$;
- i) NH—$N(C_1$-$C_6$-alkyl$)_2$;
- j) NHC(=NH)NHC(=NH)$NH_2$;
- k) $NR^a(CH_2)_pNHR^a$;
- l) $NR^aR^b$;
- m) $N(R^b)_2$;
- n) NHC(=$NR^d$)$NH_2$;
- o) NHC(=$NR^c$)NH—$C_1$-$C_6$-alkyl, wherein said alkyl is unsubstituted or substituted with phenyl, $CF_3$ or NHC(O)$C_1$-$C_6$-alkyl;
- p) NHC(=$NR^d$)NH—$C_3$-$C_6$-cycloalkyl;
- q) NHC(=$NR^d$)NH-phenyl, wherein said phenyl is unsubstituted or substituted with 1 or 2 substituents selected from halo and $CF_3$;
- r) $CO_2C_1$-$C_6$-alkyl;
- s) $OCOC_1$-$C_6$ alkyl;
- t) heteroaryl, wherein heteroaryl is a 5- or 6-membered aromatic ring having 1, 2 or 3 heteroatoms selected from N, O or S, attached through a carbon or nitrogen on the ring, and optionally substituted on a ring carbon or nitrogen that is not the point of attachment, with 1 or 2 substituents selected from $N(R^o)_2$, $OR^o$, $CO_2R^o$, $CON(R^o)_2$, and $C_1$-$C_6$ alkyl unsubstituted or substituted with 1 or 2 substituents selected from $N(R^o)_2$, NHC(=NH)$NH_2$, $OC(O)C_1$-$C_6$ alkyl, $OR^o$, and $CO_2R^o$; or
- u) CN;

p is 1, 2, 3 or 4;

$R^a$ is H or C(=NH)$NH_2$;

$R^b$ is $C_1$-$C_6$ alkyl, unsubstituted or substituted with 1 or 2 substituents selected from $N(R^o)_2$ and $OR^o$;

$R^cC$ is H or CN;

$R^d$ is H or $C_3$-$C_6$-cycloalkyl;

$R^5$ is
- a) $C_1$-$C_6$-alkyl, unsubstituted or substituted with 1 or 2 substituents selected from $N(R^o)_2$ and $OR^o$;
- b) OH;
- c) $OC_1$-$C_6$-alkyl, unsubstituted or substituted with phenyl;
- d) $OC(O)C_1$-$C_6$-alkyl;
- e) $C_3$-$C_6$-cycloalkyl;
- f) aryl, wherein aryl is phenyl or naphthyl and aryl is unsubstituted or substituted with 1 to 3 substituents selected from halo, $OCF_3$, $CF_3$, $N(R^o)_2$ and $OR^o$;
- g) heteroaryl, wherein heteroaryl is a 5- or 6-membered aromatic ring having 1, 2 or 3 heteroatoms selected from N, O or S, attached through a carbon or nitrogen on the ring, and optionally substituted on a ring carbon or nitrogen that is not the point of attachment, with 1 or 2 substituents selected from $N(R^o)_2$, $OR^o$, and $C_1$-$C_6$-alkyl; or
- h) heterocyclyl, wherein heterocyclyl is a 5- or 6-membered, saturated or unsaturated non-aromatic ring having 1, 2 or 3 heteroatoms selected from N, O or S, attached through a ring carbon or nitrogen, and optionally substituted on a ring carbon or nitrogen that is not the point of attachment, with 1 to 2 substituents selected from $N(R^o)_2$, $OR^o$, and $C_1$-$C_6$-alkyl;

$R^6$ is H or $C_1$-$C_6$-alkyl, wherein said alkyl is unsubstituted or substituted with a 5- to 6-membered saturated, unsaturated or aromatic ring having 1, 2 or 3 heteroatoms selected from N, O or S, attached through a ring carbon or nitrogen, and optionally substituted on a ring carbon or nitrogen that is not the point of attachment, with 1 to 2 substituents selected from $N(R^o)_2$, $OR^o$, $CO_2R^o$, $CON(R^o)_2$ and $C_1$-$C_6$-alkyl unsubstituted or substituted with one or two substituents selected from $OR^o$, $N(R^o)_2$, NHC(=NH)$NH_2$, $OC(O)C_1$-$C_6$-alkyl, $CO_2R^o$, $C(O)N(R^o)_2$, and $NHC(O)R^o$;

$R^7$ is
- a) H;
- b) $C_1$-$C_6$-alkyl, unsubstituted or substituted with 1 or 2 substituents selected from $N(R^o)_2$, $OR^o$, $CO_2R^o$, $OC(O)C_1$-$C_6$-alkyl, $NHC(O)R^o$, $C(O)N(R^o)_2$, phenyl, heteroaryl, and heterocyclyl, wherein heteroaryl is as defined below in (j) and heterocyclyl is as defined below in (k);
- c) C(O)H;
- d) $C(O)C_1$-$C_6$-haloalkyl;
- e) $C(O)C_1$-$C_6$-alkyl, unsubstituted or substituted with 1 or 2 substituents selected from $CO_2R^o$, $OR^o$, $OCH_2CO_2R^o$, $N(R^o)_2$, $C(O)C_1$-$C_6$-alkyl, $O(CH_2)_2OC_1$-$C_6$-alkyl, $C(O)N(R^o)_2$, $OC(O)C_1$-$C_6$ alkyl, and $NHC(O)R^o$;
- f) $C(O)OC_1$-$C_6$-alkyl;
- g) C(O)NH—$C_1$-$C_6$-alkyl;
- h) $SO_2C_1$-$C_6$-alkyl;

i) $C_3$-$C_6$-cycloalkyl;
j) aryl, wherein aryl is phenyl or naphthyl and aryl is unsubstituted or substituted with 1 to 3 substituents selected from halo, $N(R^0)_2$, $OR^0$, $C_1$-$C_6$-alkyl, $CF_3$, $OCF_3$, $CO_2R^0$, and $C(O)N(R^0)_2$;
k) heteroaryl, wherein heteroaryl is a 5- or 6-membered aromatic ring having 1, 2 or 3 heteroatoms selected from N, O or S, attached through a carbon or nitrogen on the ring, and optionally substituted on a ring carbon or nitrogen that is not the point of attachment, with 1 or 2 substituents selected from $N(R^0)_2$, $OR^0$, $CO_2R^0$, $OC(O)$$C_1$-$C_6$-alkyl, $CON(R^0)_2$, $NHC(O)R^0$, and $C_1$-$C_6$-alkyl unsubstituted or substituted with 1 or 2 substituents selected from $N(R^0)_2$, $NHC(=NH)NH_2$, $OC(O)C_1$-$C_6$ alkyl, $OR^0$, $CO_2R^0$, $C(O)N(R^0)_2$ and $NHC(O)R^0$;
l) heterocyclyl, wherein heterocyclyl is a 5- or 6-membered, saturated or unsaturated non-aromatic ring having 1, 2 or 3 heteroatoms selected from N, O or S, attached through a carbon or nitrogen on the ring, and optionally substituted on a ring carbon or nitrogen that is not the point of attachment, with 1 to 2 substituents selected from $N(R^0)_2$, imino, oxo, $OR^0$, $CO_2R^0$, $OC(O)$$C_1$-$C_6$-alkyl, $CON(R^0)_2$, $NHC(O)R^0$, and $C_1$-$C_6$-alkyl unsubstituted or substituted with 1 or 2 substituents selected from $N(R^0)_2$, $NHC(=NH)NH_2$, $OC(O)C_1$-$C_6$-alkyl, $OR^0$, $CO_2R^0$, $C(O)N(R^0)_2$ and $NHC(O)R^0$;
m) $C(=NH)C_1$-$C_6$-alkyl, wherein said alkyl is unsubstituted or substituted with 1 or 2 substituents selected from halo, $CF_3$, $N(R^0)_2$, $OR^0$, and $NHC(O)C_1$-$C_6$-alkyl;
n) $C(=NR^d)NH_2$;
o) $C(=NH)NH$—$C_1$-$C_6$-alkyl, wherein said alkyl is unsubstituted or substituted with 1 to 3 substituents selected from halo, $CF_3$, $N(R^0)_2$, $OR^0$, and $NHC(O)C_1$-$C_6$-alkyl;
p) $C(=NH)NH$—$C_3$-$C_6$-cycloalkyl;
q) $C(=NH)NH$-phenyl, wherein phenyl is unsubstituted or substituted with 1 to 3 substituents selected from halo and $CF_3$; or
r) $C(=NH)NHC(=NH)NH_2$;

$R^6$ and $R^7$ are optionally taken together with the attached nitrogen atom to form a 3- to 6-membered saturated, unsaturated or aromatic ring having 0-2 additional heteroatoms selected from N, O and S, wherein said ring is optionally substituted on a ring carbon or nitrogen that is not the point of attachment, with 1 to 2 substituents selected from halo, $N(R^0)_2$, $OR^0$, $CO_2R^0$, $CON(R^0)_2$, and $C_1$-$C_6$ alkyl unsubstituted or substituted with 1 or 2 substituents selected from $OR^0$ and $N(R^0)_2$, and wherein two adjacent substituents of said ring are optionally taken together to form a fused 5- or 6-membered saturated, unsaturated, or aromatic ring having 0-2 heteroatoms selected from N, O and S; or $R^6$ and $R^9$ are optionally taken together, with the nitrogen atom $R^6$ is attached to, to form a pyrrolidinyl ring;

$R^8$ and $R^9$ are $C_1$-$C_6$ alkyl; or $R^8$ and $R^9$ are optionally taken together to form a 3- to 6-membered saturated ring having 0-1 heteroatom selected from N, O or S;

$R^{10}$ is $C_1$-$C_6$-alkyl unsubstituted or substituted with $OR^0$, $N(R^0)_2$, $OC(O)C_1$-$C_6$ alkyl or $CO_2R^0$;

$R^{11}$ is $C_1$-$C_6$ alkyl unsubstituted or substituted with $OR^0$, $OC(O)C_1$-$C_6$ alkyl, $OC(O)$-phenyl, $CO_2R^0$, or $N(R^0)_2$;

$R^{12}$ is OH or $C_1$-$C_6$ alkyl, wherein said alkyl is unsubstituted or substituted with $OC(O)C_1$-$C_6$ alkyl or $OR^0$;

$R^{13}$ is $C_1$-$C_4$-alkyl;

$R^{17}$ is
a) $C_1$-$C_6$-alkyl, unsubstituted or substituted with 1 to 2 substituents selected from $CO_2R^0$, $OR^0$, $N(R^0)_2$, and $OC(O)C_1$-$C_6$-alkyl;
b) aryl, wherein aryl is phenyl or naphthyl and aryl is unsubstituted or substituted with 1 to 2 substituents selected from halo, $OR^0$ and $N(R^0)_2$; or
c) $C_1$-$C_6$-haloalkyl;

$R^{18}$ is H or $C_1$-$C_6$-alkyl, wherein said alkyl is unsubstituted or substituted with 1 to 2 substituents selected from $OR^0$, $N(R^0)_2$, heteroaryl, heterocyclyl, $CO_2N(R^0)_2$, and $CO_2R^0$, wherein heteroaryl is as defined in $R^{16}$ (t) and heterocyclyl is as defined in $R^{16}$ (h); and each $R^0$ is independently H or $C_1$-$C_6$ alkyl.

The present invention also includes pharmaceutical compositions comprising a compound of the present invention and methods of preparing such compositions. The present invention further includes methods of treating or preventing mycotic infections comprising administering the present compounds or compositions, either alone or in combination with a second therapeutic agent.

Other embodiments, aspects and features of the present invention are either further described in or will be apparent from the ensuing description, examples and appended claims.

DETAILED DESCRIPTION OF THE INVENTION

The present invention relates to compounds of Formula I as described above, and pharmaceutically acceptable salts thereof. These compounds are useful as (1,3)-β-D-glucan synthase inhibitors. The present invention also includes compounds of Formula I-a wherein all variables are as originally defined for Formula I or as defined in embodiment P.

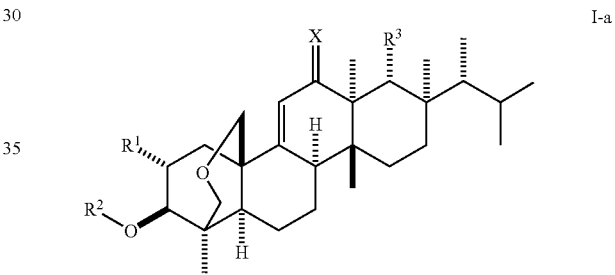

I-a

One embodiment of the present invention is a compound of Formula I or I-a, or a pharmaceutically acceptable salt thereof, wherein $R^3$ is $C(O)R^{14}$; and all other variables are as originally defined above or as defined in embodiment P.

A second embodiment of the present invention is a compound of Formula I or I-a, or a pharmaceutically acceptable salt thereof, wherein $R^3$ is $C(O)R^{14}$ and $R^{14}$ is OH or $OR^{15}$; and all other variables are as originally defined or as defined in embodiment P.

A third embodiment of the present invention is a compound of Formula II, or a pharmaceutically acceptable salt thereof, wherein $R^1$, $R^2$ and X are as originally defined for Formula I or as defined in embodiment P:

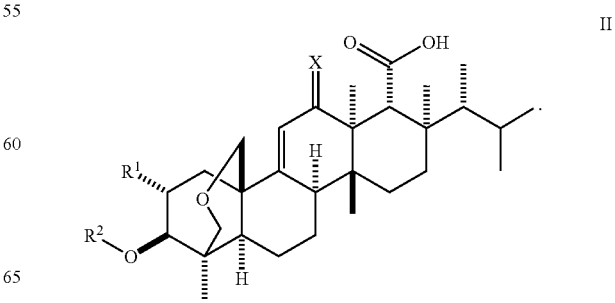

II

A fourth embodiment of the present invention is a compound of Formula I or I-a, or a pharmaceutically acceptable salt thereof, wherein X is O and all other variables are as originally defined or as defined in any one of the preceding embodiments (e.g., a compound of Formula II-1).

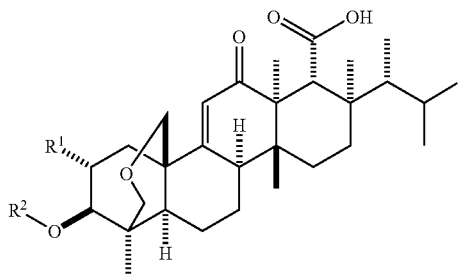

II-1

A fifth embodiment of the present invention is a compound of Formula I or I-a, or a pharmaceutically acceptable salt thereof, wherein X is $H_2$ and all other variables are as originally defined or as defined in any one of the preceding embodiments (e.g., a compound of Formula II-2).

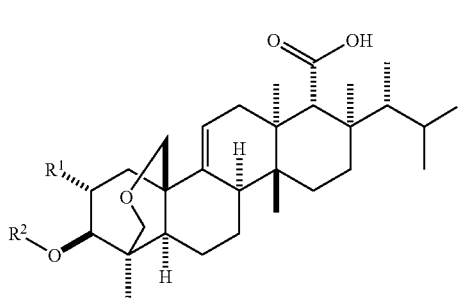

II-2

A sixth embodiment of the present invention is a compound of Formula I, I-a or II (II-1 or II-2), or a pharmaceutically acceptable salt thereof, wherein $R^1$ is $OC(O)C_1-C_{12}$ alkyl, unsubstituted or substituted with 1 or 2 substituents selected from $OR^0$, $N(R^0)_2$, and $CO_2R^0$; and all other variables are as originally defined or as defined in any one of the preceding embodiments.

A seventh embodiment of the present invention is a compound of Formula I, I-a or II (II-1 or II-2), or a pharmaceutically acceptable salt thereof, wherein $R^1$ is $OC(O)NHC_1-C_6$ alkyl, unsubstituted or substituted with phenyl; and all other variables are as originally defined or as defined in any one of the preceding embodiments.

An eighth embodiment of the present invention is a compound of Formula I, I-a or II (II-1 or II-2), or a pharmaceutically acceptable salt thereof, wherein $R^2$ is $CH_2CHR^5(CH_2)_m NR^6R^7$, $CH_2CR^8R^9(CH_2)_m NR^6R^7$, or $CHR^{13}CHR^5(CH_2)_m NR^6R^7$; and all other variables are as originally defined or as defined in any one of the preceding embodiments.

An aspect of the eighth embodiment is a compound of Formula III-1, III-2, III-3 or III-4:

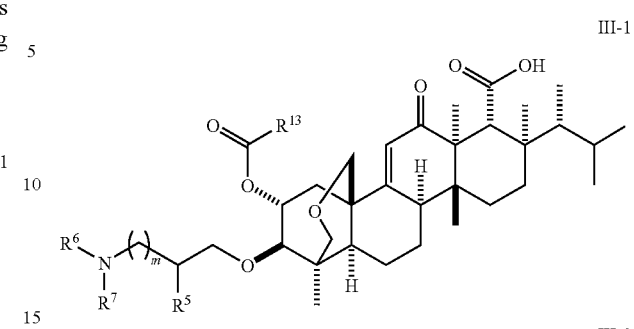

III-1

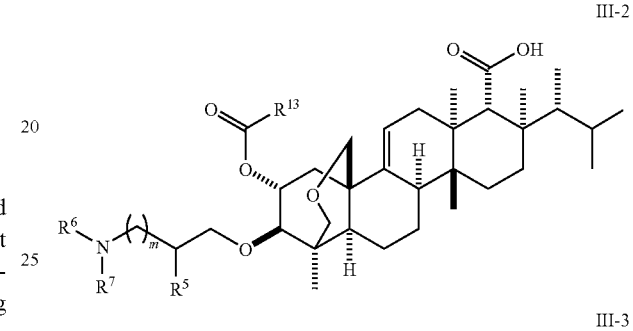

III-2

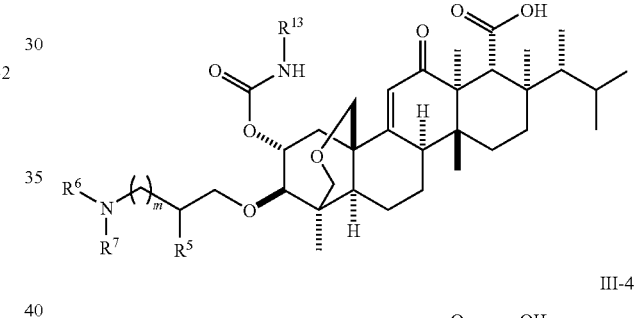

III-3

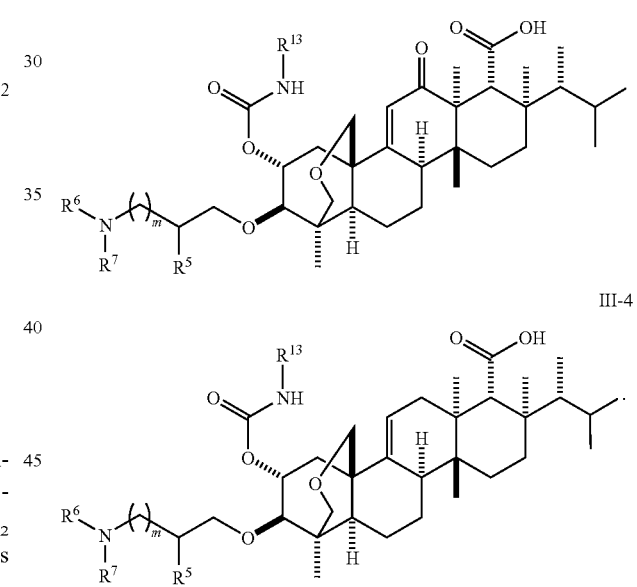

III-4

Another aspect of the eighth embodiment is a compound of Formula IV-1, IV-2, IV-3 or IV-4:

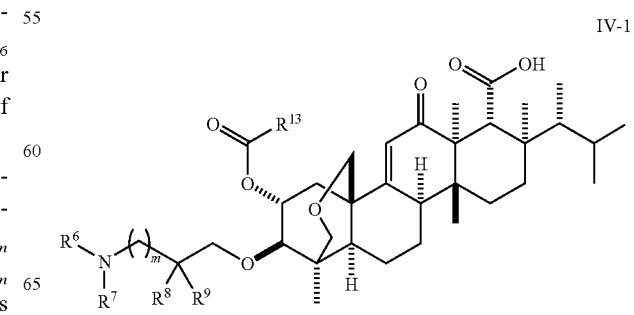

IV-1

-continued

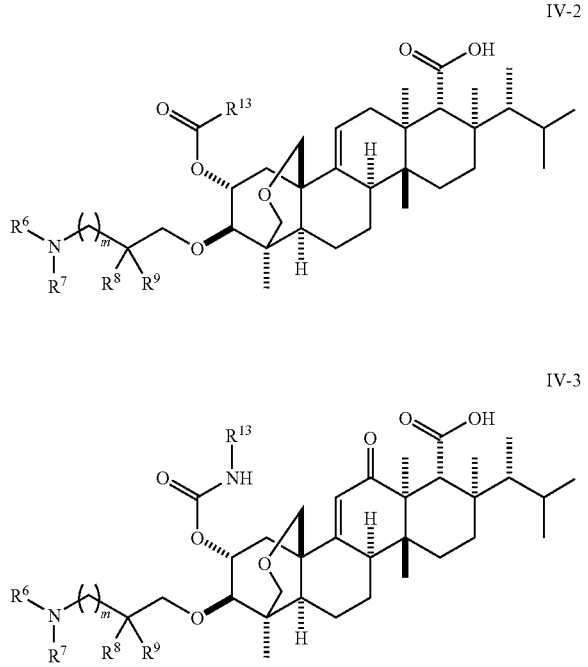

Another aspect of the eighth embodiment is a compound of Formula IV-1 wherein $R^{13}$ is —$CH_3$;

m is 0;

$R^8$ is selected from the group consisting of —$CH_3$, $CH_2CH_3$, $CH_2OCH(CH_3)_2$, and $CH(CH_3)_2$;

$R^9$ is selected from the group consisting of $CH_3$, $CH_2CH_3$, $CH_2CH_2CH_3$, $CH(CH_3)_2$, $CH(CH_3)(CH_2CH_3)$, $CH_2CH_2CH_2CH_3$, $CH_2OCH_3$, $CH_2CH_2OCH_3$, $CH_2CH_2OCH_2CH_3$, cyclohexyl, (R)$CH(CH_3)_2$, and (S)$CH(CH_3)_2$;

$R^6$ is H, —$CH_3$, $CH_2CH_3$, $CH_2CF_3$, $CH_2CH_2CH_3$, $CH_2CH_2OCH_3$, cyclobutyl, $CH_2$-cyclopropyl, $CH(CH_3)_2$, $CH_2CH_2CH_2CH_3$, $CH(CH_3)(CH_2CH_3)$, cyclopentyl, and cyclohexyl; and $R^7$ is H, —$CH_3$, $CH_2CH_3$, $CH(CH_3)_2$, and $CH_2CH_2CH_3$.

Another aspect of the eighth embodiment is a compound of Formula IV-1 wherein $R^{13}$ is —$CH_3$, m is 0, $R^8$ is —$CH_3$, $R^9$ is —$CH(CH_3)_2$, $R^6$ is H or —$CH_3$, and $R^7$ is H or —$CH_3$.

Another aspect of the eighth embodiment is a compound of Formula IV-1a:

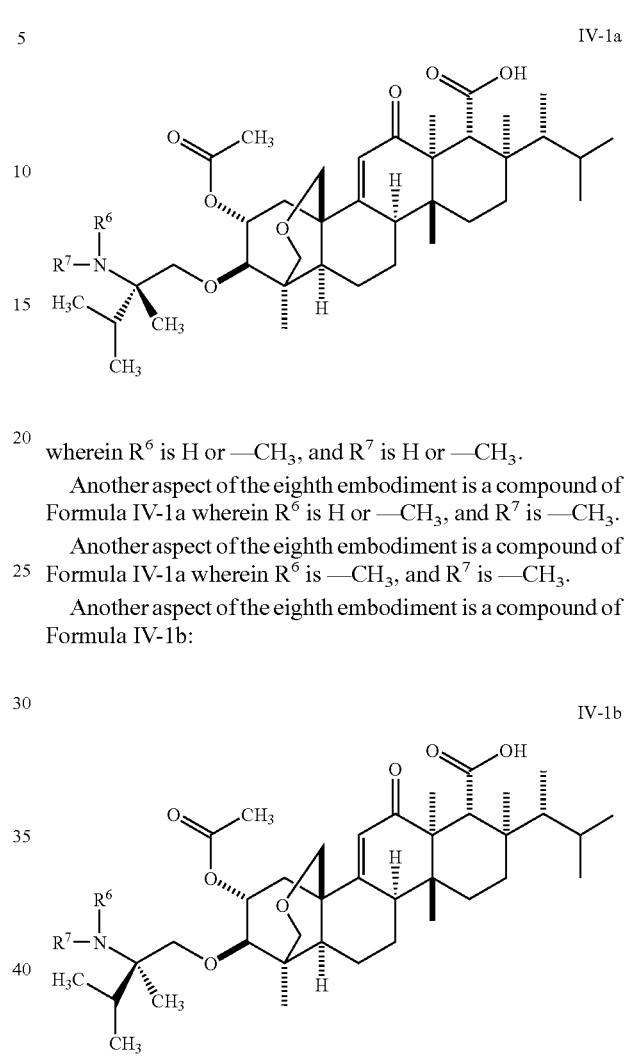

wherein $R^6$ is H or —$CH_3$, and $R^7$ is H or —$CH_3$.

Another aspect of the eighth embodiment is a compound of Formula IV-1a wherein $R^6$ is H or —$CH_3$, and $R^7$ is —$CH_3$.

Another aspect of the eighth embodiment is a compound of Formula IV-1a wherein $R^6$ is —$CH_3$, and $R^7$ is —$CH_3$.

Another aspect of the eighth embodiment is a compound of Formula IV-1b:

wherein $R^6$ is H or —$CH_3$, and $R^7$ is H or —$CH_3$.

Another aspect of the eighth embodiment is a compound of Formula IV-1b wherein $R^6$ is H or —$CH_3$, and $R^7$ is —$CH_3$.

Another aspect of the eighth embodiment is a compound of Formula Iv-1b wherein $R^6$ is —$CH_3$, and $R^7$ is —$CH_3$.

Yet another aspect of the eighth embodiment is a compound of Formula V-1, V-2, V-3 or V-4:

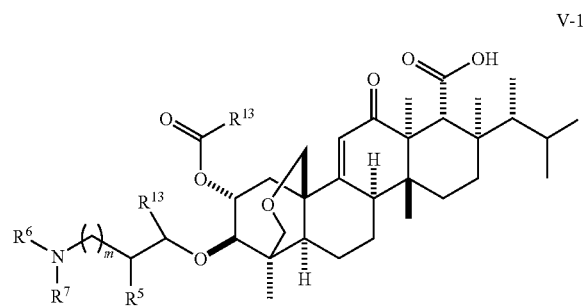

-continued

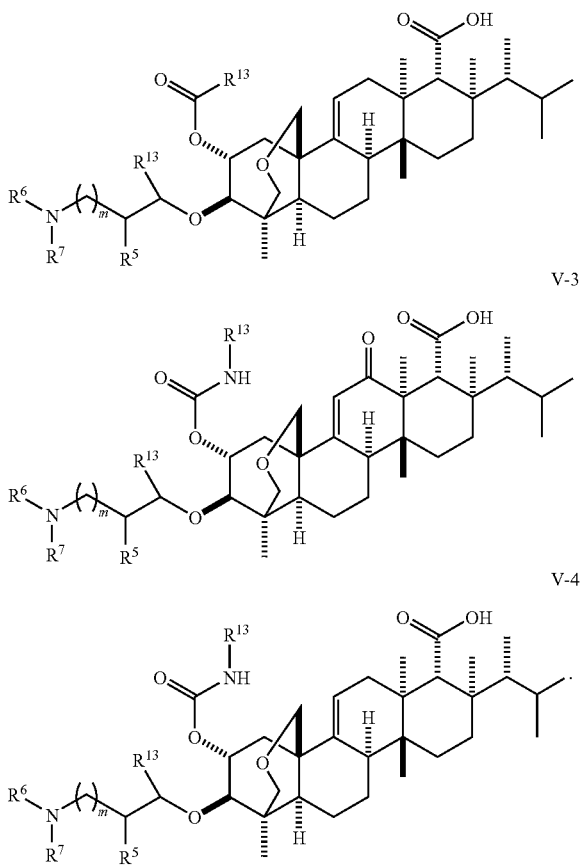

A ninth embodiment of the present invention is a compound of Formula I, I-a, II (II-1 or II-2), III-1 to III-4, IV-1 to IV-4, or V-1 to V-4, or a pharmaceutically acceptable salt thereof, wherein m is 0; and all other variables are as originally defined or as defined in any one of the preceding embodiments.

A tenth embodiment of the present invention is a compound of Formula III-1 to III-4, IV-1 to IV-4, or V-1 to V-4, or a pharmaceutically acceptable salt thereof, wherein $R^{13}$ is methyl and m is 0; and all other variables are as originally defined.

An eleventh embodiment of the present invention is a compound of Formula I, I-a II (II-1 or II-2), III-1 to III-4, or V-1 to V-4, or a pharmaceutically acceptable salt thereof, wherein $R^5$ is (i) $C_1$-$C_6$-alkyl, unsubstituted or substituted with 1 or 2 substituents selected from $N(R^o)_2$ and $OR^o$; (ii) $C_3$-$C_6$-cycloalkyl; or (iii) aryl, wherein aryl is phenyl or naphthyl and aryl is unsubstituted or substituted with 1 to 3 substituents selected from halo, $OCF_3$, $CF_3$, $N(R^o)_2$ and $OR^o$; and all other variables are as originally defined or as defined in any one of the preceding embodiments.

An aspect of the eleventh embodiment is a compound of Formula I, I-a, II (II-1 or II-2), III-1 to III-4, or V-1 to V-4, or a pharmaceutically acceptable salt thereof, wherein $R^5$ is (i) $C_1$-$C_6$-alkyl, unsubstituted or substituted with 1 substituent selected from $N(R^o)_2$ or $OR^o$, or (ii) $C_3$-$C_6$-cycloalkyl; and all other variables are as originally defined or as defined in any one of the preceding embodiments.

Another aspect of the eleventh embodiment is a compound of Formula I, I-a, II (II-1 or II-2), III-1 to III-4, or V-1 to V-4, or a pharmaceutically acceptable salt thereof, wherein $R^5$ is methyl, ethyl, n-propyl, i-propyl, n-butyl, i-butyl, n-pentyl, $CH_2NH_2$, $CH_2CH_2NH_2$, $CH_2OCH_3$, $CH_2OCH(CH_3)_2$, cyclopropyl, cyclopentyl, or cyclohexyl; and all other variables are as originally defined or as defined in any one of the preceding embodiments.

A twelfth embodiment of the present invention is a compound of Formula I, I-a, II (II-1 or II-2), III-1 to III-4, or V-1 to V-4, or a pharmaceutically acceptable salt thereof, wherein both $R^6$ and $R^7$ are H; and all other variables are as originally defined or as defined in any one of the preceding embodiments.

A thirteenth embodiment of the present invention is a compound of Formula I, I-a, II (II-1 or II-2), III-1 to III-4, or V-1 to V-4, or a pharmaceutically acceptable salt thereof, wherein $R^6$ is H and $R^7$ is (i) $C_1$-$C_6$-alkyl, unsubstituted or substituted with 1 or 2 substituents selected from $N(R^o)_2$, $OR^o$, $CO_2R^o$, $OC(O)C_1$-$C_6$-alkyl, $NHC(O)R^o$, and $C(O)N(R^o)_2$; (ii) $C_3$-$C_6$-cycloalkyl; or (iii) aryl, wherein aryl is phenyl or naphthyl and aryl is unsubstituted or substituted with 1 to 3 substituents selected from halo, $N(R^o)_2$, $OR^o$, $C_1$-$C_6$-alkyl, $CF_3$, $OCF_3$, $CO_2R^o$, and $C(O)N(R^o)_2$; and all other variables are as originally defined or as defined in any one of the preceding embodiments.

An aspect of the thirteenth embodiment is a compound of Formula I, I-a, II (II-1 or II-2), III-1 to III-4, or V-1 to V-4, or a pharmaceutically acceptable salt thereof, wherein $R^6$ is H, $R^7$ is methyl, $(CH_2)_3NH_2$, cyclopropyl, cyclobutyl, or phenyl; and all other variables are as originally defined or as defined in any one of the preceding embodiments.

A fourteenth embodiment of the present invention is a compound of Formula I, I-a, II (II-1 or II-2), III-1 to III-4, or V-1 to V-4, or a pharmaceutically acceptable salt thereof, wherein $R^6$ is H and $R^7$ is (i) $C_1$-$C_6$-alkyl substituted with 1 substituent selected from phenyl, heteroaryl or heterocyclyl; (ii) heteroaryl; (iii) $C(=NH)C_1$-$C_6$-alkyl, wherein said alkyl is unsubstituted or substituted with 1 or 2 substituents selected from halo, $CF_3$, $N(R^o)_2$, $OR^o$, and $NHC(O)C_1$-$C_6$-alkyl; (iv) $C(=NR^d)NH_2$; or (v) $C(=NH)NH$—$C_1$-$C_6$-alkyl, wherein said alkyl is unsubstituted or substituted with 1 to 3 substituents selected from halo, $CF_3$, $N(R^o)_2$, $OR^o$, and $NHC(O)C_1$-$C_6$-alkyl; and all other variables are as originally defined or as defined in any one of the preceding embodiments.

An aspect of the fourteenth embodiment is a compound of Formula I, I-a, II (II-1 or II-2), III-1 to III-4, or V-1 to V-4, or a pharmaceutically acceptable salt thereof, wherein $R^6$ is H and $R^7$ is $C(=NH)CH_3$, $C(=NH)CH_2CH_2NH_2$, $C(=NH)NH_2$, $C(=NH)NHCH_3$, benzyl, imidazolylmethyl, or triazolyl optionally substituted with an $NH_2$ group; and all other variables are as originally defined or as defined in any one of the preceding embodiments.

A fifteenth embodiment of the present invention is a compound of Formula I, I-a, II (II-1 or II-2), III-1 to III-4, or V-1 to V-4, or a pharmaceutically acceptable salt thereof, wherein both $R^6$ and $R^7$ are independently unsubstituted $C_1$-$C_6$-alkyl; or $R^6$ and $R^7$ are taken together with the attached nitrogen atom to form a 5- to 6-membered saturated, unsaturated or aromatic ring having 0-1 additional heteroatom selected from N, O or S, wherein said ring is optionally substituted on a ring carbon or nitrogen that is not the point of attachment, with 1 to 2 substituents selected from $N(R^o)_2$, $OR^o$, $CO_2R^o$, $CON(R^o)_2$, and $C_1$-$C_6$ alkyl unsubstituted or substituted with 1 or 2 substituents selected from $OR^o$ and $N(R^o)_2$, and wherein two adjacent substituents of said ring are optionally taken together to form a fused 5- or 6-membered saturated, unsaturated, or aromatic ring having 0-2 heteroatoms selected from N, O and S; and all other variables are as originally defined or as defined in any one of the preceding embodiments.

An aspect of the fifteenth embodiment is a compound of Formula I, I-a, II (II-1 or II-2), III-1 to III-4, or V-1 to V-4, or a pharmaceutically acceptable salt thereof, wherein both $R^6$ and $R^7$ are independently methyl, ethyl or propyl; or $R^6$ and $R^7$ are taken together with the attached nitrogen atom to form a piperidinyl ring; and all other variables are as originally defined or as defined in any one of the preceding embodiments.

A sixteenth embodiment of the present invention is a compound of Formula I, I-a, II (II-1 or II-2), or IV-1 to IV-4, or a pharmaceutically acceptable salt thereof, wherein both $R^8$ and $R^9$ are $C_1$-$C_3$ alkyl; or $R^8$ and $R^9$ are taken together to form a 3- to 6-membered saturated ring having 0-1 heteroatom selected from N, O or S; and all other variables are as originally defined or as defined in any one of the preceding embodiments.

An aspect of the sixteenth embodiment is a compound of Formula I, I-a, II (II-1 or II-2), or IV-1 to IV-4, or a pharmaceutically acceptable salt thereof, wherein $R^8$ is methyl and $R^9$ is methyl, ethyl or propyl; and all other variables are as originally defined or as defined in any one of the preceding embodiments.

Another aspect of the sixteenth embodiment is a compound of Formula I, I-a, II (II-1 or II-2), or IV-1 to IV-4, or a pharmaceutically acceptable salt thereof, wherein $R^8$ and $R^9$ are taken together to form a cyclobutyl or cyclopentyl; and all other variables are as originally defined or as defined in any one of the preceding embodiments.

A seventeenth embodiment of the present invention is a compound of Formula I, I-a, II (II-1 or II-2), or IV-1 to IV-4, or a pharmaceutically acceptable salt thereof, wherein both $R^6$ and $R^7$ are H; and all other variables are as originally defined or as defined in any one of the preceding embodiments.

An eighteenth embodiment of the present invention is a compound of Formula I, I-a, II (II-1 or II-2), or IV-1 to IV-4, or a pharmaceutically acceptable salt thereof, wherein $R^6$ is H and $R^7$ is unsubstituted $C_1$-$C_6$-alkyl; and all other variables are as originally defined or as defined in any one of the preceding embodiments.

An aspect of the eighteenth embodiment is a compound of Formula I, I-a, II (II-1 or II-2), or IV-1 to IV-4, or a pharmaceutically acceptable salt thereof, wherein $R^6$ is H; $R^7$ is propyl; and all other variables are as originally defined or as defined in any one of the preceding embodiments.

A nineteenth embodiment of the present invention is a compound of Formula I, I-a, II (II-1 or II-2), or IV-1 to IV-4, or a pharmaceutically acceptable salt thereof, wherein $R^6$ and $R^7$ are independently unsubstituted $C_1$-$C_6$-alkyl; and all other variables are as originally defined or as defined in any one of the preceding embodiments.

An aspect of the nineteenth embodiment is a compound of Formula I, I-a, II (II-1 or II-2), or IV-1 to IV-4, or a pharmaceutically acceptable salt thereof, wherein $R^6$ and $R^7$ are independently methyl or ethyl; and all other variables are as originally defined or as defined in any one of the preceding embodiments.

A twentieth embodiment of the present invention is a compound of Formula I, I-a, II (II-1 or II-2), III-1 to III-4, IV-1 to IV-4, or V-1 to V-4, or a pharmaceutically acceptable salt thereof, wherein m is 1; and all other variables are as originally defined or as defined in any one of the preceding embodiments.

A twenty-first embodiment of the present invention is a compound of Formula III-1 to III-4, IV-1 to IV-4, or V-1 to V-4, or a pharmaceutically acceptable salt thereof, wherein $R^{13}$ is methyl and m is 1; and all other variables are as originally defined or as defined in any one of the preceding embodiments.

A twenty-second embodiment of the present invention is a compound of Formula I, I-a, II (II-1 or II-2), III-1 to III-4, or V-1 to V-4, or a pharmaceutically acceptable salt thereof, wherein $R^5$ is OH; $OC_1$-$C_6$-alkyl, unsubstituted or substituted with phenyl; $OC(O)C_1$-$C_6$-alkyl; or $C_1$-$C_6$-alkyl, unsubstituted or substituted with 1 or 2 substituents selected from $N(R^0)_2$ and $OR^0$; and all other variables are as originally defined or as defined in any one of the preceding embodiments.

A twenty-third embodiment of the present invention is a compound of Formula I, I-a, II (II-1 or II-2), III-1 to III-4, or V-1 to V-4, or a pharmaceutically acceptable salt thereof, wherein $R^6$ is H and $R^7$ is (i) H; (ii) $C_1$-$C_6$-alkyl substituted with a heteroaryl; (iii) C(O)H; (iv) $C(O)C_1$-$C_6$-haloalkyl; (v) $C(O)C_1$-$C_6$-alkyl, unsubstituted or substituted with 1 or 2 substituents selected from $CO_2R^0$, $OR^0$, $OCH_2CO_2R^0$, $N(R^0)_2$, $C(O)C_1$-$C_6$-alkyl, $O(CH_2)_2OC_1$-$C_6$-alkyl, $C(O)N(R^0)_2$, $OC(O)C_1$-$C_6$ alkyl, and $NHC(O)R^0$; (vi) $C(O)OC_1$-$C_6$-alkyl; (vii) $C(O)NH$—$C_1$-$C_6$-alkyl; or (viii) $SO_2C_1$-$C_6$-alkyl; and all other variables are as originally defined or as defined in any one of the preceding embodiments.

An aspect of the twenty-third embodiment is a compound of Formula I, I-a, II (II-1 or II-2), III-1 to III-4, or V-1 to V-4, or a pharmaceutically acceptable salt thereof, wherein $R^6$ is H and $R^7$ is H; C(O)H; $C(O)C_1$-haloalkyl; $C(O)C_1$-$C_2$-alkyl unsubstituted or substituted with 1 or 2 substituents selected from $CO_2R^0$, $OR^0$, $OCH_2CO_2R^0$, $N(R^0)_2$, $C(O)C_1$-$C_6$-alkyl, and $O(CH_2)_2OC_1$-$C_2$-alkyl; $C(O)OC_1$-$C_2$-alkyl; $C(O)NH$—$C_1$-$C_2$-alkyl; $SO_2C_1$-$C_2$-alkyl; or $CH_2$-furanyl wherein furanyl is optionally substituted with $C_1$-$C_6$-alkyl which is unsubstituted or substituted with an $OR^0$; and all other variables are as originally defined or as defined in any one of the preceding embodiments.

Another aspect of the twenty-third embodiment is a compound of Formula I, I-a, II (II-1 or II-2), III-1 to III-4, or V-1 to V-4, or a pharmaceutically acceptable salt thereof, wherein $R^6$ is H and $R^7$ is H, C(O)H, $C(O)CF_3$, $C(O)CH_3$, $C(O)CH_2OH$, $C(O)CH_2NH_2$, $C(O)CH_2C(O)CH_3$, $C(O)CH_2O(CH_2)_2OCH_3$, $C(O)CH_2OCH_2CO_2H$, $C(O)(CH_2)_2CO_2H$, $C(O)(CH_2)_2CO_2CH_3$, $CO_2CH_3$, C(O)NH-ethyl, $SO_2CH_3$, $CH_2$-furanyl wherein furanyl is optionally substituted with hydroxymethyl; and all other variables are as originally defined or as defined in any one of the preceding embodiments.

A twenty-fourth embodiment the present invention is a compound of Formula I, I-a, II (II-1 or II-2), or IV-1 to IV-4, or a pharmaceutically acceptable salt thereof, wherein m is 1; both $R^8$ and $R^9$ are $C_1$-$C_4$ alkyl; or $R^8$ and $R^9$ are taken together to form a 3- to 6-membered saturated ring having 0-1 heteroatom selected from N, O or S; and all other variables are as originally defined or as defined in any one of the preceding embodiments.

An aspect of the twenty-fourth embodiment is a compound of Formula I, I-a, II (II-1 or II-2), or IV-1 to IV-4, or a pharmaceutically acceptable salt thereof, wherein m is 1; $R^8$ is methyl and $R^9$ is methyl, ethyl or propyl; and all other variables are as originally defined or as defined in any one of the preceding embodiments.

Another aspect of the twenty-fourth embodiment is a compound of Formula I, I-a, II (II-1 or II-2), or IV-1 to IV-4, or a pharmaceutically acceptable salt thereof, wherein m is 1; $R^8$ and $R^9$ are taken together to form a cyclobutyl or cyclopentyl; and all other variables are as originally defined or as defined in any one of the preceding embodiments.

A twenty-fifth embodiment of the present invention is a compound of Formula I, I-a, II (II-1 or II-2), or IV-1 to IV-4, or a pharmaceutically acceptable salt thereof, wherein m is 1; both $R^6$ and $R^7$ are H; and all other variables are as originally defined or as defined in any one of the preceding embodiments.

A twenty-sixth embodiment of the present invention is a compound of Formula I, I-a, II (II-1 or II-2), or IV-1 to IV-4, or a pharmaceutically acceptable salt thereof, wherein m is 1; $R^6$ is H and $R^7$ is unsubstituted $C_1$-$C_6$-alkyl; and all other variables are as originally defined or as defined in any one of the preceding embodiments.

An aspect of the twenty-sixth embodiment is a compound of Formula I, I-a, II (II-1 or II-2), or IV-1 to IV-4, or a pharmaceutically acceptable salt thereof, wherein m is 1; $R^6$ is H; $R^7$ is propyl; and all other variables are as originally defined or as defined in any one of the preceding embodiments.

A twenty-seventh embodiment of the present invention is a compound of Formula I, I-a, II (II-1 or II-2), or IV-1 to IV-4, or a pharmaceutically acceptable salt thereof, wherein m is 1; $R^6$ and $R^7$ are independently unsubstituted $C_1$-$C_6$-alkyl; and all other variables are as originally defined or as defined in any one of the preceding embodiments.

An aspect of the twenty-seventh embodiment is a compound of Formula I, I-a, II (II-1 or II-2), or IV-1 to IV-4, or a pharmaceutically acceptable salt thereof, wherein m is 1; $R^6$ and $R^7$ are independently methyl or ethyl; and all other variables are as originally defined or as defined in any one of the preceding embodiments.

A twenty-eighth embodiment of the present invention is a compound of Formula I or I-a, or a pharmaceutically acceptable salt thereof, wherein $R^2$ is $CH_2R^4$ and $R^4$ is $(CH_2)_{1-6}$—$R^{16}$ or heterocyclyl, wherein heterocyclyl is a 5- or 6-membered, saturated or unsaturated non-aromatic ring having 1, 2 or 3 heteroatoms selected from N, O or S, attached through a carbon or nitrogen on the ring, and optionally substituted on a ring carbon or nitrogen that is not the point of attachment, with 1 to 2 substituents selected from oxo, $N(R^0)_2$, $OR^0$, $CO_2R^0$, $CON(R^0)_2$, and $C_1$-$C_6$-alkyl unsubstituted or substituted with 1 or 2 substituents selected from $N(R^0)_2$, NHC(=NH)$NH_2$, OC(O)$C_1$-$C_6$-alkyl and $CO_2R^0$; and all other variables are as originally defined.

An aspect of the twenty-eighth embodiment is a compound of Formula I or I-a, or a pharmaceutically acceptable salt thereof, wherein $R^4$ is pyrrolidinyl optionally substituted with 1 to 2 substituents selected from oxo, $N(R^0)_2$, $OR^0$, $CO_2R^0$, $CON(R^0)_2$, and $C_1$-$C_6$-alkyl unsubstituted or substituted with 1 or 2 substituents selected from $N(R^0)_2$, NHC(=NH)$NH_2$, OC(O)$C_1$-$C_6$-alkyl and $CO_2R^0$; and all other variables are as originally defined.

A twenty-ninth embodiment of the present invention is a compound of Formula VI-1, VI-2, VI-3, or VI-4:

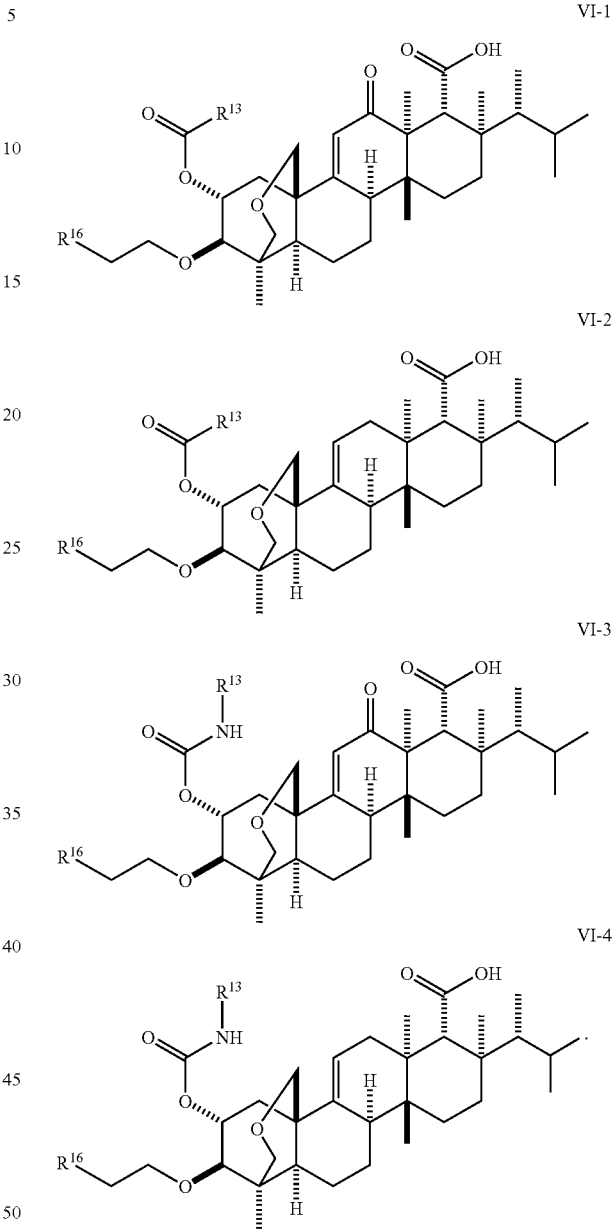

A thirtieth embodiment of the present invention is a compound of Formula VI-1, VI-2, VI-3, or VI-4, wherein $R^{13}$ is methyl and $R^{16}$ is as originally defined.

A thirty-first embodiment of the present invention is a compound of Formula VI-1, VI-2, VI-3, or VI-4, wherein $R^{13}$ is methyl or as originally defined and $R^{16}$ is $NR^a R^b$.

An aspect of the thirty-first embodiment is a compound of Formula VI-1, VI-2, VI-3, or VI-4, wherein $R^a$ is H and $R^b$ is $C_1$-$C_6$ alkyl unsubstituted or substituted with 1 or 2 $N(R^0)_2$ substituents.

A thirty-second embodiment of the present invention is a compound or a pharmaceutically acceptable salt thereof, selected from Tables A-H and J-M and 3a below. An aspect of the thirty-second embodiment is a compound or a pharmaceutically acceptable salt thereof, selected from compounds set forth in Examples 1 to 114 and 124 to 179.

A thirty-third embodiment of the present invention is a compound, or a pharmaceutically acceptable salt thereof, selected from the group consisting of
(1S,2R,3R,4aR,6aS,7R,8R,10aR,10bR,12aR)-3-(acetyloxy)-2-[(2S)-2-amino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid,
(1S,2R,3R,4aR,6aS,7R,8R,10aR,10bR,12aR)-3-(acetyloxy)-2-[(2S)-2-methylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4-a-(methanooxymethano)chrysene-7-carboxylic acid,
(1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4-a-(methanooxymethano)chrysene-7-carboxylic acid,
(1S,2R,3R,4aR,6aS,7R,8R,10aR,10bR,12aR)-3-acetoxy-2-[[(2R)-2-amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4-a-(methanooxymethano)chrysene-7-carboxylic acid,
(1S,2R,3R,4aR,6aS,7R,8R,10aR,10bR,12aR)-3-acetoxy-2-[[(2R)-2-methylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4-a-(methanooxymethano)chrysene-7-carboxylic acid, and
(1S,2R,3R,4aR,6aS,7R,8R,10aR,10bR,12aR)-3-acetoxy-2-[[(2R)-2-dimethylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid.

A thirty-fourth embodiment of the present invention is a compound, or a pharmaceutically acceptable salt thereof, which is
(1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid.

A thirty-fifth embodiment of the invention includes hydrates of any of the embodiments and aspects defined above.

The compounds set forth in each of Tables A-H and J-M and 3a are further embodiments of the invention, and the compounds individually are aspects of the embodiments.

TABLE A

I-a

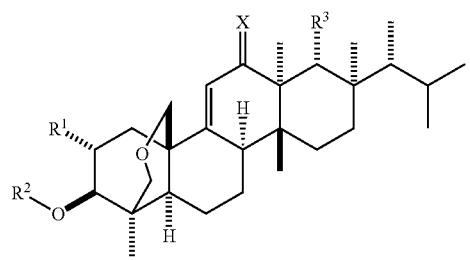

| Compound No. | X | R¹ | R² | R³ |
|---|---|---|---|---|
| A-1 | $H_2$ | HO | $CH_3$ | $C(O)OCH_2$-phenyl |
| A-2 | $H_2$ | $CH_3O$ | $CH_3$ | $CH_2OH$ |
| A-3 | O | $CH_3C(O)O$ | 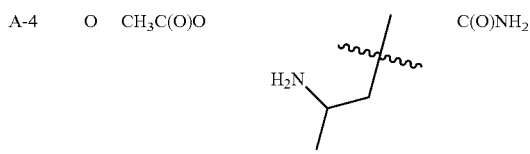 | 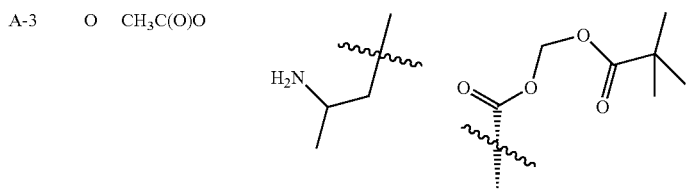 |
| A-4 | O | $CH_3C(O)O$ | 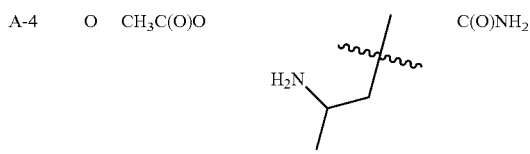 | $C(O)NH_2$ |

TABLE A-continued
I-a
| Compound No. | X | R¹ | R² | R³ |
|---|---|---|---|---|
| A-5 | O | CH₃C(O)O | 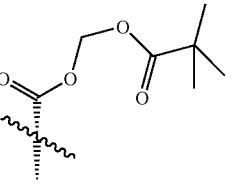 | 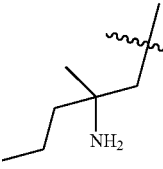 |
| A-6 | O | CH₃O | 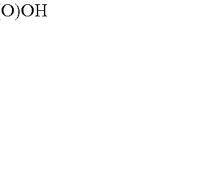 | C(O)OH |
| A-7 | H₂ | CH₃C(O)O | 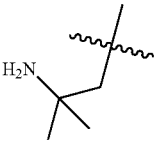 | C(O)OCH₃ |
| A-8 | H₂ | CH₃O | 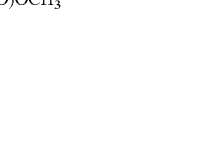 | CH₂OH |
| A-9 | H₂ | CH₃C(O)O | 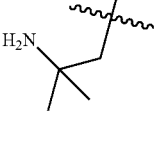 | C(O)NH₂ |

TABLE A-continued
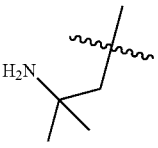
I-a
| Compound No. | X | R¹ | R² | R³ |
|---|---|---|---|---|
| A-10 | $H_2$ | $CH_3C(O)O$ | 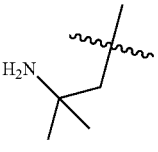 | $CH_2OC(O)CH_3$ |
| A-11 | O | $CH_3C(O)O$ | 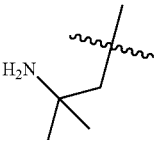 | $C(O)OCH_3$ |
| A-12 | O | $CH_3C(O)O$ | 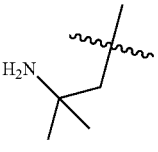 | $C(O)NH_2$ |
| A-13 | $H_2$ | $CH_3C(O)O$ | 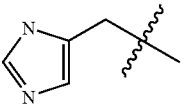 | $C(O)OH$ |
| A-14 | $H_2$ | $CH_3O$ | $NH_2CH_2CH_2$ | $C(O)OH$ |
| A-15 | $H_2$ | $CH_3O$ | $(CH_3)_2NCH_2CH_2$ | $C(O)OH$ |
| A-16 | $H_2$ | $(CH_3)_3CC(O)O$ | $CH_3NHCH_2CH_2$ | $C(O)OH$ |
| A-17 | $H_2$ | $CH_3CH_2C(O)O$ | $CH_3NHCH_2CH_2$ | $C(O)OH$ |
| A-18 | $H_2$ | $CH_3(CH_2)_2C(O)O$ | $CH_3NHCH_2CH_2$ | $C(O)OH$ |
| A-19 | $H_2$ | $(CH_3)_2CHC(O)O$ | $CH_3NHCH_2CH_2$ | $C(O)OH$ |
| A-20 | $H_2$ | $CH_3C(O)O$ | $NCCH_2CH_2$ | $C(O)OH$ |

TABLE B

II-1

[Structure of compound II-1 with R¹ and R²O substituents on pentacyclic triterpene scaffold with ketone and carboxylic acid groups]

| Cpd. No. | R¹ | R² |
|---|---|---|
| B-1 | CH₃C(O)O | -CH₂-C(OH)(CH₂OH)(CH₂NH₂) group |
| B-2 | CH₃C(O)O | -CH₂-C(OH)(CH₂OH)(CH₂CH₂NH₂) group |
| B-3 | CH₃C(O)O | pyrrolidin-2-ylmethyl group |

TABLE C

II-2

[Structure of compound II-2 with R¹ and R²O substituents on pentacyclic triterpene scaffold with C=C double bond and carboxylic acid group]

| Cpd. # | R¹ | R² |
|---|---|---|
| C-1 | CH₃C(O)O | benzyl (CH₂-C₆H₅) |
| C-2 | NH₂(CH₂)₂O | CH₂CH₂NH₂ |
| C-3 | CH₃C(O)O | HOCH₂CH₂ |
| C-4 | HO(CH₂)₂O | HOCH₂CH₂ |
| C-5 | HO | HOCH₂CH₂ |
| C-6 | CH₃OC(O)O | HOCH₂CH₂ |
| C-7 | HO | CH₃CH₂CH₂ |

TABLE C-continued

II-2

| Cpd. # | R¹ | R² |
|---|---|---|
| C-10 | | 2,2-dimethyl-1,3-dioxolane-4,5-diyl group |
| C-39 | CH₃C(O)NH | -CH(CH₃)-CH₂-NH₂ group |
| C-12 | CF₃C(O)O | -C(CH₃)₂-NH-C(O)-CH(NH₂)-CH₂OH group |
| C-13 | HO | -C(CH₃)₂-CH₂-NH-C(O)-NH₂ group |
| C-14 | CH₃C(O)O | -C(CH₃)(CH₂OH)(CH₂OH) with additional CH₂OH group |
| C-15 | CH₃C(O)O | -CH₂-CH(OH)-CH₂-OH group |
| C-16 | CH₃C(O)O | -C(CH₃)(CH₂OH)(CH₂OH)(CH₂OC(O)CH₃) group |

TABLE C-continued
II-2
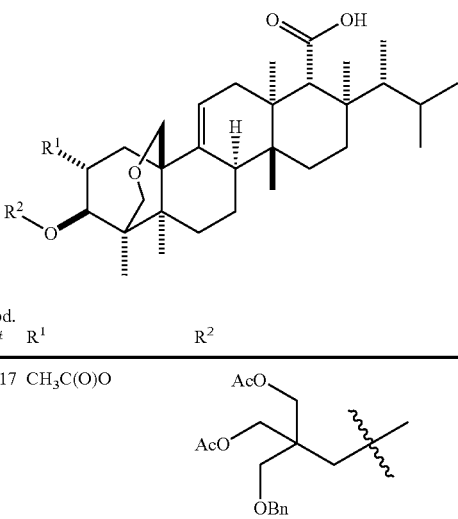
| Cpd. # | R¹ | R² |
|---|---|---|
| C-17 | CH₃C(O)O | 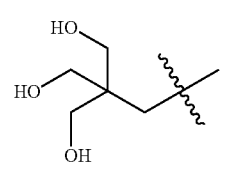 |
| C-18 | CH₃C(O)O | 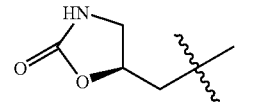 |
| C-19 | CH₃C(O)O | 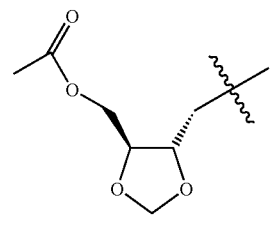 |
| C-20 | CH₃C(O)O | 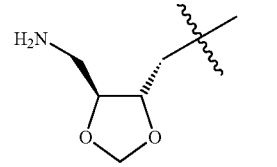 |
| C-21 | CH₃C(O)O | 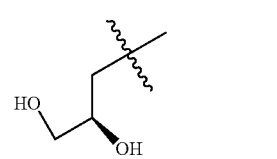 |
| C-22 | CH₃C(O)O | 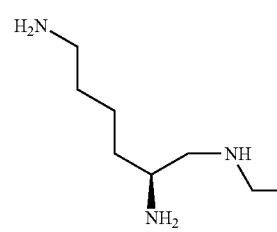 |
| C-23 | CH₃O | 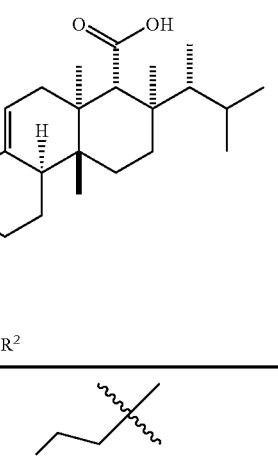 |
TABLE C-continued
II-2
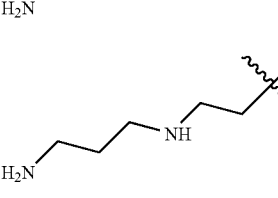
| Cpd. # | R¹ | R² |
|---|---|---|
| C-24 | CH₃O | 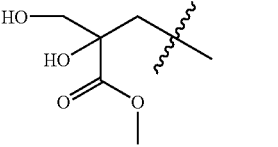 |
| C-25 | CH₃O | 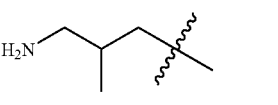 |
| C-26 | CH₃C(O)O | 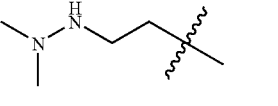 |
| C-27 | CH₃O | 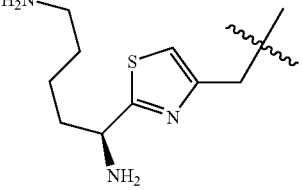 |
| C-28 | CH₃O | 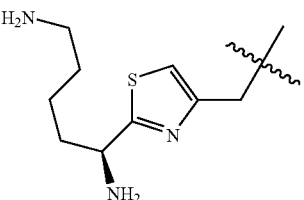 |
| C-29 | CH₃C(O)O | 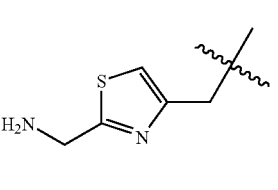 |
| C-30 | CH₃O | |
| C-31 | CH₃O | |

TABLE C-continued

II-2

| Cpd. # | R¹ | R² |
|---|---|---|
| C-32 | CH₃O | guanidino-propyl group (H₂N-C(=NH)-NH-C(=NH)-NH-CH₂CH₂-) |
| C-33 | CH₃O | 2-(1-aminoethyl)thiazol-4-ylmethyl |
| C-34 | CH₃O | 2-(guanidinomethyl)thiazol-4-ylmethyl |
| C-35 | CH₃O | 2-(1-guanidinoethyl)thiazol-4-ylmethyl |
| C-36 | CH₃O | 2-amino-1-methylpropyl |
| C-37 | CH₃O | 2-amino-3-hydroxypropylaminoethyl |
| C-38 | cyclopropanecarbonyloxy | 2-aminoethyl |

TABLE D

III-1A

| Cpd. # | R⁵ | R⁶ | R⁷ |
|---|---|---|---|
| D-1 | CH₃ | H | imidazol-2-ylmethyl |
| D-2 | CH₃ | H | amidino (C(=NH)NH₂) |
| D-3 | CH₃ | H | H |
| D-4 | CH₃ | CH₃ | CH₃ |
| D-5 | CH₃ | H | N-methylamidino |
| D-6 | CH₃ | H | 1-imino-2-aminoethyl |
| D-7 | CH₃(CH₂)₂ | H | H |
| D-8 | (CH₃)₂CH | H | 3-amino-1H-1,2,4-triazol-5-yl |
| D-9 | CH₃ | H | 3-amino-1H-1,2,4-triazol-5-yl |
| D-10 | CH₃CH₂ | H | H |
| D-11 | (CH₃)₂CH | H | H |
| D-12 | CH₃ | | thieno[2,3-c]pyrrol-5-yl |

TABLE D-continued

III-1A

| Cpd. # | R⁵ | R⁶ | R⁷ |
|---|---|---|---|
| D-13 | phenyl | H | H |
| D-14 | CH₃CH₂ | CH₃ | CH₃ |
| D-15 | i-propyl | Et | Et |
| D-16 | i-propyl | CH₃ | CH₃ |
| D-17 | Et | Et | Et |
| D-18 | CH₃ | Et | Et |
| D-19 | i-propyl | NR⁶R⁷ = piperidinyl | |
| D-20 | CH₃ | H | 5-(hydroxymethyl)furan-2-ylmethyl |
| D-21 | CH₃ | R⁶ = R⁷ = 5-(hydroxymethyl)furan-2-ylmethyl | |
| D-22 | ethyl | H | 5-(hydroxymethyl)furan-2-ylmethyl |
| D-23 | HOCH₂ | H | H |
| D-24 | n-propyl | CH₃ | CH₃ |
| D-25 | 4-(trifluoromethoxy)phenyl | H | H |
| D-26 | CH₃OCH₂ | H | H |
| D-27 | cyclopentyl | H | H |
| D-28 | n-heptyl | H | H |
| D-29 | ethyl | R⁶ = R⁷ = n-propyl | |
| D-30 | ethyl | H | benzyl |
| D-31 | CH₃ | H | H₂N(CH₂)₃— |
| D-32 | cyclopropyl | H | H |
| D-33 | n-pentyl | H | H |
| D-34 | n-butyl | H | H |
| D-35 | sec-butyl(2-methylbutyl) | H | H |
| D-36 | cyclopentyl | CH₃ | CH₃ |
| D-37 | cyclohexyl | H | H |
| D-38 | cyclohexyl | CH₃ | CH₃ |

TABLE D-continued

III-1A

| Cpd. # | R⁵ | R⁶ | R⁷ |
|---|---|---|---|
| D-39 | 4-fluorophenyl | H | H |
| D-40 | n-butyl | CH₃ | CH₃ |
| D-41 | CH₃OCH₂ | CH₃ | CH₃ |
| D-42 | sec-butyl (1-methylpropyl) | CH₃ | CH₃ |
| D-43 | sec-butyl (1-methylpropyl) | H | i-propyl |
| D-44 | isopropoxymethyl | H | H |
| D-45 | CH₃ | H | cyclopropyl |
| D-46 | 4-aminobutyl | H | H |
| D-47 | isopropoxymethyl | CH₃ | CH₃ |
| D-48 | n-propyl | H | -C(CH₃)₂-NH-C(=NH)-NH-CH₂CH₂-NH-C(=O)CH₃ |
| D-49 | CH₃ | H | 1-cyclobutyl-1-methyl |
| D-50 | ethyl | H | 1-cyclobutyl-1-methyl |
| D-51 | ethyl | H | CH₃ |
| D-52 | isobutyl | H | H |
| D-53 | cyclopentyl | H | -C(CH₃)₂-NH-C(=NH)-NH-CH₂CF₃ |
| D-54 | CH₃ | H | -C(CH₃)(–)-N=C(NH₂)-NH-(2-CF₃-phenyl) |

TABLE D-continued

III-1A

[Structure of III-1A]

| Cpd. # | R⁵ | R⁶ | R⁷ |
|---|---|---|---|
| D-55 | [isobutyl-methyl branched group] | CH₃ | CH₃ |
| D-56 | [cyclohexyl-methyl group] | H | [t-butyl-HN-C(=NH)- guanidino group] |
| D-57 | n-propyl | H | n-propyl |
| D-58 | n-pentyl | H | [H₂N-C(=NH)- amidino group] |
| D-59 | CH₃ | H | [H₂C=C(CH₃)-N= group] |
| D-60 | n-propyl | H | ethyl |
| D-61 | ethyl | H | ethyl |

TABLE E

III-1B

[Structure of III-1B]

| Cpd. # | R⁵ | R⁶ | R⁷ |
|---|---|---|---|
| E-1 | [CH₂-N(CH₃)₂ group] | H | H |
| E-2 | CH₃ | Et | Et |
| E-3 | H | H | H |
| E-4 | H | H | [H₂N-C(=NH)- amidino group] |
| E-5 | CH₃ | H | H |

TABLE F

III-2A

[Structure of III-2A]

| Cpd. No. | R⁵ | R⁶ | R⁷ |
|---|---|---|---|
| F-1 | CH₃ | H | H |
| F-2 | n-butyl | H | H |
| F-3 | i-propyl | H | H |
| F-4 | [cyclopentyl group] | H | H |
| F-5 | [cyclohexyl-methyl group] | H | H |

TABLE F-continued

III-2A

| Cpd. No. | R⁵ | R⁶ | R⁷ |
|---|---|---|---|
| F-6 | 2-thiazolyl | H | H |
| F-7 | i-propyl | H | 3-amino-1H-1,2,4-triazol-5-yl |
| F-8 | n-pentyl | H | H |

TABLE G

III-2b

| Cpd. # | R⁵ | R⁶ | R⁷ |
|---|---|---|---|
| G-1 | –CH(OC(O)CH₃)– (methyl-acetate substituent) | H | –C(O)NHCH₂CH₃ (N-ethyl amide) |
| G-2 | –CH(OC(O)CH₃)– | H | CH₃SO₂ |
| G-3 | –CH(OC(O)CH₃)– | H | –C(O)CF₃ |
| G-4 | –CH(OH)– | H | CH₃C(O) |
| G-5 | –CH(OH)– | H | CH₃SO₂ |
| G-6 | –CH(OH)– | H | –C(O)NHCH₂CH₃ |
| G-7 | –CH(OC(O)CH₃)– | H | CH₃C(O) |
| G-8 | –CH(OH)– | H | –C(O)CH₂CH₂C(O)OH |
| G-9 | –CH(OH)– | H | –C(O)CH₂CH₂C(O)OCH₃ |
| G-10 | –CH(OH)– | H | –C(O)CH₂OH |
| G-11 | –CH(OH)– | H | –C(O)CH₂OCH₂C(O)OH |
| G-12 | –CH(OH)– | H | H |
| G-13 | –CH(OH)– | H | –C(O)OCH₃ |

TABLE G-continued

III-2b

Structure III-2b

| Cpd. # | R⁵ | R⁶ | R⁷ |
|---|---|---|---|
| G-14 | (wavy)-OH | H | H₃C-O-CH₂CH₂-O-CH₂-C(=O)-(wavy) |
| G-15 | (wavy)-OH | H | H₃C-C(CH₃)₂-C(=O)-(wavy) |
| G-16 | (wavy)-O-CH₂-C₆H₅ | H | H₂N-CH₂-C(=O)-(wavy) |
| G-17 | (wavy)-OH | H | H₃C-C(=O)-CH₂-C(=O)-(wavy) |
| G-18 | (wavy)-OH | H | EtNH-C(=O)-CH(CH₃)-(wavy) |
| G-19 | (wavy)-OH | H | OHC-CH(CH₃)-(wavy) |
| G-20 | CH₃ | H | H |
| G-21 | CH₃ | H | (CH₃)₂-C-C(=O)-CH₃ |
| G-22 | CH₃ | H | H |

TABLE H

III-3A

Structure III-3A

| Cpd. No. | R⁵ | R⁶ | R⁷ |
|---|---|---|---|
| H-1 | i-propyl | H | H |

TABLE J

IV-1A

Structure IV-1A

| Cpd. No. | R⁶ | R⁷ | R⁸ | R⁹ |
|---|---|---|---|---|
| J-1 | H | H | CH₃ | CH₃ |
| J-2 | CH₃ | CH₃ | CH₃ | CH₃ |
| J-3 | H | H | CH₃ | n-propyl |
| J-4 | ethyl | ethyl | CH₃ | CH₃ |
| J-5 | CH₃ | CH₃ | CH₃ | n-propyl |
| J-6 | H | i-propyl | CH₃ | CH₃ |
| J-7 | H | H | CH₃ | i-propyl |
| J-8 | ethyl | ethyl | CH₃ | n-propyl |
| J-9 | H | H | CH₃ | ethyl |
| J-10 | CH₃ | CH₃ | CH₃ | ethyl |
| J-11 | CH₃ | CH₃ | CH₃ | i-propyl |
| J-12 | H | CH₃ | CH₃ | CH₃ |
| J-13 | H | CF₃CH₂ | CH₃ | n-propyl |
| J-14 | H | H | CH₃ | i-butyl |
| J-15 | CH₃ | CH₃ | CH₃ | i-butyl |
| J-16 | H | H | ethyl | ethyl |
| J-17 | H | H | CH₃ | CH₂O-(i-propyl) |
| J-18 | CH₃ | CH₃ | CH₃ | CH₂O-(i-propyl) |
| J-19 | ethyl | ethyl | CH₃ | ethyl |
| J-20 | n-propyl | n-propyl | CH₃ | ethyl |
| J-21 | H | CH₃ | cyclopropyl | |
| J-22 | H | H | cyclobutyl | |
| J-23 | H | CH₃ | 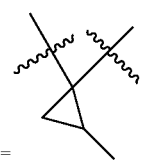 | |
| | | | CR⁸R⁹ = | |
| J-24 | CH₃ | CH₃ | 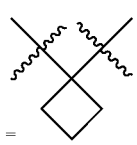 | |
| | | | CR⁸R⁹ = | |
| J-25 | H | H | CH₂OCH(CH₃)₂ | CH₃ |
| J-26 | CH₃ | CH₃ | CH₂OCH(CH₃)₂ | CH₃ |

TABLE J-continued

IV-1A

| Cpd. No. | R⁶ | R⁷ | R⁸ | R⁹ |
|---|---|---|---|---|
| J-27 | H | H | CH₂OCH₃ | CH₃ |
| J-28 | CH₃ | CH₃ | CH₂OCH₃ | CH₃ |
| J-29 | H | H | CH₂OCH₂CH₃ | CH₃ |
| J-30 | CH₃ | CH₃ | CH₂OCH₂CH₃ | CH₃ |
| J-31 | CH₃ | CH₃ | CH₂CH₂OCH₃ | CH₃ |
| J-32 | H | H | CH₂CH₂OCH₃ | CH₃ |
| J-33 | H | H | CH₂OCH₃ | CH₂OCH₃ |
| J-34 | CH₂CH₃ | CH₂CH₃ | CH₂OCH₂CH₃ | CH₃ |
| J-35 | H | H | CH₂CH₂OCH₂CH₃ | CH₃ |
| J-36 | CH₃ | CH₃ | CH₂CH₂OCH₂CH₃ | CH₃ |
| J-37 | CH₂CH₃ | CH₂CH₃ | CH₂OCH₃ | CH₃ |
| J-38 | H | CH₂CH₃ | CH₂CH₂OCH₃ | CH₃ |
| J-39 | H | H | CH₂CH₂SO₂CH₃ | CH₃ |
| J-40 | H | H | CH₃ | 4-F-C₆H₄ |
| J-41 | CH₃ | CH₃ | CH₃ | 4-F-C₆H₄ |

TABLE K

VI-1, VI-2

TABLE K-continued

VI-4 wherein R¹³ of VI-1, VI-2 or VI-4 is methyl.

| Cpd. # | Formula | R¹⁶CH₂CH₂ |
|---|---|---|
| K-1 | VI-2 | CH₃C(O)NHCH₂CH₂ |
| K-2 | VI-2 | 2,3-dihydroxybenzoyl-NHCH₂CH₂ |
| K-3 | VI-2 | CH₃SO₂NHCH₂CH₂ |
| K-4 | VI-2 | CH₃CH₂NHC(O)NHCH₂CH₂ |
| K-5 | VI-2 | H₂NCH₂C(O)NHCH₂CH₂ |
| K-6 | VI-2 | CF₃C(O)NHCH₂CH₂ |
| K-7 | VI-2 | imidazol-1-yl-CH₂CH₂ |
| K-8 | VI-2 | L-histidyl-NHCH₂CH₂ |
| K-9 | VI-2 | HOOC-CH₂CH₂-C(O)NHCH₂CH₂ |

TABLE K-continued
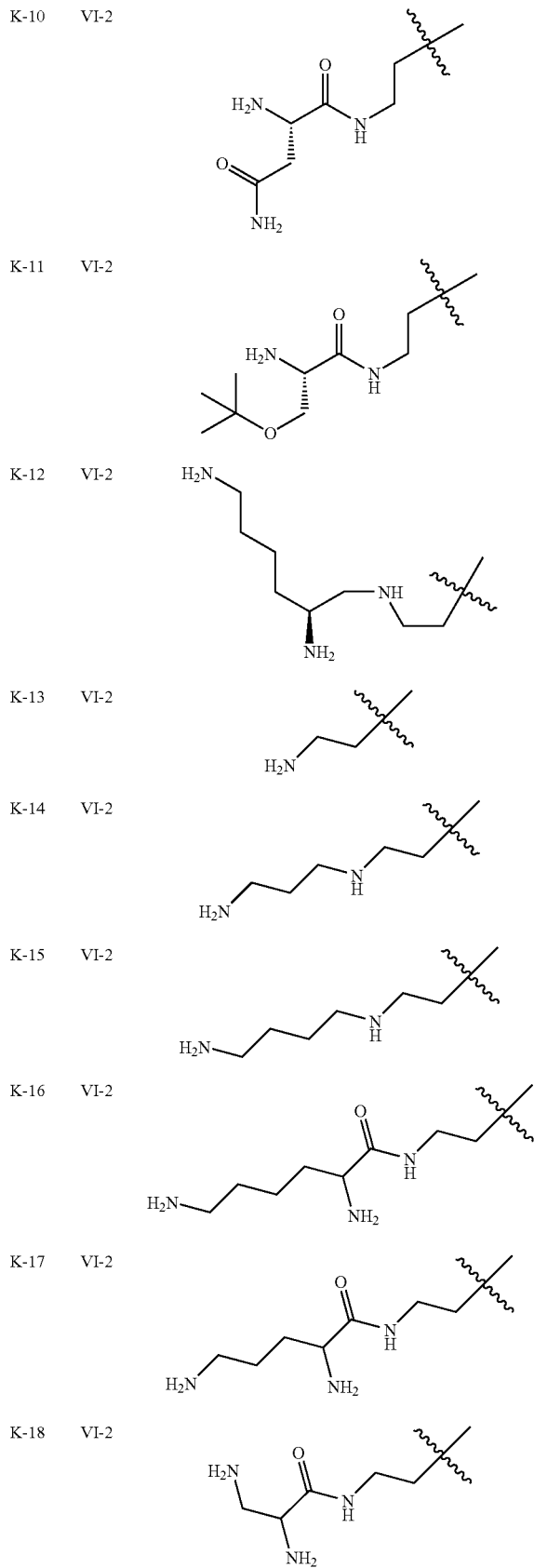
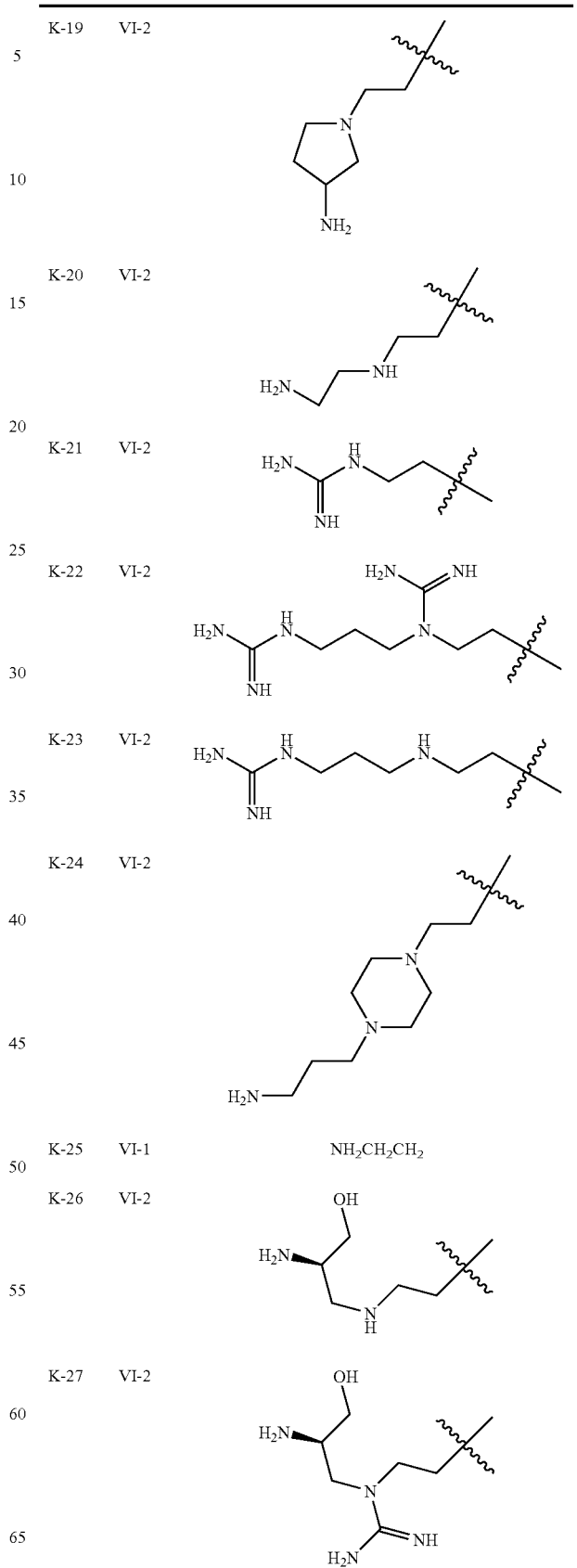

TABLE K-continued
| | | |
|---|---|---|
| K-28 | VI-2 | 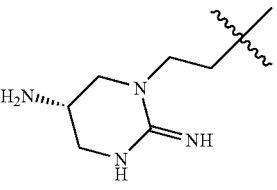 |
| K-29 | VI-2 | 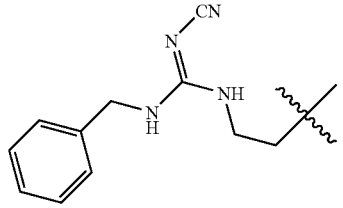 |
| K-30 | VI-2 | 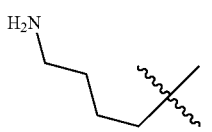 |
| K-31 | VI-2 | 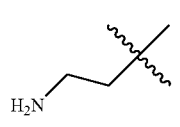 |
| K-32 | VI-2 | 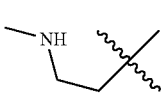 |
| K-33 | VI-2 | 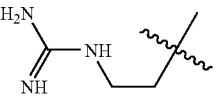 |
| K-34 | VI-2 | 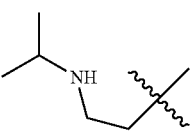 |
| K-35 | VI-2 | 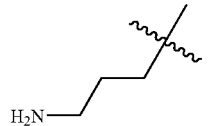 |
| K-36 | VI-2 | 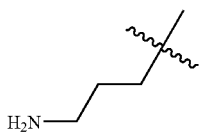 |
| K-37 | VI-2 | 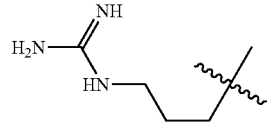 |
| K-38 | VI-2 | 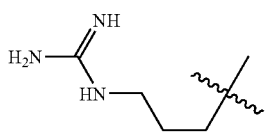 |
| K-39 | VI-4 | 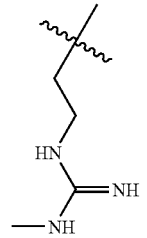 |
| K-40 | VI-1 | 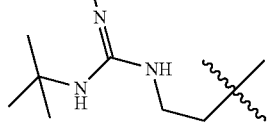 |
| K-41 | VI-1 | 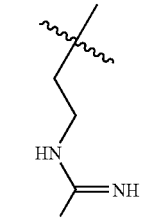 |
| K-42 | VI-1 | 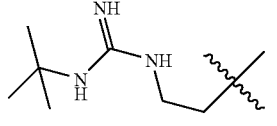 |
| K-43 | VI-2 | 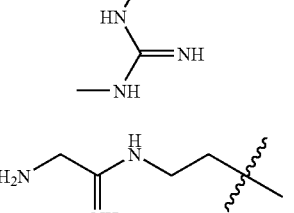 |
| K-44 | VI-1 | 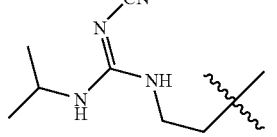 |
| K-45 | VI-1 | 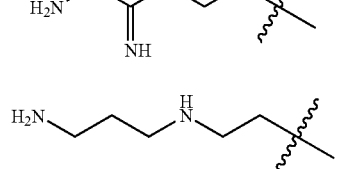 |
| K-46 | VI-1 | 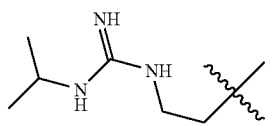 |
| K-47 | VI-1 | 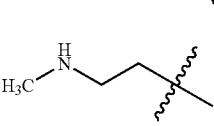 |

TABLE K-continued

| | | |
|---|---|---|
| K-48 | VI-1 | 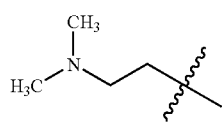 |
| K-49 | VI-1 | 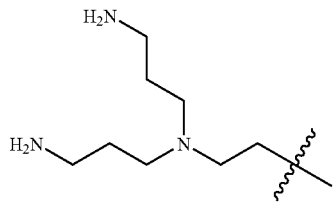 |
| K-50 | VI-1 | 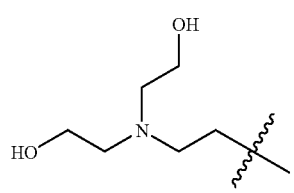 |

TABLE L

IV-1B

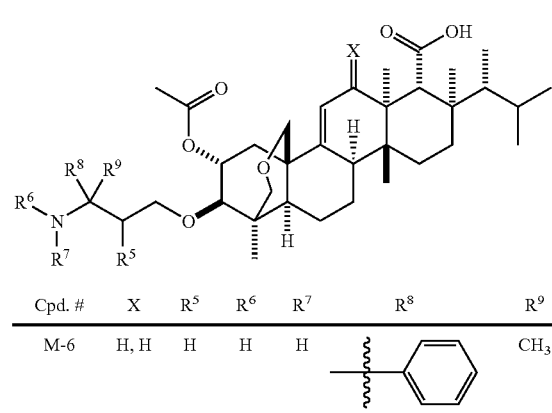

| Cpd. No. | $R^6$ | $R^7$ | $R^8$ | $R^9$ |
|---|---|---|---|---|
| L-1 | H | H | $CH_3$ | ethyl |
| L-2 | H | H | $CH_3$ | $CH_3$ |
| L-3 | H | H | $CH_3$ | i-propyl |
| L-4 | H | H | $CH_2CH_2SO_2CH_3$ | $CH_3$ |

TABLE M

VII

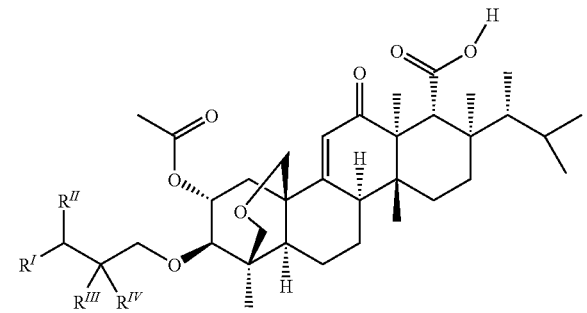

| Cpd. # | X | $R^5$ | $R^6$ | $R^7$ | $R^8$ | $R^9$ |
|---|---|---|---|---|---|---|
| M-1 | H, H | H | H | H | H | $CH_3$ |
| M-2 | H, H | H | H | H | H | $CH_2CH_3$ |
| M-3 | H, H | H | H | H | H | $CH_2CH_2CH_3$ |
| M-4 | H, H | H | H | $CH_3$ | $CH_3$ | $CH_2CH_3$ |
| M-5 | O | H | H | H | H | $CH_3$ |

TABLE M-continued

VII

| Cpd. # | X | $R^5$ | $R^6$ | $R^7$ | $R^8$ | $R^9$ |
|---|---|---|---|---|---|---|
| M-6 | H, H | H | H | H | (phenyl) | $CH_3$ |
| M-7 | O | OH | H | H | H | $CH_3$ |
| M-8 | O | OH | H | H | $CH_3$ | $CH_3$ |
| M-9 | O | OH | H | H | $CH_3$ | $CH_3$ |

TABLE 3a

| Ex./cpd | $R^{III}$ | $R^{IV}$ | $R^{I}$ | $R^{II}$ | MS |
|---|---|---|---|---|---|
| 154 | Et | Et | Me | Me | 672 (M + H)+ |
| 155 | n-Bu | Me | Me | Me | 672 (M + H)+ |
| 156 | $CH_2OMe$ | Me | Me | Me | 660 (M + H)+ |
| 157 | $CH_2CH_2OMe$ | Me | H | H | 660 (M + H)+ |
| 158 | $CH_2CH_2OMe$ | Me | Me | Me | 688 (M + H)+ |
| 159 | $CH_2CH_2OEt$ | Me | H | H | 674 (M + H)+ |
| 160 | $CH_2CH_2OEt$ | Me | Me | Me | MH+ = 716 |
| 161 | $CH_2CH_2OEt$ | Me | Et | H | 688 (M + H)+ |
| 162 | Cyclohexyl | | H | H | 656 (M + H)+ |
| 163 | (R) i-Pr | Me | Et | Et | 700 (M + H)+ |
| 164 | (R) i-Pr | Me | Et | H | 672 (M + H)+ |
| 165 | (R) i-Pr | Me | $CH_2CH_2OMe$ | H | 702 (M + H)+ |
| 166 | (R) i-Pr | Me | $(CH_2)_3OMe$ | H | 716 (M + H)+ |
| 167 | (R) i-Pr | Me | nPr | H | 686 (M + H)+ |
| 168 | (R) i-Pr | Me | cycloBu | H | 698 (M + H)+ |
| 169 | (S) i-Pr | Me | Et | H | 672 (M + H)+ |
| 170 | (S) i-Pr | Me | Et | Et | 700 (M + H)+ |
| 171 | (S) i-Pr | Me | nPr | H | 686 (M + H)+ |
| 172 | (S) i-Pr | Me | cPrCH2 | H | 698 (M + H)+ |
| 173 | (S) i-Pr | Me | Et | Me | 672 (M + H)+ |
| 174 | (S) i-Pr | Me | iPr | H | 686 (M + H)+ |
| 175 | (S) i-Pr | Me | nBu | H | 700 (M + H)+ |
| 176 | (S) i-Pr | Me | iBu | H | 700 (M + H)+ |
| 177 | (S) i-Pr | Me | c-Butyl | H | 698 (M + H)+ |
| 178 | (S) i-Pr | Me | cPentyl | H | 712 (M + H)+ |
| 179 | (S) i-Pr | Me | cHexyl | H | 726 (M + H)+ |

Other embodiments of the present invention include the following:

(a) A composition comprising a compound of Formula I or I-a and a carrier, adjuvant, or vehicle;

(b) A pharmaceutical composition comprising a compound of Formula I or I-a and a pharmaceutically acceptable carrier, adjuvant, or vehicle;

(c) The pharmaceutical composition of (b), further comprising a second therapeutic agent;

(d) The pharmaceutical composition of (c), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(e) The pharmaceutical composition of (d), wherein the second therapeutic agent is itraconazole, ketoconazole, miconazole, fluconazole, voriconazole, posaconazole, amphotericin B, flucytosine, anidulafungin, micafungin, or caspofungin;

(f) A pharmaceutical combination which is (1) a compound of Formula I or I-a and (2) a second therapeutic agent, wherein the compound of Formula I or I-a and the second therapeutic agent are each employed in an amount that renders the combination effective for treating or preventing fungal/bacterial infections;

(g) The combination of (f), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(h) The combination of (g), wherein the second therapeutic agent is itraconazole, ketoconazole, miconazole, fluconazole, voriconazole, posaconazole, amphotericin B, flucytosine, anidulafungin, micafungin, or caspofungin;

(i) A method of inhibiting (1,3)-β-D-glucan synthase in a subject in need thereof comprising administering to the subject an effective amount of a compound of Formula I or I-a;

(j) A method of treating or preventing mycotic infections in a subject in need thereof comprising administering to the subject an effective amount of a compound of Formula I or I-a;

(k) The method of (j), wherein the compound of Formula I or I-a, is administered in combination, either sequentially or concurrently, with a second therapeutic agent effective against fungal/bacterial infections;

(l) The method of (k), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(m) The method of (l), wherein the second therapeutic agent is itraconazole, ketoconazole, miconazole, fluconazole, voriconazole, posaconazole, amphotericin B, flucytosine, anidulafungin, micafungin, or caspofungin;

(n) A method of inhibiting (1,3)-β-D-glucan synthase in a subject in need thereof comprising administering to the subject a pharmaceutical composition of (b), (c), (d), or (e) or the combination of (f), (g) or (h); and (O) A method of treating or preventing mycotic infections in a subject in need thereof comprising administering to the subject a pharmaceutical composition of (b), (c), (d), or (e) or the combination of (f), (g) or (h).

The present invention also includes a compound of the present invention (i) for use in, (ii) for use as a medicament for, or (iii) for use in the preparation of a medicament for: (a) inhibiting (1,3)-β-D-glucan synthase in a subject in need thereof, or (b) treating or preventing mycotic infections. In these uses, the compounds of the present invention can optionally be employed in combination, either sequentially or concurrently, with one or more therapeutic agents effective against fungal/bacterial infections.

Additional embodiments of the invention include the pharmaceutical compositions, combinations and methods set forth in (a)-(O) above and the uses set forth in the preceding paragraph, wherein the compound of the present invention employed therein is a compound of one of the embodiments or aspects of the compounds described above. In all of these embodiments as well as those described hereinbelow, the compound may optionally be used in the form of a pharmaceutically acceptable salt or hydrate when appropriate.

The present compounds (including pharmaceutical acceptable salt and/or hydrate forms) have or are expected to have antimicrobial (e.g., antifungal) activities against yeasts and fungi, including *Acremonium, Absidia* (e.g., *Absidia corymbifera*), *Alternaria, Aspergillus* (e.g., *Aspergillus clavatus, Aspergilius flavus, Aspergillus fumigatus, Aspergillus nidulans, Aspergillus niger, Aspergillus terreus,* and *Aspergillus versicolor*), *Bipolaris, Blastomyces* (e.g., *Blastomyces dermatitidis*), *Blastoschizomyces* (e.g., *Blastoschizomyces capitatus*), *Candida* (e.g., *Candida albicans, Candida glabrata* (*Torulopsis glabrata*), *Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cladosporium* (e.g., *Cladosporium carrionii* and *Cladosporium trichloides*), *Coccidioides* (e.g., *Coccidioides immitis*), *Cryptococcus* (e.g., *Cryptococcus neoformans*), *Curvularia, Cunninghamella* (e.g., *Cunninghamella elegans*), *Dermatophyte, Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Histoplasma* (e.g., *Histoplasma capsulatum* var. *capsulatum*), *Malassezia* (e.g., *Malassezia furfur*), *Microsporum* (e.g., *Microsporum canis* and *Microsporum gypseum*), *Mucor, Paracoccidioides* (e.g., *Paracoccidioides brasiliensis*), *Penicillium* (e.g., *Penicillium marneffei*), *Phialophora, Pityrosporum ovale, Pneumocystis* (e.g., *Pneumocystis carinii*), *Pseudallescheria* (e.g., *Pseudallescheria boydii*), *Rhizopus* (e.g., *Rhizopus microsporus* var. *rhizopodiformis* and *Rhizopus oryzae*), *Saccharomyces* (e.g., *Saccharomyces cerevisiae*), *Scedosporium* (e.g., *Scedosporium apiosperum*), *Scopulariopsis, Sporothrix* (e.g., *Sporothrix schenckii*), *Trichoderma, Trichophyton* (e.g., *Trichophyton mentagrophytes* and *Trichophyton rubrum*), and *Trichosporon* (e.g., *Trichosporon asahii, Trichosporon beigelii* and *Trichosporon cutaneum*). The present compounds may also be used to treat infections caused by protozoa such as *Toxoplasma, Cryptosporidium, Leishmania, Tripanosoma, Giardia* and *Trichomonas*. The present compounds are not only useful against organisms causing systemic human pathogenic mycotic infections, but also useful against organisms causing superficial fungal infections such as *Trichoderma* sp. and other *Candida* spp. The compounds of the present invention are particularly effective against *Aspergilius flavus, Aspergillus fumigatus, Candida albicans, Candida parapsilosis, Cryptococcus neoformans, Saccharomyces cerevisiae,* and *Trichophyton mentagrophytes.*

In view of their antifungal activity, compounds of formula I are useful for the treatment and/or prevention of a variety of superficial, cutaneous, subcutaneous and systemic mycotic infections in skin, eye, hair, nail, oral mucosa, gastrointestinal tract, bronchus, lung, endocardium, brain, meninges, urinary organ, vaginal portion, oral cavity, ophthalmus, systemic, kidney, bronchus, heart, external auditory canal, bone, nasal cavity, paranasal cavity, spleen, liver, hypodermal tissue, lymph duct, gastrointestine, articulation, muscle, tendon, interstitial plasma cell in lung, blood, and so on.

Therefore, compounds of the present invention are useful for preventing and treating various infectious diseases, such as dermatophytosis (e.g., trichophytosis, ringworm or tinea infections), athletes foot, paronychia, pityriasis versicolor, erythrasma, intertrigo, fungal diaper rash, candida vulvitis, candida balanitis, otitis externa, candidiasis (cutaneous and mucocutaneous), chronic mucocandidiasis (e.g. thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia. The present compounds may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states.

Examples of azoles that may be used in combination with the present compounds include, but are not limited to, fluconazole, voriconazole, itraconazole, ketoconazole, miconazole, ravuconazole, detoconazole, clotrimazole, and posaconazole. Examples of polyenes that may be used in combination with the present compounds include, but are not limited to, amphotericin B, nystatin, liposamal and lipid forms thereof such as Abelcet™, AmBisome™, and Amphocil™. Examples of purine or pyrimidine nucleotide inhibitors that may be used in combination with the present compounds include, but are not limited to, flucytosine or polyxins such as nikkomycines, in particular nikkomycine Z or nikkomycine X. Another class of therapeutic agents that may be used in combination with the present compounds includes chitin inhibitors. Examples of elongation factor inhibitors that may be used in combination with the present compounds include, but are not limited to, sordarin and analogs thereof. Examples of pneumocandin or echinocandin derivatives that may be used in combination with the present compounds include, but are not limited to, cilofungin, anidulafungin, micafungin, and caspofungin. Examples of mannan inhibitors that may be used in combination with the present compounds include but are not limited to predamycin. Examples of bactericidal/permeability-inducing (BPI) protein products that may be used in combination with the present compounds include but are not limited to XMP.97 and XMP.127. Examples of immunomodulators that may be used in combination with the present compounds include, but are not limited to, an interferon, (e.g., IL-1, IL-2, IL-3 and IL-8), defensines, tacrolimus and G-CSF (Granulocyte-colony stimulating factor).

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkoxy" refers to an —O-alkyl group wherein alkyl is as defined above.

The term "cycloalkyl" refers to any cyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. Suitable haloalkyls include the series $(CH_2)_{0-5}CF_3$ (i.e., trifluoromethyl, 2,2,2-trifluoroethyl, 3,3,3-trifluoro-n-propyl, etc.).

The term "silylalkyl" refers to an alkyl group as defined above in which one or more of the carbon atoms have been replaced with a silicon atom.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

Any of the various cycloalkyl and heterocyclic/heteroaryl rings and ring systems defined herein may be attached to the rest of the compound at any ring atom (i.e., any carbon atom or any heteroatom) provided that a stable compound results. Suitable 5- or 6-membered heteroaromatic rings include, but are not limited to, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable 3- to 6-membered heterocyclyls include, but are not limited to, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. Unless otherwise indicated, all isomeric forms of these compounds, whether isolated or in mixtures, are within the scope of the present invention. Also included within the scope of the present invention are tautomeric forms of the present compounds as depicted.

When any variable occurs more than one time in any constituent or in Formula I or I-a or in any other formula depicting and describing compounds of the invention, its definition on each occurrence is independent of its definition at every other occurrence. Also, combinations of substituents and/or variables are permissible only if such combinations result in stable compounds.

The term "substituted" includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., an aryl, a cycloalkyl, a heteroaryl, or a heterocyclyl) provided such ring substitution is chemically allowed and results in a stable compound.

The compounds of this invention are also useful in the preparation and execution of screening assays for antifungal compounds. For example, the compounds of this invention are useful for isolating mutants, which are excellent screening tools for more powerful antifungal compounds.

All compounds of the present invention may be administered in the form of pharmaceutically acceptable salts or hydrates as appropriate. The term "pharmaceutically acceptable salt" refers to a salt which possesses the approximate effectiveness of the parent compound and which is suitable for administration to a patient. Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, and benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the subject in need of treatment. When a compound of the invention or a prodrug thereof is provided in combination with one or more other active agents (e.g., other antifungal/antibacterial agents useful for treating fungal/bacterial infections), "administration" and its variants are each understood to include concurrent and sequential provision of the compound or prodrug and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented or for reducing the likelihood of occurrence. The term also includes herein the amount of active compound sufficient to inhibit (1,3)-$\beta$-D-glucan synthase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting (1,3)-$\beta$-D-glucan synthase or preventing or treating fungal infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation (e.g., nasal or buccal inhalation spray, aerosols from metered dose inhalator, and dry powder inhalator), by nebulizer, ocularly, topically, transdermally, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 19$^{th}$ edition, edited by A. R. Gennaro, Mack Publishing Co., 1995.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention also includes processes for making compounds of formula I or Ia. The compounds of the present invention may be prepared according to the following reaction schemes and examples, or modifications thereof, from starting material enfumafungin. Enfumafungin is a natural product produced from a fungus strain of *Hormonema* sp. (deposited under the Budapest Treaty in the culture collection of the American Type Culture Collection and assigned accession number ATCC 74360) that was isolated from living leaves of an unidentified shrub collected in Navalquejigo, province of Madrid, Spain, as described in U.S. Pat. No. 5,756,472, content of which is incorporated by reference in its entirety.

General Schemes

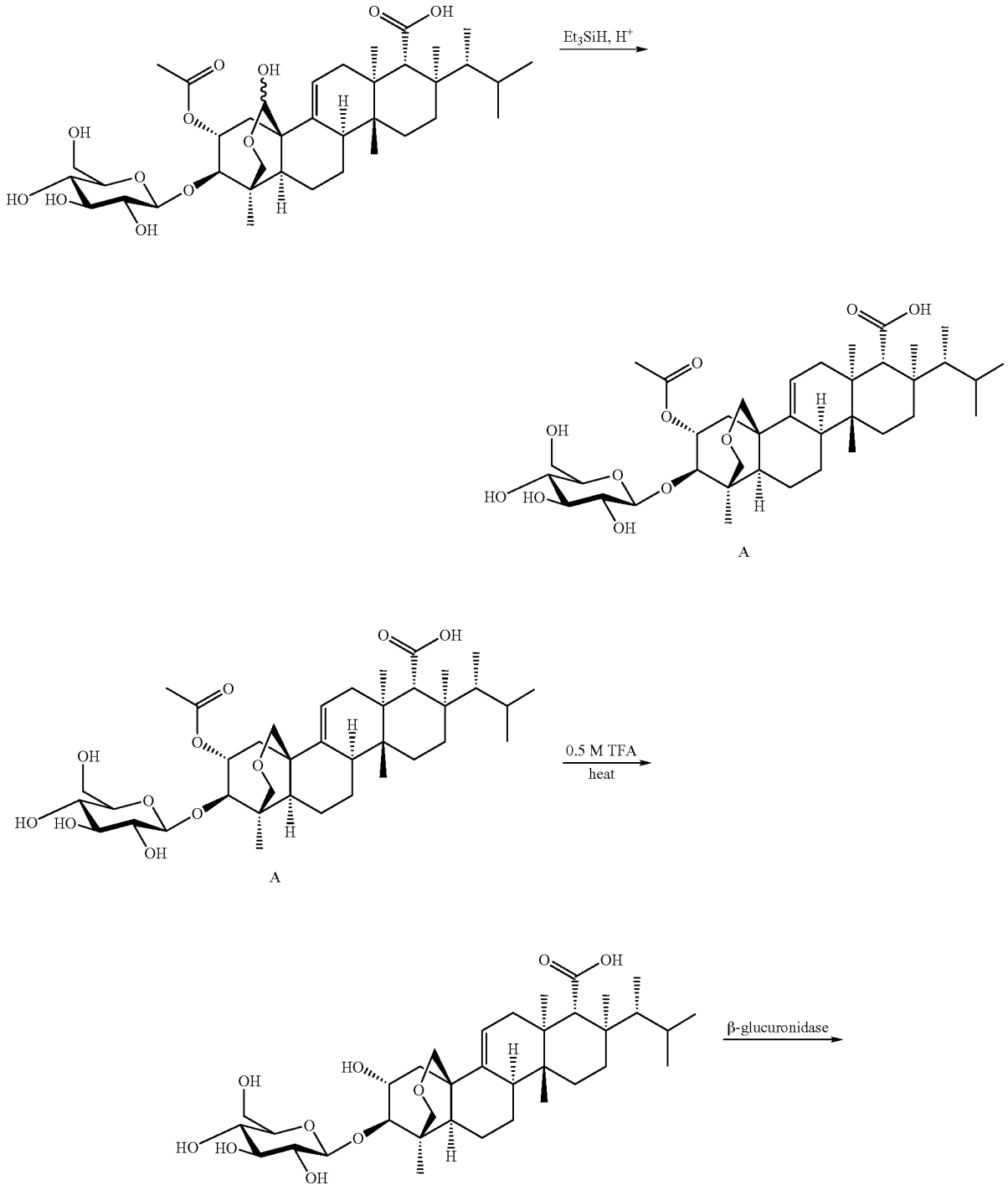

-continued

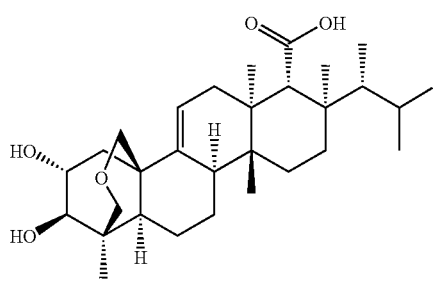
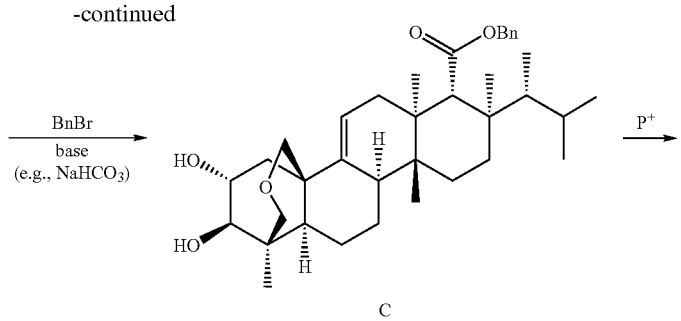

C

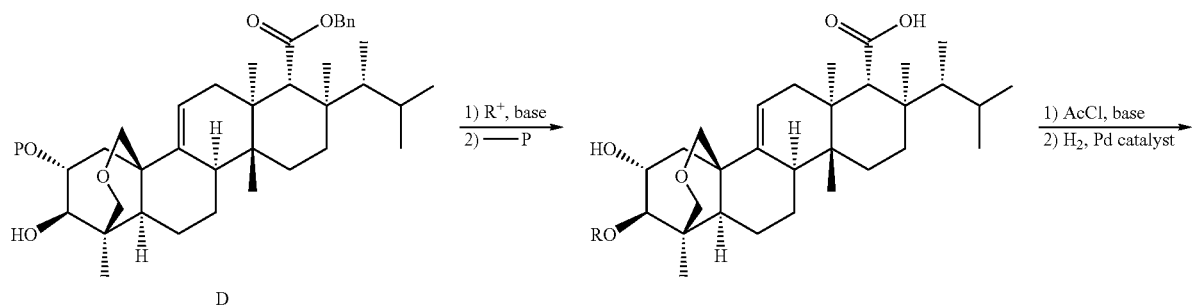

D

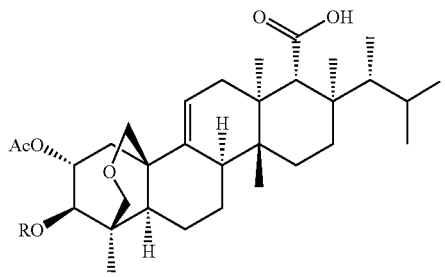

Scheme A outlines methods for preparing C-3 derivatives of enfumafungin (compound A). The C-25 hydroxyl group of enfumafungin may be reduced by treatment of enfumafungin with a suitable reducing agent such as triethylsilane under acidic conditions (e.g., trifluoroacetic acid) to give A (Shafiee et al., *J. Molecular Catalysis B: Enzymatic*, 2001(16), pp. 27-32). Heating A with aqueous trifluoroacetic acid (TFA) achieves selective hydrolysis of the 2-acetyl group. Treatment of that intermediate in an appropriate aqueous buffer with a β-glucuronidase (Shafiee et al., *J. Molecular Catalysis B: Enzymatic*, 2001(16), pp. 27-32) hydrolyzes the 3-glucose moiety to give the diol which can be selectively protected on the C-18 carboxylic acid utilizing benzyl bromide (BnBr) and a suitable base such as sodium hydrogen carbonate or cesium carbonate to give C. Selective protection of the 2-hydroxyl group may be carried out with bulky electrophiles such as trityl chloride and an acid catalyst, tert-butyldiphenylsilyl chloride and base or with acetyl chloride and base. Once the 2-position is suitably protected (group P), treatment of D an electrophile gives derivitization of the 3-position. Deprotection at the 2-position followed by acetylation and hydrogenolysis give analogs substituted at the 3-position. Alternatively, A may be protected on the C-18 carboxyl by treatment with benzyl bromide and base. Next, hydrolysis of the 2-acetate followed by hydrolysis of the 3-glucose gives the diol C. Selective acetylation with acetyl chloride gives D which may be reacted at the 3-hydroxyl group with various electrophiles and derivatizing agents which after hydrogenolysis of the C-18 benzyloxycarbonyl group yields 3-substituted analogs of enfumafungin and A.

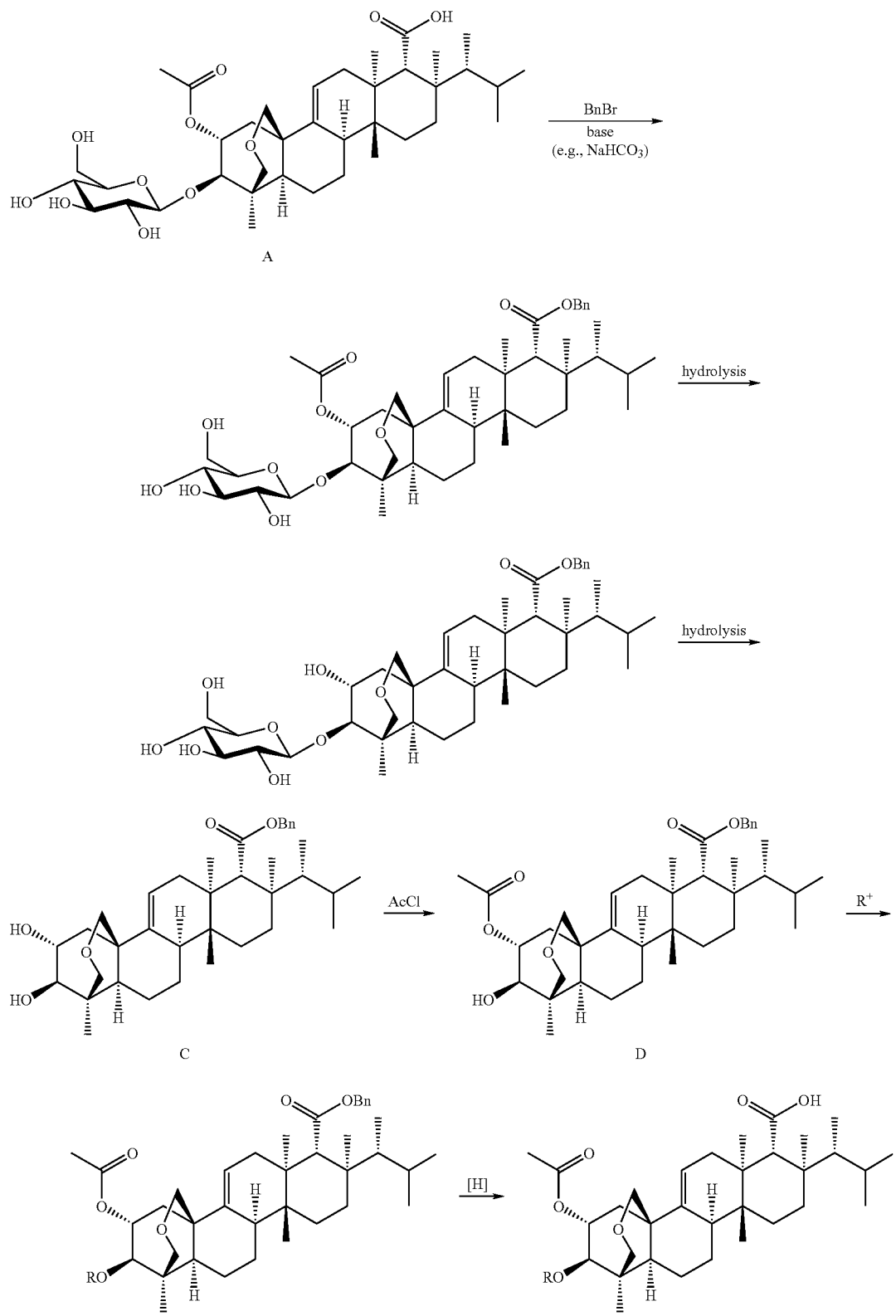
R can be, for example, $C_1$-$C_4$ alkyl.

Alternatively, as outlined in Scheme B, compound C is prepared from enfumafungin by a process that involves initial reductive dehydration of the cyclic hemi-acetal followed by treatment of the reduced enfumafungin derivative with benzyl bromide and a base such as sodium hydrogen carbonate in a suitable solvent such as dimethylformamide. The resulting benzyl ester mixture is then treated with a mild acid in a suitable solvent, with optional heating, to effect removal of the glucose ring and afford compound C. The mild acid can be p-toluenesulfonic acid, camphorsulfonic acid and the like and the solvent is toluene or benzene. Most preferably the acid is camphorsulfonic acid in toluene and the reaction mixture is heated at about 60° C. for about 1 hour. The electrophile (R$^+$) may then be introduced under acidic, neutral or mildly basic conditions.

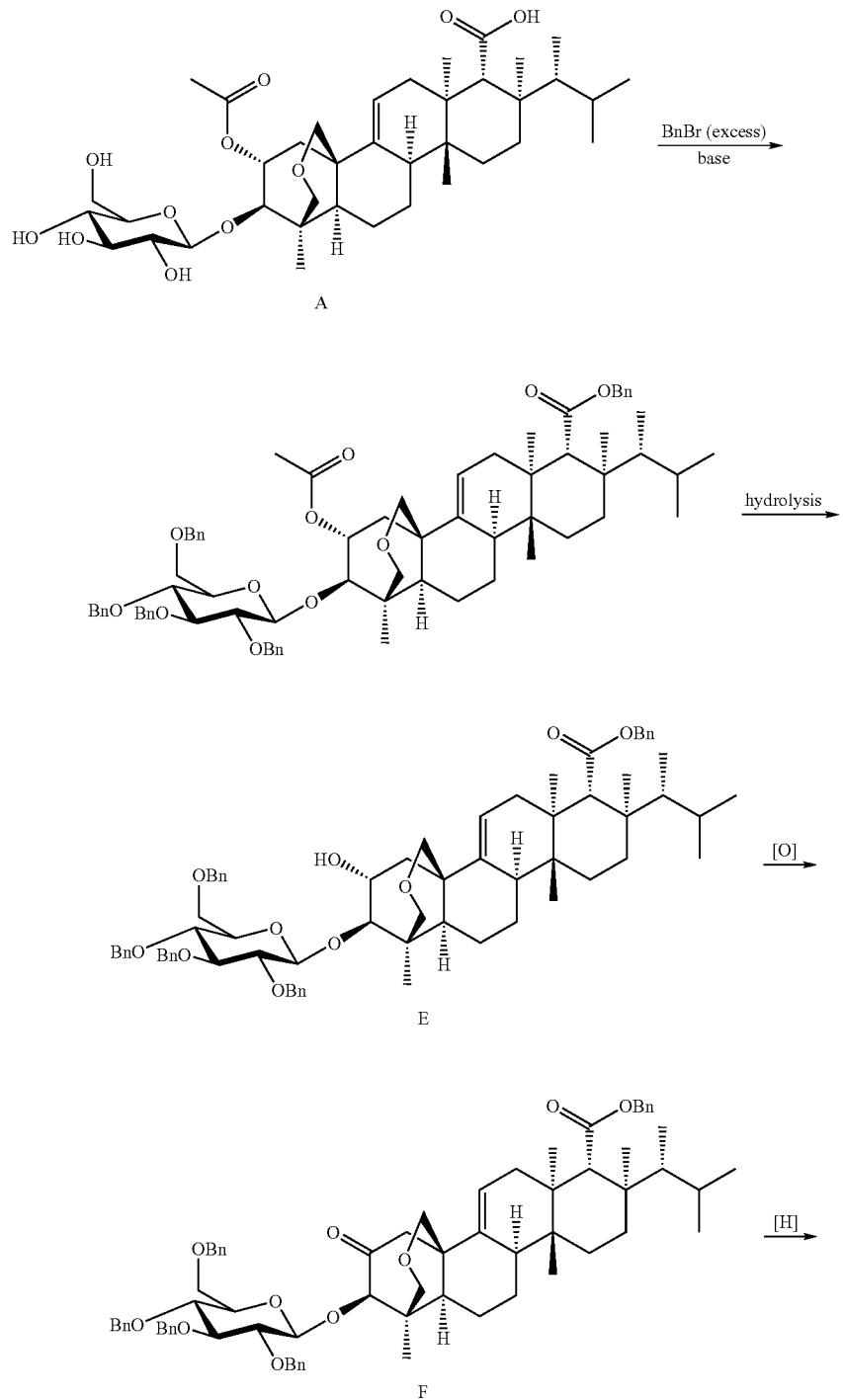

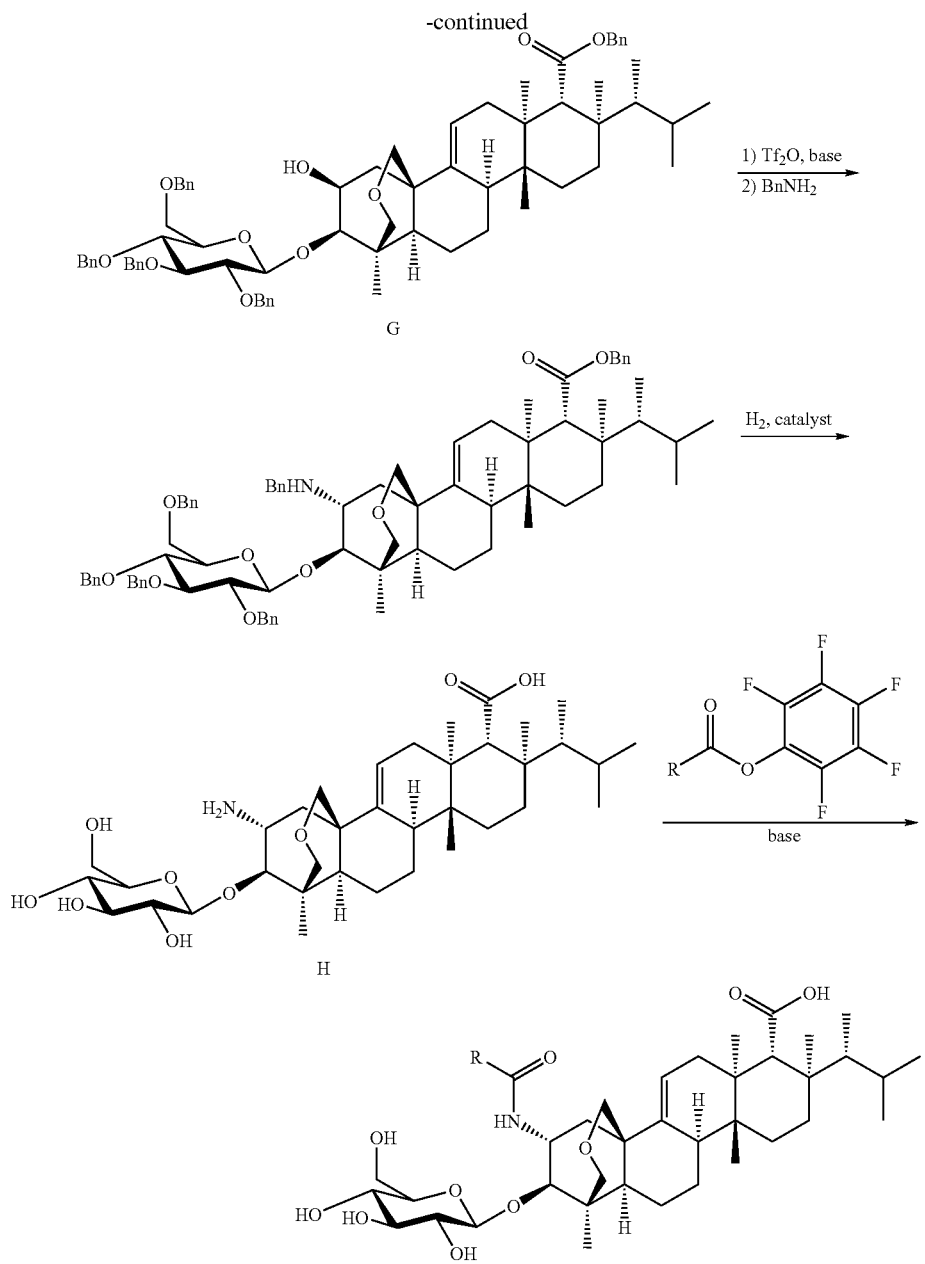

In Scheme C, perbenzylation of A with excess benzyl bromide followed by base hydrolysis gives 2-hydroxy compound E. The 2-hydroxy group of E may be oxidized to give ketone intermediate F. The fully protected 2-oxo intermediate F may be reduced to give a 2β-hydroxy analog utilizing a reducing agent such as DIBAL-H to give G. The hydroxyl group of G may be activated by derivatizing as a trifluoromethylsulfonate or other leaving group and displaced with amines such as benzylamine to give the 2-benzyl amino analog. Hydrogenolysis of the benzyl group produces the primary amine and simultaneously removes the benzyl protecting groups to give H. Selective acylation of the amino group may be accomplished with relatively unreactive reagents such as pentafluorophenyl esters and the like to give 2-amido derivatives of enfumafungin.

Scheme D

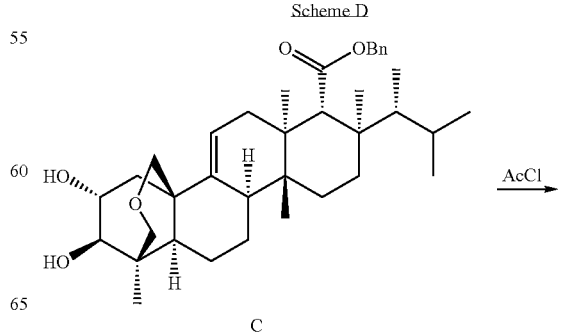

-continued

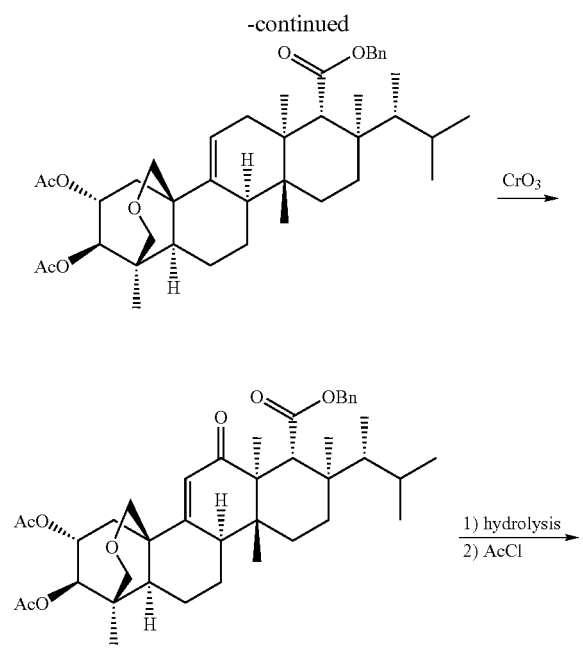

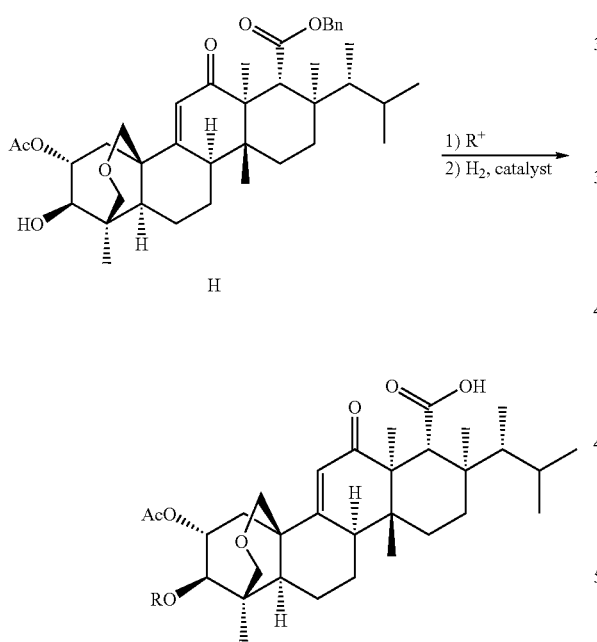

Scheme D outlines a method for preparing 12-oxo derivatives wherein intermediate C may be acetylated at the 2- and 3-positions to protect the hydroxyl groups from inadvertent oxidation. Treatment of the product with an allylic oxidizing reagent such as chromium trioxide and dimethylpyrazole gives the desired 12-oxo modification. Hydrolysis, selective acetylation, derivitization at the 3-position followed by hydrogenolysis of the benzyl ester or any other cleavable protecting groups gives 12-oxo derivatives of enfumafungin or its 3-derivatives.

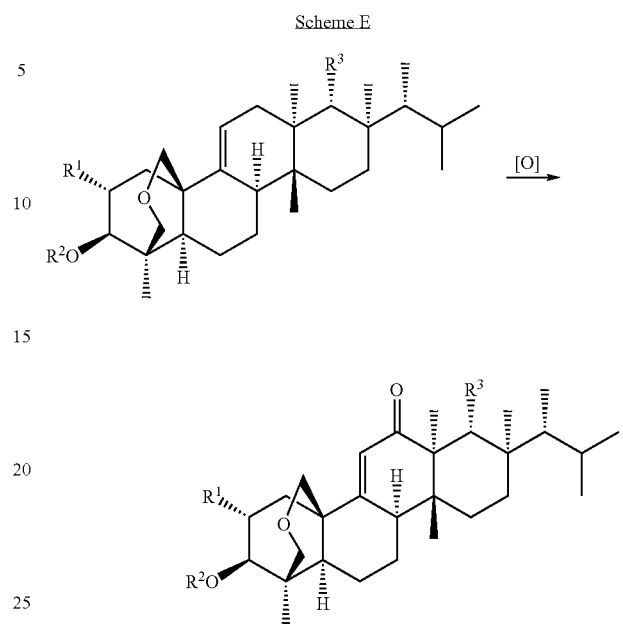

Scheme E outlines an alternative way to introduce a 12-oxo substituent directly into the final product or a suitably protected precursor. Treatment of an enfumafungin derivative with an allylic oxidation reagent such as chromium trioxide and dimethylpyrazole may yield the desired product. Deprotection may be carried out at this step to unmask any desired functional groups.

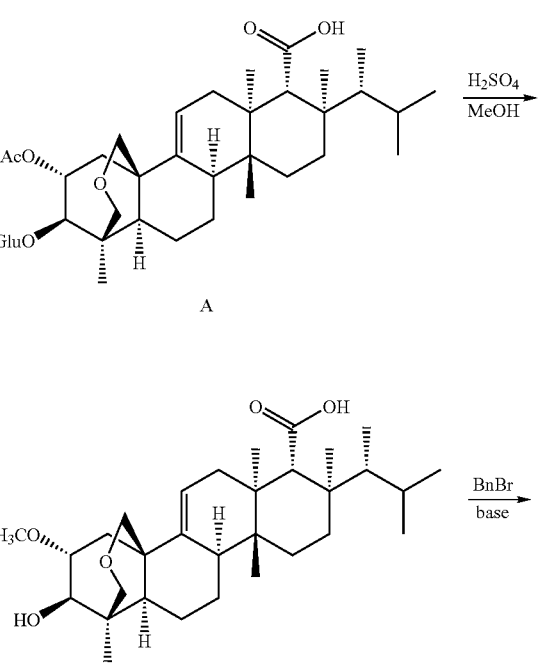

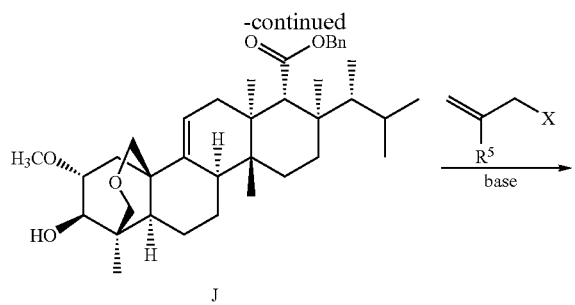

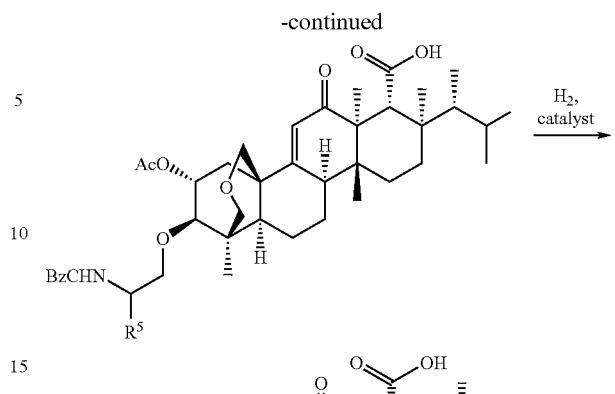

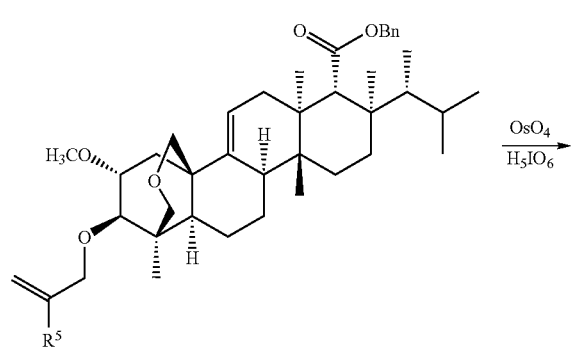

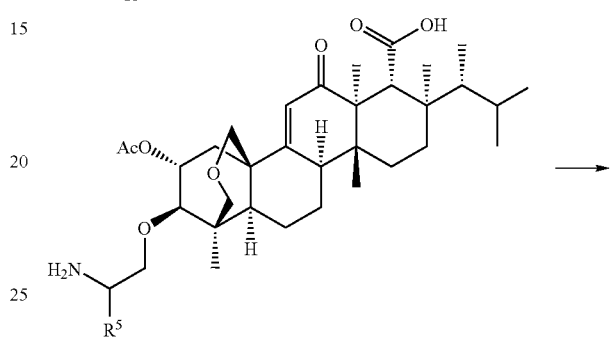

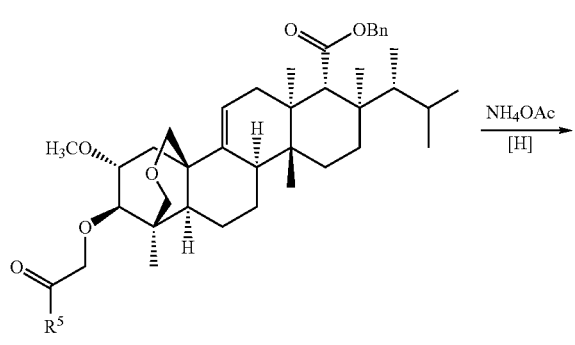

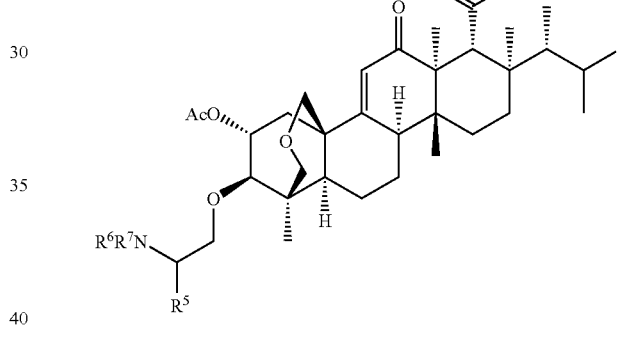

Variables $R^5$, $R^6$ and $R^7$ are as previously defined or are corresponding precursor groups. X is halogen or a leaving group.

Scheme F describes a route for preparing another subset of especially useful compounds of the present invention wherein compound A is treated with sulfuric acid in methanol to hydrolyze the acetate and glucose and give substitution at the 2-position to a methyl ether. Protection of the carboxylic acid is accomplished by treatment with benzyl bromide and a suitable base such as sodium carbonate to give J. Alkylation with an allylic halide or other activated allylic species gives the 2-allyl ether. Oxidative cleavage of the vinyl group gives the keto-ether analog and reductive amination under standard conditions gives the 3-(2'-aminoether) derivative. Exchange of the 2-methoxy group with an acetate followed by protection of the amine with a carbobenzyloxy group or other suitable amine protecting group allows oxidation of the 12-position with chromium trioxide. Hydrogenolysis of the carbobenzyloxy group gives aminoethyl ether analogs. The amine may be further substituted by derivitization by standard procedures.

Scheme G

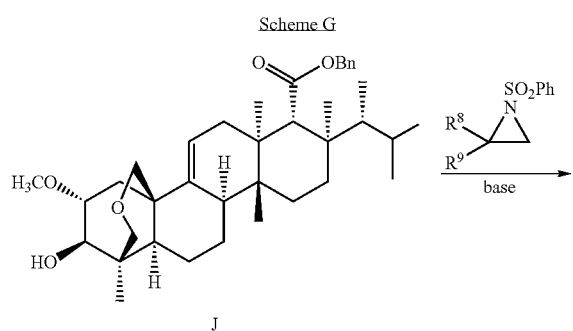

J

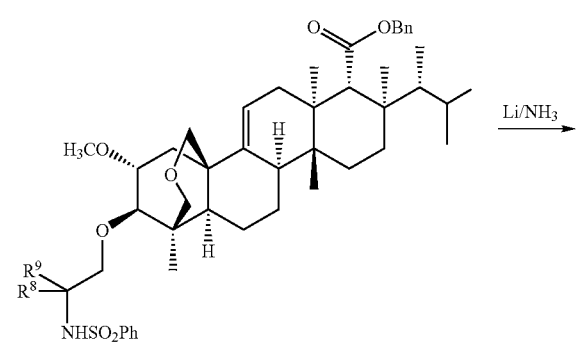

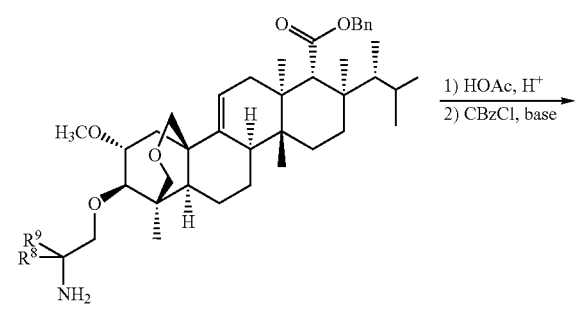

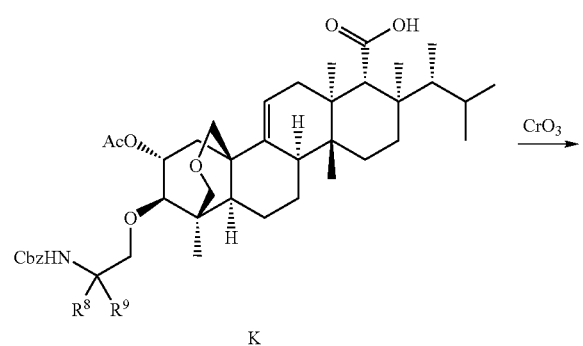

K

L

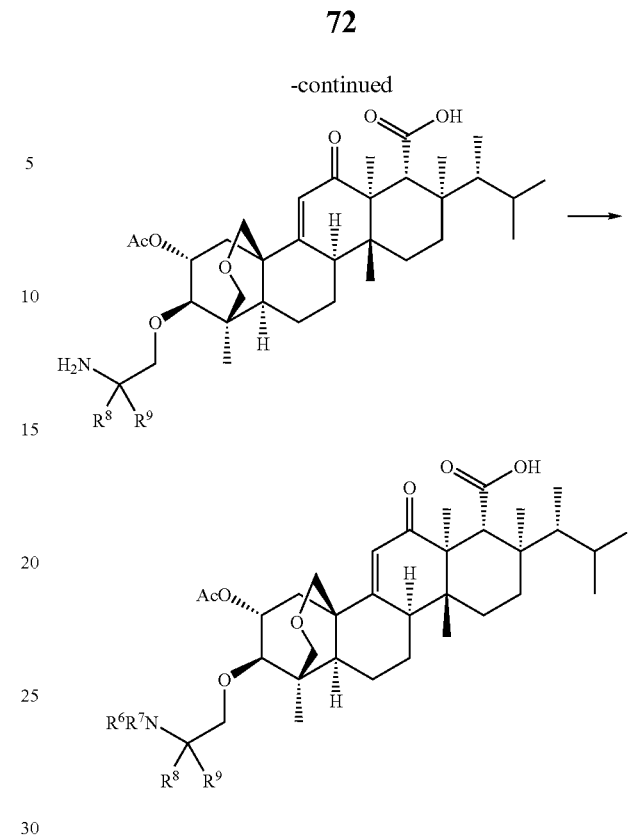

-continued

Variables $R^6$, $R^7$, $R^8$ and $R^9$ are as previously defined or are corresponding precursor groups.

Scheme G outlines a method complementary to Scheme F and useful for the preparation of 2',2'-disubstituted 2'-aminoethyl ethers shown in Scheme F. Reaction of J with an N-sulfonyl aziridine and base gives 2'-aminoethyl ethers after reductive removal of the N-sulfonyl group. Then, in a manner described above, 2'-aminoethyl ether derivatives may be prepared.

Scheme J

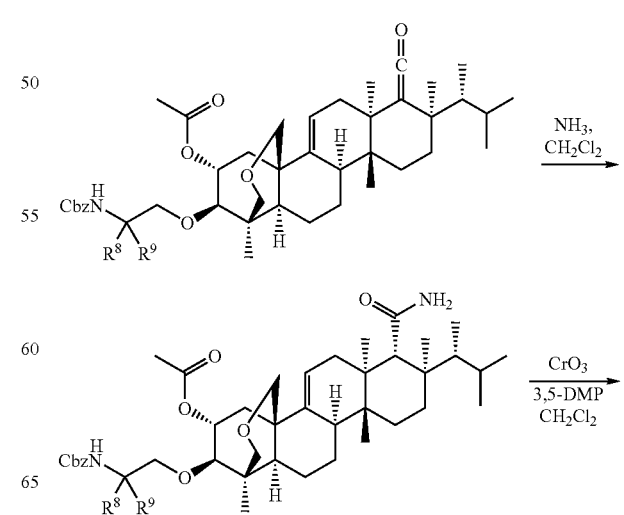

-continued

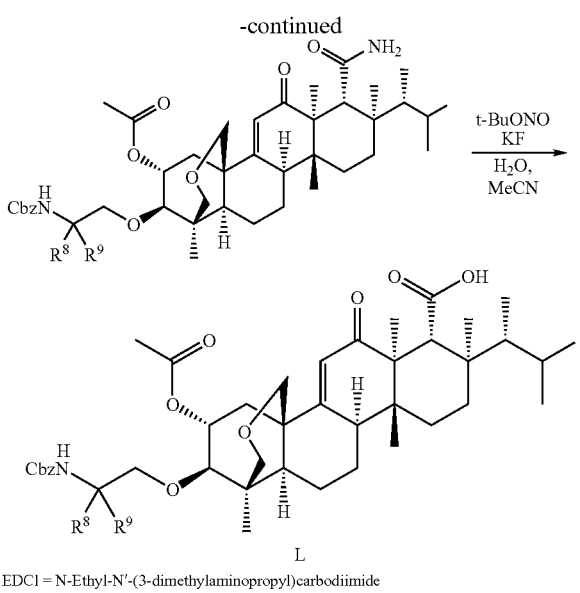

L

EDCl = N-Ethyl-N'-(3-dimethylaminopropyl)carbodiimide

Variables $R^8$ and $R^9$ are as previously defined or are corresponding precursor groups.

The antifungal activity of the present compounds can be demonstrated by various assays known in the art, for example, by their glucan synthesis inhibitory acticity ($IC_{50}$), minimum inhibitory concentration (MIC-100) or minimum prominent inhibition (MIC-80) against yeasts and minimum effective concentration (MEC) against filamentous moulds and dermatophytes in a broth microdilution assay, or in vivo anti-*Candida* activity in a mouse (TOKA). Compounds of the present invention were found to inhibit the growth of *Candida* spp. in the range of <0.03-32 µg/mL or to give an MEC against *Aspergillus fumigatus* in the range of <0.03-32 µg/mL.

Glucan Synthase Inhibition

The in vitro evaluation of glucan synthase inhibitory activity of compounds was measured in a polymerization assay in 96-well format. Each well contained 100 µL of $^3$H-UDPG at 0.5 mM (6000 to 8000 dpm/nmol), 50 mM HEPES pH 7.5 (Sigma), 10% w/v glycerol (Sigma), 1.5 mg/mL bovine serum albumin (Sigma A 9647. Lot 44H0190), 25 mM KF (Fisher), 1 mM EDTA (Gibco Ultrapure), 25 µM GTP-γ-S, enzyme sufficient to give 3 to 6 nmoles incorporation during the 60 min incubation at 22° C., and test compound added from wells in 3-fold serial dilutions in 100% DMSO (1 µL/well). The reaction was stopped by the addition of 100 µL of 20% trichloroacetic acid. Plates were chilled for a minimum of 10 min, and precipitated glucan collected by filtration on GF/C plates (Packard Unifilter®-96), washed with 5 cycles of water (about 1 mL/well each cycle) using a Packard Filtermate Harvester. 40 µL/well scintillation fluid (Packard Ultima Gold TM-XR) was added and the sealed plates counted in a Wallac Beta counter in top-counting mode at an efficiency of approximately 40%.

Stock solutions were stored at 10 mg/mL in DMSO at -20° C. For each new enzyme preparation, the initial titration performed started at 1 mg/mL, which was prepared by making a 10-fold dilution in DMSO (5 µL to 50 µL). 40 µL of this stock was placed in column 12 of a round-bottomed 96-well microtiter plate. 40 µL DMSO was added to columns 1 to 11 in the same row and ten 3-fold serial dilutions performed, by transferring 20 µL from column 12 to column 11 etc., with 4 mixings before each transfer. No test compound was transferred to from column 2 to column 1. Duplicate aliquots of 1 µL of all 12 dilutions were then transferred to the side walls of a 96-well Bioblock 1.1 mL plate (Fisherbrand) to create two rows.

The results were tabulated and a standard plate background was subtracted and the net count transpose-pasted into a Prism file, with final compound concentrations used in ng/mL. Graphs were created in Prism software, using the average of two determinations, and using Prism's curve fitting program (sigmoidal dose response non-linear regression).

Routine analysis was performed with glucan synthase (GS) prepared from *Candida albicans* MY1055 by the following procedure: MY1055 was grown in 10 liters YPD medium (10 g yeast extract, 20 g tryptone, 20 g glucose per liter) with vigorous shaking at 30° C., to early stationary phase. Cells were harvested by centrifugation, the pellet was washed and frozen at -70° C. until breakage. Thawed pellets were shaken with an equal volume of breakage buffer (50 mM HEPES pH 7.4, 10% glycerol, 1 mM EDTA, 1 mM PMSF, 1 mM DTT) and 4 times their weight of 0.5 mm acid washed glass beads for 2 hours at 4° C. Extent of breakage was assessed visually at 40× magnification. For *C. parapsilosis* strains, shaking was extended to 3 hours to maximize breakage. After low speed centrifugation to remove cell debris, the supernatant was centrifuged at 100,000×g for 60 min. to separate membranes plus ribosomes from cytoplasmic components. Membranes were further washed two additional times with breakage buffer using the same centrifugation conditions and finally suspended in breakage buffer at 25 to 30 mg/mL protein (Biorad) for storage at -70° C. Extraction of GS activity from membranes was performed at a protein concentration of 5 mg/mL in extraction buffer (50 mM $NaPO_4$ pH 7.5, 0.1 M KCl, 0.1M Na citrate, 20% glycerol, 5 µM GTP-γ-S, 1 mM DTT, 1 mM PMSF, 3 µg/mL pepstatin) plus 0.25% W1 by gentle mixing at 4° C. for 60 min, followed by centrifugation at 100,000×g for 60 min. After centrifugation, clear supernatant was removed from a pellet consisting of a hard layer usually with small amounts of gelatinous unextracted membranes above it.

Trapping was initiated immediately by 5-fold dilution in trapping buffer (50 mM HEPES pH 7.5, 10 mM KF, 1 mM EDTA, 2 mg/mL BSA) plus 2.5 mM UDPG and 10 µM GTP-γ-S. After incubation at 25° C. for 60 to 90 minutes, glucan was harvested by low speed centrifugation (3,000×g, 10 min). The soft pellet was washed 3 times with wash buffer (50 mM HEPES, 20% glycerol, 1 mM EDTA) plus 2.5 mM UDPG and 5 µM GTP-γ-S, once without UDPG, and suspended in about 5 volumes of PE extraction buffer (50 mM HEPES, 30% glycerol, 1 mM EDTA, 20 µM GTP-γ-S, 0.4% CHAPS, 0.08% cholesterol hemisuccinate) using a Dounce homogenizer. The suspension was frozen overnight at -70° C., and then sedimented at 100,000×g for 10 min.

Susceptibility Testing

To each well of a 96 well plate 100 µL of appropriate test medium (example: RPMI-1640 containing 0.165 molar MOPS+3 g/L glutamine w/o sodium bicarbonate or RPMI-1640 containing 0.165 molar MOPS+3 g/L glutamine w/o sodium bicarbonate with 3.2% DMSO or 2×RPMI-1640 containing 0.33 molar MOPS+6 g/L glutamine w/o sodium bicarbonate with 6.4% DMSO for the plates with final concentration of 50% serum) was added.

The test compound was dissolved at concentration of 10 mg/mL in DMSO and diluted 1:78 into appropriate test medium with no DMSO or 1.92% DMSO or 5.12% DMSO. Example: added 25 µL of 10 mg/ml compound stock solution to 1925 µL of RPMI-1640 containing 0.165 molar MOPS+3 g/L glutamine w/o sodium bicarbonate with 1.92% DMSO. The test compound concentration achieved was 128 µg/ml and DMSO concentration of 3.2%. To the first well of each row of appropriate test medium plate 100 µL of the compound stock solutions (128 µg/mL) were added. Compounds were serially diluted two-fold across the plate to column 11 (column 12 was the growth control well) and the last 100 µL was discarded yielding compound concentrations of 64 to 0.06 µg/mL. For plates with dermatophytes the last 100 µL were placed in the first row of a second plate and serial diluted two-fold and yielding compound concentrations of 64-0.00004 µg/mL. Amphotericin B and caspofungin, the control compounds, were prepared as a stock solution of 10 mg/mL in DMSO and prepared in micro-titer plate as stated above for test compounds.

Yeasts

In the microbroth dilution assay for yeasts, microorganisms *Candida* spp., *Cryptococcus neoformans* (MY2062) and *Saccharomyces cerevisiae* (MY2255) were selected by streaking a yeast culture on Sabouraud Dextrose Agar (SDA) incubating for 24-48 hours at 35-37° C., thereafter selecting 1 characteristic colony and transferring to a fresh plate and incubating under same conditions. From the regrowth, 3 to 5 colonies were selected and suspended in 5-mL of sterile normal saline (BBL) and adjusted to match the turbidity of a 0.5 McFarland standard using Dade/Behring turbidity meter (preferred OD of 0.06 to 0.12). This resulted in a concentration of approximately $1-5\times10^6$ CFU/mL. The inocula were further diluted 1:1000 into RPMI-1640 containing 0.165 molar MOPS+3 g/L glutamine w/o sodium bicarbonate with 3.2% DMSO. Assay plates previously titrated with test compound in RPMI-1640 containing 0.165 molar MOPS+3 g/L glutamine w/o sodium bicarbonate with 3.2% DMSO were then inoculated with 100 µL/well of this dilution of culture. This resulted in a final organism concentration of $5\times10^2$ to $2.5\times10^3$ CFU/mL and final compound concentrations of 32 to 0.03 µg/mL. In addition *C. albicans* (MY1055) was also tested with heat inactivated (1 hour at 55° C.) mouse serum which was filtered twice using 0.22 micron GP Express PLUS Millipore filtration system. This standardized suspension was diluted 1:1000 into mouse serum. Assay plates previously titrated with drug in 2×RPMI-1640 containing 0.33 molar MOPS+6 g/l glutamine w/o sodium bicarbonate with 6.4% DMSO were then inoculated with 100 µl/well of this dilution of culture. This resulted in a final organism concentration of $5\times10^2$ to $2.5\times10^3$ CFU/mL and final compound concentration of 32 to 0.03 µg/ml and 50% mouse serum. Plates were incubated at 35-37° C. and MICs were read at 24 hours for *Candida* and 48 hours for *Cryptococcus neoformans*.

Filamentous Fungi

In the microbroth dilution assay for filamentous fungi *Aspergillus fumigatus* (MF5668) and dermatophyte *Trichophyton mentagrophytes* (MF7004) these microorganisms were grown on Sabouraud Dextrose Agar (SDA) slants at 35-37° C. for *Aspergillus fumigatus* and at 30° C. for *Trichophyton mentagrophytes* for 7 days prior to use. Inocula for filamentous fungi were prepared by adding 5 mL of sterile normal saline to slant followed by gently scraping the surface of stock slants growth with a sterile Dacron swab suspending the spores (conidia) in saline. Each spore suspension was then transferred to another tube and adjusted to match the turbidity of a 0.5 McFarland standard using the Dade/Behring turbidity meter (preferred OD of 0.06-0.09) for *A. fumigatus* and (preferred OD of 0.13-0.17) for dermatophyte *T. mentagrophytes*. This resulted in a concentration of approximately $1-5\times10^6$ CFU/mL. A spore count was performed on each culture suspension with a hemocytometer to insure the correct inoculum. This standardized suspension for *A. fumigatus* was diluted 1:500 in RPMI-1640 containing 0.165 molar MOPS+3 g/L glutamine w/o sodium bicarbonate with 3.2% DMSO. This standardized suspension for *T. mentagrophytes* was diluted 1:500 in RPMI-1640 containing 0.165 molar MOPS+3 g/L glutamine w/o sodium bicarbonate. Assay plates previously titrated with test compound in either RPMI-1640 containing 0.165 molar MOPS+3 g/L glutamine w/o sodium bicarbonate with 3.2% DMSO or RPMI-1640 containing 0.165 molar MOPS+3 g/L glutamine w/o sodium bicarbonate were then inoculated with 100 µL/well of this dilution. In addition *A. fumigatus* (MF5668) was also tested with heat inactivated human serum which was filtered once using 0.22 micron GP Express PLUS Millipore filtration system. This standardized suspension was diluted 1:500 in human serum. Assay plates previously titrated with test compound in 2×RPMI-1640 containing 0.33 molar MOPS+6 g/L glutamine w/o sodium bicarbonate were then inoculated with 100 µl/well of this dilution of culture. Plates were incubated at 35° C. and MICs were read at 48 hours for *Aspergillus fumigatus*, and plates incubated at 30° C. and MICs were read at 96 hours for Dermatophyte *T. mentagrophytes*.

In the above testing, viable cell counts were performed on 0.5 McFarland samples to verify the CFU/mL. Serial dilutions (1:10) with the 0.5 McFarland were made in saline. One-hundred micro-liters of each dilution ($10^4, 10^5, 10^6$) was spread onto a Sabouraud Dextrose Agar (SDA) plates which were then incubated for 24 to 48 or 96 (dermatophytes) hours at 35° C. or 30° C. After incubation colonies were counted and recorded. Growth and sterility controls for each organism were also carried out. Column 12 was the growth control and contains no test compound. Row H was not inoculated with organism or test compound and was used as sterility control for each plate.

The minimum inhibitory concentration (MIC-100) for all test compounds is determined to be the lowest concentration of compound at which there was no visible growth as compared to growth control without test compound. The minimum prominent inhibition (MIC-80) in growth is indicated as 80% inhibition in growth compared to growth control without test compound. For *Aspergillus* and dermatophyte *T. mentagrophytes* minimum effective concentration (MEC) was determined as narly morphology of hyphae both macroscopic and microscopic.

In Vivo Anti-Candida Activity

A disseminated *Candida* infection is induced in DBA/2 mice by the I.V. inoculation of 0.2 mL of a yeast cell suspension containing $3.0\times10^4$ CFU of *C. albicans* MY1055 into their lateral tail vein. Therapy is initiated within 15 to 30 minutes after challenge. Mice are treated with test compound either 1) I.P., b.i.d. for a total of 2 days or 2) P.O., b.i.d. for a total of 2 days. For each route of administration and diluent, an appropriate sham-treated control group is included.

Kidneys from euthanized mice (4-5/group) are removed four days after challenge using aseptic techniques, weighed and placed in sterile Whirl Pak bags containing 5 mL sterile saline. Kidneys are homogenized in the bags, serially diluted in saline and aliquots are plated on SDA. Plates are incubated at 35° C. and enumerated after 30 to 48 hours for *C. albicans* CFUs. Means from CFU/g of paired kidneys of treated groups are compared to the means from sham-treated controls. Percent sterilization is indicated by the number of mice with no detectable yeast, where the limit of detection because of the dilution scheme, is 50 yeast cells per pair of kidneys. For data from individual mice where no detectable yeast are recovered from paired kidneys, 9.8 is entered into the Microsoft Excel spread sheets formula [Log 10 ((5×raw count)/paired kidney weight)] so that the counts would be one less than the limit of detection (49 cells per pair of kidneys).

Mean log 10 yeast CFU/g of paired kidneys are compared to the sham treated controls using Student's t-test (two tailed, unpaired) on Microsoft Excel. Comparisons are deemed significant at the p=0.05 level. Mean percent reduction in CFU/g of paired kidneys for treated groups at 4 days following challenge relative to control are computed. A linear trend is typically evident when dose and CFU are both expressed in log 10 scale. Inverse regression (2) is subsequently used to estimate $ED_{90}$ and $ED_{99}$ values, defined as the doses (mg/kg) that reduced the number of CFU per organ by 90 and 99%, respectively.

Compounds of the present invention have GS $IC_{50}$s less than 500 nM and MIC-100s of <0.03-32 μg/mL (e.g., 0.03-8 μg/mL). Compounds of the present invention have MIC-80s in the range of <0.03-32 μg/mL (e.g., 0.03-4 μg/mL) and MECs of <0.03-32 μg/mL (e.g., 0.03-2 μg/mL). As for activity in the disseminated *Candida* infection, useful compounds will lower the CFU/g in kidneys by greater than 1 log 10 unit compared to sham treated controls and compounds that lower CFU/g by 2 log 10 units are especially useful. Example Number correspond to the examples described in the Examples section following description of Intermediates.

| EXAMPLE NUMBER | *Candida albicans* GS $IC_{50}$ (ng/mL) |
|---|---|
| 1 | 47 |
| 2 | 23 |
| 5 | 83 |
| 6 | 12 |
| 8 | 16 |
| 21 | 41 |
| 24 | 22 |
| 35 | 28 |
| 40 | 31 |
| 44 | 391 |
| 47 | 46 |
| 48 | 18 |
| 65 | 106 |
| 68 | 135 |
| 71 | 244 |
| 81 | 348 |
| 89 | 116 |
| 109 | 93 |
| 114 | 52 |
| 128 | 60 |
| 148 | 13 |
| 149 | 13 |
| 150 | 14 |
| 151 | 11 |
| 152 | 9 |
| 153 | 18 |

The following examples serve only to illustrate the invention and its practice. The examples are not to be construed as limitations on the scope or spirit of the invention.

Intermediate 1

Benzyl (1S,2R,3R,4aR,6aS,7R,8R,10aR,10bR, 12aR)-3-(acetyloxy)-8-[(1R)-1,2-dimethylpropyl]-2-hydroxy-1,6a,8,10a-tetramethyl-1,3,4,6,6a,7,8,9,10, 10a,10b,11,12,12a-tetradecahydro-2H-1,4a-(methanooxymethano)chrysene-7-carboxylate

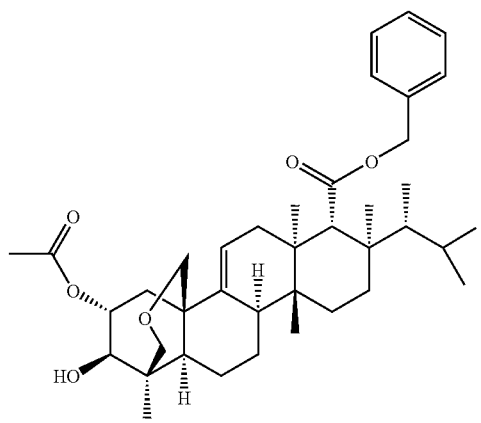

A flask was charged with enfumafungin (16 g, 22.5 mmol) and triethylsilane (120 mL) and the mixture was stirred until complete dissolution occurred. Trifluoroacetic acid (180 mL) was added and the solution was stirred at room temperature for 10 minutes. Toluene (150 mL) was added and the solvents were evaporated to leave a solid that was used directly.

A solution of the solid from above (22.5 mmol) in DMF (200 mL) was treated with benzyl bromide (16 mL) and sodium bicarbonate (28 g). The mixture was heated to 70° C. for 48 hours. The reaction mixture was allowed to cool to room temperature and then filtered through a pad of Celite. The Celite was washed with dichloromethane, toluene, and methanol. The resulting solution was concentrated to an oily residue which was purified by flash chromatography (silica gel, 100% dichloromethane to 92:8 dichloromethane:methanol) to afford the benzyl ester as a white powder.

To a solution of the solid from above (11 mmol) in toluene (500 mL) was added camphorsulfonic acid (4.2 g) and the mixture was heated at 70° C. for about 1 hour. The reaction was cooled to room temperature and pyridine (20 mL) was added. The reaction mixture was concentrated under reduced pressure and the residue was purified by flash chromatography (silica gel, 100% dichloromethane followed by 98:2 dichloromethane:methanol followed by 95:5 $CH_2Cl_2$:methanol) to give the title compound as a white solid (6.2 g). $^1H$ NMR (400 MHz, $CDCl_3$, ppm) δ 0.71-0.74 (m, 6H), 0.78 (d, J=6.83 Hz, 3H), 0.80-0.84 (m, 6H), 1.15 (s, 3H), 1.16-1.21 (m, 1H), 1.23 (s, 3H), 1.25-1.29 (m, 1H), 1.33-1.63 (m, 7H), 1.70-1.82 (m, 3H), 1.89 (m, 1H), 1.98-2.06 (m, 1H), 2.08 (s, 3H), 2.09-2.16 (m, 1H), 2.33-2.39 (m, 1H), 2.87 (s, 1H), 3.32 (d, J=4.69 Hz, 1H), 3.34 (br. S, 1H), 3.43 (m, 2H), 3.81 (d, J=11.91 Hz, 1H), 4.96 (d, J=12.25 Hz, 1H), 5.12 (d, J=12.25 Hz, 1H), 5.39 (d, J=5.81 Hz, 1H), 5.66-5.74 (m, 1H), and 7.35 (s, 5H).

Intermediate 2

Benzyl (1S,2R,3R,4aR,6aS,7R,8R,10aR,10b,12aR)-8-[(1R)-1,2-dimethylpropyl]-2,3-(dihydroxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate

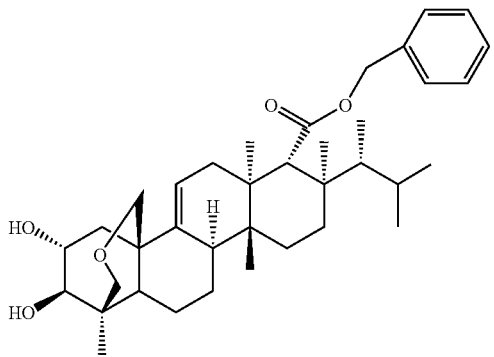

To a solution of benzyl (1S,2R,3R,4aR,6aS,7R,8R,10aR,10bR,12aR)-3-(acetyloxy)-8-[(1R)-1,2-dimethylpropyl]-2-hydroxy-1,6a,8,10a-tetramethyl-1,3,4,6,6a,7,8,9,10,10a,10b,11,12,12a-tetradecahydro-2H-1,4-a-(methanooxymethano)chrysene-7-carboxylate (Intermediate 1, 1.2 mmol; 750 mg) in methanol (30 mL) was added potassium carbonate (198 mg). The reaction mixture was stirred for about 16 hours at room temperature. The reaction was concentrated under reduced pressure to about 10 mL and diluted with dichloromethane. The solution was washed with water and saturated NaCl solution and then dried over anhydrous sodium sulfate. The solvents were evaporated to yield the title compound (700 mg) as a white solid. $^1$H NMR (400 MHz, CDCl$_3$, ppm) δ 0.72 (s, 3H), 0.73 (d, 3H), 0.78 (d, J=6.87 Hz, 3H), 0.80 (s, 3H), 0.81 (d, J=6.70 Hz, 3H), 1.14 (s, 3H), 1.14-1.21 (m, 2H), 1.23 (s, 3H), 1.24-1.27 (m, 1H), 1.47 (m, 6H), 1.69-1.82 (m, 3H), 1.84-1.93 (m, 1H), 1.99-2.06 (m, 1H), 2.07-2.15 (m, 1H), 2.28-2.35 (m, 1H), 2.87 (s, 1H), 3.15 (d, J=8.95 Hz, 1H), 3.32 (d, J=11.92 Hz, 1H), 3.37-3.46 (m, 2H), 3.71 (d, J=11.98 Hz, 1H), 4.57 (m, 1H), 4.98 (d, J=12.25 Hz, 1H), 5.13 (d, J=12.25 Hz, 1H), 5.37-5.41 (m, 1H), and 7.36 (m, 5H).

Intermediate 3

Benzyl (1S,2R,3R,4aR,6aS,7R,8R,10aR,10bR,12aR)-8-[(1R)-1,2-dimethylpropyl]-2-(hydroxyl)-3-(methoxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate

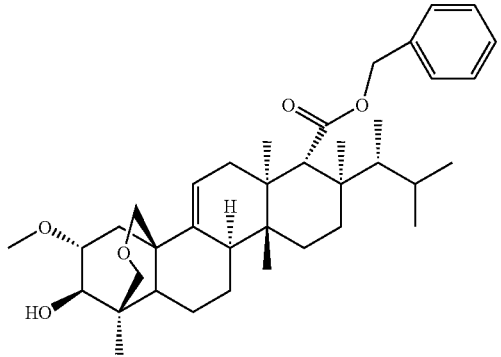

To a stirred solution of benzyl (1S,2R,3R,4aR,6aS,7R,8R,10aR,10bR,12aR)-8-[(1R)-1,2-dimethylpropyl]-2,3-(dihydroxy)-1,6a,8,10a-tetramethyl-1,3,4,6,6a,7,8,9,10,10a,10b,11,12,12a-tetradecahydro-2H-1,4-a-(methanooxymethano) chrysene-7-carboxylate (Intermediate 2, 0.26 mmol; 150 mg) in dichloromethane (8 mL) was added methanol (800 μL) and trifluoromethanesulfonic acid (1.02 mmol). The reaction mixture was stirred at room temperature for about 16 hours. Triethylamine (400 μL) was added and the solvents were evaporated under reduced pressure. The residue was purified by flash chromatography (silica gel, 90:10 to 80:20 heptane:ethyl acetate) to afford the title compound (122 mg). $^1$H NMR (400 MHz, CDCl$_3$, ppm) δ 0.71-0.74 (m, 6H), 0.78 (d, J=6.83 Hz, 3H), 0.80-0.83 (m, 6H), 1.15 (s, 3H), 1.16-1.21 (m, 1H), 1.23 (s, 3H), 1.24-1.29 (m, 2H), 1.32-1.53 (m, 4H), 1.56-1.62 (m, 1H), 1.70-1.81 (m, 3H), 1.87-1.95 (m, 1H), 1.99-2.04 (m, 1H), 2.07-2.16 (m, 1H), 2.30 (d, J=2.25 Hz, 1H), 2.40-2.47 (m, 1H), 2.88 (s, 1H), 3.18 (d, J=8.88 Hz, 1H), 3.31 (d, J=11.76 Hz, 1H), 3.40-3.42 (m, 2H), 3.43 (s, 3H), 3.77 (d, J=11.81 Hz, 1H), 4.09-4.19 (m, 1H), 4.98 (d, 1H), 5.12 (d, 1H), 5.39-5.43 (m, 1H), and 7.32-7.39 (m, 5H).

Intermediate 3 (Alternative Process)

To a slurry of enfumafungin (90.0 g, 126.9 mmol) in 846 ml of toluene with mechanical stirring at room temperature was added Et$_3$SiH (202.2 ml, 1269.5 mmol) in one portion. Trifluoroacetic acid (202.4 ml, 2627.8 mmol) was then added dropwise at a rapid rate. Once the trifluoroacetic acid addition was complete, the resulting amber colored solution was allowed to stir at room temperature for 2.5 hours. The TFA/toluene solution was then concentrated to dryness. Fresh toluene (300-500 ml) was added and the mixture was once again concentrated to dryness. The toluene stripping procedure was repeated two additional times. The crude solid was then dried overnight on a high vacuum line to yield 120 g of a purple brown solid. This material was carried on to the next step without additional purification.

To a solution of the solid from above (120 g crude material, ~126.9 mmol) in MeOH (1.27 L) with mechanical stirring, H$_2$SO$_4$ (31.2 ml, 585.3 mmol) was added dropwise at a fast rate. Once the addition was complete, the resulting solution was warmed to 65 deg C. and was allowed to stir for 4.5 hours. During the course of the reaction a white solid precipitated. The reaction was cooled to room temperature and the white solid was isolated by filtration. The solid was then washed with MeOH (2×200 ml) and CH$_3$CN (2×200 ml). After drying, 47.91 g white solid was recovered.

Additional material was isolated from the initial filtrate and subsequent washings as follows. The total liquid volume was reduced to ⅓ by evaporation in vacuo. An excess of water was added and a purple white solid precipitated. The solid was filtered, washed with 3:7 MeOH:water (2×100 mL) and CH$_3$CN (2×100 mL) and dried to give an additional 7.30 g of product as a brownish white solid. The combined yield of product was 55.21 g (86.5%).

This product (55.21 g, 109.8 mmol), NaHCO$_3$ (147.5 g, 1756.8 mmol) and benzyl bromide (65.29 ml, 549.0 mmol) were combined in 550 ml DMF with mechanical stirring. The mixture was warmed to 65 deg C. and was allowed to stir for 4.5 hours. The DMF was removed in vacuo and the resulting crude material was dissolved in 1 L of 3:2 water/MeOH. The mixture was vigorously stirred for 2-3 hours. During this time a brownish white solid formed. The precipitate was filtered and washed with additional 3:2 water/MeOH (2×250 mL). The solid was then rinsed with heptane and was allowed to air aspirate to initial dryness. The white solid recovered was then Intermediate 4

Benzyl (1S,2R,3R,4aR,6aS,7R,8R,10aR,10bR,
12aR)-8-[(1R)-1,2-dimethylpropyl]-2-(☐ydroxyl)-3-
(trityloxy)-1,6a,8,10a-tetramethyl-1,3,4,6,6a,7,8,9,
10,10a,10b,11,12,12a-tetradecahydro-2H-1,4-a-
(methanooxymethano)chrysene-7-carboxylate

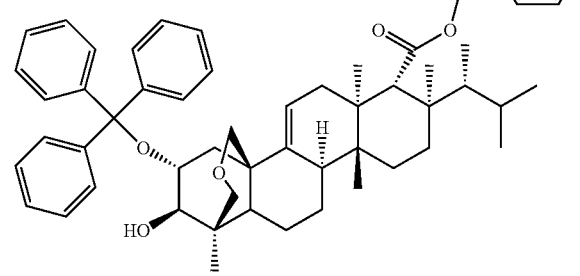

To a solution of benzyl (1S,2R,3R,4aR,6aS,7R,8R,10aR, 10bR,12aR)-8-[(1R)-1,2-dimethylpropyl]-2,3-(dihydroxy)-1,6a,8,10a-tetramethyl-1,3,4,6,6a,7,8,9,10,10a,10b,11,12, 12a-tetradecahydro-2H-1,4a-(methanooxymethano) chrysene-7-carboxylate (Intermediate 2, 230 mg; 0.4 mmol) in dichloromethane (20 mL) was added diisopropylethylamine (348 µL), trityl bromide (646 mg), and dimethylaminopyridine (10 mg). The reaction was stirred at room temperature for about 16 hours. The volatiles were removed under reduced pressure and the residue was purified by flash chromatography (silica gel, 100:0 to 70:30 heptane:ethyl acetate) to yield the title compound (330 mg). $^1$H NMR (400 MHz, CDCl$_3$, ppm) δ 0.59 (s, 3H), 0.67 (d, J=7.13 Hz, 3H), 0.71 (s, 3H), 0.73 (d, J=6.83 Hz, 3H), 0.76 (d, J=6.69 Hz, 3H), 1.06 (s, 3H), 1.07-1.17 (m, 2H), 1.18 (s, 3H), 1.20-1.30 (m, 5H), 1.32-1.51 (m, 2H), 1.58-1.66 (m, 3H), 1.67-1.76 (m, 1H), 1.84 (d, J=2.20 Hz, 1H), 1.90 (d, J=12.84 Hz, 1H), 2.00-2.12 (m, 1H), 2.79 (s, 1H), 2.82 (d, J=11.52 Hz, 1H), 3.06-3.12 (m, 2H), 3.38-3.47 (m, 2H), 4.37-4.46 (m, 1H), 4.69-4.75 (m, 1H), 4.93 (d, J=12.30 Hz, 1H), 5.13 (d, J=12.30 Hz, 1H), 7.10-7.37 (m, 15H), and 7.44-7.52 (m, 5H).

Intermediate 5

Benzyl (1S,2R,3R,4aR,6aS,7R,8R,10aR,10bR,
12aR)-8-[(1R)-1,2-dimethylpropyl]-2-(2-methane-
sulfonyloxy-ethoxy)-3-(methoxy)-1,6a,8,10a-tetram-
ethyl-1,3,4,6,6a,7,8,9,10,10a,10b,11,12,12a-
tetradecahydro-2H-1,4a-(methanooxymethano)
chrysene-7-carboxylate

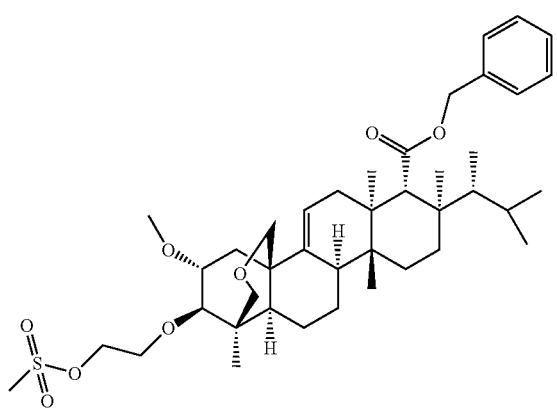

To a solution of Intermediate 3 (835 mg; 1.4 mmol) in dimethylformamide (10 mL) was added sodium hydride (170 mg). 2-Chloroethyl 4-methoxybenzylether (948 mg; 2.8 mmol) was added and the reaction stirred for 1 hour at room temperature. Over the course of 48 hours, sodium hydride (500 mg) and 2-chloroethyl 4-methoxybenzylether (1.9 g) were added portionwise to the stirring reaction solution until the reaction was judged complete by TLC analysis. Ethyl acetate, methanol, and water were slowly added to the reaction solution until all bubbling subsided. Ethyl acetate (1170 mL) and water (150 mL) were added to the reaction mixture. The aqueous phase was washed twice with ethyl acetate. The organic phases were combined and washed with water and saturated NaCl before being dried over sodium sulfate and concentrated. Residue was flash chromatographed (silica gel; 95:5 heptane:ethyl acetate). Purified material (1.4 g) was dissolved in dichloromethane (66 mL) and water (4 mL) and 2,3-dichloro-5,6-dicyano-1,4-benzoquinone (576 mg) were added. The reaction solution was stirred at room temperature for 16 hours and judged complete by TLC analysis. Ethyl acetate (20 mL) and water (70 mL) were added to the reaction solution. The organic phase was washed with water and saturated NaCl solution, dried over sodium sulfate, and concentrated. The residue was flash chromatographed (silica gel; 95:5 heptane:ethyl acetate) to give purified material (578 mg). A portion of the purified material (500 mg) was dissolved in dichloromethane (30 mL) and triethylamine (277 µL) was added. The reaction solution was cooled to 4° C. and methanesulfonyl chloride (84 µL) was added. The reaction solution was stirred for 2 hours, warming to room temperature. The reaction was judged complete by TLC analysis. The reaction solution was washed with water and saturated NaCl solution, dried over sodium sulfate, and concentrated. The residue was flash chromatographed (silica gel, 93:7 to 80:20 heptane:ethyl acetate) to give the title compound (456 mg).

1H NMR (400 MHz, CDCl3, ppm) δ 0.59 (s, 3H), 0.67 (d, J=7.13 Hz, 3H), 0.71 (s, 3H), 0.73 (d, J=6.83 Hz, 3H), 0.76 (d, J=6.69 Hz, 3H), 1.06 (s, 3H), 1.07-1.17 (m, 2H), 1.18 (s, 3H), 1.20-1.30 (m, 5H), 1.32-1.51 (m, 2H), 1.58-1.66 (m, 3H), 1.67-1.76 (m, 1H), 1.84 (d, J=2.20 Hz, 1H), 1.90 (d, J=12.84 Hz, 1H), 2.00-2.12 (m, 1H), 2.79 (s, 1H), 2.82 (d, J=11.52 Hz, 1H), 3.06-3.12 (m, 2H), 3.38-3.47 (m, 2H), 4.37-4.46 (m, 1H), 4.69-4.75 (m, 1H), 4.93 (d, J=12.30 Hz, 1H), 5.13 (d, J=12.30 Hz, 1H), 7.10-7.37 (m, 15H), and 7.44-7.52 (m, 5R).

Intermediate 6

Benzyl (1S,2R,3R,4aR,6aS,7R,8R,10aR,10bR, 12aR)-3-(acetyloxy)-8-[(1R)-1,2-dimethylpropyl]-2-(hydroxyl)-1,6a,8,10a-tetramethyl-6-oxo-1,3,4,6,6a, 7,8,9,10,10a,10b,11,12,12a-tetradecahydro-2H-1,4a-(methanooxymethano)chrysene-7-carboxylate

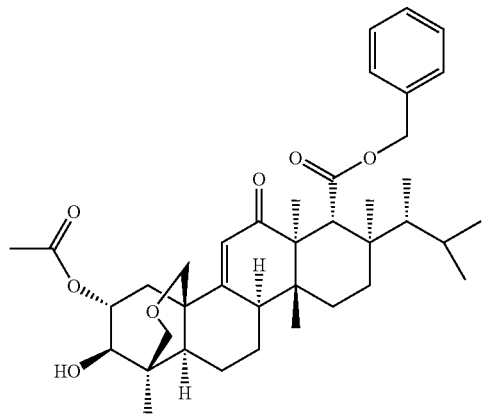

a) Benzyl (1S,2R,3R,4aR,6aS,7R,8R,10 aR,10bR,12aR)-2,3-bis(acetyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylate To a stirred solution of benzyl (1S,2R,3R,4aR,6aS,7R,8R, 10aR,10bR,12aR)-3-(acetyloxy)-8-[(1R)-1,2-dimethylpropyl]-2-hydroxy-1,6a,8,10a-tetramethyl-1,3,4,6,6a,7,8,9,10, 10a,10b,11,12,12a-tetradecahydro-2H-1,4a-(methanooxymethano)chrysene-7-carboxylate (Intermediate 1, 2.2 g, 3.5 mmol) in dichloromethane (150 mL) was added pyridine (5 mL), acetyl chloride (2.1 mL), and dimethylaminopyridine (200 mg). The reaction mixture was stirred at room temperature for about 2 hours. Dichloromethane (200 mL) was added and the organic solution was washed with aqueous HCl (1.0 N), saturated sodium bicarbonate solution, and saturated NaCl solution. The organic phase was dried over anhydrous sodium sulfate, filtered and the solvents evaporated under reduced pressure. The residue was purified by flash chromatography (silica gel; 80:20 heptane:ethyl acetate) to afford benzyl (1S,2R,3R,4aR,6aS,7R,8R,10aR, 10bR,12aR)-2,3-bis(acetyloxy)-8-[(1R)-1,2-dimethylpropyl]-1,6a,8,10a-tetramethyl-1,3,4,6,6a,7,8,9,10,10a,10b,11, 12,12a-tetradecahydro-2H-1,4a-(methanooxymethano) chrysene-7-carboxylate (2.0 g).

b) (1S,2R,3R,4aR,6aS,7R,8R,10aR,10bR,12aR)-2,3-Bis (acetyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid The diacetate from above (2.0 g) was dissolved in methanol (120 mL) and palladium hydroxide (700 mg) was added. A hydrogen atmosphere was secured (balloon) and the reaction mixture was stirred at room temperature for about 1 hour. The palladium catalyst was removed by filtration and the solvent was evaporated to leave a carboxylic acid (1.7 g).

c) The carboxylic acid from above (1.7 g) was added to a chilled (−20° C.) round bottom flask containing chromium trioxide (12 g) and dimethylpyrazole (11.4 g) in dichloromethane (400 mL). The reaction solution was stirred for 16 hours and allowed to warm to room temperature. The reaction was judged complete by TLC analysis. The reaction contents were diluted by additional dichloromethane (400 mL) and washed with saturated sodium bicarbonate. The aqueous phase was washed with additional dichloromethane and ethyl acetate. All organic phases were combined and dried over sodium sulfate before being concentrated. The residue was flash chromatographed (silica gel, 80:20 heptane:ethyl acetate). Purified material was dissolved in dichloromethane and washed with aqueous hydrochloric acid (10% solution) and saturated NaCl before being dried over sodium sulfate and concentrated. Purified material (820 mg) was dissolved in dimethylformamide (70 mL) with benzyl bromide (1.7 mL) and sodium bicarbonate (2.3 g). The reaction mixture was stirred at 50° C. for 16 hours and judged complete by TLC. The reaction mixture was cooled to room temperature and ethyl acetate was added. The organic phase was washed with water and twice with 10% aqueous ammonium chloride solution before being dried over sodium sulfate and concentrated. The residue was flash chromatographed (silica gel; 88:12 heptane:ethyl acetate) to yield purified material (560 mg). Purified material was dissolved in methanol (50 mL) and potassium carbonate (112 mg) was added. The reaction solution was stirred at room temperature for 3 hours and judged complete by TLC. Ethyl acetate was added to the reaction solution and the organic phase was washed with water and saturated NaCl solution before being dried over sodium sulfate and concentrated. The resulting material (450 mg) was dissolved in acetic acid (27 mL) and concentrated sulfuric acid (270 µL) was added. The reaction was stirred at room temperature for 2 hours and judged complete by TLC analysis. Water (1 mL) and ethyl acetate were added to the reaction solution. The organic phase was gently washed (stirring Erlenmayer flask) with saturated sodium bicarbonate solution and saturated NaCl before being dried over sodium sulfate and concentrated. The residue was flash chromatographed (86:14 heptane:ethyl acetate) to yield the title compound (300 mg). 1H NMR (400 MHz, CDCl3, ppm) δ 0.70 (d, J=7.14 Hz, 3H), 0.73 (d, J=6.70 Hz, 3H), 0.78-0.82 (m, 6H), 0.85 (s, 3H), 0.85-0.91 (m, 1H), 1.10 (s, 3H), 1.20-1.41 (m, 3H), 1.43-1.72 (m, 4H), 1.73 (s, 3H), 1.81-1.94 (m, 3H), 2.09 (s, 3H), 2.13-2.20 (m, 1H), 2.38 (dd, J=13.38, 7.11 Hz, 1H), 2.51-2.59 (m, 1H), 3.14 (s, 1H), 3.30-3.37 (m, 2H), 3.43-3.57 (m, 2H), 3.87 (d, J=12.03 Hz, 1H), 5.00 (d, J=12.31 Hz, 1H), 5.26 (d, J=12.25 Hz, 1H), 5.69-5.78 (m, 1H), 5.79 (d, J=2.58 Hz, 1H), 7.29-7.40 (m, 3H), and 7.45-7.51 (m, 2H).

Intermediate 7

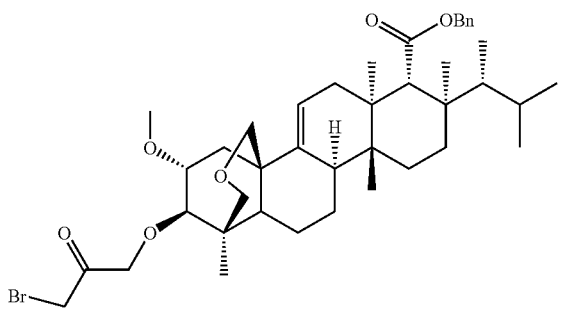

To a chilled solution of Intermediate 3 (410 mg; 0.69 mmol) in anhydrous dimethylformamide (6 mL) was added sodium hydride (110 mg; 8.6 mmol) and 3-chloro-2-methoxymethoxy-propene (188 mg). The reaction solution was stirred for 16 hours, gradually warming to room temperature. The reaction was judged complete by TLC analysis. Water was added dropwise until bubbling ceased and the reaction contents were concentrated. The residue was flash chromatographed (silica gel; 80:20 heptane:ethyl acetate). Purified material (440 mg) was dissolved in tetrahydrofuran (17.6 mL) and water (4.4 mL) and N-bromosuccinimide (130 mg) were added. The reaction stirred for 4 hours at room temperature and was judged complete by TLC analysis. The reaction contents were concentrated and the residue was flash chromatographed (silica gel; 80:20 heptane:ethyl acetate) to yield a white solid (370 mg). MS: 727, found: 651 (M–Br)$^+$. $^1$H NMR (400 MHz, CDCl$_3$, ppm) δ 0.65 (s, 3H), 0.66 (s, 3H), 0.71 (d, J=6.83 Hz, 3H), 0.72-0.73 (m, 3H), 0.74 (d, J=6.74 Hz, 3H), 1.07 (s, 3H), 1.16 (s, 3H), 1.17-1.21 (m, 2H), 1.26-1.51 (m, 5H), 1.57-1.74 (m, 4H), 1.80-1.88 (m, 1H), 1.90-1.98 (m, 1H), 1.99-2.11 (m, 1H), 2.37 (dd, J=13.40, 6.91 Hz, 1H), 2.80 (s, 1H), 2.85 (d, J=8.40 Hz, 1H), 3.27 (s, 3H), 3.29-3.38 (m, 4H), 3.67 (d, J=11.76 Hz, 1H), 4.08 (d, J=14.6 Hz, 1H), 4.14 (d, J=14.6 Hz, 1H), 4.17-4.24 (m, 1H), 4.32 (d, J=15.2 Hz, 1H), 4.46 (d, J=15.2 Hz, 1H), 4.91 (d, J=12.3 Hz, 1H), 5.04 (d, J=12.3 Hz, 1H), 5.35 (s, 1H), and 7.23-7.42 (m, 5H).

Intermediate 8

2-isopropyl-2-methyl-1-[(4-methylphenyl)sulfonyl]aziridine

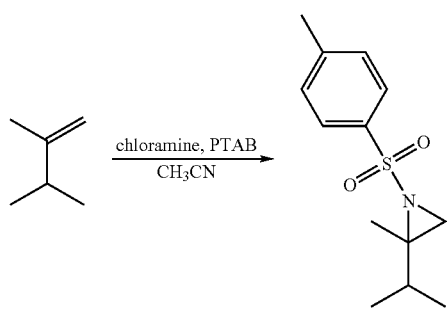

To a solution of 2,3-dimethyl butene (300 ml, 2.42 mol) in 7.8 L of dry acetonitrile was added Chloramine-T (749.9 g, 1.1 eq) portionwise over 90 min. The temperature was maintained at approximately 20° C. To this reaction mixture was added phenyltrimethylammonium tribromide (91.4 g, 0.1 eq) in 10 g portions over 90 min. The temperature increased to 26° C. during the addition. The reaction mixture was stirred at room temperature for 2 days. The reaction mixture was concentrated down to approximately 15% of the initial volume and was them filtered, washing the solid with 1 L of acetonitrile. The organic liquid phase was concentrated and the residue dissolved in 2.5 L of EtOAc. The resulting solution was washed twice with water, dried over MgSO$_4$, and concentrated to give a solid. The crude was purified on a large plug of celite using gradient elution 5% to 25% EtOAc/heptanes to afford 317 g of 2-isopropyl-2-methyl-1-[(4-methylphenyl)sulfonyl]aziridine as a solid.

Intermediate 9

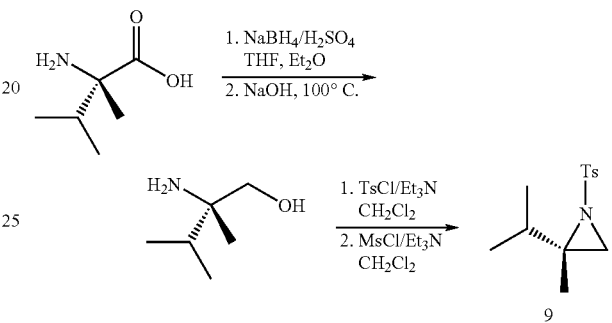

(2S)-2-isopropyl-2-methyl-1-[(4-methylphenyl)sulfonyl]aziridine (a) NaBH$_4$ (94.5 g, 2.498 mol) was charged into a 5 L three-necked flask containing 540 ml of dry THF. This solution was cooled with an ice bath. The L-α-Me-Val-OH (75 g, 0.572 mol) was added to this solution. The mixture was stirred for 20 min under N$_2$ then a solution of H$_2$SO$_4$ (66.7 ml, 1.252 mol) in 160 ml of dry ether was added dropwise over a period of 3.5 h. The reaction mixture was stirred for one hour while in the ice bath then allowed to warm to rt overnight. TLC in CH$_2$Cl$_2$MeOH (70/30) indicated the reaction was complete. The reaction was cooled with an ice bath and quenched by the slow addition of 250 ml of MeOH over 45 min. The mixture was then stirred at rt for 15 min then NaOH (5N, 700 ml) was added very slowly. The flask was equipped with a distillation head and heated to 100° C. with a heating mantle. The volatiles (bp<100° C.) were removed by distillation. The resulting mixture was heated to 100° C. (internal temp.) for 3 h then cooled to rt. Water (1 L) was added and the mixture was extracted with CH$_2$Cl$_2$ (6×500 ml). The combined organic layers were dried over Na$_2$SO$_4$, filtered and concentrated to afford the amino alcohol product as a yellow oil (64.2 g). $^1$H NMR (400 MHz, CDCl$_3$) δ ppm 0.87 (d, J=6.93 Hz, 3H) 0.91 (d, J=6.93 Hz, 3H) 0.95 (s, 3H) 1.57-1.68 (m, 1H) 3.30 (d, J=10.30 Hz, 1H) 3.34 (d, J=10.30 Hz, 1H).

(b) A solution of amino alcohol from above (32 g, 273.5 mmol) in dry CH$_2$Cl$_2$ (1.7 L) was cooled with an ice bath and Et$_3$N (198 ml, 1422 mmol) was added. A solution p-toluenesulfonyl chloride (62.5 g, 328.2 mmol) in CH$_2$Cl$_2$ (250 ml) was added dropwise over a period of 3 h. The ice bath was removed and the solution was stirred at rt overnight. The mixture was cooled in an ice bath and Et$_3$N (61.6 ml, 442 mmol) was added followed by the dropwise addition of methanesulfonyl chloride (40 ml, 516.8 mmol). The reaction mixture was stirred for 4 h while keeping the temperature below 12° C. Water (600 ml) was added to the mixture followed by brine (350 ml). The aqueous layer was extracted with CH$_2$Cl$_2$ (3×500 ml). The combined organic layers were dried over Na$_2$SO$_4$, filtered concentrated. The crude product was purified over a pad of silica gel (EtOAc/Heptanes:5/95 then 10/90) to afford the aziridine as a white solid (36 g). $^1$H NMR (400 MHz, CDCl$_3$) δ ppm 0.94 (d, J=6.78 Hz, 3H) 0.98 (d, J=6.78 Hz, 3H) 1.44-1.53 (m, 1H) 1.59 (s, 3H) 2.20 (s, 1H) 2.42 (s, 3H) 2.60 (s, 1H) 7.30 (d, J=7.90 Hz, 2H) 7.83 (d, J=7.90 Hz, 2H).

Intermediate 10

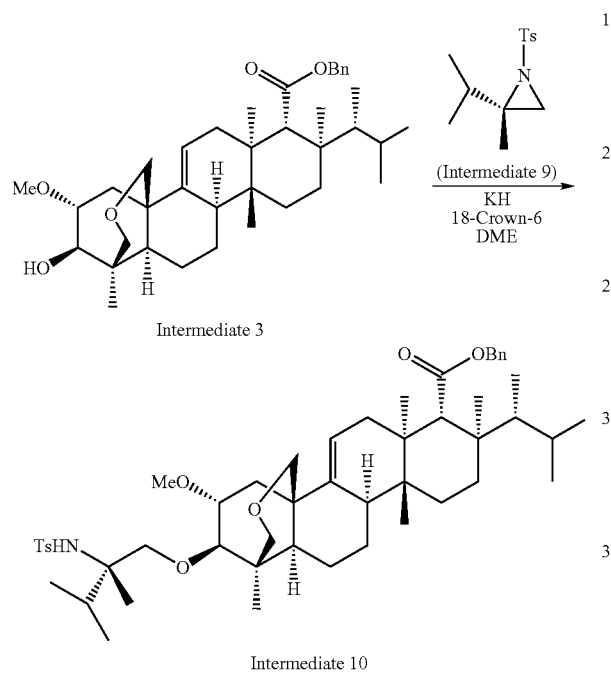

Benzyl (1S,2R,3R,4aR,6aS,7R,8R,10aR,10bR, 12aR)-8-[(1R)-1,2-dimethylpropyl]-2-[[(2S)-2,3-dimethyl-2-[(p-tolylsulfonyl)amino]butyl]oxy]-3-(methoxy)-1,6a,8,10a-tetramethyl-1,3,4,6,6a,7,8,9, 10,10a,10b,11,12,12a-tetradecahydro-2H-1,4a-(methanooxymethano)chrysene-7-carboxylate To a stirred solution of Intermediate 3 (60 g, 101 mmol) in anhydrous dimethoxyethane (800 mL) was added 18-crown-6 (67.4 g, 255 mmol) and the aziridine (42.8 g, 169.2 mmol). The mixture was stirred under nitrogen for 30 min until all solids were dissolved. Potassium hydride (30% in oil, 34.0 g, 255 mmol) was added portionwise (ca. 5 g portions) over a period of about 1 hour. The reaction temperature increased from 18° C. to 27° C. After the completion of the addition the resulting suspension was stirred at room temperature for about 3 h. The reaction was carefully quenched by the dropwise addition of methanol (80 mL). Following an initial period of bubbling, the rate of addition of methanol addition can be increased and a clear solution was obtained. The reaction mixture was then diluted with water (600 mL) and extracted with EtOAc (900 mL). The organic solution was diluted with CH$_2$Cl$_2$ (1 L) and dried over anhydrous MgSO$_4$. The drying agent was removed by filtration and the organic solvent was removed under reduced pressure to afford the crude compound (143.4 g). This material was purified on silica gel using ethyl acetate/heptanes to give the desired compound 75.4 g).

EXAMPLES

Example 1

(1S,2R,3R,4aR,6aS,7R,8R,10aR,10bR,12aR)-3-(acetyloxy)-2-(2-aminoethoxy)-8-[(1R)-1,2-dimethylpropyl]-1,6a,8,10a-tetramethyl-1,3,4,6,6a,7,8,9,10, 10a,10b,11,12,12a-tetradecahydro-2H-1,4a-(methanooxymethano)chrysene-7-carboxylic acid (K-25)

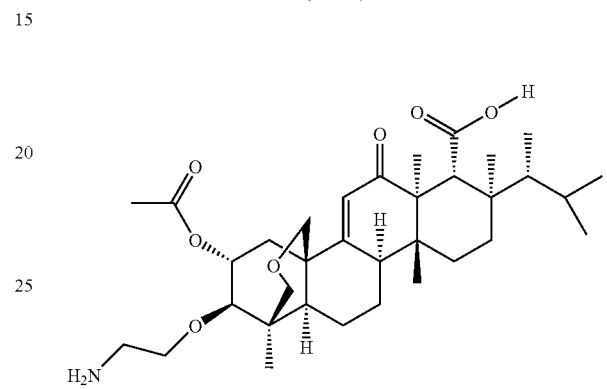

a) Benzyl (1S,2R,3R,4aR,6aS,7R,8R,10aR,10bR,12aR)-8-[(1R)-1,2-dimethylpropyl]-3-(methoxy)-2-(allyloxy)-1,6a, 8,10a-tetramethyl-1,3,4,6,6a,7,8,9,10,10a,10b,11,12,12a-tetradecahydro-2H-1,4a-(methanooxymethano)chrysene-7-carboxylate To a chilled solution of Intermediate 3 (611 mg; 1.025 mmol) in dimethylformamide (9 mL) was added sodium hydride (328 mg; 8.2 mmol) and allyl bromide (355 µL). The reaction was stirred at room temperature for 16 hours. The reaction was judged complete by TLC analysis. The reaction contents were concentrated and the residue was flash chromatographed (silica gel; 80:20 heptane:ethyl acetate). Purified material (529 mg).

b) Benzyl (1S,2R,3R,4aR,6aS,7R,8R,10aR,10bR,12aR)-8-[(1R)-1,2-dimethylpropyl]-3-(methoxy)-2-(2-oxoethoxy)-1, 6a,8,10a-tetramethyl-1,3,4,6,6a,7,8,9,10,10a,10b,11,12, 12a-tetradecahydro-2H-1,4a-(methanooxymethano) chrysene-7-carboxylate The material from above (529 mg) was dissolved in acetone (6.8 mL) and water (0.8 mL). Osmium tetroxide (4% solution; 531 µL; 0.08 mmol) and 4-methylmorpholine N-oxide ((196 mg) were added and the reaction stirred at room temperature for 16 hours. The reaction was judged complete by TLC analysis. Florisil (550 mg) and sodium bisulfite (550 mg) were added and the reaction solution was stirred for 1 hour at room temperature. The reaction contents were filtered over a pad of Celite and concentrated. The residue was dissolved in tetrahydrofuran (12 mL) and water (3 mL) and sodium periodate (490 mg) was added. The reaction solution was stirred for 2 hours at room temperature and judged complete by TLC analysis. Water (5 mL) was added and the aqueous phase was thrice washed with ethyl acetate. The organic phase was dried over magnesium sulfate and concentrated. The residue was flash chromatographed (silica gel; 70:30 heptane:ethyl acetate) to yield the title compound (550 mg).

c) Benzyl (1S,2R,3R,4aR,6aS,7R,8R,10aR,10bR,12aR)-8-[(1R)-1,2-dimethylpropyl]-3-(methoxy)-2-(2-aminoethoxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate To a solution of the compound from Example 1(b) (0.373 g, 0.59 mmol) in isopropanol (33 mL) was added ammonium acetate (2.8 g, 35 mmol). Sodium cyanoborohydride (0.55 g, 8.23 mmol) was added and the mixture was stirred under nitrogen at reflux (100° C.). After 1 h, TLC (10% methanol in DCM) indicated the reaction to be complete. The solvent was evaporated and the mixture was diluted with sodium bicarbonate (40 ml). The solution was extracted with dichloromethane (3×20 ml). The combined organic layers were washed with brine (20 ml), dried over sodium sulfate and evaporated. The crude material was purified by column chromatography (SepPack, 10 g, silica gel) using dichloromethane/methanol as eluant to afford the desired compound (94.6 mg).

d) Benzyl (1S,2R,3R,4aR,6aS,7R,8R,10aR,10bR,12aR)-8-[(1R)-1,2-dimethylpropyl]-3-(acetyloxy)-2-(2-aminoethoxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate To a stirred solution of the compound from Example 1 (c) (0.095 g, 0.15 mmol) in acetic acid (13 mL) was added p-toluenesulfonic acid (0.072 g, 0.3 mmol) and the solution was heated at about 110° C. for 60 minutes. The solvent was evaporated under reduced pressure, toluene (10 mL) was added to the residue and the volatiles again removed under vacuum. The resulting yellow oil was diluted with ethyl acetate (20 ml) and washed with sodium bicarbonate (2×10 ml) and brine (10 ml). The water layers were extracted with ethyl acetate (3×10 ml) and the combined organic layers were dried over sodium sulfate and evaporated. The crude oil was purified by column chromatography (SepPack, 2 g, silica gel) using dichloromethane/methanol as solvent to yield the title compound (33.6 mg).

e) (1S,2R,3R,4aR,6aS,7R,8R,10aR,10bR,12aR)-3-(acetyloxy)-2-(2-aminoethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid A solution of the compound from Example 1(d) (0.034 g, 0.05 mmol) in methanol (5 mL) was purged with nitrogen several times then palladium hydroxide (0.06 g) was added. The solution was placed under a hydrogen atmosphere and stirred for about 3 h until the reaction was judged to be complete by TLC analysis. The mixture was filtered through a short plug of Celite and the pad was washed with methanol and dichloromethane. The solvents were evaporated to give the title compound as a white solid, 0.022 g. Calculated for $C_{34}H_{55}NO_6$: 573; observed: 574 $(M+H)^+$. $^1H$ NMR (400 MHz, methanol-$d_4$) δ ppm 0.77 (s, 3H), 0.78 (d, J=7.22 Hz, 3H), 0.83 (s, 3H), 0.87 (d, J=6.64 Hz, 3H), 0.91 (d, J=6.69 Hz, 3H), 1.18 (s, 3H), 1.22 (s, 3H), 1.24-1.90 (m, 13H), 1.93 (s, 6H), 2.06 (s, 3H), 2.08-2.13 (m, 1H), 2.16-2.26 (m, 1H), 2.40-2.49 (m, 1H), 2.82-2.88 (m, 1H), 3.05-3.12 (m, 2H), 3.17-3.23 (m, 1H), 3.34-3.40 (m, 1H), 3.41-3.50 (m, 2H), 3.72-3.81 (m, 2H), 3.84-3.93 (m, 1H), 5.45-5.50 (m, 1H), and 5.72-5.84 (m, 1H).

Example 2

(1S,2R,3R,4aR,6aS,7R,8R,10aR,10bR,12aR)-3-(Acetyloxy)-2-(2-aminopropoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-1)

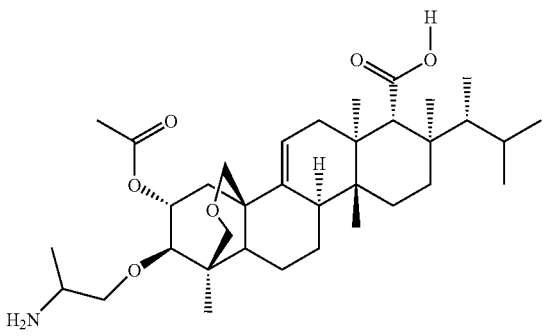

a) In a similar manner as described in Example 1(a), from benzyl (1S,2R,3R,4aR,6aS,7R,8R,10aR, 10bR,12aR)-8-[(1R)-1,2-dimethylpropyl]-2-(hydroxyl)-3-(methoxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate (Intermediate 3, 1.48 g, 2.48 mmol) and 3-bromo-2-methylpropene (9.9 mmol) was obtained benzyl (1S,2R,3R,4aR,6aS,7R,8R,10aR,10bR,12aR)-8-[(1R)-1,2-dimethylpropyl]-3-(methoxy)-2-(2-methyl-allyloxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate (1.89 g).

b) In a similar manner as described in Example 1(b), from benzyl (1S,2R,3R,4aR,6aS,7R,8R,10aR, 10bR,12aR)-8-[(1R)-1,2-dimethylpropyl]-3-(methoxy)-2-(2-methyl-allyloxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate (3.3 g, 5.1 mmol) was obtained benzyl (1S,2R,3R,4aR,6aS,7R,8R,10aR,10bR,12aR)-8-[(1R)-1,2-dimethylpropyl]-3-(methoxy)-2-(2-oxopropoxy)-1,6a,8,10a-tetramethyl-1,3,4,6,6a,7,8,9,10,10a,10b, 11,12,12a-tetradecahydro-2H-1,4a-(methanooxymethano)chrysene-7-carboxylate (2.8 g).

c) In a similar manner as described in Example 1(c). Ketone from Example 2(b) (2.8 g) was dissolved in isopropanol (200 mL) and ammonium acetate (20 g) and sodium cyanoborohydride (3.75 g) were added. The reaction solution was refluxed for about 16 hours and judged complete by TLC analysis. The reaction contents were cooled to room temperature and concentrated. The residue was suspended in water and the solution was adjusted to pH 10 using solid sodium carbonate and saturated sodium bicarbonate solution. The aqueous phase was extracted with dichloromethane (5×) and the combined organic extracts were dried over magnesium sulfate and concentrated to yield benzyl (1S,2R,3R,4aR,6aS, 7R,8R,10aR,10bR,12aR)-8-[(1R)-1,2-dimethylpropyl]-3-

(methoxy)-2-(2-aminopropoxy)-1,6a,8,10a-tetramethyl-1,3,4,6,6a,7,8,9,10,10a,10b,11,12,12a-tetradecahydro-2H-1,4a-(methanooxymethano)chrysene-7-carboxylate as a white solid (2.9 g).

d) In a similar manner as described in Example 1(d), the amino compound above (2.9 g) was dissolved in acetic acid (250 mL) and p-toluenesulfonic acid (1.33 g) was added. The reaction solution was stirred at 110° C. for 2 hours and judged complete by TLC analysis. The reaction solution was cooled to room temperature and concentrated. The residue was dissolved in dichloromethane, washed with saturated sodium bicarbonate solution, dried over magnesium sulfate, and concentrated to yield benzyl (1S,2R,3R,4aR,6aS,7R,8R,10aR,10bR,12aR)-3-(acetyloxy)-2-(2-aminopropoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylate as a white solid (2.15 g).

e) In a similar manner as described in Example 1 (e), the benzyl ester from above (2.15 g) was dissolved in methanol (80 mL) and dichloromethane (1 mL). Palladium hydroxide (1.2 g) was added and a hydrogen atmosphere was secured (balloon). The reaction mixture was stirred at room temperature for 1 hour and judged complete by TLC analysis. The reaction mixture was filtered through a pad of Celite and the filtrate was concentrated to yield the title compound (1.8 g). Calculated for $C_{35}H_{57}NO_6$: 587; observed: 588 (M+H)+. $^1$H NMR (400 MHz, methanol-$d_4$) δ ppm 0.75-0.77 (m, 3H), 0.82-0.84 (m, 3H), 0.85 (d, J=6.69 Hz, 3H), 0.91 (d, J=6.78 Hz, 3H), 1.15-1.23 (m, 3H), 1.24 (s, 3H), 1.27-1.41 (m, 6H), 1.44-1.66 (m, 6H), 1.70-1.87 (m, 4H), 2.03-2.09 (m, 3H), 2.21-2.32 (m, 1H), 2.36-2.47 (m, 1H), 2.75-2.81 (m, 1H), 2.86 (s, 1H), 3.10-3.22 (m, 1H), 3.22-3.36 (m, 3H), 3.35-3.50 (m, J=55.01 Hz, 4H), 3.61-3.81 (m, 3H), 5.45-5.54 (m, 1H), and 5.67-5.87 (m, 1H).

Example 3

(1S,2R,3R,4aR,6aS,7R,8R,10aR,10bR,12aR)-3-(acetyloxy)-2-[2-(2,6-diaminohexanoylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-16)

Benzyl (1S,2R,3R,4aR,6aS,7R,8R,10aR,10bR,12aR)-3-(acetyloxy)-2-(2-aminoethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylate, Example 1(d) (5 mg) was dissolved in dimethylformamide (1.5 mL) and Cbz-(ε-Cbz)-Lys-OH (12.5 mg; 0.03 mmol), dicyclohexylcarbodiimide (6.2 mg; 0.03 mmol), and dimethylaminopyridine (3 mg) were added. The reaction was stirred at room temperature for about 16 hours and judged complete by TLC analysis. The reaction contents were concentrated and purified by reverse phase HPLC (40:60 to 100:0 methanol:water). A portion of the purified material (7.4 mg) was dissolved in methanol (2 mL) and acetic acid (15 μL) was added. Palladium hydroxide (65 mg) was added and a hydrogen atmosphere was secured (balloon). The reaction was stirred at room temperature for 30 minutes and judged complete by TLC analysis. The reaction contents were filtered over celite and concentrated to give the title compound as an acetate salt (1.8 mg). Calculated for $C_{40}H_{67}N_3O_7$: 701; observed: 702 (M+H)+. $^1$H NMR (400 MHz, methanol-$d_4$) δ ppm 0.76 (s, 3H), 0.78 (d, J=7.17 Hz, 3H), 0.82 (s, 3H), 0.87 (d, J=6.69 Hz, 3H), 0.91 (d, J=6.78 Hz, 3H), 1.17 (s, 3H), 1.22 (s, 3H), 1.24-1.38 (m, 3H), 1.41-1.57 (m, 3H), 1.57-1.71 (m, 5H), 1.72-1.87 (m, 3H), 1.95 (s, 3H), 2.06 (s, 3H), 2.09 (s, 3H), 2.10-2.13 (m, 1H), 2.16-2.24 (m, 1H), 2.32-2.41 (m, 1H), 2.85 (s, 1H), 2.91-2.99 (m, 2H), 3.08-3.17 (m, 1H), 3.23-3.28 (m, 2H), 3.34-3.38 (m, 2H), 3.39-3.54 (m, 4H), 3.56-3.65 (m, 1H), 3.70 (d, J=11.23 Hz, 1H), 3.73-3.83 (m, 1H), 4.41 (s, 1H), 5.47 (d, J=6.20 Hz, 1H), and 5.71-5.84 (m, 1H).

Example 4

(1S,2R,3R,4aR,6aS,7R,8R,10aR,10bR,12aR)-3-(acetyloxy)-2-[2-(2,5-diaminopentanoylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-17)

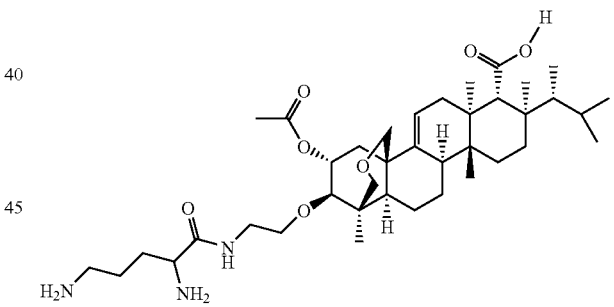

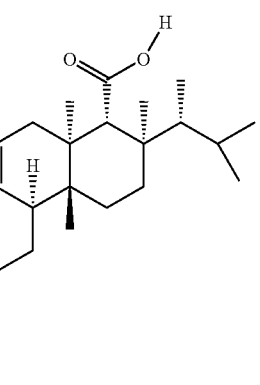

Prepared in a similar manner as described in Example 3, using Cbz-(δ-Cbz)-Orn-OH yielded the title compound, 4.8 mg as the acetate salt. Calculated for $C_{39}H_{65}N_3O_7$: 687; observed: 688 (M+H)+. $^1$H NMR (400 MHz, methanol-$d_4$) δ ppm 0.76 (s, 3H), 0.78 (d, J=7.17 Hz, 3H), 0.82 (s, 3H), 0.87 (d, J=6.69 Hz, 3H), 0.91 (d, J=6.83 Hz, 3H), 1.17 (s, 3H), 1.22 (s, 3H), 1.23-1.46 (m, 5H), 1.46-1.68 (m, 5H), 1.69-1.90 (m, 5H), 1.91-1.95 (m, 1H), 2.06 (s, 3H), 2.07-2.15 (m, 2H), 2.17-2.25 (m, 1H), 2.30-2.40 (m, 1H), 2.85 (s, 1H), 2.93-3.01 (m, 1H), 3.08-3.16 (m, 1H), 3.34-3.39 (m, 3H), 3.39-3.54 (m, 5H), 3.56-3.65 (m, 1H), 3.67-3.83 (m, 2H), 5.47 (d, J=5.61 Hz, 1H), and 5.69-5.80 (m, 1H).

Example 5

(1S,2R,3R,4aR,6aS,7R,8R,10aR,10bR,12aR)-3-(acetyloxy)-2-[2-(2,3-diaminopropionylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-18)

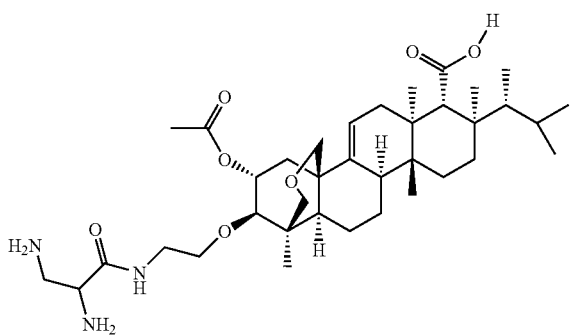

Prepared in a similar manner as described in Example 3, using N-α-N-β-di-Cbz-diaminopropionic acid and yielded the title compound, 8.4 mg as an acetate salt. Calculated for $C_{37}H_{61}N_3O_7$: 659; observed: 660 (M+H)+. $^1$H NMR (400 MHz, methanol-$d_4$) δ ppm 0.76 (s, 3H), 0.78 (d, J=7.22 Hz, 3H), 0.81 (s, 3H), 0.87 (d, J=6.69 Hz, 3H), 0.91 (d, J=6.83 Hz, 3H), 1.17 (s, 3H), 1.22 (s, 3 H), 1.24-1.45 (m, 5H), 1.45-1.69 (m, 4H), 1.72-1.90 (m, 3H), 1.98-2.00 (m, 1H), 2.05 (s, 3H), 2.07-2.14 (m, 1H), 2.17-2.26 (m, 1H), 2.31-2.41 (m, 1H), 2.85 (s, 1H), 2.89-2.97 (m, 1H), 3.07-3.22 (m, 2H), 3.33-3.41 (m, 2H), 3.43-3.47 (m, 2H), 3.48-3.55 (m, 1H), 3.57-3.66 (m, 2H), 3.68-3.82 (m, 2H), 3.83-4.22 (m, 2H), 5.47 (d, J=5.76 Hz, 1H), and 5.70-5.84 (m, 1H).

Example 6

(1S,2R,3R,4aR,6aS,7R,8R,10aR,10bR,12aR)-3-(acetyloxy)-2-(2-guanidino-ethoxy)-8-[(1R)-1,2-dimethylpropyl]-1,6a,8,10a-tetramethyl-1,3,4,6,6a,7,8,9,10,10a,10b, 11,12,12a-tetradecahydro-2H-1,4a-(methanooxymethano)chrysene-7-carboxylic acid (K-21)

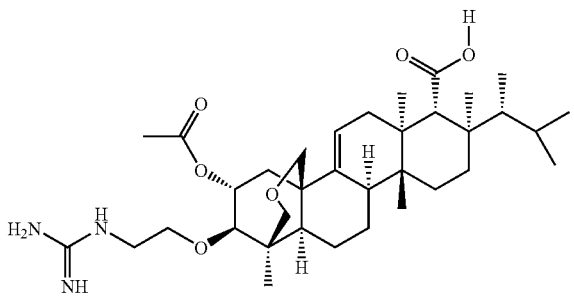

The compound described in Example 1(d) (15 mg; 0.022 mmol) was dissolved in dimethylformamide (2 mL) and 1,3-bis(benzyloxycarbonyl)-2-methyl-2-thiopseudourea (40 mg) and triethylamine (30 μL) were added. The reaction contents were stirred at room temperature for 16 hours. Mercuric chloride (2 mg) was added and the reaction stirred for 2 hours at room temperature. The reaction was judged complete by TLC analysis and purified by reverse phase HPLC (60:40 to 100:0 methanol:water). Purified material (15 mg) was dissolved in methanol (2 mL) and ethyl acetate (2 mL). Acetic acid (10 μL) and palladium hydroxide (25 mg) were added and a hydrogen atmosphere was secured (balloon). The reaction mixture was stirred at room temperature for 1 hour and judged complete by TLC analysis. The reaction contents were filtered through Celite and concentrated to yield the title compound as an acetate salt (1.5 mg). Calculated for $C_{35}H_{57}N_3O_6$: 615; observed: 616 (M+H)+. $^1$H NMR (400 MHz, methanol-$d_4$) δ ppm 0.77 (s, 3H), 0.78 (d, J=7.22 Hz, 3H), 0.82 (s, 3H), 0.87 (d, J=6.69 Hz, 3H), 0.91 (d, J=6.83 Hz, 1H), 1.17 (s, 3H), 1.22 (s, 3H), 1.23-1.45 (m, 5H), 1.45-1.70 (m, 4H), 1.69-1.91 (m, 3H), 1.92-1.96 (m, 1H), 1.97 (s, 3H), 2.05 (s, 3H), 2.06-2.14 (m, 1H), 2.16-2.26 (m, 1H), 2.35-2.45 (m, 1H), 2.86 (s, 1H), 3.16 (d, J=9.08 Hz, 1H), 3.33-3.52 (m, 5H), 3.64-3.74 (m, 2H), 3.77-3.84 (m, 1H), 5.47 (d, J=5.86 Hz, 1H), and 5.74-5.84 (m, 1H).

Example 7

(1S,2R,3R,4aR,6aS,7R,8R,10aR,10bR,12aR)-3-(methoxy)-2-[2-(3-aminopropylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-25)

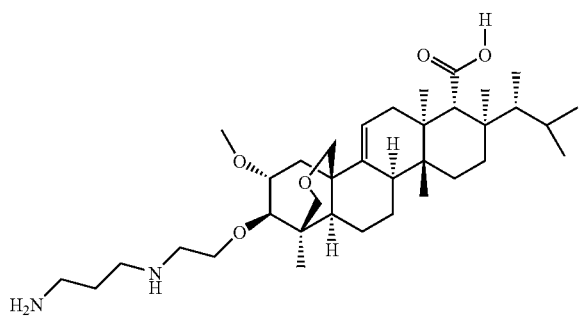

(a) To a solution of Intermediate 5 (80 mg; 0.11 mmol) in tetrahydrofuran (4 mL) and methanol (4 mL) was added 1,3-diaminopropane (2.3 mL). The reaction solution was heated to 70° C. and stirred for 2 hours. The reaction was judged complete by TLC analysis. The reaction contents were concentrated and purified by reverse phase HPLC (40:60 to 100:0 methanol:water) to yield purified material (77 mg).

(b) A portion of the material from step (a) (15 mg) was subjected to hydrogenolysis in a similar manner as described in Example 1(e) to afford the title compound as the acetate salt (12.9 mg). Calculated for $C_{36}H_{62}N_2O_5$: 602; observed: 603 (M+H)+. $^1$H NMR (400 MHz, methanol-$d_4$) δ ppm 0.75-0.82 (m, 9H), 0.87 (d, J=6.69 Hz, 3H), 0.92 (d, J=6.83 Hz, 3H), 1.19 (s, 3H), 1.23 (s, 3H), 1.24-1.35 (m, 3H), 1.38-1.69 (m, 5H), 1.69-1.89 (m, 3H), 1.96-2.03 (m, 4H), 2.06-2.14 (m, 1H), 2.16-2.26 (m, 1H), 2.48-2.58 (m, 1H), 2.86 (s, 1H), 2.92-3.16 (m, 5H), 3.34-3.36 (m, 1H), 3.41 (s, 3H), 3.43 (s, 2H), 3.62-3.77 (m, 2H), 3.82-3.89 (m, 1H), 3.91-4.09 (m, 2H), 4.17-4.28 (m, 1H), and 5.55 (d, J=5.71 Hz, 1 H).

Example 8

(1S,2R,3R,4aR,6aS,7R,8R,10aR,10bR,12aR)-3-(acetyloxy)-2-[2-(3-aminopropylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-14)

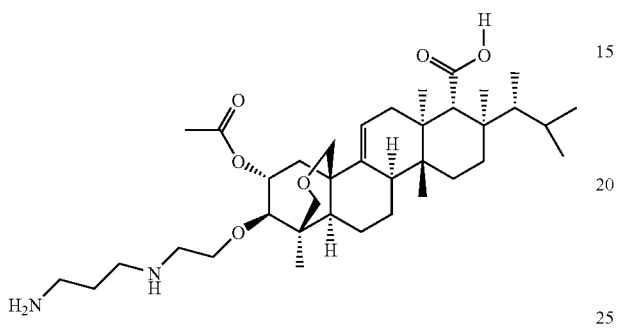

The material from Example 7 (a) (30 mg) was subjected to the conditions described in Example 1 (d) and Example 1 (e) to afford the title compound as a tosylate salt (27.4 mg). Calculated for $C_{37}H_{62}N_2O_6$: 630; observed: 631 $(M+H)^+$. $^1H$ NMR (400 MHz, methanol-$d_4$) δ ppm 0.71-0.82 (m, 9H), 0.87 (d, J=6.69 Hz, 3H), 0.91 (d, J=6.78 Hz, 3H), 1.17 (s, 3H), 1.22 (s, 3H), 1.24-1.45 (m, 5H), 1.46-1.70 (m, 4H), 1.71-1.90 (m, 3H), 1.92-1.96 (m, 1H), 2.06 (s, 3H), 2.09-2.16 (m, 2H), 2.17-2.25 (m, 1H), 2.38 (s, 6H), 2.39-2.45 (m, 1H), 2.86 (s, 1H), 2.90-2.96 (m, 1H), 3.02-3.27 (m, 5H), 3.39-3.50 (m, 2H), 3.63-3.71 (m, 1H), 3.72-3.78 (m, 1H), 3.78-3.97 (m, 2H), 3.98-4.12 (m, 1H), 5.47 (d, J=5.76 Hz, 1H), 5.72-5.86 (m, 1H), 7.25 (d, J=7.91 Hz, 4H), and 7.71 (d, J=8.20 Hz, 4H).

Example 9

(1S,2R,3R,4aR,6aS,7R,8R,10aR,10bR,12aR)-3-(acetyloxy)-2-[2-(3-guanidinopropylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-23)

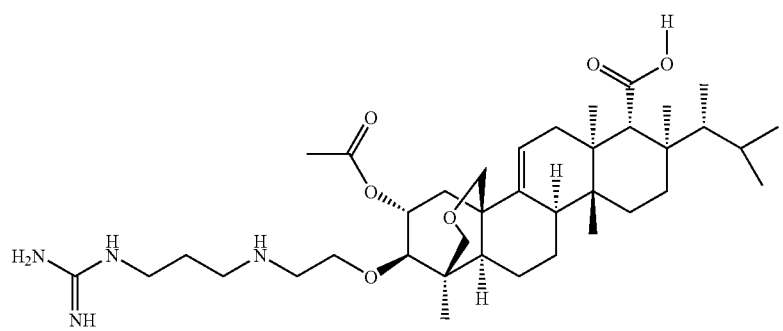

The material from Example 7 (a) (85 mg) was subjected to the conditions described in Example 1 (d). This product was converted to a guanidine derivative in a similar manner as described in Example 6 to give the title compound as the tosylate salt (3.0 mg). Calculated for $C_{38}H_{64}N_4O_6$: 672; observed: 673 $(M+H)^+$. $^1H$ NMR (400 MHz, methanol-$d_4$) δ ppm 0.77 (s, 3H), 0.78 (d, J=7.22 Hz, 3H), 0.83 (s, 3H), 0.87 (d, J=6.69 Hz, 3H), 0.91 (d, J=6.78 Hz, 3H), 1.18 (s, 3H), 1.22 (s, 3H), 1.24-1.33 (m, 3H), 1.32-1.46 (m, 3H), 1.45-1.69 (m, 3H), 1.70-1.91 (m, 5H), 2.05 (s, 3H), 2.06-2.09 (m, 3H), 2.10-2.14 (m, 1H), 2.15-2.26 (m, 1H), 2.33-2.44 (m, 5H), 2.51-2.57 (m, 1H), 2.85 (s, 1H), 2.92-3.00 (m, 1H), 3.09-3.19 (m, 2H), 3.34-3.41 (m, 2H), 3.42-3.51 (m, 4H), 3.57-3.82 (m, 3H), 3.82-3.93 (m, 1H), 5.45-5.51 (m, J=5.42 Hz, 1H), 5.73-5.87 (m, 1H), 7.24 (d, J=7.96 Hz, 2H), and 7.71 (d, J=8.20 Hz, 2H).

Example 10

(1S,2R,3R,4aR,6aS,7R,8R,10aR,10bR,12aR)-3-(acetyloxy)-2-{2-[N-(3-guanidinopropyl)-guanidino]-ethoxy}-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-22)

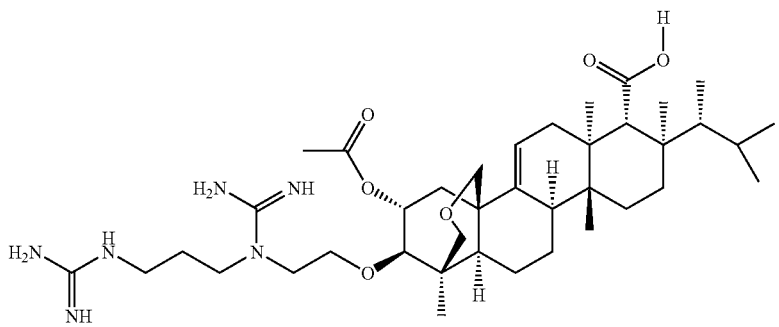

Isolated as a second product from Example 9, 7.5 mg of the title compound as the acetate salt. Calculated for $C_{39}H_{66}N_6O_6$: 714; observed: 715 (M+H)+. $^1$H NMR (400 MHz, methanol-$d_4$) δ ppm 0.77 (s, 3H), 0.78 (d, J=7.22 Hz, 3H), 0.81 (s, 3H), 0.86 (d, J=6.69 Hz, 3H), 0.91 (d, J=6.78 Hz, 3H), 1.18 (s, 3H), 1.23 (s, 3H), 1.25-1.35 (m, 3H), 1.35-1.45 (m, 2H), 1.46-1.70 (m, 4H), 1.71-1.88 (m, 3H), 1.93 (s, 9H), 1.94-1.97 (m, 2H), 1.97-2.02 (m, 1H), 2.05 (s, 3H), 2.07-2.15 (m, 1H), 2.18-2.26 (m, 1H), 2.33-2.42 (m, 1H), 2.83 (s, 1H), 3.16 (d, J=9.03 Hz, 1H), 3.21 (t, J=6.81 Hz, 2H), 3.40 (d, J=12.06 Hz, 1H), 3.42-3.51 (m, 4H), 3.53-3.60 (m, 2H), 3.62 (d, J=11.81 Hz, 1H), 3.74-3.83 (m, 1H), 3.84-3.93 (m, 1H), 5.48 (d, J=5.61 Hz, 1H), and 5.73-5.86 (m, 1H).

Example 11

(1S,2R,3R,4aR,6aS,7R,8R,10aR,10bR,12aR)-3-(methoxy)-2-[2-(N',N'-dimethylhydrazino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-28)

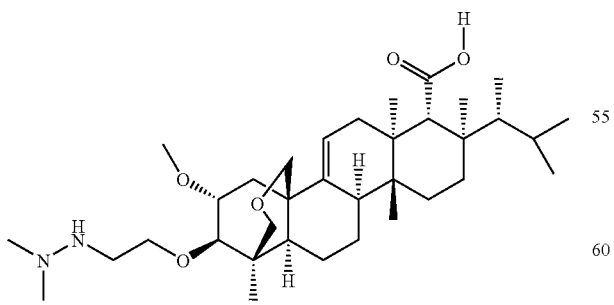

To a solution of Intermediate 5 (60 mg; 0.08 mmol) in methanol (3 mL) and ethyl acetate (3 mL) was added acetic acid (10 µL) and palladium hydroxide (50 mg). A hydrogen atmosphere was secured (balloon) and the reaction mixture was stirred at room temperature for 30 minutes. The reaction was judged complete by TLC analysis and the reaction mixture was filtered over a pad of Celite. The filtrate was concentrated to give a white solid (55 mg). A portion of this material (28 mg) was dissolved in tetrahydrofuran (2 mL) and methanol (3.5 mL) and N,N-dimethylhydrazine (170 uL) were added. The reaction solution was heated to 65° C. and stirred for 16 hours. The reaction was judged complete by TLC analysis and the reaction contents were concentrated. The residue was purified by reverse phase HPLC (40:60 to 100:0 methanol:water) to give the title compound (14 mg) which was isolated as the acetate salt. Calculated for $C_{35}H_{60}N_2O_5$: 588; observed: 589 (M+H)+. $^1$H NMR (400 MHz, methanol-$d_4$) δ ppm: 0.76-0.80 (m, 6H), 0.82 (s, 3H), 0.87 (d, J=6.69 Hz, 3H), 0.92 (d, J=6.83 Hz, 3H), 1.19 (s, 3H), 1.23 (s, 3H), 1.25-1.37 (m, 3H), 1.37-1.70 (m, 6H), 1.72-1.88 (m, 3H), 1.95-2.03 (m, 1H), 2.06-2.14 (m, 1H), 2.17-2.28 (m, 1H), 2.57 (dd, J=13.28, 6.74 Hz, 1H), 2.85 (s, 1H), 2.98 (d, J=8.64 Hz, 1H), 3.34-3.36 (m, 1H), 3.38 (s, 3H), 3.39-3.41 (m, 6H), 3.43 (s, 2H), 3.57-3.71 (m, 2H), 3.74-3.82 (m, 1H), 3.99-4.08 (m, 1H), 4.19-4.28 (m, 1H), 4.29-4.38 (m, 1H), and 5.55 (d, J=5.86 Hz, 1H).

Example 12

(1S,2R,3R,4aR,6aS,7R,8R,10aR,10bR,12aR)-3-(acetyloxy)-2-(2-methylaminoethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-30)

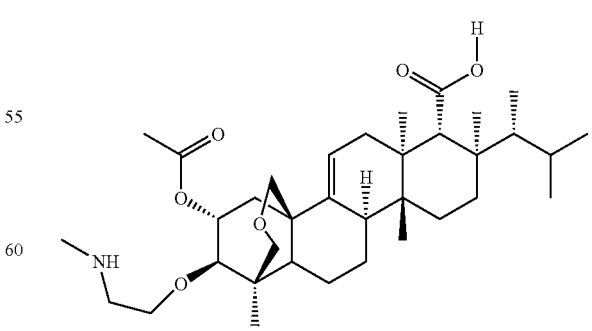

In a similar manner as described in Example 1 (c), (d) and (e), from aldehyde Example 1(b) (50 mg) and methylamine was obtained the title compound as a tosylate salt (8 mg).

Calculated for $C_{35}H_{57}NO_6$: 587; observed: 588 $(M+H)^+$. $^1H$ NMR (400 MHz, methanol-$d_4$) δ ppm 0.77 (s, 3H), 0.83 (s, 3H), 0.87 (d, J=6.69 Hz, 3H), 0.91 (d, J=6.74 Hz, 3H), 1.17 (s, 3H), 1.22 (s, 3H), 1.29 (s, 3H), 1.37-1.67 (m, 7H), 1.79 (s, 6H), 2.06 (s, 3H), 2.15-2.25 (m, 3H), 2.37 (s, 3H), 2.43-2.50 (m, 1H), 2.71 (s, 3H), 2.86 (s, 1H), 3.10-3.23 (m, 3H), 3.32-3.51 (m, 3H), 3.72-3.83 (m, 1H), 3.89-4.00 (m, 1H), 5.47 (s, 1H), 5.69-5.88 (m, 1H), 7.24 (d, J=8.00 Hz, 2H), and 7.71 (d, J=8.15 Hz, 2H).

Example 13

(1S,2R,3R,4aR,6aS,7R,8R,10aR,10bR,12aR)-3-(acetyloxy)-2-(2-isopropylaminoethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-31)

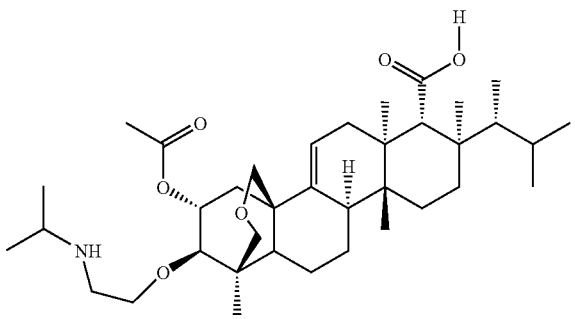

In a similar manner as described in Example 1 (c), (d) and (e), from aldehyde Example 1(b) (30 mg) and 2-propylamine was obtained the title compound as a tosylate salt (24 mg). Calculated for $C_{37}H_{61}NO_6$: 615; observed: 616 $(M+H)^+$. $^1H$ NMR (400 MHz, methanol-$d_4$) δ ppm 0.75-0.78 (m, 3H), 0.83 (s, 3H), 0.87 (d, J=6.69 Hz, 3H), 0.91 (d, J=6.78 Hz, 3H), 1.17 (s, 3H), 1.22 (s, 3H), 1.24-1.31 (m, 3H), 1.34 (d, J=6.49 Hz, 3H), 1.46-1.66 (m, 5H), 1.72-1.85 (m, 6H), 1.88-2.03 (m, 3H), 2.07 (s, 3H), 2.14-2.26 (m, 2H), 2.37 (s, 3H), 2.40-2.49 (m, 1H), 2.85 (s, 1H), 3.13-3.23 (m, 3H), 3.46 (s, 6H), 3.81-3.89 (m, 2H), 3.88-4.05 (m, 1H), 5.47 (s, 1H), 5.68-5.92 (m, 1H), 7.24 (d, J=7.91 Hz, 2H), and 7.71 (d, J=8.10 Hz, 2H).

Example 14

(1S,2R,3R,4aR,6aS,7R,8R,10aR,10bR,12aR)-3-(methoxy)-2-[2-(I-2-amino-3-hydroxypropylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-37)

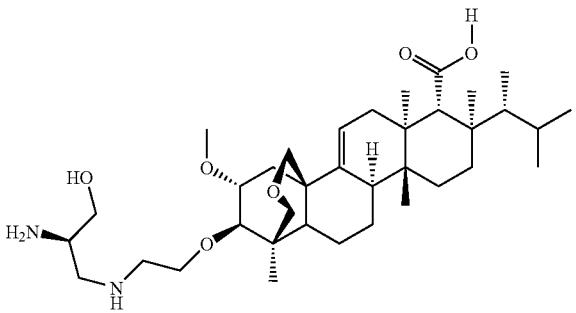

(a) To a solution of the aldehyde described in Example 1(b) (30 mg) dissolved in methanol (1.6 mL) was added (R)-(1-aminomethyl-2-benzyloxyethyl)-carbamic acid tert-butyl ester (16 mg) and sodium triacetoxyborohydride (20 mg). Acetic acid (2 mL) was added and the reaction was stirred for 16 hours at room temperature. Additional (R)-(1-aminomethyl-2-benzyloxyethyl)-carbamic acid tert-butyl ester (6 mg) and sodium triacetoxyborohydride (64 mg) were added and the reaction solution was stirred at 60° C. for 2 hours. The reaction was judged complete by TLC analysis and the reaction contents were concentrated. The residue was flash chromatographed (silica gel; 97:3 dichloromethane:methanol).

(b) The material from the above (21 mg) was dissolved in dichloromethane:trifluoroacetic acid (1:1, 2 ml) and the reaction solution was stirred at room temperature for 30 minutes to effect a deprotection of the Boc group. The reaction was judged complete by TLC analysis and the reaction contents were concentrated.

(c) The residue was dissolved in methanol (2 mL) and palladium hydroxide (100 mg) was added. A hydrogen atmosphere was secured (balloon) and the reaction was stirred at room temperature for 4 hours. The reaction was judged complete by TLC analysis and the reaction contents were filtered through a pad of Celite. The filtrate was concentrated to yield the title compound (12 mg) as the trifluoroacetate salt. Calculated for $C_{36}H_{62}N_2O_6$: 618; observed: 619 $(M+H)^+$. $^1H$ NMR (400 MHz, methanol-$d_4$) δ ppm 0.75-0.78 (m, 3H), 0.78-0.82 (m, 3H), 0.87 (d, J=6.64 Hz, 3H), 0.92 (d, J=6.74 Hz, 3H), 1.18 (s, 3H), 1.22 (s, 3H), 1.25-1.34 (m, J=7.37 Hz, 3H), 1.38-1.48 (m, 3H), 1.48-1.68 (m, 7H), 1.69-1.87 (m, 5H), 1.93-2.01 (m, 1H), 2.12-2.28 (m, 3H), 2.46-2.57 (m, 1H), 2.85 (s, 1H), 2.93-3.05 (m, 1H), 3.07-3.16 (m, 1H), 3.18-3.23 (m, 1H), 3.31 (s, 3H), 3.34-3.50 (m, 4H), 3.55-3.73 (m, 2H), 4.01-4.13 (m, 1H), 4.52-4.58 (m, 1H), and 5.48-5.63 (m, 1H).

Example 15

(1S,2R,3R,4aR,6aS,7R,8R,10aR,10bR,12aR)-3-(acetyloxy)-2-[2-(2-aminoethylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-20)

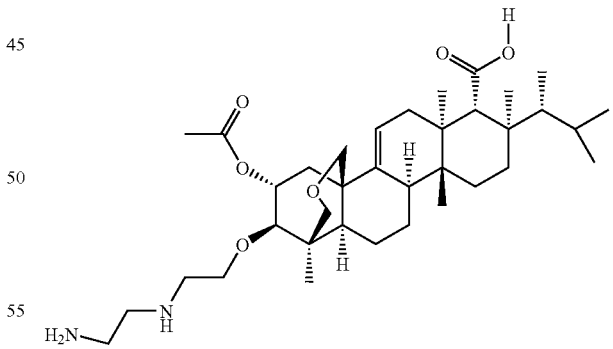

(a) Benzyl (1S,2R,3R,4aR,6aS,7R,8R,10aR,10bR,12aR)-3-(acetyloxy)-2-(allyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylate.

In a similar manner as described in Example 1 (a) and (d), from Intermediate 3 (2 g, 3.2 mmol) and allyl bromide (16.1 mmol) was obtained the desired allyl ether (1.1 g). $^1H$ NMR (400 MHz, chloroform-d) δ ppm 0.65 (d, 3H), 0.64 (s, 3H), 0.69 (s, 3H), 0.71 (d, J=6.88 Hz, 2H), 0.74 (d, J=6.64 Hz, 3H), 0.77-0.86 (m, 3H), 0.99-1.28 (m, 3H), 1.07 (s, 3H), 1.16 (s, 3H), 1.20 (s, 6H), 1.28-1.45 (m, 7H), 1.48 (s, 3H), 1.55-2.12 (m, 2H), 2.80 (s, 1H), 3.25-3.38 (m, 2H), 3.43 (s, 1H), 3.93-4.37 (m, 2H), 4.86-4.94 (m, 1H), 5.00-5.09 (m, 1H), 5.20-5.35 (m, 2H), 5.82-5.96 (m, 1H), and 7.26-7.35 (m, 5H).

(b) To a solution of the allyl ether from above (70 mg) in tetrahydrofuran (7 mL) and water (1 mL) was added osmium tetroxide (4% solution; 43 µL) and sodium periodate (84 mg). The reaction solution was stirred at room temperature for 3 hours and judged complete by TLC analysis. Ethyl acetate (20 mL) and water (20 mL) were added to the reaction solution. The aqueous phase was washed with ethyl acetate. The organic phases were combined and dried over magnesium sulfate and concentrated. The residue was purified by reverse phase HPLC to yield purified material (35 mg). To a portion of this material (15 mg) dissolved in methanol (0.5 mL) was added acetic acid (3 µL), 1,2-diaminoethane (12 mg) and sodium cyanoborohydride (20 mg). The reaction was stirred at room temperature for 3 hours and was judged complete by TLC analysis. Concentrated ammonium hydroxide (0.1 mL) and water (15 mL) were added to the reaction solution and the aqueous phase was thrice washed with ethyl acetate. The organic phase was dried over magnesium sulfate and concentrated. The residue was purified by reverse phase HPLC to give the desired compound, 5.6 mg.

(c) The benzyl ester from above (5.6 mg) was dissolved in ethyl acetate (3 mL) and methanol (3 mL). Acetic acid (1 drop) and palladium hydroxide (10 mg) were added and a hydrogen atmosphere was secured (balloon). The reaction stirred at room temperature for 1 hour and was judged complete by TLC analysis. The reaction contents were filtered over Celite and concentrated to yield the title compound as an acetate salt (4 mg). Calculated for $C_{36}H_{60}N_2O_6$: 616; observed: 617 $(M+H)^+$. $^1$H NMR (400 MHz, methanol-$d_4$) δ ppm 0.77 (s, 3H), 0.78 (d, J=7.37 Hz, 3H), 0.82 (s, 3H), 0.87 (d, J=6.69 Hz, 3H), 0.91 (d, J=6.78 Hz, 3H), 1.18 (s, 3H), 1.22 (s, 3H), 1.27-1.50 (m, 4H), 1.51-1.71 (m, 6H), 1.72-1.89 (m, J=6.54 Hz, 3H), 2.01 (s, 3H), 2.03-2.16 (m, 3H), 2.15-2.27 (m, 1H), 2.27-2.43 (m, 1H), 2.78-2.99 (m, 3H), 3.00 (s, 1H), 3.01-3.16 (m, 2H), 3.38-3.58 (m, 3H), 3.59-3.80 (m, 3H), 5.48 (s, 1H), and 5.72-5.97 (m, 1H).

Example 16

(1S,2R,3R,4aR,6aS,7R,8R,10aR,10bR,12aR)-3-(acetyloxy)-2-{2-[4-(3-aminopropyl)-piperazin-1-yl]-ethoxy}-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-24)

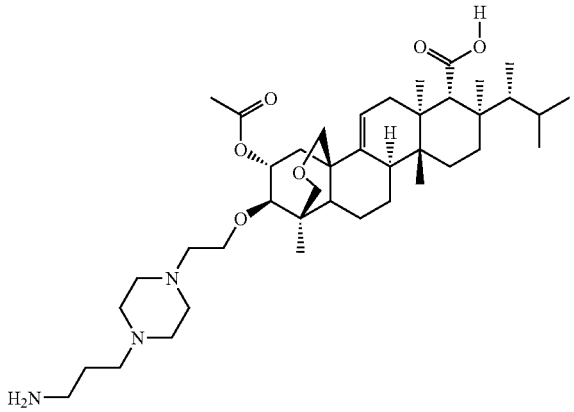

In a similar manner as described in Example 15, from the allyl ether (80 mg) and 3-piperazin-1-yl proprionitrile (20.2 mg) was obtained the title compound (1.5 mg). Calculated for $C_{41}H_{69}N_3O_6$: 699; observed: 700 $(M+H)^+$. $^1$H NMR (400 MHz, chloroform-d) δ ppm 0.67 (s, 3H), 0.71 (s, 3H), 0.78 (d, J=6.59 Hz, 3H), 0.84 (d, J=6.78 Hz, 3H), 1.08 (s, 3H), 1.13 (s, 3H), 1.15-1.25 (m, 7H), 1.28-1.35 (m, 4H), 1.43-1.59 (m, 5H), 1.55-1.78 (m, 6H), 1.82-1.94 (m, J=17.67 Hz, 4H), 1.99 (s, 3H), 2.06-2.16 (m, 2H), 2.31-2.50 (m, 1H), 2.81 (s, 1H), 3.02 (d, J=8.98 Hz, 2H), 3.20-3.52 (m, 8H), 3.50-3.72 (m, 3H), 5.38 (s, 1H), and 5.63-5.86 (m, 1H).

Example 17

(1S,2R,3R,4aR,6aS,7R,8R,10aR,10bR,12aR)-3-(acetyloxy)-2-[2-(I-2-amino-3-hydroxypropylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-26)

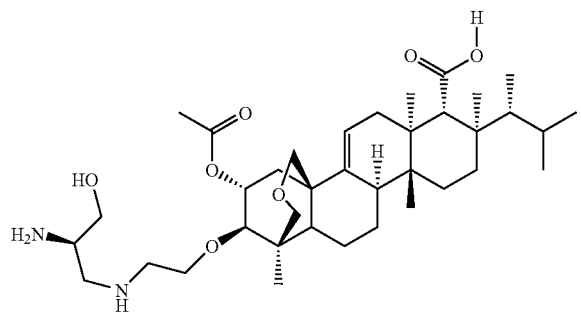

In a similar manner as described in Example 15 (a) and (b), Example 14 (b) and Example 15 (c), from allyl ether (430 mg; 0.65 mmol) and 1-(1-aminomethyl-2-benzyloxyethyl)-carbamic acid tert-butyl ester (21 mg) was obtained the title compound (10 mg) as a trifluoroacetate salt. Calculated for $C_{37}H_{62}N_2O_7$: 646; observed: 647 $(M+H)^+$. $^1$H NMR (400 MHz, methanol-$d_4$) δ ppm 0.73-0.78 (m, 3H), 0.84 (s, 3H), 0.87 (d, J=6.69 Hz, 3H), 0.91 (d, J=6.78 Hz, 3H), 1.17 (s, 3H), 1.22 (s, 3H), 1.24-1.31 (m, 4H), 1.31-1.46 (m, 4H), 1.48-1.68 (m, 5H), 1.71-1.98 (m, 7H), 2.09 (s, 3H), 2.11-2.27 (m, 3H), 2.31-2.54 (m, 1H), 2.86 (s, 1H), 3.10-3.25 (m, 2H), 3.35-3.53 (m, 3H), 3.68-3.92 (m, 3H), 3.95-4.06 (m, 1H), 5.48 (s, 1H), and 5.71-5.91 (m, 1H).

Example 18

(1S,2R,3R,4aR,6aS,7R,8R,10aR,10bR,12aR)-3-(acetyloxy)-2-{2-[N—(I-2-amino-3-hydroxypropyl)-guanidino]-ethoxy}-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-27)

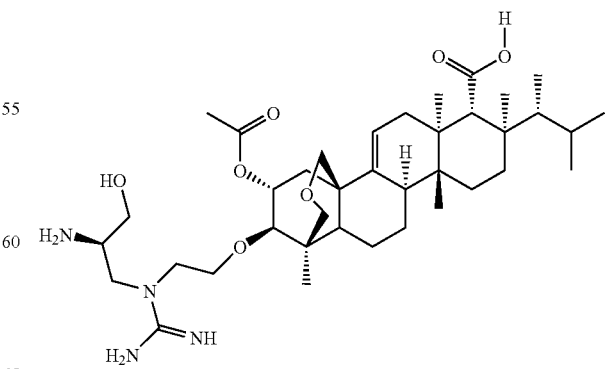

The benzyl ester of the compound described in Example 17 (53 mg) was subjected a guanidinylation procedure as described in Example 6 followed by deprotection of the Boc group as described in Example 14 (b) and de-benzylation as described in Example 15 (c) to give the title compound as the trifluoroacetate salt (16 mg). Calculated for $C_{38}H_{64}N_4O_7$: 688; observed: 689 (M+H)+. $^1$H NMR (400 MHz, methanol-$d_4$) δ ppm 0.75-0.79 (m, 3H), 0.78-0.82 (m, 3H), 0.87 (d, J=6.69 Hz, 3H), 0.91 (d, J=6.69 Hz, 3H), 1.17 (s, 3H), 1.22 (s, 3H), 1.36-1.58 (m, 8H), 1.46-1.75 (m, 7H), 1.73-2.00 (m, 6H), 2.06 (s, 3H), 2.15-2.24 (m, 1H), 2.30-2.46 (m, 1H), 2.70-2.92 (m, 1H), 3.09-3.19 (m, 1H), 3.36-3.51 (m, 5H), 3.54-3.97 (m, 4H), 5.49 (s, 1H), and 5.70-5.97 (m, 1H).

Example 19

(1S,2R,3R,4aR,6aS,7R,8R,10aR,10bR,12aR)-3-(acetyloxy)-2-[2-((S)-5-amino-2-iminotetrahydropyrimidin-1-yl)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-28)

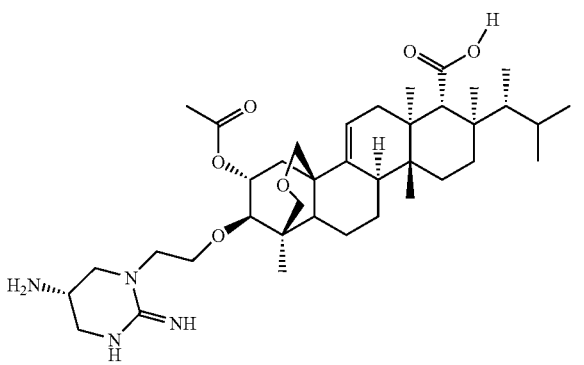

In a similar manner as described in Example 15 (a) and (b), from allyl ether (439 mg, 0.66 mmol) and I-(1-aminomethyl-2-benzyloxyethyl)-carbamic acid tert-butyl ester was obtained a protected amino ether. This material (80 mg) was dissolved in tetrahydrofuran (9.8 mL) and 1,3-bis(tert-butoxycarbonyl)-2-methyl-2-thiopseudourea (67 mg) was added. Mercuric chloride (65 mg) and triethylamine (120 μL) were added and the reaction was stirred at room temperature for 16 hours. The reaction was judged complete by TLC analysis and the reaction contents were concentrated. The residue was suspended in water and thrice washed with dichloromethane. The organic phase was dried over magnesium sulfate and concentrated. The residue was flash chromatographed (silica gel; 80:20 heptane:ethyl acetate). Purified material (43 mg) was dissolved in methanol (2 mL) and palladium hydroxide (100 mg) was added. A hydrogen atmosphere was secured (balloon) and the reaction stirred at room temperature for 1.5 hours. The reaction was judged complete by TLC analysis and the reaction contents were filtered over a pad of Celite. The filtrate was concentrated to yield 26 mg material. A portion (13 mg) of this material was dissolved in tetrahydrofuran (500 μL). Triphenylphosphine (10 mg) and diisopropyl azodicarboxylate (8 μL) were added and the reaction was stirred at room temperature for 16 hours. The reaction was judged complete by TLC analysis and the reaction contents were concentrated. The residue was purified by reverse phase HPLC. Purified material (13 mg) was dissolved in trifluoroacetic acid:dichloromethane (1:1; 2 mL) and the reaction solution was stirred for 1 hour at room temperature. The reaction was judged complete by TLC analysis and the reaction contents were concentrated to yield the title compound as the trifluoroacetate salt (1.5 mg). Calculated for $C_{38}H_{62}N_4O_6$: 670; observed: 671 (M+H)+. $^1$H NMR (400 MHz, methanol-$d_4$) δ ppm 0.76-0.78 (m, 3H), 0.83 (s, 3H), 0.87 (d, J=6.69 Hz, 3H), 0.91 (d, J=5.86 Hz, 3H), 1.18 (s, 3H), 1.21 (s, 3H), 1.26-1.49 (m, 7H), 1.49-1.72 (m, 6H), 1.72-1.89 (m, 7H), 2.06 (s, 3H), 2.10-2.26 (m, 1H), 2.26-2.39 (m, 1H), 2.84-2.89 (m, 1H), 3.12-3.24 (m, 1H), 3.34-3.53 (m, 3H), 3.58-3.68 (m, 3H), 3.69-3.95 (m, 3H), 4.21 (d, 1H), 5.38-5.55 (m, 1H), and 5.76-5.94 (m, 1H).

Example 20

(1S,2R,3R,4aR,6aS,7R,8R,10aR,10bR,12aR)-3-(methoxy)-2-[2-((S)-2,6-diaminohexylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-23)

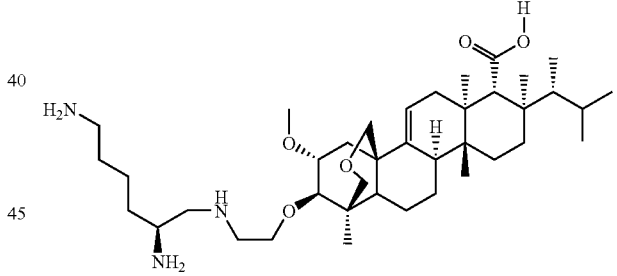

In a similar manner as described in Example 1 (c) and (e), from the aldehyde described in Example 1(b) (100 mg) and (S)-1-aminomethyl-5-benzyloxycarbonylamino-pentyl)-carbamic acid benzyl ester (75 mg), was obtained the title compound (16 mg). Calculated for $C_{39}H_{69}N_3O_5$: 659; observed: 660 (M+H)+. $^1$H NMR (400 MHz, methanol-$d_4$) δ ppm 0.77 (s, 3H), 0.80 (s, 3H), 0.87 (d, J=6.69 Hz, 3H), 0.92 (d, J=6.78 Hz, 3H), 1.19 (s, 3H), 1.23 (s, 3H), 1.22-1.34 (m, 4H), 1.38-1.60 (m, 7H), 1.58-1.84 (m, 7H), 1.93 (s, 3H), 2.01-2.16 (m, 1H), 2.17-2.26 (m, 1H), 2.46-2.57 (m, 1H), 2.62-2.84 (m, 3H), 2.85 (s, 1H), 2.88-3.00 (m, 4H), 2.98-3.13 (m, 1H), 3.32-3.39 (m, 1H), 3.41 (s, 3H), 3.51-3.71 (m, 2H), 3.72-3.82 (m, 1H), 3.86-3.99 (m, 1H), 4.01-4.10 (m, 1H), 4.05-4.26 (m, 2H), and 5.55 (s, 1H).

Example 21

(1S,2R,3R,4aR,6aS,7R,8R,10aR,10bR,12aR)-3-(acetyloxy)-2-[2-((S)-2,6-diaminohexylamino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-12)

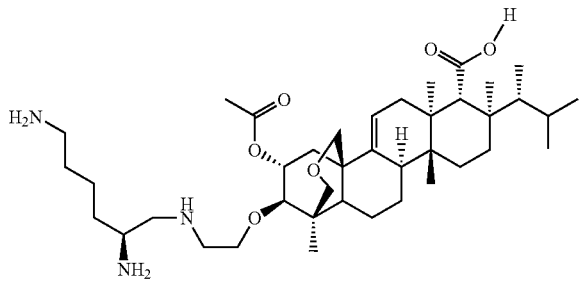

In a similar manner as described in Example 1(c), (d) and (e), from aldehyde (100 mg) and (S)-1-aminomethyl-5-benzyloxycarbonylamino-pentyl)-carbamic acid benzyl ester (75 mg) was obtained the title compound (36 mg). Calculated for $C_{40}H_{69}N_3O_6$: 687; observed: 688 (M+H)$^+$. $^1$H NMR (400 MHz, methanol-$d_4$) δ ppm 0.77 (s, 3H), 0.83 (s, 3H), 0.87 (d, J=6.69 Hz, 3H), 0.91 (d, J=6.83 Hz, 3H), 1.18 (s, 3H), 1.22 (s, 3H), 1.21-1.42 (m, 6H), 1.48-1.75 (m, 7H), 1.70-1.85 (m, 4H), 1.98 (s, 3H), 2.02-2.14 (m, 3H), 2.15-2.24 (m, 1H), 2.31-2.44 (m, 1H), 2.66-2.78 (m, 1H), 2.85 (s, 1H), 2.86-2.91 (m, 2H), 2.93-3.08 (m, 3H), 3.14 (d, J=8.83 Hz, 1H), 3.18-3.30 (m, 1H), 3.24-3.41 (m, 3H), 3.40-3.54 (m, J=4.73 Hz, 3H), 3.62-3.75 (m, 2H), 3.78-3.94 (m, 1H), 5.48 (s, 1H), and 5.74-5.89 (m, 1H).

Example 22

(1S,2R,3R,4aR,6aS,7R,8R,10aR,10bR,12aR)-3-(acetyloxy)-2-[2-(3-aminopyrrolidin-1-yl)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-19)

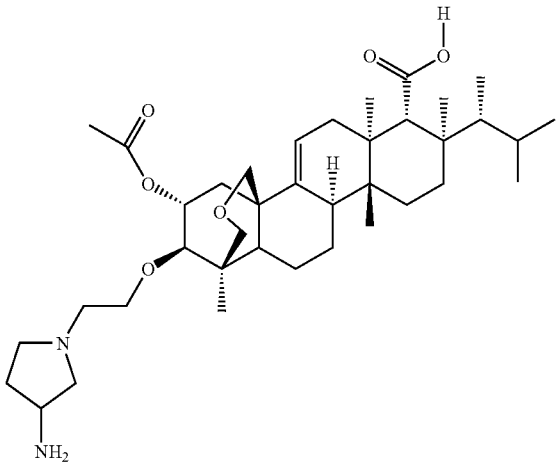

In a similar manner as described in Example 1(c), reductive amination of the aldehyde (38 mg, 0.06 mmol) and pyrrolidin-3-yl carbamic acid tert-butyl ester (14 mg) gave the desired amino compound (23 mg). This was subjected to a deprotection reaction as described in Example 14 (b), acetate exchange as described in Example 1 (d) and final deprotection as described in Example 1 (e) to give the title compound as a trifluoroacetate salt (1.5 mg). Calculated for $C_{38}H_{62}N_2O_6$: 642; observed: 643 (M+H)$^+$. $^1$H NMR (400 MHz, methanol-$d_4$) δ ppm 0.68 (s, 3H), 0.70-0.73 (m, 3H), 0.78 (d, J=6.74 Hz, 3H), 0.83 (d, J=6.78 Hz, 3H), 1.06-1.10 (m, 3H), 1.13 (s, 3H), 1.14-1.26 (m, 4H), 1.29-1.43 (m, 3H), 1.39-1.55 (m, 3H), 1.59-1.81 (m, 7H), 1.77-1.97 (m, 4H), 2.03 (s, 3H), 2.09-2.17 (m, 3H), 2.24-2.39 (m, 1H), 2.77 (s, 1H), 3.02-3.17 (m, 1H), 3.22-3.42 (m, 5H), 3.48-3.72 (m, 2H), 3.78 (s, 1H), 3.98 (s, 1H), 5.38 (s, 1H), and 5.65-5.85 (m, 1H).

Example 23

(1S,2R,3R,4aR,6aS,7R,8R,10aR,10bR,12aR)-3-(acetyloxy)-2-[2-(N'-tert-butyl-N''-cyano-guanidino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-34)

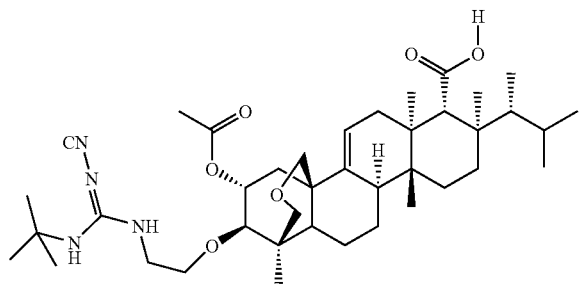

The compound described in Example 1 (d) (50 mg) was dissolved in isopropanol (2.5 mL) and dimethylformamide (0.5 mL), diphenyl cyanocarbonimidate (20 mg) and triethylamine (42 µL) were added and the reaction for 3 hours at room temperature. The reaction was judged complete by TLC analysis and the reaction contents were concentrated. The residue was flash chromatographed (silica gel; 80:20 heptane:ethyl acetate). Purified material (60 mg) was dissolved in isopropanol (4 mL) and dimethylformamide (0.5 mL). Tert-butyl amine (0.3 mL) was added and the reaction was refluxed for 3 hours. The reaction was judged nearly complete by TLC analysis and the reaction was cooled to room temperature. The reaction contents were concentrated and the residue was flash chromatographed (silica gel; 50:50 to 0:100 heptane:ethyl acetate). Purified material (41 mg) was dissolved in methanol (3 mL) and dichloromethane (0.5 mL). Palladium hydroxide (60 mg) was added and a hydrogen atmosphere was secured (balloon). The reaction mixture was stirred at room temperature for 30 minutes and judged complete by TLC analysis. The reaction mixture was filtered over a pad of Celite and the filtrate was concentrated. The residue was flash chromatographed (silica gel; 90:10 dichloromethane:methanol then 63:34:3 dichloromethane:methanol:ammonium hydroxide) to yield the title compound (11 mg).

Calculated for $C_{40}H_{64}N_4O_6$: 696; observed: 697 (M+H)$^+$. $^1$H NMR (400 MHz, chloroform-d) δ ppm 0.72 (s, 3H), 0.79 (s, 3H), 0.83 (d, J=6.69 Hz, 3H), 0.89 (d, J=6.78 Hz, 3H), 1.13 (s, 3H), 1.16 (s, 3H), 1.19-1.27 (m, 3H), 1.36 (s, 9H), 1.43-1.65 (m, 5H), 1.66-1.82 (m, 5H), 1.86 (s, 3H), 1.92-2.19 (m, 3H), 2.44-2.61 (m, 1H), 2.80 (s, 1H), 3.06 (d, J=9.37 Hz, 1H), 3.26-3.39 (m, 5H), 3.43-3.68 (m, 4H), 3.77-3.92 (m, 1H), 5.37 (s, 1H), and 5.59-5.74 (m, 1H).

Example 24

(1S,2R,3R,4aR,6aS,7R,8R,10aR,10bR,12aR)-3-(acetyloxy)-2-[2-(N'-tert-butylguanidino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-35)

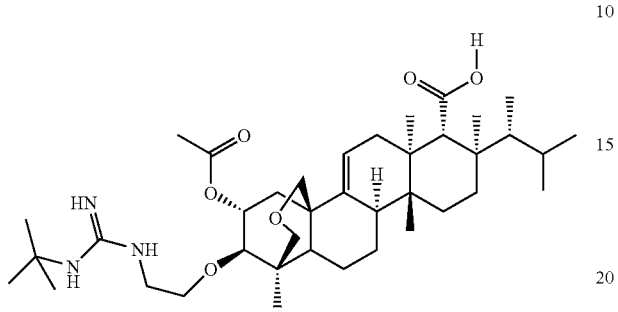

Isolated as a by-product from Example 23 (22 mg). Calculated for $C_{39}H_{65}N_3O_6$: 671; observed: 611 (M−HOAc)$^+$. $^1$H NMR (400 MHz, methanol-$d_4$) δ ppm 0.77 (s, 3H), 0.82 (s, 3H), 0.87 (d, J=6.64 Hz, 3H), 0.91 (d, J=6.78 Hz, 3H), 1.18 (s, 3H), 1.22 (s, 3H), 1.25-1.37 (m, 5H), 1.42 (s, 9H), 1.63 (s, 5H), 1.81 (s, 3H), 2.03 (s, 3H), 2.06-2.14 (m, 2H), 2.15-2.29 (m, 1H), 2.32-2.53 (m, 1H), 2.85 (s, 1H), 3.18 (d, J=8.83 Hz, 1H), 3.35-3.56 (m, 7H), 3.67 (d, J=11.86 Hz, 1H), 3.78 (s, 1H), 5.47 (s, 1H), 5.66-5.92 (m, 1H), and 7.92 (s, 1H).

Example 25

(1S,2R,3R,4aR,6aS,7R,8R,10aR,10bR,12aR)-3-(acetyloxy)-2-[2-(N'-isopropyl-N''-cyano-guanidino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-36)

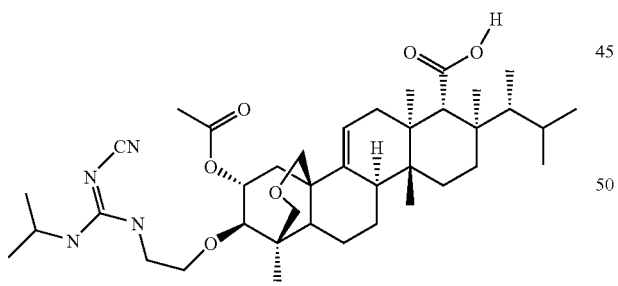

Prepared in a similar fashion to Example 23 using isopropyl amine in place of tert-butyl amine to yield the title compound (7 mg). Calculated for $C_{39}H_{62}N_4O_6$: 682; observed: 721 (M+K)$^+$. $^1$H NMR (400 MHz, methanol-$d_4$) δ ppm 0.75-0.78 (m, 3H), 0.81 (s, 3H), 0.87 (d, J=6.69 Hz, 3H), 0.91 (d, J=6.78 Hz, 3H), 1.17 (s, 3H), 1.22 (s, 3H), 1.23 (s, 3H), 1.25 (s, 3H), 1.27-1.44 (m, 3H), 1.52-1.68 (m, 4H), 1.70-1.88 (m, 4H), 1.94 (s, 3H), 2.04 (s, 3H), 2.07-2.13 (m, 1H), 2.15-2.25 (m, 1H), 2.28-2.48 (m, 1H), 2.85 (s, 1H), 3.12 (d, J=8.83 Hz, 1H), 3.38-3.52 (m, 4H), 3.62-3.76 (m, J=11.62 Hz, 3H), 3.73-3.83 (m, 2H), 5.47 (s, 1H), 5.69-5.87 (m, 1H), 7.28-7.48 (m, 1H), and 7.93 (s, 1H).

Example 26

(1S,2R,3R,4aR,6aS,7R,8R,10aR,10bR,12aR)-3-(acetyloxy)-2-[2-(N'-isopropylguanidino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-37)

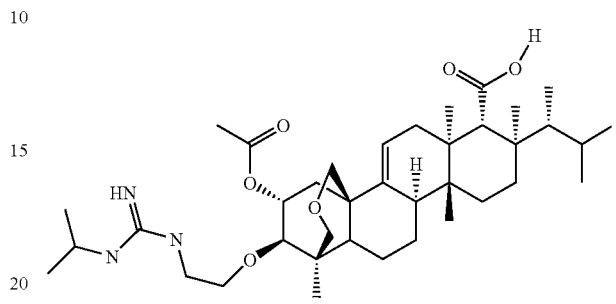

Isolated as a by-product from Example 25 (27 mg). Calculated for $C_{38}H_{63}N_3O_6$: 657; observed: 696 (M+K)$^+$. $^1$H NMR (400 MHz, methanol-$d_4$) δ ppm 0.75-0.77 (m, 3H), 0.80 (s, 3H), 0.87 (d, J=6.69 Hz, 3H), 0.91 (d, J=6.78 Hz, 3H), 1.17 (s, 3H), 1.22 (s, 3H), 1.23 (s, 3H), 1.25 (s, 3H), 1.31-1.49 (m, 4H), 1.48-1.68 (m, 6H), 1.72-1.90 (m, 5H), 2.03 (s, 3H), 2.07-2.16 (m, 1H), 2.17-2.27 (m, 1H), 2.33-2.46 (m, 1H), 2.85 (s, 1H), 3.12 (d, J=8.30 Hz, 1H), 3.38-3.52 (m, 5H), 3.61-3.87 (m, J=41.34 Hz, 4H), 5.34-5.52 (m, 1H), 5.64-5.86 (m, 1H), and 7.93 (s, 1H).

Example 27

(1S,2R,3R,4aR,6aS,7R,8R,10aR,10bR,12aR)-3-(acetyloxy)-2-[2-(N'-benzyl-N''-cyano-guanidino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-38)

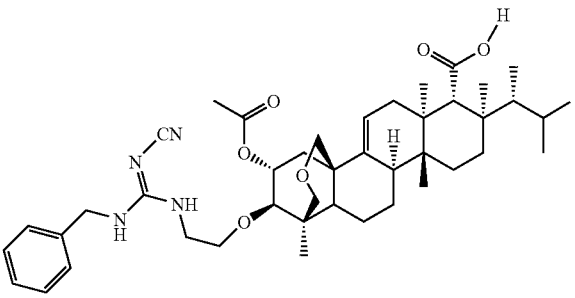

Prepared in a similar manner as described in Example 23 using benzylamine in place of tert-butyl amine to yield the title compound (1.5 mg). Calculated for $C_{43}H_{62}N_4O_6$: 730; observed: 660 (M−HOAc)$^+$. $^1$H NMR (400 MHz, chloroform-d) δ ppm 0.65 (s, 3H), 0.71 (s, 3H), 0.77 (d, J=6.59 Hz, 3H), 0.84 (d, J=6.74 Hz, 3H), 1.08 (s, 3H), 1.10 (s, 3H), 1.14-1.35 (m, 3H), 1.41-1.57 (m, 5H), 1.60-1.79 (m, 4H), 1.89 (s, 3H), 1.92-2.01 (m, 3H), 2.01-2.20 (m, 1H), 2.26-2.45 (m, 1H), 2.77 (s, 1H), 2.95 (d, J=9.18 Hz, 1H), 3.15-3.23 (m, 1H), 3.29 (s, 4H), 3.39-3.56 (m, 3H), 3.65-3.79 (m, 1H), 4.09-4.24 (m, 1H), 4.37-4.55 (m, 1H), 5.29-5.43 (m, 1H), 5.66-5.87 (m, 1H), 6.27 (s, 1H), and 7.27 (s, 5H).

Example 28

(1S,2R,3R,4aR,6aS,7R,8R,10aR,10bR,12aR)-3-(acetyloxy)-2-[2-(N'-methylguanidino)-ethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-43)

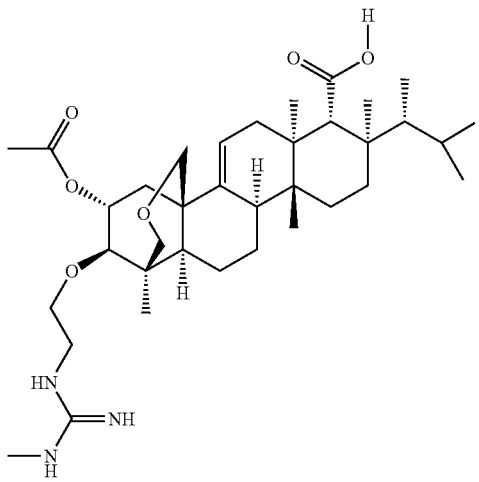

To a solution of the compound described in Example 1 (50 mg; 0.08 mmol) in dimethylformamide (2 mL) was added N,N'-bis(benzyloxycarbonyl)-1,2-dimethyl-isothiourea (122 mg) and triethylamine (110 μL). The reaction solution was stirred at room temperature for 16 hours and judged complete by TLC analysis. The reaction solution was purified by reverse phase HPLC (60:40 to 100:0 methanol:water). Purified material (23 mg) was dissolved in methanol (2.5 mL) and acetic acid (20 μL). Palladium hydroxide (34 mg) was added and a hydrogen atmosphere was secured (balloon). The reaction solution was stirred at room temperature for 1 hour and judged complete by TLC analysis. The reaction contents were filtered over a pad of Celite and the filtrate was concentrated. The residue was flash chromatographed ($C_{18}$ resin; 60:40 to 100:0 methanol (0.05% acetic acid/water) to yield the title compound as an acetate salt (16.4 mg). Calculated for $C_{36}H_{59}N_3O_6$: 629; observed: 630 (M+H)$^+$. $^1$H NMR (400 MHz, methanol-$d_4$) δ ppm 0.77 (s, 3H), 0.78 (d, J=7.22 Hz, 3H), 0.81 (s, 3H), 0.86 (d, J=6.69 Hz, 3H), 0.91 (d, J=6.78 Hz, 3H), 1.18 (s, 3H), 1.23 (s, 3H), 1.24-1.45 (m, 5H), 1.45-1.70 (m, 5H), 1.71-1.89 (m, 3H), 1.92 (s, 3H), 1.93-2.01 (m, 1H), 2.04 (s, 3H), 2.06-2.13 (m, 1H), 2.17-2.27 (m, 1H), 2.38 (dd, J=13.25, 7.05 Hz, 1H), 2.81-2.86 (m, 4H), 3.16 (d, J=8.98 Hz, 1H), 3.33-3.51 (m, 5H), 3.66 (d, J=11.76 Hz, 1H), 3.69-3.81 (m, 2H), 5.47 (d, J=5.81 Hz, 1H), and 5.74-5.84 (m, 1H).

Example 29

(1S,2R,3R,4aR,6aS,7R,8R,10aR,10bR,12aR)-3-(methoxy)-2-[2-((S)-1,5-diaminopentyl)-thiazol-4-ylmethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-30)

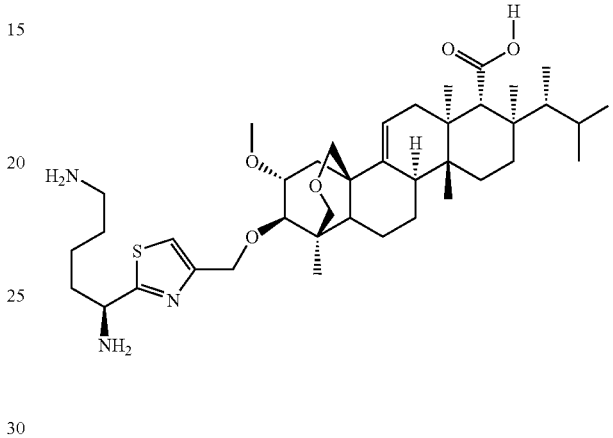

Intermediate 7 (73 mg) was dissolved in acetone (4 mL) and ((S)-5-tert-butoxycarbonyl amino-1-thiocarbamoyl-pentyl)-carbamic acid tert-butyl ester (36 mg) was added. The reaction solution was refluxed for 21 hours and judged complete by TLC analysis. The reaction contents were concentrated and the residue was flash chromatographed (silica gel; 90:10 heptane:ethyl acetate) to yield a white solid (45 mg). A portion of this material (10 mg) was dissolved in trifluoroacetic acid (1 mL) and dichloromethane (1 mL). The reaction was stirred for 30 minutes at room temperature and judged complete by TLC analysis. To this solution was added palladium hydroxide and a hydrogen atmosphere was secured (balloon). The reaction mixture was stirred at room temperature for 30 minutes and judged complete by TLC analysis. The reaction contents were filtered through a pad of Celite and the filtrate was concentrated to yield the title compound as a trifluoroacetate salt (15 mg). Calculated for $C_{40}H_{65}N_3O_5S$: 699; observed: 700 (M+H)$^+$. $^1$H NMR (400 MHz, methanol-$d_4$) δ ppm 0.77 (s, 3H), 0.79 (s, 3H), 0.87 (d, J=6.69 Hz, 3H), 0.92 (d, J=6.78 Hz, 3H), 1.19 (s, 2H), 1.20-1.26 (m, 3H), 1.25-1.32 (m, 4H), 1.33-1.64 (m, 6H), 1.61-1.85 (m, 7H), 1.92-2.02 (m, 1H), 2.02-2.15 (m, 2H), 2.21 (s, 1H), 2.42-2.65 (m, 1H), 2.87 (s, 1H), 2.88-2.96 (m, 1H), 3.02-3.20 (m, J=12.15 Hz, 2H), 3.31 (s, 3H), 3.33-3.51 (m, 6H), 3.60-3.77 (m, 2H), 4.10-4.35 (m, 1H), 4.63-4.80 (m, 2H), 5.03 (d, J=12.50 Hz, 1H), 5.55 (s, 1H), and 7.55 (s, 1H).

Example 30

(1S,2R,3R,4aR,6aS,7R,8R,10aR,10bR,12aR)-3-(methoxy)-2-(2-aminomethyl-thiazol-4-ylmethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-31)

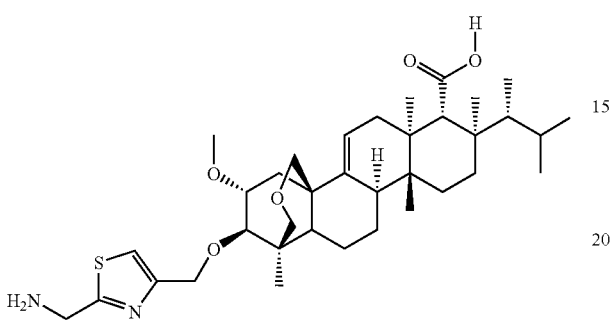

In a similar manner as described for Example 29, using thiocarbamoylmethylcarbamic acid tert-butyl ester was obtained the title compound as a trifluoroacetate salt (16 mg). Calculated for $C_{36}H_{56}N_2O_5S$: 628; observed: 629. $^1$H NMR (400 MHz, methanol-$d_4$) δ ppm 0.76 (s, 3H), 0.77 (s, 3H), 0.87 (d, J=6.69 Hz, 3H), 0.92 (d, J=6.78 Hz, 3H), 1.19 (s, 3H), 1.22 (s, 3H), 1.24-1.34 (m, 4H), 1.37-1.47 (m, 1H), 1.47-1.65 (m, 4H), 1.69-1.87 (m, 4H), 1.92-2.05 (m, 2H), 2.05-2.14 (m, 2H), 2.14-2.25 (m, 1H), 2.47-2.59 (m, 1H), 2.86 (s, 1H), 3.07 (d, J=8.44 Hz, 1H), 3.40 (s, 3H), 3.40-3.52 (m, 3H), 3.69 (d, J=11.71 Hz, 1H), 4.27 (dd, 1H), 4.47 (s, 2H), 4.73 (d, J=12.50 Hz, 1H), 5.02 (d, J=12.49 Hz, 1H), 5.54 (s, 1H), and 7.53 (s, 1H).

Example 31

(1S,2R,3R,4aR,6aS,7R,8R,10aR,10bR,12aR)-3-(methoxy)-2-[2-((S)-1-aminoethyl)-thiazol-4-yl-methoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-33)

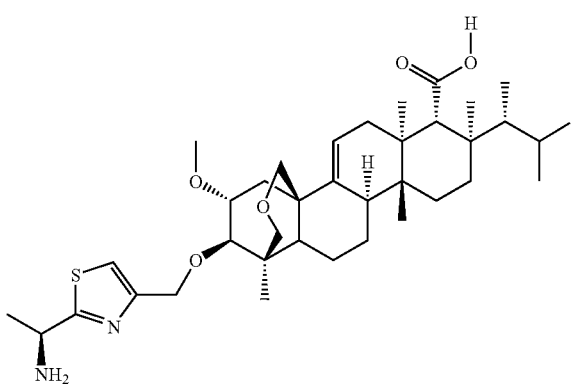

In a similar manner as described for Example 29, using (S)-1-thiocarbamoyl-ethyl)-carbamic acid benzyl ester was obtained the title compound as a trifluoroacetate salt (22 mg). Calculated for $C_{37}H_{58}N_2O_5S$: 642; observed: 643 (M+H)$^+$. $^1$H NMR (400 MHz, methanol-$d_4$) δ ppm 0.77 (s, 3H), 0.79 (s, 3H), 0.87 (d, J=6.69 Hz, 3H), 0.91 (d, J=6.83 Hz, 3H), 1.18 (s, 3H), 1.22 (s, 3H), 1.24-1.34 (m, 5H), 1.41 (s, 3H), 1.46-1.67 (m, 4H), 1.72 (d, J=6.88 Hz, 3H), 1.74-1.89 (m, J=13.67 Hz, 3H), 1.92-2.05 (m, 1H), 2.05-2.14 (m, 1H), 2.14-2.28 (m, 1H), 2.46-2.57 (m, 1H), 2.86 (s, 1H), 3.08 (dd, J=8.59 Hz, 1H), 3.40 (s, 3H), 3.69 (d, J=11.67 Hz, 1H), 3.98 (s, 2H), 4.05-4.14 (m, 1H), 4.17-4.32 (m, 1H), 4.73 (d, J=12.45 Hz, 1H), 4.84 (d, 1H), 5.02 (d, J=12.54 Hz, 1H), 5.55 (s, 1H), and 7.52 (s, 1H).

Example 32

(1S,2R,3R,4aR,6aS,7R,8R,10aR,10bR,12aR)-3-(methoxy)-2-(2-guanidinomethyl-thiazol-4-yl-methoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-34)

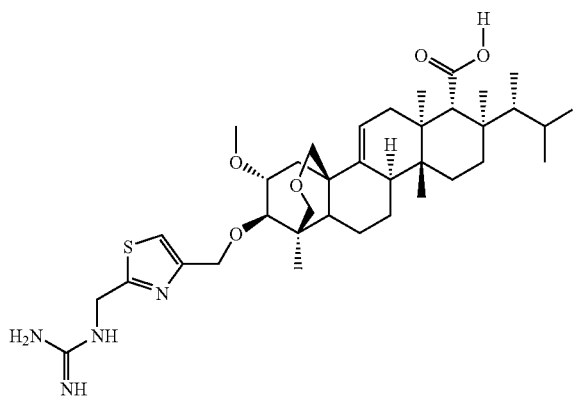

The benzyl ester derived from the compound described in Example 30 (40 mg) was dissolved in tetrahydrofuran (2 mL) and 1,3-bis(benzyloxycarbonyl)-2-methyl-2-thiopseudourea (23 mg) and triethylamine (40 μL) were added. Mercuric chloride (18 mg) was added and the reaction solution stirred at room temperature for 3 hours. The reaction was judged complete by TLC analysis and the reaction solution was concentrated. The residue was flash chromatographed (85:15 heptane:ethyl acetate) to yield a white sticky solid (50 mg). A portion of this material (25 mg) was dissolved in trifluoroacetic acid (2 mL) and dichloromethane (2 mL). Palladium hydroxide (150 mg) was added and a hydrogen atmosphere was secured (balloon). The reaction mixture was stirred at room temperature for 1 hour and judged complete by TLC analysis. The reaction contents were filtered through a pad of Celite and the filtrate was concentrated to yield the title compound as a trifluoroacetate salt (16 mg). Calculated for $C_{37}H_{58}N_4O_5S$: 670; observed: 671 (M+H)$^+$. $^1$H NMR (400 MHz, methanol-$d_4$) δ ppm 0.77 (s, 3H), 0.79 (s, 3H), 0.86 (d, J=6.69 Hz, 3H), 0.91 (d, J=6.78 Hz, 3H), 1.18 (s, 3H), 1.22 (s, 3H), 1.25-1.31 (m, 4 H), 1.30-1.46 (m, 2H), 1.45-1.68 (m, 4H), 1.70-1.84 (m, 3H), 1.92-1.97 (m, 1H), 2.04-2.13 (m, 1H), 2.16-2.27 (m, 1H), 2.47-2.59 (m, 1H), 2.86 (s, 1H), 3.06 (d, J=8.49 Hz, 1H), 3.40 (s, 3H), 3.41-3.45 (m, 5H), 3.64-3.81 (m, 2H), 4.19-4.31 (m, 1H), 4.64-4.77 (m, 2H), 4.98 (d, J=12.45 Hz, 1H), 5.53 (s, 1H), and 7.44 (s, 1H).

Example 33

(1S,2R,3R,4aR,6aS,7R,8R,10aR,10bR,12aR)-3-(methoxy)-2-[2-((S)-1-guanidinoethyl)-thiazol-4-ylmethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-35)

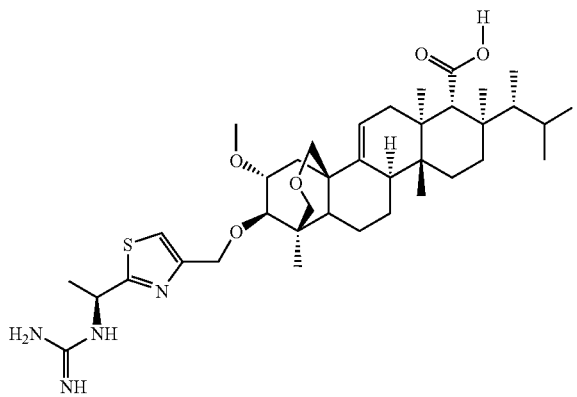

In a similar manner as described in Example 32, from the benzyl ester of the compound described in Example 31 (14 mg) was obtained the title compound as a trifluoroacetate salt (5 mg). Calculated for $C_{38}H_{60}N_4O_5S$: 684; observed: 685 (M+H)+. 1H NMR (400 MHz, methanol-$d_4$) δ ppm 0.76 (s, 3H), 0.79 (s, 3H), 0.87 (d, J=6.69 Hz, 3H), 0.91 (d, J=6.78 Hz, 3H), 1.18 (s, 3H), 1.22 (s, 3H), 1.26-1.36 (m, 6H), 1.40-1.54 (m, 4H), 1.56-1.63 (m, 2H), 1.75-1.85 (m, 2H), 2.01-2.13 (m, 1H), 2.13-2.27 (m, 1H), 2.47-2.59 (m, 1H), 2.99 (s, 1H), 3.01-3.13 (m, 1H), 3.35 (s, 3H), 3.37-3.49 (m, J=13.62 Hz, 3H), 3.64-3.74 (m, J=11.67 Hz, 1H), 3.98 (s, 2H), 4.04-4.21 (m, 1H), 4.20-4.31 (m, 1H), 4.31-4.46 (m, 1H), 4.71 (dd, J=12.40 Hz, 1H), 5.08 (s, 1H), 5.54 (s, 2H), 7.43 (s, 1H), and 7.99 (s, 1H).

Example 34

(1S,2R,3R,4aR,6aS,7R,8R,10aR,10bR,12aR)-3-(acetyloxy)-2-[2-((S)-1,5-diaminopentyl)-thiazol-4-ylmethoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-29)

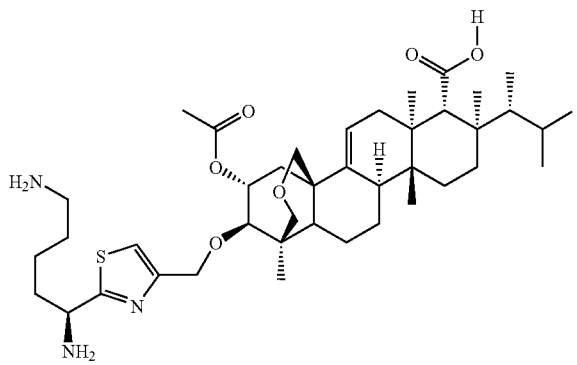

Intermediate 7 (73 mg) was dissolved in acetone (4 mL) and (S)-5-tert-butoxycarbonyl amino-1-thiocarbamoyl-pentyl)-carbamic acid tert-butyl ester (36 mg) was added. The reaction solution was refluxed for 21 hours and judged complete by TLC analysis. The reaction contents were concentrated and the residue was flash chromatographed (silica gel; 90:10 heptane:ethyl acetate) to yield a white solid (45 mg). A portion of this material (35 mg) was dissolved in trifluoroacetic acid (2 mL) and dichloromethane (2 mL) and the reaction was stirred at room temperature for 30 minutes. The reaction was judged complete by TLC analysis and the reaction contents were concentrated. The residue was dissolved in acetic acid (3 mL) and paratoluenesulfonic acid (20 mg) was added. The reaction mixture was heated to 115° C. and stirred for 2 hours. The reaction was judged complete by TLC analysis and cooled to room temperature, then concentrated. The residue was twice redissolved in toluene and concentrated. The residue was then dissolved in dichloromethane (2 mL) and trifluoroacetic acid (2 mL) and palladium hydroxide (150 mg) was added. A hydrogen atmosphere was secured (balloon) and the reaction was stirred for 30 minutes at room temperature. The reaction was judged complete and the reaction contents were filtered through a pad of Celite. The filtrate was concentrated and purified by reverse phase HPLC (40:60 methanol:water) to yield the title compound as the tosylate salt (7 mg). Calculated for $C_{41}H_{65}N_3O_6S$: 727; observed: 728 (M+H)+. 1H NMR (400 MHz, methanol-$d_4$) δ ppm 0.76-0.78 (m, 3H), 0.81 (s, 3H), 0.87 (d, J=6.64 Hz, 3H), 0.92 (d, J=6.78 Hz, 3H), 1.14-1.20 (m, 3H), 1.21 (s, 3H), 1.26-1.33 (m, 2H), 1.35-1.50 (m, 3H), 1.58-1.73 (m, 3H), 1.79 (s, 3H), 1.99 (s, 3H), 2.05-2.16 (m, 2H), 2.14-2.25 (m, 2H), 2.36-2.39 (m, 2H), 2.41-2.47 (m, 1H), 2.86 (s, 1H), 2.88-3.00 (m, 1H), 3.14 (s, 1H), 3.27-3.44 (m, 5H), 3.43-3.55 (m, 1H), 3.70 (d, J=12.59 Hz, 1H), 4.67-4.84 (m, 3H), 4.83-4.96 (m, 1H), 5.49 (s, 1H), 5.71-5.94 (m, 1H), 7.24 (d, J=7.91 Hz, 2H), 7.54 (d, J=2.88 Hz, 1H), and 7.71 (d, J=8.20 Hz, 2H).

Example 35

(1S,2R,3R,4aR,6aS,7R,8R,10aR,10bR,12aR)-3-(acetyloxy)-2-(3-aminopropoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-32)

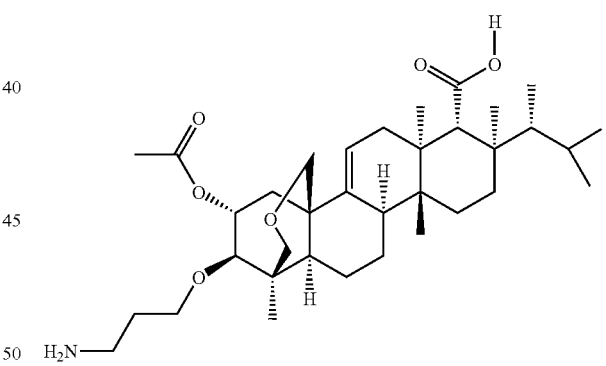

(a) In a similar manner as described in Example 1 (a) from Intermediate 3 and allyl bromide was obtained the desired prop-2-enyl ether.

(b) The prop-2-enyl ether from above was dissolved in dry THF (20 mL) and borane tetrahydrofuran complex was added (1.0 M; 1.2 mL). The reaction solution was stirred at room temperature for 2.5 hours then aqueous sodium hydroxide (3.0 M; 20 mL) was added followed by aqueous hydrogen peroxide (30%; 0.5 mL). The reaction solution was stirred at room temperature for 16 hours. Additional hydrogen peroxide (1 mL) was added and the reaction was refluxed for 2 hours. The reaction solution was cooled to room temperature and ethyl acetate (60 mL) and water (60 mL) were added. The aqueous phase was twice washed with ethyl acetate. The organic phases were combined and dried over magnesium sulfate, then concentrated. The residue was dissolved in dichloromethane (30 mL) and triethylamine (600 mg) and methanesulfonyl chloride (0.14 g) were added. The reaction solution was stirred at room temperature for 1.5 hours and judged complete by TLC analysis. Additional dichloromethane (30 mL) and water (30 mL) were added to the reaction solution. The aqueous phase was twice washed with dichloromethane. The combined organic phases were dried over magnesium sulfate and concentrated. The residue was purified by flash chromatography (80:20 heptane:ethyl acetate) to give the desired methanesulfonyloxyethoxy derivarive (0.24 g).

(c) The mesylate from above (240 mg) was dissolved in tetrahydrofuran (5 mL) and methanol (15 mL) in a high-pressure vessel. The solution was chilled and ammonia was bubbled through the solution for 5 minutes. The vessel was sealed and the reaction solution was heated to 45° C. and stirred for 6 hours. The reaction was judged complete by TLC analysis. Ethyl acetate (50 mL) and water (30 mL) were added. The aqueous phase was twice washed with ethyl acetate. The organic phases were combined and dried over magnesium sulfate, then concentrated. The residue was flash chromatographed (50:50 heptane:ethyl acetate, then 90:10 dichloromethane:methanol) to yield the desired amino compound (190 mg).

(d) A portion of the amino derivative from above (50 mg) was dissolved in acetic acid (6 mL) and paratoluenesulfonic acid (31 mg) was added. The reaction was heated to 110° C. and stirred for 15 minutes, then judged complete by TLC analysis. The reaction contents were concentrated and the residue was purified by reverse phase HPLC. Purified material (35 mg) was dissolved in methanol (7 mL) and ethyl acetate (7 mL). Acetic acid (0.1 mL) and palladium hydroxide (35 mg) were added and a hydrogen atmosphere was secured (balloon). The reaction was stirred at room temperature for 1 hour and judged complete by TLC analysis. The reaction mixture was filtered through a pad of Celite and the filtrate was concentrated. The residue was purified by reverse phase HPLC (50:50 to 100:0 methanol:water) to yield the title compound as a tosylate salt (31 mg). Calculated for $C_{35}H_{57}NO_6$: 587; observed: 588 (M+H)+. $^1$H NMR (400 MHz, methanol-$d_4$) δ ppm 0.77 (s, 3H), 0.78 (d, 3H), 0.81 (s, 3H), 0.87 (d, J=6.69 Hz, 3H), 0.91 (d, J=6.78 Hz, 3H), 1.18 (s, 3H), 1.22 (s, 3H), 1.24-1.32 (m, 3H), 1.32-1.49 (m, 3H), 1.49-1.71 (m, 3H), 1.73-1.95 (m, 5H), 1.98 (s, 3H), 2.08-2.14 (m, 1H), 2.15-2.24 (m, 1H), 2.30-2.37 (m, 1H), 2.37 (s, 3H), 2.86 (s, 1H), 2.96-3.05 (m, 2H), 3.10 (d, J=8.74 Hz, 1H), 3.38 (d, J=11.76 Hz, 1H), 3.42-3.51 (m, 2H), 3.66 (d, J=11.76 Hz, 1H), 3.69-3.77 (m, 2H), 5.48 (s, 1H), 5.71-5.88 (m, 1H), 7.23 (d, J=7.96 Hz, 2H), and 7.71 (d, J=8.20 Hz, 2H).

Example 36

(1S,2R,3R,4aR,6aS,7R,8R,10aR,10bR,12aR)-3-(acetyloxy)-2-(3-guanidinopropoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid
(K-42)

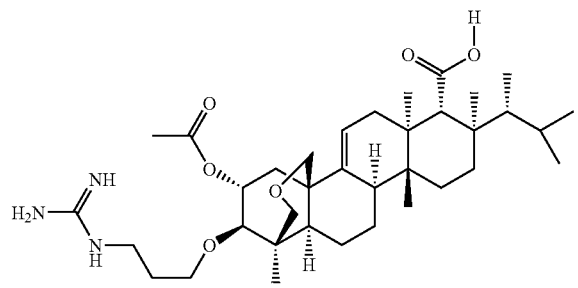

The aminopropyl ether derivative described in Example 35 (c) (50 mg) was dissolved in dimethylformamide (4 mL) and triethylamine (58 μL) and 1,3-bis(benzyloxycarbonyl)-2-methyl-2-thiopseudourea (102 mg) were added. The reaction solution was stirred at room temperature for 72 hours and judged complete by TLC analysis. The reaction solution was concentrated and the residue was purified by reverse phase HPLC (50:50 to 100:0 methanol:water). Purified material (11 mg) was dissolved in methanol (3 mL) and ethyl acetate (3 mL). Acetic acid (50 μL) and palladium hydroxide (12 mg) were added and a hydrogen atmosphere was secured (balloon). The reaction was stirred at room temperature for 1.5 hours and judged complete by TLC analysis. The reaction mixture was filtered through a pad of Celite and concentrated to yield the title compound as an acetate salt (6.1 mg). Calculated for $C_{36}H_{59}N_3O_6$: 629; observed: 630 (M+H)+. $^1$H NMR (400 MHz, methanol-$d_4$) δ ppm 0.77 (s, 3H), 0.78 (d, J=7.22 Hz, 3H), 0.81 (s, 3H), 0.87 (d, J=6.69 Hz, 3H), 0.91 (d, J=6.83 Hz, 3H), 1.15-1.19 (m, 3H), 1.22 (s, 3H), 1.27-1.52 (m, 3H), 1.52-1.71 (m, 4H), 1.73-1.90 (m, 6H), 1.90-1.95 (m, 1H), 1.98 (s, 6H), 2.01 (s, 3H), 2.05 (s, 3H), 2.06-2.14 (m, 1H), 2.17-2.24 (m, 1H), 2.36-2.43 (m, J=20.35 Hz, 1H), 2.86 (s, 1H), 3.11 (d, J=8.54 Hz, 1H), 3.22-3.30 (m, 1H), 3.42-3.52 (m, 2H), 3.63-3.70 (m, 2H), 3.70-3.80 (m, 3H), 5.45-5.49 (m, J=5.76 Hz, 1H), and 5.76 (s, J=26.94 Hz, 1H).

Example 37

(1S,2R,3R,4aR,6aS,7R,8R,10aR,10bR,12aR)-3-(methoxy)-2-(3-amino-2-methylpropoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid
(C-27)

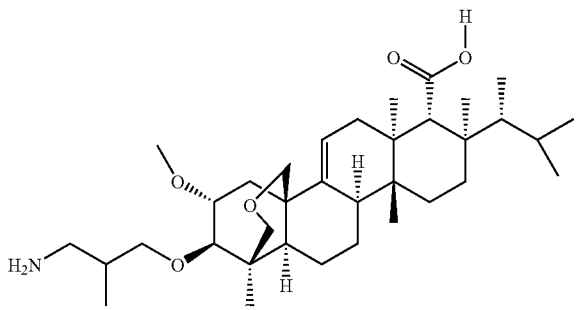

In a similar manner as described in Example 1(a), from Intermediate 3 (0.67 g, 1.1 mmol) and 3-chloro-2-chloromethylpropene (650 mg) was obtained the desired 2-chloromethyl-2-propenyl derivative. A portion of the chloromethyl derivative (200 mg) was dissolved in tetrahydrofuran (2 mL) and methanol (6 mL) in a high-pressure vessel and the solution was chilled to −50° C. Ammonia gas was bubbled through the solution for five minutes and the vessel was sealed. The vessel was allowed to warm to room temperature and stirred for 48 hours. The reaction was judged complete by TLC analysis and the vessel was unsealed. The reaction contents were concentrated and the residue was flash chromatographed (50:50 heptane:ethyl acetate; then 85:15 dichloromethane:methanol (0.02% concentrated ammonium hydroxide) to yield the desired amino derivative (158 mg). A portion of this material (40 mg) was dissolved in methanol (4 mL) and ethyl acetate (4 mL). Acetic acid (3 drops) and palladium hydroxide (40 mg) were added and a hydrogen atmosphere was secured (balloon). The reaction was stirred at room temperature for 1 hour and judged complete by TLC analysis. The reaction mixture was filtered through a pad of Celite and concentrated to give the title compound as an acetate salt (40 mg). Calculated for $C_{35}H_{59}NO_5$: 573; observed: 574 (M+H)+. $^1$H NMR (400 MHz, methanol-$d_4$) δ ppm 0.77 (s, 3H), 0.78 (d, J=5.08 Hz, 3H), 0.79 (s, 3H), 0.87

(d, J=6.69 Hz, 3H), 0.92 (d, J=6.78 Hz, 3H), 0.99 (d, J=6.93 Hz, 1H), 1.05 (d, J=6.93 Hz, 2H), 1.18 (s, 3H), 1.23 (s, 3H), 1.23-1.35 (m, 4H), 1.35-1.66 (m, 5H), 1.66-1.89 (m, 3H), 1.96 (s, 3H), 2.00 (s, 1H), 2.05-2.15 (m, 2H), 2.16-2.28 (m, 1H), 2.44-2.56 (m, 1H), 2.86 (s, 1H), 2.87-2.94 (m, 1H), 2.98-3.14 (m, 1H), 3.32-3.37 (m, 1H), 3.38-3.40 (m, 3H), 3.42 (s, 2H), 3.51-3.59 (m, 1H), 3.59-3.70 (m, 2H), 3.69-3.85 (m, 1H), 4.10-4.27 (m, 1H), and 5.54 (m, 1H).

Example 38

(1S,2R,3R,4aR,6aS,7R,8R,10aR,10bR,12aR)-3-(acetyloxy)-2-(3-amino-2-methylpropoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (G-22)

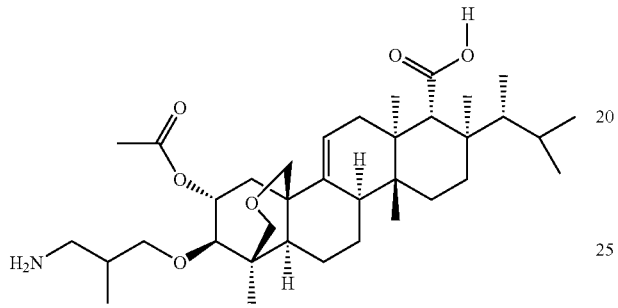

To a solution of Example 37 (15 mg; 0.02 mmol) in acetic acid (1.5 mL) was added paratoluenesulfonic acid (13 mg). The reaction solution was heated to 110° C. for 50 minutes and judged complete by TLC analysis. The reaction contents were cooled and concentrated; the residue was purified by reverse phase HPLC to yield the title compound as an acetate salt (5.9 mg). Calculated for $C_{36}H_{59}NO_6$: 601; observed: 602 (M+H)$^+$. $^1$H NMR (400 MHz, methanol-$d_4$) δ ppm 0.77 (s, 3H), 0.78 (d, J=7.22 Hz, 3H), 0.81 (d, J=2.54 Hz, 3H), 0.87 (d, J=6.69 Hz, 3H), 0.91 (d, J=6.78 Hz, 3H), 0.96 (d, J=6.88 Hz, 1H), 1.05 (d, J=6.98 Hz, 2H), 1.18 (s, 3H), 1.22 (s, 3H), 1.23-1.32 (m, 3H), 1.32-1.52 (m, 4H), 1.52-1.69 (m, 3H), 1.69-1.91 (m, 3H), 1.95 (s, 3H), 1.97-2.04 (m, 1H), 2.06 (s, 2H), 2.09 (s, 1H), 2.10-2.14 (m, 1H), 2.14-2.26 (m, 1H), 2.30-2.36 (m, 1H), 2.37 (s, 3H), 2.80-2.96 (m, 2H), 3.02-3.14 (m, 2H), 3.35-3.59 (m, 4H), 3.61-3.71 (m, 2H), 5.47-5.49 (m, 1H), 5.76-5.89 (m, 1H), 7.21-7.26 (m, 2H), and 7.68-7.74 (m, J=8.25 Hz, 2H).

Example 39

(1S,2R,3R,4aR,6aS,7R,8R,10aR,10bR,12a-R)-3-(acetyloxy)-2-(3-acetylamino-2-methyl-propoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (G-21)

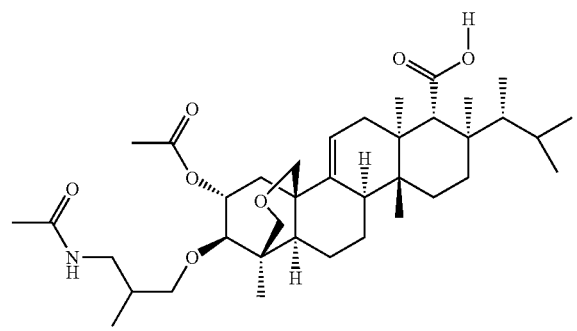

Isolated as a by-product from Example 38. Calculated for $C_{38}H_{61}NO_7$: 643; observed: 644 (M+H)$^+$. $^1$H NMR (400 MHz, chloroform-d) δ ppm 0.69-0.69 (m, 3H), 0.70-0.76 (m, 6H), 0.78-0.83 (m, 6H), 0.83-0.92 (m, 3H), 1.10 (s, 3H), 1.15 (s, 3H), 1.25-1.45 (m, 4H), 1.45-1.60 (m, 4H), 1.63-1.78 (m, 5H), 1.88 (s, 1H), 1.92 (s, 3H), 1.94 (s, 3H), 2.07-2.12 (m, 2H), 2.27-2.41 (m, 1H), 2.81-2.85 (m, 2H), 2.90-2.97 (m, 2H), 3.23-3.36 (m, 2H), 3.37-3.52 (m, 2H), 3.57-3.70 (m, 2H), 5.39 (s, 1H), 5.75-5.86 (m, 1H), and 6.12-6.36 (m, 1H).

Example 40

(1S,2R,3R,4aR,6aS,7R,8R,10aR,10bR,12aR)-3-(acetyloxy)-2-(4-aminobutoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (K-29)

To a solution of the compound described in Example 1 (b) (71 mg, 0.11 mmol) in ethylene glycol dimethyl ether (4 mL) was added sodium hydride (24 mg; 0.55 mmol). The reaction solution was cooled to −78° C. and diethyl cyanomethylphosphonate (100 μL; 0.55 mmol). The reaction was stirred, warming to room temperature, for 2 hours and judged complete by TLC analysis. Saturated sodium bicarbonate solution was added to the reaction mixture and the aqueous phase was thrice washed with dichloromethane. The organic phases were combined, dried over magnesium sulfate, and concentrated. The residue was flash chromatographed (silica gel; 75:25 heptane:ethyl acetate). Purified material (64 mg) was dissolved in methanol (5 mL) and ammonium hydroxide (1 mL) and Raney-Ni (100 mg) were added. A hydrogen atmosphere was secured (balloon) and the reaction mixture was stirred for 16 hours at room temperature. The reaction was judged complete by TLC analysis and the reaction contents were filtered through a pad of Celite. The filtrate was concentrated and the residue was dissolved in dichloromethane (50 mL) and water. The aqueous phase was thrice washed with dichloromethane. The organic phases were combined, dried over magnesium sulfate, and concentrated. The residue (50 mg) was subjected to the conditions described in Example 1 (d) and (e) to yield the title compound as a tosylate salt (18 mg). Calculated for $C_{36}H_{59}NO_6$: 601; observed: 602 (M+H)$^+$. $^1$H NMR (400 MHz, methanol-$d_4$) δ ppm 0.76 (s, 3H), 0.79-0.81 (m, 3H), 0.87 (d, J=6.64 Hz, 3H), 0.91 (d, J=6.74 Hz, 3H), 1.17 (s, 3H), 1.22 (s, 3H), 1.26-1.44 (m, 6H), 1.56-1.65 (m, 5H), 1.69-1.88 (m, 5H), 1.99 (s, 3H), 2.11-2.13 (m, 1H), 2.14-2.28 (m, 3H), 2.37 (s, 3H), 2.85 (s, 1H), 2.89-3.02 (m, 2H), 3.08 (d, J=8.93 Hz, 1H), 3.32-3.50 (m, 5H), 3.54-3.80 (m, 3H), 4.03-4.25 (m, 1H), 5.47 (s, 1H), 5.78 (s, 1H), 7.24 (d, J=7.91 Hz, 2H), and 7.71 (d, J=8.10 Hz, 2H).

Example 41

(1S,2R,3R,4aR,6aS,7R,8R,10aR,10bR,12aR)-3-(acetyloxy)-2-(2-amino-3-methylbutoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-3)

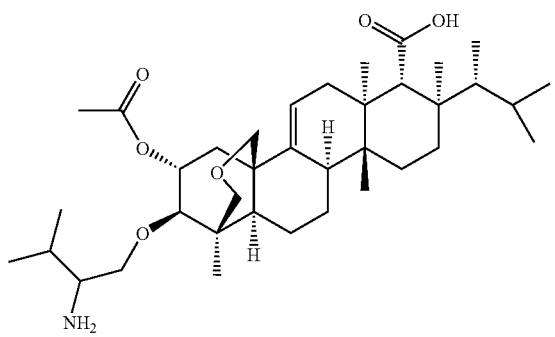

In a similar manner as described in Example 1(a), from Intermediate 3 (2.5 g) and 2-bromomethyl-3-methyl-but-2-ene was obtained the desired butenyl derivative. This derivative was subjected to the conditions outlined in Example 1(b-e) to yield the title compound (1.09 g) which was converted to the acetate salt. Calculated for $C_{37}H_{61}NO_6$: 615; observed: 616 (M+H)$^+$. $^1$H NMR (400 MHz, chloroform-d) δ ppm 0.73 (s, 3H), 0.77 (d, J=7.13 Hz, 6H), 0.80-0.82 (m, 3H), 0.82-0.87 (m, J=6.54 Hz, 6H), 0.88-0.93 (m, 3H), 0.94 (dd, J=6.74, 2.44 Hz, 1H), 1.01-1.06 (m, J=6.64 Hz, 2H), 1.11-1.16 (m, 6H), 1.20 (s, 3H), 1.22-1.29 (m, 3H), 1.33-1.42 (m, 2H), 1.43-1.50 (m, 3H), 1.53-1.64 (m, 2H), 1.69-1.79 (m, 4H), 1.90-1.94 (m, 1H), 2.02-2.06 (m, 1H), 2.10 (s, 1H), 2.15 (s, 3H), 2.17 (s, 3H), 2.19-2.27 (m, 1H), 2.44-2.52 (m, 1H), 2.85-2.91 (m, 1H), 3.10-3.17 (m, 1H), 3.25-3.40 (m, 1H), 3.72-3.80 (m, 1H), 3.82-3.91 (m, 1H), and 5.40-5.48 (m, 1H).

Example 42

(1S,2R,3R,4aR,6aS,7R,8R,10aR,10bR,12aR)-3-(acetyloxy)-2-[2-(5-amino-2H-[1,2,4]triazol-3-ylamino)-3-methylbutoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-7)

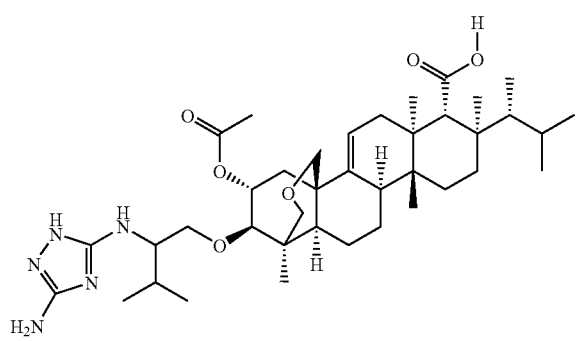

To a solution of Example 41 (50 mg) dissolved in isopropanol (3 mL) and dimethylformamide (6.5 mL) was added diphenyl cyanocarbonimidate (26 mg) and triethylamine (26 μL). The reaction solution was stirred at room temperature for 60 hours and the reaction was judged complete by TLC analysis. The reaction solution was concentrated and the residue was flash chromatographed (silica gel; 80:20 heptane:ethyl acetate). Purified material (36 mg) was dissolved in ethanol (2.5 mL) and hydrazine hydrate (1.0 M in ethanol; 193 μL) was added. The reaction stirred for 1 hour at room temperature. Additional hydrazine hydrate (1.0 M in ethanol; 193 μL) was added and the reaction solution stirred at room temperature for 16 hours. The reaction was judged complete by TLC analysis and the reaction contents were concentrated. The residue was flash chromatographed (95:5 dichloromethane:methanol) to yield the title compound (33 mg). Calculated for $C_{39}H_{63}N_5O_6$: 697; observed: 698 (M+H)$^+$. $^1$H NMR (400 MHz, methanol-d$_4$) δ ppm 0.74-0.77 (m, 6H), 0.79 (s, 3H), 0.81 (s, 3H), 0.86 (d, J=6.69 Hz, 3H), 0.91 (d, J=6.83 Hz, 3H), 0.93-1.00 (m, 6H), 1.16 (s, 3H), 1.22 (s, 3H), 1.24-1.34 (m, 3H), 1.54-1.65 (m, 3H), 1.72-1.83 (m, 2H), 1.89-1.99 (m, 3H), 2.01 (s, 3H), 2.05-2.11 (m, 1H), 2.20 (s, 1H), 2.36-2.44 (m, 1H), 2.84 (s, 1H), 3.03-3.13 (m, 1H), 3.25-3.31 (m, 1H), 3.38-3.51 (m, 2H), 3.56-3.67 (m, 1H), 3.72 (d, J=11.76 Hz, 1H), 3.81-3.90 (m, 1H), 4.10 (dd, 1H), 5.46 (s, 1H), and 5.66-5.83 (m, 1H).

Example 43

(1S,2R,3R,4aR,6aS,7R,8R,10aR,10bR,12aR)-3-(acetyloxy)-2-[(S)-2,3-dihydroxy-propoxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-22)

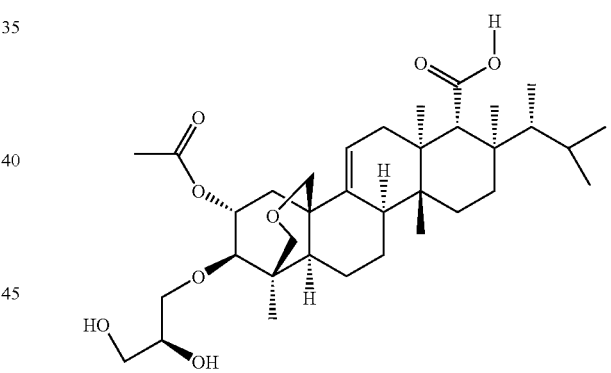

The allyl ether described in Example 1 (a) was converted to an acetate derivative in a similar manner as described in Example 1(d). To this allyl ether (120 mg; 0.18 mmol) in acetone (1 mL) was added a solution of tert-butanol (10 mL), water (10 mL) and AD-mix-beta (500 mg) at 0° C. The reaction solution was stirred at 0° C. for 16 hours. Additional AD-mix-beta (250 mg) was added and the reaction was stirred at 15° C. for 16 hours. The reaction was judged complete by TLC analysis. Sodium sulfite (300 mg) was added and the reaction was stirred for 30 minutes, warming to room temperature. The reaction solution was thrice extracted with ethyl acetate. The organic phases were combined, washed with saturated NaCl solution, dried over magnesium sulfate, and concentrated. The residue was flash chromatographed (silica gel; 80:20 dichloromethane:methanol) to yield a white powder (85 mg). A portion of this material (5 mg) was subjected to hydrogenolysis conditions described in Example 1(e) to yield the title compound (5 mg) which was converted to an acetate salt. Calculated for $C_{35}H_{56}O_6$: 604; observed: 627 (M+23)⁺. ¹H NMR (400 MHz, chloroform-d) δ ppm 0.73 (s, 3H), 0.77 (d, J=7.13 Hz, 3H), 0.79-0.82 (2s, 3H), 0.85 (d, J=6.64 Hz, 3H), 0.90 (d, J=6.69 Hz, 3H), 1.14 (s, 3H), 1.20 (s, 3H), 1.21-1.31 (m, 3H), 1.31-1.51 (m, 4H), 1.51-1.65 (m, 3H), 1.69-1.82 (m 3H), 1.89-2.05 (m, 2H), 2.05-2.08 (2s, 3H), 2.11-2.21 (m, 2H), 2.38-2.47 (m, 1H), 2.87 (s, 1H), 3.07 (d, J=9.13 Hz, 1H), 3.28-3.42 (m, 2H), 3.48-3.53 (m, 2H), 3.54-3.62 (m, 1H), 3.65-3.75 (m, 3H), 3.75-3.88 (m, 1H), 5.42-5.46 (m, 1H), and 5.78-5.89 (m, 1H).

Example 44

(1S,2R,3R,4aR,6aS,7R,8R,10aR,10bR,12aR)-3-(acetyloxy)-2-(2,3-dihydroxy-2-hydroxymethylpropoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-14)

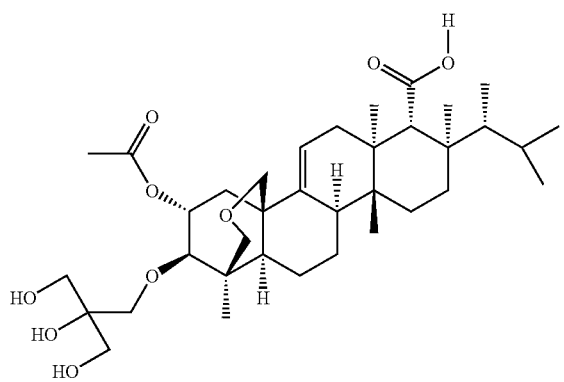

In a similar manner as described in Example 1 (a), using 3-chloro-2-chloromethyl propene yielded the desired propenyl ether.

The propenyl ether from above (0.2 mmol) was dissolved in dimethylformamide (10 mL) and benzyl alcohol (0.22 g) and sodium hydride (0.12 g) were added. The reaction solution stirred at room temperature for 1.5 hours and was judged complete by TLC analysis. Ethyl acetate (40 mL), methanol (5 mL) and water (20 mL) were slowly added to the reaction solution. The aqueous phase was twice washed with ethyl acetate. The organic phases were combined, dried over magnesium sulfate, and concentrated. The residue was purified by reverse phase HPLC (50:50 to 100:0 methanol:water) to afford the desired allyl benzyl ether. This allyl benzyl ether (120 mg) was dissolved in acetic acid (24 mL). Paratoluenesulfonic acid (24 mg) was added and the stirred reaction solution was heated to 110° C. for 20 minutes. The reaction was judged complete by TLC analysis, cooled to room temperature, and concentrated. The residue was flash chromatographed (silica gel; 80:20 heptane:ethyl acetate). Purified material (43 mg) was dissolved in tetrahydrofuran (8 mL) and osmium tetroxide (4%; 300 μL) and 4-methylmorpholine N-oxide (60 mg) were added. The reaction solution was stirred at room temperature for 4 hours and judged complete by TLC analysis. Ethyl acetate (50 mL) and water (20 mL) were added to the reaction solution. The aqueous phase was twice washed with ethyl acetate. The organic phases were combined, washed with water, dried over magnesium sulfate and concentrated. The residue was purified by reverse phase HPLC. Purified material (46 mg) was dissolved in methanol (5 mL) and ethyl acetate (5 mL). Palladium hydroxide (80 mg) was added and a hydrogen atmosphere was secured (balloon). The reaction mixture stirred at room temperature for 1.5 hours and was judged complete by TLC analysis. The reaction contents were filtered over a pad of Celite and the filtrate was concentrated. The residue was flash chromatographed (C18; 60:40 to 100:0 methanol:water) to yield the title compound (16 mg). Calculated for $C_{36}H_{58}O_9$: 634; observed; 657 (M+Na)⁺. ¹H NMR (400 MHz, methanol-d₄) δ ppm 0.76 (s, 3H), 0.78 (d, J=7.22 Hz, 3H), 0.84 (s, 3H), 0.87 (d, J=6.69 Hz, 3H), 0.91 (d, J=6.78 Hz, 3 H), 1.17 (s, 3H), 1.22 (s, 3H), 1.24-1.32 (m, 4H), 1.32-1.45 (m, 2H), 1.46-1.69 (m, 3H), 1.69-1.87 (m, 3H), 1.87-2.02 (m, 1H), 2.05 (s, 3H), 2.06-2.15 (m, 1H), 2.15-2.27 (m, 1H), 2.30-2.44 (m, 1H), 2.86 (s, 1H), 2.98 (d, J=21.92 Hz, 2H), 3.10 (d, J=8.83 Hz, 1H), 3.33-3.39 (m, 1H), 3.39-3.50 (m, 2H), 3.50-3.62 (m, 3H), 3.65-3.76 (m, 2H), 5.42-5.49 (m, 1H), and 5.70-5.83 (m, 1H).

Example 45

(1S,2R,3R,4aR,6aS,7R,8R,10aR,10bR,12aR)-3-(acetyloxy)-2-(2,3-dihydroxy-2-methoxycarbonyl-propoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (C-26)

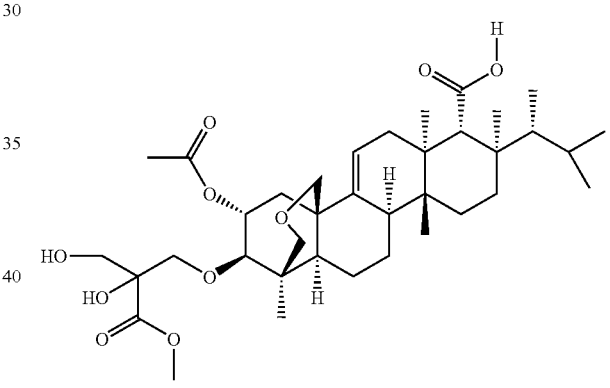

In a similar manner as described in Example 1 (a), using Intermediate 1 (100 mg, 0.12 mmol) and methyl-2-bromoethyl acrylate (125 mg) yielded the desired propenyl ether (86 mg). A portion of this material (20 mg) was dissolved in tetrahydrofuran (1 mL) and water (1 mL). Osmium tetroxide (4%; 62 μL) and 4-methylmorpholine N-oxide (13 mg) were added and the reaction was stirred at room temperature for 3.5 hours. The reaction was judged complete by TLC analysis and the reaction contents were concentrated. The residue was purified by reverse phase HPLC. Purified material (7 mg) was dissolved in methanol (2 mL) and ethyl acetate (2 mL). Palladium hydroxide (10 mg) was added and a hydrogen atmosphere was secured (balloon). The reaction stirred at room temperature for 1 hour and was judged complete by TLC analysis. The reaction contents were filtered over a pad of Celite and concentrated to yield the title compound (4.2 mg). Calculated for $C_{37}H_{58}O_{10}$: 662; observed: 685 (M+Na)⁺. ¹H NMR (400 MHz, methanol-d₄) δ ppm 0.76 (s, 3H), 0.77 (s, 3H), 0.79-0.82 (m, 3H), 0.86 (d, J=6.69 Hz, 3H), 0.91 (d, J=6.78 Hz, 3H), 1.17 (s, 3H), 1.22 (s, 3H), 1.24-1.68 (m, 7H), 1.68-1.87 (m, 4H), 1.89-2.04 (m, 2H), 2.05-2.07 (m, 3H), 2.07-2.13 (m, 1H), 2.16-2.26 (m, 1H), 2.33-2.43 (m, 1H), 2.83-2.87 (m, 1H), 2.99-3.14 (m, 1H), 3.33-3.49 (m, 2H), 3.53-3.66 (m, 2H), 3.69-3.74 (m, 4H), 3.74-3.99 (m, 2H), 3.97 (d, J=8.74 Hz, 1H), 5.40-5.49 (m, 1H), and 5.65-5.80 (m, 1H).

Example 46

(1S,2R,3R,4aR,6aS,7R,8R,10aR,10bR,12aR)-3-(acetyloxy)-2-(2-amino-2-thiazol-2-yl-ethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-6)

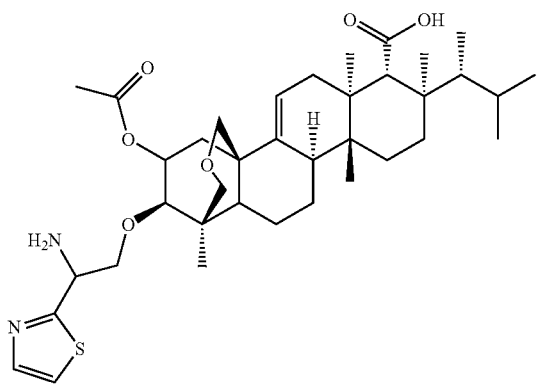

The aldehyde described in Example 1 (b) (200 mg) was dissolved in anhydrous dichloromethane and chilled to 0° C. under a nitrogen atmosphere. 2-Trimethylsilanyl-thiazole (200 µL) was added and the reaction solution was stirred for 16 hours and judged complete by TLC analysis. Tetrabutylammonium fluoride solution (1 M in tetrahydrofuran; 4 mL) was added and the reaction solution stirred at room temperature for 7 hours. Water and saturated sodium bicarbonate solution were added; the aqueous phase was washed with dichloromethane. The organic phase was dried over sodium sulfate and concentrated. The residue was flash chromatographed (70:30 heptane:ethyl acetate) to yield a white solid (175 mg). Purified material was dissolved in anhydrous tetrahydrofuran (5 mL) and triphenylphosphine (307 mg) was added. The reaction solution was chilled to −20° C. and diethylazodicarboxylate (213 µL) and diphenylphosphoryl azide (253 µL) were added. The reaction was stirred for 16 hours, warming to room temperature. The reaction was judged complete by TLC analysis and the reaction contents were concentrated. The residue was redissolved in tetrahydrofuran (2 mL) and water (2 mL). Triphenylphosphine (70 mg) was added and the reaction solution was stirred for 60 hours at room temperature. The reaction was judged complete by TLC analysis and the reaction contents were concentrated. The residue was flash chromatographed (95:5 dichloromethane:methanol) to yield an orange gum (80 mg). The material was then subjected to conditions outlined in Example 1 (e) to yield the title compound as an orange glassy solid (52 mg) that was converted to a trifluoroacetate salt. Calculated for $C_{37}H_{56}N_2O_6S$: 656; observed: 657 (M+H)$^+$. $^1$H NMR (400 MHz, methanol-d$_4$) δ ppm 0.77 (s, 3H), 0.79 (s, 3H), 0.86 (d, J=6.64 Hz, 3H), 0.91 (d, J=6.78 Hz, 3H), 1.19 (s, 3H), 1.23 (s, 3H), 1.27-1.39 (m, 5H), 1.44-1.55 (m, 2H), 1.53-1.67 (m, 4H), 1.68-1.86 (m, 3H), 1.89-1.96 (m, 1H), 1.98 (s, 3H), 2.06-2.13 (m, 1H), 2.17-2.29 (m, 1H), 2.41 (dd, 2H), 2.81 (s, 1H), 3.21 (d, J=8.54 Hz, 1H), 3.38-3.47 (m, 2H), 3.65 (d, J=11.71 Hz, 1H), 3.72 (d, J=11.81 Hz, 1H), 3.86-3.97 (m, 1H), 3.99-4.12 (m, 1H), 4.50-4.67 (m, 1H), 5.45 (s, 1H), 5.66-5.89 (m, 1H), 7.57 (d, J=3.27 Hz, 1H), and 7.77 (d, J=3.22 Hz, 1H).

Example 47

(1S,2R,3R,4aR,6aS,7R,8R,10aR,10bR,12aR)-3-(acetyloxy)-2-(2-aminoethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (K-25)

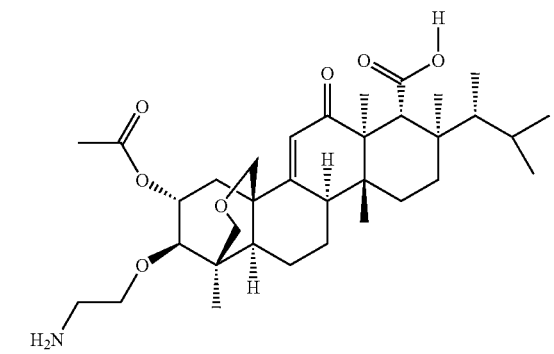

To a solution of Example 1 (260 mg; 0.41 mmol) in dimethylformamide (50 mL) was added pyridine (1.325 mL) and benzyl chloroformate (1.17 µL). The reaction was stirred at room temperature for 1 hour and judged complete by TLC analysis. Water (200 mL) and ethyl acetate (200 mL) were added to the reaction solution. The aqueous phase was twice washed with ethyl acetate. The organic phases were combined, washed with saturated NaCl solution, dried over sodium sulfate, and concentrated. The residue was flash chromatographed (silica gel; 99:1 dichloromethane:methanol).

The protected amino derivative from above (117 mg) was subjected to the oxidation procedure in the manner described in Intermediate 6 (c) using chromium trioxide (0.68 g) and dimethylpyrazole (0.66 g) to afford the desired enone (32 mg).

The enone from above (32 mg) was dissolved in methanol (4 mL) and acetic acid (15 µL) and palladium hydroxide (25 mg) were added. A hydrogen atmosphere was secured (balloon) and the reaction mixture was stirred at room temperature for 1 hour. The reaction was judged complete by TLC analysis. The reaction contents were filtered over a pad of Celite and the filtrate was concentrated to yield the title compound as an acetate salt (25.3 mg). Calculated for $C_{34}H_{53}NO_7$: 587; observed: 588 (M+H)$^+$. $^1$H NMR (400 MHz, methanol-d$_4$) δ ppm 0.77-0.81 (m, 3H), 0.81 (s, 3H), 0.86-0.92 (m, 6H), 0.97 (d, J=6.69 Hz, 3H), 1.11 (s, 3H), 1.15-1.37 (m, 3H), 1.37-1.61 (m, 4H), 1.72 (s, 3H), 1.73-1.83 (m, 2H), 1.84-1.94 (m, 2H), 2.03-2.06 (m, 1H), 2.07 (s, 3H), 2.20 (s, 3H), 2.22-2.30 (m, 1H), 2.42-2.54 (m, 1H), 2.71 (s, 1H), 3.08-3.16 (m, 3H), 3.25 (d, J=8.83 Hz, 1H), 3.40 (d, J=11.76 Hz, 1H), 3.46-3.57 (m, 2H), 3.75-4.00 (m, 3H), 5.76 (d, J=2.64 Hz, 1H), and 5.78-5.89 (m, 1H).

Example 48

(1S,2R,3R,4aR,6aS,7R,8R,10aR,10bR,12aR)-3-(acetyloxy)-2-(2-guanidinoethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (K-40)

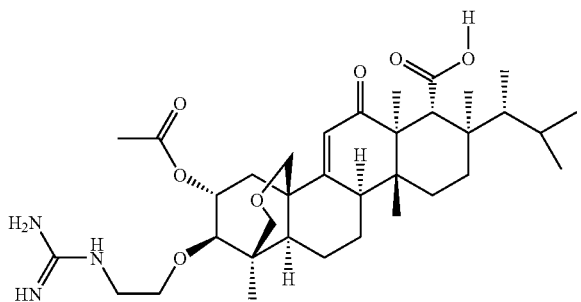

In a similar manner as described in Example 6, from the compound described in Example 47 was obtained the title compound as an acetate salt (13.6 mg). Calculated for $C_{35}H_{55}N_3O_7$: 629; observed: 630 (M+H)$^+$. $^1$H NMR (400 MHz, methanol-$d_4$) δ ppm 0.76-0.80 (m, 3H), 0.81 (s, 3H), 0.85 (s, 3H), 0.88 (d, J=6.59 Hz, 3H), 0.97 (d, J=6.69 Hz, 3H), 1.11 (s, 3H), 1.17-1.24 (m, 1H), 1.29-1.41 (m, 3H), 1.41-1.59 (m, 3H), 1.72 (s, 3H), 1.72-1.83 (m, 3H), 1.84-1.92 (m, 2H), 1.94 (s, 6H), 2.05 (s, 3H), 2.19-2.29 (m, 1H), 2.43 (dd, J=13.30, 7.10 Hz, 1H), 2.64-2.73 (m, 1H), 3.11 (s, 1H), 3.20 (d, J=8.93 Hz, 1H), 3.33-3.44 (m, 4H), 3.52 (s, 2H), 3.67-3.76 (m, 2H), 3.78-3.85 (m, 1H), 5.76 (d, J=2.49 Hz, 1H), and 5.78-5.87 (m, 1H).

Example 49

(1S,2R,3R,4aR,6aS,7R,8R,10aR,10bR,12aR)-3-(acetyloxy)-2-(2-methylaminoethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (K-47)

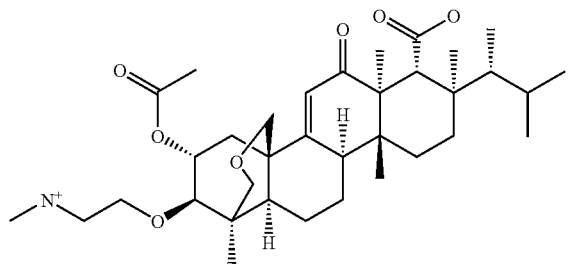

To a solution of the compound described in Example 47 (100 mg; 0.15 mmol) in methanol (6 mL) was added paraformaldehyde (4.6 mg; 0.15 mmol) and sodium bicarbonate (19 mg). The reaction solution was stirred at room temperature for 40 minutes, then heated to 60° C. and stirred for 1 hour. The reaction solution was cooled to room temperature and palladium hydroxide (80 mg) and acetic acid (30 μL) were added. A hydrogen atmosphere was secured and the reaction mixture was stirred for 1 hour at room temperature. The reaction mixture was filtered over a pad of Celite and the filtrate was concentrated. The residue was flash chromatographed (silica gel; 95:5 dichloromethane:methanol) to yield the title compound as an acetate salt (27 mg). Calculated for $C_{35}H_{55}NO_7$: 602; observed: 603 (M+H)$^+$. $^1$H NMR (400 MHz, methanol-$d_4$) δ ppm 0.78 (d, J=7.17 Hz, 3H), 0.82 (s, 3H), 0.84-0.94 (m, 6H), 0.97 (d, J=6.64 Hz, 3H), 1.11 (s, 3H), 1.15-1.58 (m, 5H), 1.65-1.71 (m, 1H), 1.73 (s, 3H), 1.75-1.89 (m, 2H), 1.90 (s, 3H), 1.91-1.98 (m, 1H), 2.07 (s, 3H), 2.08-2.13 (m, 1H), 2.19-2.31 (m, 1H), 2.39-2.51 (m, 1H), 2.63 (s, 3H), 2.65-2.71 (m, 1H), 3.02-3.09 (m, 2H), 3.09 (s, 1H), 3.23 (d, J=8.98 Hz, 1H), 3.39 (d, J=11.96 Hz, 1H), 3.45-3.60 (m, 2H), 3.73-3.84 (m, 3H), 3.88-3.96 (m, 1H), 5.76 (d, J=2.49 Hz, 1H), and 5.78-5.87 (m, 1H).

Example 50

(1S,2R,3R,4aR,6aS,7R,8R,10aR,10bR,12aR)-3-(acetyloxy)-2-(2-dimethylaminoethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (K-48)

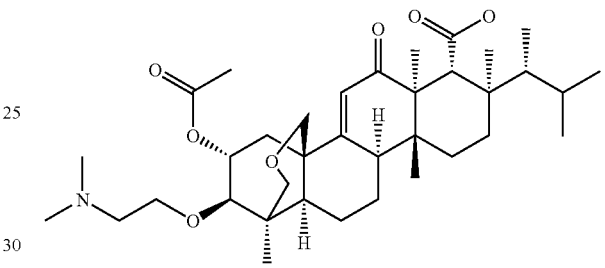

Isolated as a by-product from Example 49 (5 mg) and was converted to an acetate salt. Calculated for $C_{36}H_{57}NO_7$: 616; observed: 617 (M+H)$^+$. $^1$H NMR (400 MHz, methanol-$d_4$) δ ppm 0.78 (d, J=7.22 Hz, 3H), 0.81 (s, 3H), 0.85-0.92 (m, 6H), 0.97 (d, J=6.74 Hz, 3H), 1.11 (s, 3H), 1.14-1.37 (m, 3H), 1.36-1.58 (m, 3H), 1.65-1.71 (m, 1H), 1.72 (s, 3H), 1.82-1.92 (m, 3H), 1.94 (s, 3H), 2.07 (s, 3H), 2.08-2.12 (m, 1H), 2.20-2.29 (m, 1H), 2.41-2.50 (m, J=20.26 Hz, 1H), 2.65-2.72 (m, 7H), 2.98-3.15 (m, 3H), 3.23 (d, J=8.98 Hz, 1H), 3.40 (d, J=11.91 Hz, 1H), 3.49-3.56 (m, 2H), 3.74-3.86 (m, 2H), 3.93-4.03 (m, 1H), 5.76 (d, J=2.59 Hz, 1H), and 5.78-5.89 (m, 1H).

Example 51

(1S,2R,3R,4aR,6aS,7R,8R,10aR,10bR,12aR)-3-(acetyloxy)-2-[2-(3-aminopropylamino)-ethoxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (K-46)

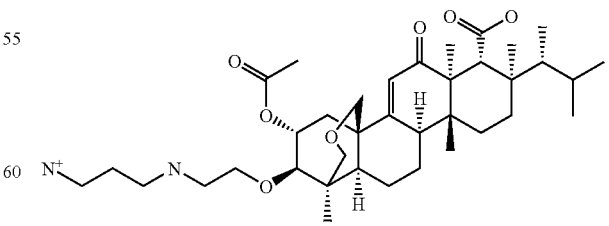

To a solution of the compound described in Example 47 (100 mg; 0.15 mmol) in methanol (8 mL) was added (3-oxopropyl)carbamic acid benzyl ester (32 mg), portion-wise, and sodium cyanoborohydride (29 mg), portion-wise. The reaction solution was stirred at room temperature for 1 hour and judged complete by TLC analysis. Ethyl acetate (80 mL) and saturated sodium bicarbonate solution (20 mL) were added. The aqueous phase was twice washed with ethyl acetate. The organic phases were combined, washed with saturated NaCl solution, dried over sodium sulfate and concentrated. The residue was flash chromatographed (silica gel; 97:3 dichloromethane:methanol). Purified material (38.2 mg) was dissolved in methanol (3 mL) and palladium hydroxide (25 mg) and acetic acid (20 μL) were added. A hydrogen atmosphere was secured (balloon) and the reaction was stirred at room temperature for 30 minutes. The reaction was judged complete by TLC analysis and the reaction contents were filtered over a pad of Celite. The filtrate was concentrated to yield the title compound as the acetate salt (33 mg). Calculated for $C_{37}H_{60}N_2O_7$: 645; observed: 646 $(M+H)^+$. $^1$H NMR (400 MHz, methanol-$d_4$) δ ppm 0.78 (d, J=7.22 Hz, 3H), 0.81 (s, 3H), 0.86-0.91 (m, 6H), 0.97 (d, J=6.69 Hz, 3H), 1.05 (d, J=19.87 Hz, 1H), 1.11 (s, 3H), 1.14-1.58 (m, 5H), 1.70 (d, J=8.49 Hz, 1H), 1.72 (s, 3H), 1.73-1.92 (m, 3H), 1.96 (s, 6H), 1.97-2.04 (m, 2H), 2.08 (s, 3H), 2.09-2.13 (m, 1H), 2.20-2.28 (m, 1H), 2.40-2.47 (m, 1H), 2.65-2.73 (m, 1H), 2.98-3.13 (m, 7H), 3.22 (d, J=8.83 Hz, 1H), 3.40 (d, J=11.86 Hz, 1H), 3.49-3.57 (m, 2H), 3.76-3.86 (m, 2H), 3.88-3.99 (m, 1H), 5.77 (d, J=2.54 Hz, 1H), and 5.80-5.89 (m, 1H).

Example 52

(1S,2R,3R,4aR,6aS,7R,8R,10aR,10bR,12aR)-3-(acetyloxy)-2-{2-[bis-(3-amino-propyl)-amino]-ethoxy}-8-[(1R)-1,2-dimethylpropyl]-1,6a,8,10a-tetramethyl-6-oxo-1,3,4,6,6a,7,8,9,10,10a, 10b,11, 12,12a-tetradecahydro-2H-1,4a-(methanooxymethano)chrysene-7-carboxylic acid (K-49)

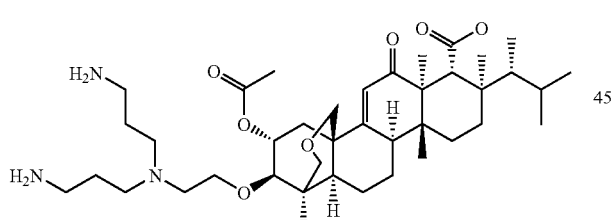

Isolated as a by-product from Example 51 (5 mg) and was converted to an acetate salt.

Calculated for $C_{40}H_{67}N_3O_7$: 702; observed: 703 $(M+H)^+$. $^1$H NMR (400 MHz, methanol-$d_4$) δ ppm 0.79 (d, J=7.22 Hz, 3H), 0.81 (s, 3H), 0.85-0.91 (m, 6H), 0.97 (d, J=6.69 Hz, 3H), 1.11 (s, 3H), 1.13-1.59 (m, 7H), 1.65-1.71 (m, 1H), 1.72 (s, 3H), 1.73-1.92 (m, 7H), 1.96 (s, 9H), 2.09 (s, 3H), 2.10-2.13 (m, 1H), 2.19-2.29 (m, 1H), 2.33-2.41 (m, 1H), 2.61-2.73 (m, 6H), 2.99 (t, J=7.20 Hz, 4H), 3.11 (s, 1H), 3.17 (d, J=8.64 Hz, 1H), 3.42 (d, J=11.62 Hz, 1H), 3.49-3.59 (m, 2H), 3.61-3.75 (m, 2H), 3.77-3.86 (m, 2H), 5.76 (d, J=2.54 Hz, 1H), and 5.78-5.87 (m, 1H).

Example 53

(1S,2R,3R,4aR,6aS,7R,8R,10aR,10bR,12aR)-3-(acetyloxy)-2-{2-[bis-(2-hydroxyethyl)-amino]-ethoxy}-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (K-50)

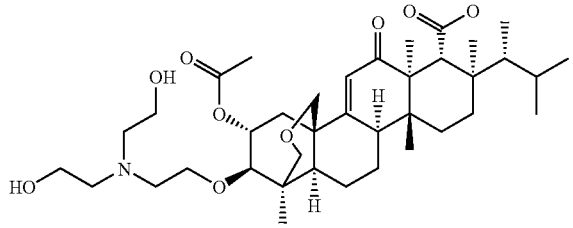

In a similar manner as described in Example 51 using hydroxyacetaldehyde (15 mg), sodium cyanoborohydride (20.2 mg), and acetic acid (21 μL) to give the title compound as an acetate salt (22 mg). Calculated for $C_{38}H_{61}NO_9$: 675; observed: 676 $(M+H)^+$. $^1$H NMR (400 MHz, methanol-$d_4$) δ ppm 0.81 (s, 3H), 0.87 (s, 3H), 0.89 (d, J=6.74 Hz, 3H), 0.97 (d, J=6.69 Hz, 3H), 1.11 (s, 3H), 1.18-1.26 (m, 3H), 1.24-1.37 (m, 4H), 1.39-1.57 (m, 4H), 1.72 (s, 3H), 1.75-1.91 (m, 3H), 1.94 (s, 3H), 1.99-2.07 (m, 2H), 2.07 (s, 3H), 2.14-2.29 (m, 2H), 2.37-2.51 (m, 1H), 2.63-2.74 (m, 1H), 2.95-3.06 (m, 3H), 3.07-3.13 (m, 1H), 3.19 (d, J=8.83 Hz, 1H), 3.32-3.45 (m, 3H), 3.65-3.83 (m, 6H), 3.88-4.01 (m, 1H), 5.76 (s, 1H), and 5.79-5.87 (m, 1H).

Example 54

(1S,2R,3R,4aR,6aS,7R,8R,10aR,10bR,12aR)-3-(acetyloxy)-2-(2-aminopropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-3)

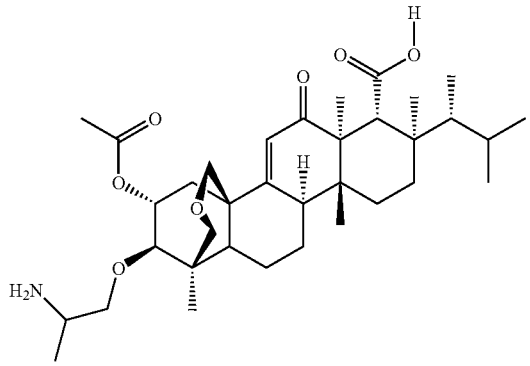

In a similar manner as described in Example 47 starting with Example 2 and yielding 37 mg. Calculated for $C_{35}H_{55}NO_7$: 601; observed: 602 $(M+H)^+$. $^1$H NMR (400 MHz, methanol-$d_4$) δ ppm 0.81 (s, 3H), 0.85-0.92 (m, J=6.93 Hz, 6H), 0.97 (d, J=6.69 Hz, 3H), 1.11 (s, 3H), 1.22-1.36 (m, J=6.88 Hz, 3H), 1.35-1.52 (m, 3H), 1.52-1.60 (m, 2H), 1.64-1.76 (m, 3H), 1.64-1.76 (m, 3H), 1.73-1.81 (m, 2H), 1.90 (s, 3H), 2.02-2.11 (m, 3H), 2.17-2.32 (m, 2H), 2.40-2.53 (m, 1H), 2.62-2.77 (m, 1H), 3.11 (s, 1H), 3.26 (d, J=8.98 Hz, 1H), 3.34-3.49 (m, 3H), 3.53 (s, 2H), 3.70-3.90 (m, J=46.76 Hz, 2H), 5.77 (s, 1H), and 5.80-5.92 (m, 1H).

Example 55

(1S,2R,3R,4aR,6aS,7R,8R,10aR,10bR,12aR)-3-(acetyloxy)-2-(2-guanidinopropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-2)

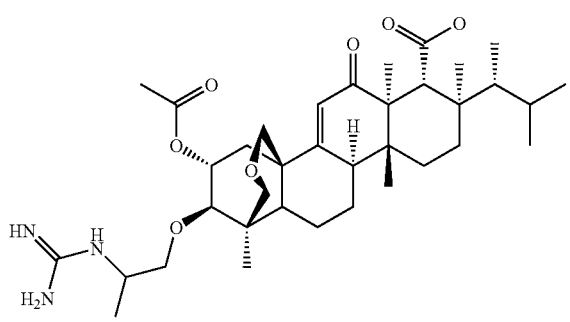

The title compound (23 mg) was prepared in a similar manner as described in Example 48 using the compound described in Example 54 (75 mg). Calculated for $C_{36}H_{57}N_3O_7$: 643; observed: 644 (M+H)$^+$. $^1$H NMR (400 MHz, methanol-$d_4$) δ ppm 0.81 (s, 3H), 0.86 (s, 3H), 0.89 (d, J=6.64 Hz, 3H), 0.97 (d, J=6.74 Hz, 3H), 1.11 (s, 3H), 1.15-1.26 (m, 3H), 1.27-1.40 (m, 2H), 1.42-1.57 (m, 5H), 1.63-1.82 (m, 3H), 1.70-1.80 (m, 2H), 1.82-1.93 (m, 4H), 2.06 (s, 3H), 2.16-2.28 (m, 1H), 2.32-2.52 (m, 1H), 2.69 (d, J=12.79 Hz, 1H), 3.11 (s, 1H), 3.20 (t, J=8.86 Hz, 2H), 3.41 (d, J=11.76 Hz, 1H), 3.52 (s, 2H), 3.64 (d, 1H), 3.68-3.85 (m, 3H), 5.76 (s, 1H), and 5.80-5.94 (m, 1H).

Example 56

(1S,2R,3R,4aR,6aS,7R,8R,10aR,10bR,12aR)-3-(acetyloxy)-2-(2-acetimidoylaminopropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-59)

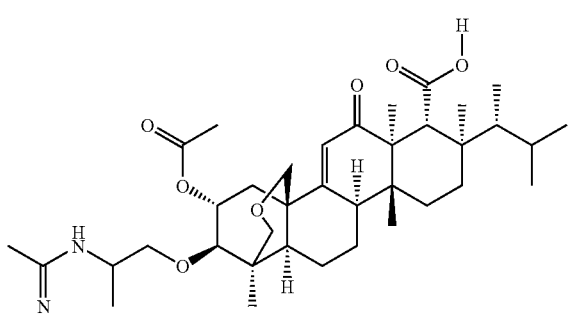

To a solution of the compound described in Example 54 (90 mg) in acetonitrile (5 mL) was added mercuric chloride (560 mg), triethylamine (2.5 mL), and methyl-2-methyl-thiopseudourea triflate (650 μL). The reaction solution was refluxed for 7 hours. Additional methyl-2-methyl-thiopseudourea (3 mL), mercuric chloride (400 mg) and triethylamine (1 mL) were added and the reaction solution was refluxed for 3 hours and judged complete by TLC analysis. The reaction mixture was filtered through Celite and the filtrate was concentrated. The residue was flash chromatographed (95:5 dichloromethane:methanol) and the residue was dissolved in the ethyl acetate. The organic phase was washed with sodium bicarbonate solution, dried over sodium sulfate, and concentrated. The residue was finally purified by reverse phase HPLC to yield the title compound (1.5 mg). Calculated for $C_{37}H_{58}N_2O_7$: 642; observed: 643 (M+H)$^+$. $^1$H NMR (400 MHz, methanol-$d_4$) δ ppm 0.81 (s, 3H), 0.85 (s, 3H), 0.88 (d, J=6.69 Hz, 3H), 0.97 (d, J=6.74 Hz, 3H), 1.11 (s, 3H), 1.24 (d, J=6.69 Hz, 3H), 1.26-1.41 (m, 4H), 1.41-1.61 (m, 5H), 1.71 (s, 3H), 1.75-1.81 (m, 1H), 1.89-1.96 (m, 3H), 1.92 (s, 3H), 2.21 (d, J=5.03 Hz, 3H), 2.25-2.29 (m, 1H), 2.31-2.45 (m, 1H), 3.11 (s, 1H), 3.17 (d, J=8.74 Hz, 1H), 3.34-3.45 (m, 2H), 3.47-3.57 (m, 2H), 3.69-3.76 (m, 2H), 3.82-3.87 (m, 1H), 3.87-3.98 (m, 1H), 5.76 (s, 1H), 5.82-5.92 (m, 1H), and 8.34-8.69 (m, 1H).

Example 57

(1S,2R,3R,4aR,6aS,7R,8R,10aR,10bR,12aR)-3-(acetyloxy)-2-{2-[(2-amino-acetimidoyl)-amino]-propoxy}8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-6)

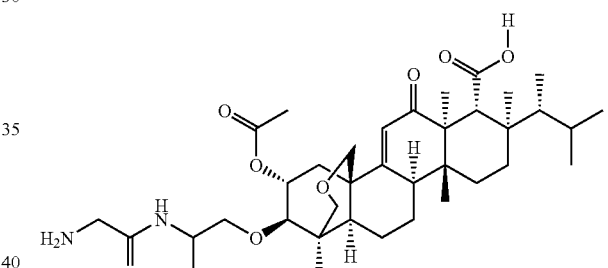

To a solution of the compound described in Example 54 (99 mg, 0.16 mmol) in dimethylformamide (5 mL) was added 2-benzyloxycarbonylamino-acetimidic acid ethyl ester (92 mg) and triethylamine (100 μL). The reaction solution was stirred at room temperature for 16 hours. The reaction was judged nearly complete by LCMS analysis and the reaction contents were concentrated. The residue was purified by reverse phase HPLC (75:25 to 100:0 methanol (0.05% acetic acid:water).

Purified material (37 mg) was dissolved in methanol (3 mL) and palladium hydroxide (80 mg) was added. A hydrogen atmosphere was secured (balloon) and the reaction stirred at room temperature for 1 hour. The reaction was judged complete and the reaction contents were filtered through a pad of Celite. The filtrate was concentrated to yield the title compound (28 mg). Calculated for $C_{37}H_{59}N_3O_7$: 657; observed: 658 (M+H)$^+$. $^1$H NMR (400 MHz, methanol-$d_4$) δ ppm 0.81 (s, 3H), 0.86 (s, 3H), 0.89 (d, J=6.69 Hz, 3H), 0.97 (d, J=6.69 Hz, 3H), 1.11 (s, 3H), 1.21-1.33 (m, 6H), 1.38-1.61 (m, J=38.22 Hz, 4H), 1.61-1.76 (m, 3H), 1.72-1.81 (m, 2H), 1.83-1.91 (m, 2H), 1.93 (s, 3H), 2.07 (s, 3H), 2.18-2.31 (m, 1H), 2.27-2.44 (m, 1H), 2.59-2.75 (m, 1H), 3.11 (s, 1H), 3.19 (d, J=8.88 Hz, 1H), 3.39 (d, J=11.86 Hz, 1H), 3.59 (s, 2H), 3.67-3.80 (m, 3H), 4.10-4.33 (m, 2H), 5.75 (s, 1H), 5.81-5.97 (m, 1H), and 7.98 (s, 1H).

Example 58

(1S,2R,3R,4aR,6aS,7R,8R,10aR,10bR,12aR)-3-(acetyloxy)-2-[2-[(N'-methylguanidino)-propoxy]8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-5)

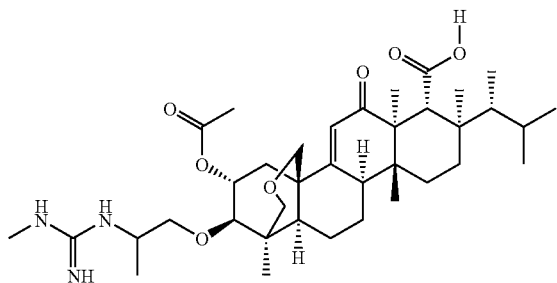

The title compound (23 mg, isolated as an acetate salt) was prepared in a similar manner as described in Example 28 using the compound described in Example 54 (100 mg). Calculated for $C_{37}H_{59}N_3O_7$: 658; observed: 659 (M+H4)+. $^1$H NMR (400 MHz, methanol-$d_4$) δ ppm 0.78 (d, J=7.17 Hz, 3H), 0.81 (s, 3H), 0.83-0.87 (m, 3H), 0.88 (d, J=6.69 Hz, 3H), 0.97 (d, J=6.69 Hz, 3H), 1.11 (s, 3H), 1.16-1.25 (m, 4H), 1.25-1.58 (m, 10H), 1.64-1.80 (m, 5H), 1.90 (s, 5H), 2.04 (s, 3H), 2.18-2.33 (m, 1H), 2.34-2.48 (m, 1H), 2.62-2.74 (m, 1H), 2.84 (s, 3H), 3.07-3.12 (m, 1H), 3.20 (t, 1H), 3.36-3.45 (m, 1H), 3.47-3.54 (m, 2H), 3.55-3.63 (m, 1H), 3.67-3.82 (m, 3H), 5.71-5.78 (m, 1H), and 5.77-5.94 (m, 1H).

Example 59

(1S,2R,3R,4aR,6aS,7R,8R,10aR,10bR,12aR)-3-(acetyloxy)-2-[2-(3-aminopropylamino)-propoxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-31)

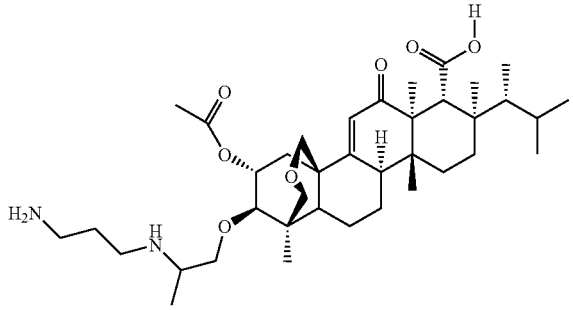

The title compound (24 mg, isolated as an acetate salt) was prepared in a similar manner as described in Example 51 using the compound described in Example 54 (85 mg). Calculated for $C_{38}H_{62}N_2O_7$: 658; observed: 659 (M+H)+. $^1$H NMR (400 MHz, methanol-$d_4$) δ ppm 0.78 (d, J=7.22 Hz, 3H), 0.81 (s, 3H), 0.86 (d, J=2.98 Hz, 3H), 0.88 (d, J=6.74 Hz, 3H), 0.91-0.94 (m, 2H), 0.97 (d, J=6.64 Hz, 3H), 1.11 (s, 3H), 1.14-1.20 (m, J=6.49 Hz, 1H), 1.21-1.44 (m, 5H), 1.45-1.59 (m, 3H), 1.64-1.72 (m, 2H), 1.73 (s, 3H), 1.76-1.82 (m, 2H), 1.82-1.90 (m, 3H), 1.91 (s, 6H), 2.07 (s, 4H), 2.17-2.32 (m, 2H), 2.34-2.48 (m, 1H), 2.63-2.74 (m, 1H), 2.80-2.97 (m, 1H), 2.96-3.06 (m, 2H), 3.07-3.12 (m, 1H), 3.14-3.24 (m, 2H), 3.35-3.45 (m, 1H), 3.47-3.56 (m, 2H), 3.55-3.67 (m, 2H), 3.68-3.84 (m, 2H), 5.76-5.81 (m, 1H), and 5.81-5.90 (m, 1H).

Example 60

(1S,2R,3R,4aR,6aS,7R,8R,10aR,10bR,12aR)-3-(acetyloxy)-2-[2-(5-amino-2H-[1,2,4]-triazol-3-ylamino)-propoxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-9)

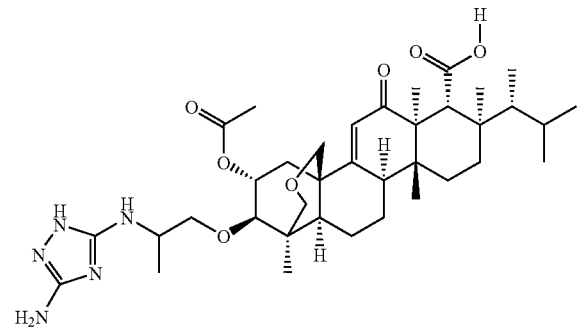

In a similar manner as described in Example 43 using the compound described in Example 55 was obtained the title compound. Calculated for $C_{37}H_{57}N_5O_7$: 683; observed: 684 (M+H)+. $^1$H NMR (400 MHz, methanol-$d_4$) δ ppm 0.79 (s, 3H), 0.81 (s, 3H), 0.88 (d, J=6.64 Hz, 3H), 0.96 (d, J=6.69 Hz, 3H), 1.11 (s, 3H), 1.16-1.24 (m, J=5.76, 5.76 Hz, 5H), 1.26-1.36 (m, 2H), 1.45-1.59 (m, 4H), 1.71 (s, 3H), 1.73-1.76 (m, 1H), 1.83-1.98 (m, 4H), 2.04 (s, 3H), 2.26 (s, 1H), 2.37-2.48 (m, 1H), 2.62-2.72 (m, 1H), 3.11 (s, 1H), 3.15 (d, J=9.08 Hz, 1H), 3.38 (s, 1H), 3.46-3.57 (m, 2H), 3.54-3.60 (m, 1H), 3.64-3.73 (m, 3H), 3.74-3.83 (m, 1H), 5.76 (s, 1H), and 5.79-5.86 (m, 1H).

Example 61

(1S,2R,3R,4aR,6aS,7R,8R,10aR,10bR,12aR)-3-(acetyloxy)-2-(2-amino-2-phenylethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-13)

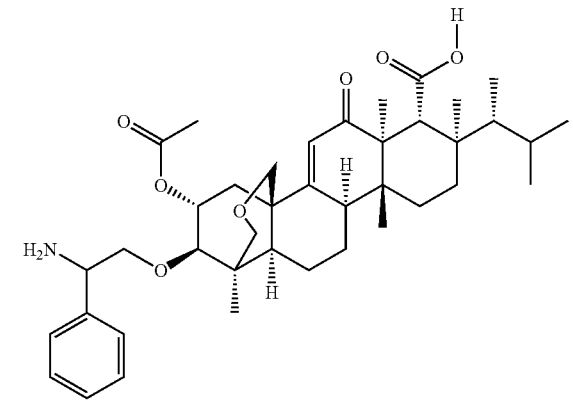

(a) Chromium dichloride (216 mg) and nickel dichloride (catalytic) were added to a round-bottomed flask under argon, anhydrous dimethylformamide (5 mL) was added and the mixture was stirred at room temperature for fifteen minutes.

To this mixture was added a solution of the compound described in Example 1(b) (200 mg) and iodobenzene (110 µL) in anhydrous dimethylformamide (5 mL). The reaction mixture was stirred at room temperature for 22 hours and judged complete by TLC. Ethyl acetate (50 mL) was added to the reaction solution and the organic phase was washed with water and saturated NaCl solution, dried over sodium sulfate, and concentrated. The residue was flash chromatographed (silica gel; 91:9 heptane:ethyl acetate) to yield a benzyl alcohol (100 mg). This transformation was repeated using 365 mg material and yielding 261 mg material.

(b) To a solution of the alcohol from above (361 mg) in tetrahydrofuran (15 mL) was added triphenylphosphine (640 mg). The reaction solution was stirred for 15 minutes and then chilled to −25° C. Diethyl azodicarboxylate (384 µL) and diphenylphosphoryl azide (525 µL) were added. The reaction solution was stirred at −25° C. for 6 hours and then, warmed to room temperature, stirred for 16 hours. The reaction solution was concentrated and the residue was flash chromatographed (94:6 heptane:ethyl acetate).

(c) The benzyl amine from above (640 mg) was dissolved in ethyl acetate (5 mL) and 10% palladium on carbon (500 mg) was added. A solution of Boc-anhydride (700 mg) in ethyl acetate (25 mL) was added, a hydrogen atmosphere (balloon) was secured and the reaction mixture was stirred at room temperature for 60 hours and judged complete by TLC analysis. The reaction mixture was filtered over a pad of Celite and the filtrate was concentrated. The residue was flash chromatographed (88:12 heptane:ethyl acetate) to yield the desired Boc protected amine (260 mg).

The protected amino compound from above was subjected to the chromium trioxide oxidation in a similar manner as described in Intermediate 6 (c) and removal of the Boc protecting group to afford the title compound as a trifluoroacetate salt (19 mg). Calculated for $C_{40}H_{57}NO_7$: 663; observed: 664 (M+H)$^+$. $^1$H NMR (400 MHz, chloroform-d) δ ppm 0.73-0.78 (m, 6H), 0.79 (s, 3H), 0.85 (d, J=6.59 Hz, 3H), 0.94 (d, J=6.64 Hz, 3H), 1.13 (s, 3H), 1.23-1.40 (m, 5H), 1.44-1.93 (m, 10H), 2.02 (d, J=9.76 Hz, 3H), 2.13-2.27 (m, 1H), 2.40-2.58 (m, 2H), 3.07 (d, J=8.88 Hz, 2H), 3.16 (s, 1H), 3.31 (d, J=11.76 Hz, 1H), 3.43 (d, J=11.47 Hz, 1H), 3.57 (d, J=11.18 Hz, 1H), 3.63-3.87 (m, 3H), 4.07-4.25 (m, 1H), 5.80 (s, 1H), 5.81-5.96 (m, 1H), and 7.29-7.42 (m, 5H).

Example 62

(1S,2R,3R,4aR,6aS,7R,8R,10aR,10bR,12aR)-3-(acetyloxy)-2-(2,5-diaminopentyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-46)

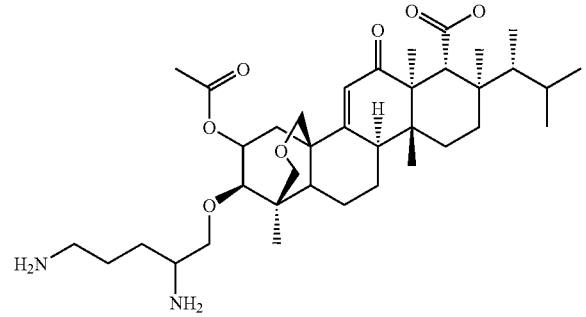

In a similar manner as described in Example 61(a), from the aldehyde described in Example 1(b) (700 mg) and tribu-tyl-((E)-3-iodo-allyloxy)-silane (1.05 g) was obtained the desired allyl alcohol (400 mg).

The alcohol was transformed to an amino group in a similar manner as described in Example 61 (b).

The amino compound from above (572 mg) was dissolved in anhydrous tetrahydrofuran (10 mL) and tetrabutylammonium fluoride (1.0 M in tetrahydrofuran; 3 mL) was added. The reaction solution was stirred at room temperature for 16 hours and judged complete by TLC analysis. Water (50 mL) was added to the reaction mixture and the aqueous phase was twice washed with ethyl acetate. The organic phases were combined, washed with saturated NaCl solution, dried over magnesium sulfate, and concentrated. The residue was flash chromatographed (silica gel; 84:16 heptane:ethyl acetate) to give the desired alcohol (477 mg).

The above amino alcohol was converted to a diamino compound in a similar manner as described in Example 61(b). The resulting diamine was subjected to the Boc protection sequence described in Example 61(c) and the protected amino compound from above was subjected to the chromium trioxide oxidation in a similar manner as described in Intermediate 6(c) and removal of the Boc protecting group to afford the title compound as a trifluoroacetate salt (18 mg). Calculated for $C_{37}H_{60}N_2O_7$: 644; observed: 645 (M+H)$^+$. $^1$H NMR (400 MHz, methanol-d$_4$) δ ppm 0.79 (d, J=7.32 Hz, 3H), 0.81 (s, 3H), 0.84-0.91 (m, 6H), 0.97 (d, J=6.54 Hz, 3H), 1.11 (s, 3H), 1.15-1.60 (m, 5H), 1.63-1.82 (m, 8H), 1.82-1.98 (m, 2H), 2.03-2.11 (m, 3H), 2.17-2.30 (m, 1H), 2.32-2.55 (m, 1H), 2.90-3.03 (m, 1H), 3.08-3.19 (m, 1H), 3.20-3.28 (m, 1H), 3.34-3.62 (m, 3H), 3.62-3.95 (m, 3H), 5.75-5.78 (m, 1H), and 5.78-5.92 (m, 1H).

Example 63

(1S,2R,3R,4aR,6aS,7R,8R,10aR,10bR,12aR)-3-(acetyloxy)-2-(2-amino-3-hydroxypropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-23)

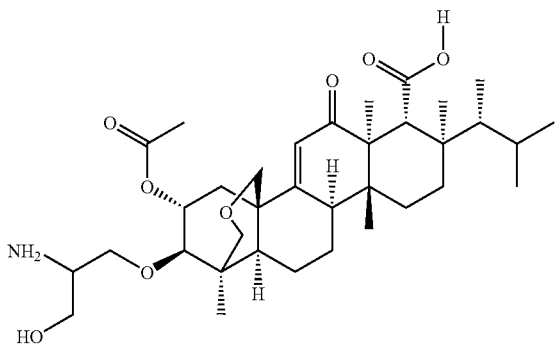

(a) The allyl ether described in Example 1 (a) (494 mg; 0.76 mmol) was dissolved in acetone (32 mL) and water (8 mL). To this solution was added 4-methylmorpholine N-oxide (230 mg) and osmium tetroxide (4%; 0.95 mL). The reaction solution stirred at room temperature for 16 hours and was judged complete by TLC analysis. Water (40 mL) was added and the acetone was removed under reduced pressure. The aqueous phase was washed with ethyl acetate (75 mL); the organic phase was washed with saturated NaCl solution, dried over sodium sulfate, and concentrated. The residue was flash chromatographed (silica gel; 60:40 heptane:ethyl acetate) to give the desired diol (490 mg).

(b) The diol from above (490 mg) was dissolved in dichloromethane (15 mL) and the solution was chilled to 0° C. Tert-butyldiphenylsilyl chloride (210 µL) was added; imidazole (110 mg) and 4-dimethylaminpyridine (catalytic) in a solution of dichloromethane (5 mL) was added and the reaction stirred for 2 hours. The reaction solution was gradually warmed to room temperature and stirred for 1 hour. The reaction was judged complete by TLC analysis and dichloromethane (30 mL) and water (50 mL) were added. The aqueous phase was washed with dichloromethane; the organic phases were combined, washed with saturated NaCl solution, and concentrated. The residue was flash chromatographed (silica gel; 88:12 heptane:ethyl acetate) to give a mono-silyl ether (600 mg).

(c) Hydroxyether (600 mg) from above was converted to an amino derivative in a similar manner as described in Example 61 (b).

(d) The amino compound described above was converted to a Boc protected derivative in a similar manner as described in Example 61(c).

(e) A portion of this material (250 mg) was dissolved in dichloromethane (10 mL) and the solution was chilled to 0° C. Trifluoroacetic acid (10 mL) was added dropwise and the reaction solution stirred for 45 minutes. The reaction was judged complete by TLC analysis and the reaction contents were concentrated. The residue was dissolved in acetone (10 mL) and water (5 mL) and carbonic acid benzyl ester 2,5-dioxo-pyrrolidin-1-yl ester (80 mg) and sodium bicarbonate (250 mg) were added. The reaction mixture stirred at room temperature for 3 hours and was judged complete by TLC analysis. The acetone was removed under reduced pressure and ethyl acetate (50 mL) and water (30 mL) were added. The organic phase was washed with saturated NaCl solution, dried over sodium sulfate, and concentrated. The residue was flash chromatographed (silica gel; 80:20 heptane:ethyl acetate). The protected amino derivative from above (200 mg) was subjected to the oxidation procedure in the manner described in Intermediate 6(c) using chromium trioxide (0.82 g) and dimethylpyrazole (0.79 g) to afford the desired enone (55 mg). The next transformation was done twice: A portion of this material (27 mg) was dissolved in tetrahydrofuran (3 mL) and the solution was chilled to 0° C. Acetic acid (16 µL) and tetrabutylammonium fluoride (1.0 M in tetrahydrofuran; 140 µL) were added and the reaction stirred, warming gradually to room temperature for 6 hours. The reaction was judged complete by TLC analysis and the reaction contents were concentrated. The residue was flash chromatographed (1:1 heptane:ethyl acetate; then 95:5 dichloromethane:methanol) to yield a total of 33 mg purified material which was submitted to the hydrogenolysis conditions outlined in Example 1 (e) to yield the title compound as an acetate salt (22 mg). Calculated for $C_{35}H_{55}NO_8$: 617; observed: 618 (M+H)$^+$. $^1$H NMR (400 MHz, methanol-$d_4$) δ ppm 0.78 (d, J=7.17 Hz, 3H), 0.82 (s, 3H), 0.87 (s, 3H), 0.88 (d, J=6.88 Hz, 3H), 0.97 (d, J=6.59 Hz, 3H), 1.12 (s, 3H), 1.18-1.60 (m, 6H), 1.65-1.83 (m, 5H), 2.07 (s, 3H), 2.18-2.35 (m, 1H), 2.41-2.53 (m, 1H), 2.63-2.73 (m, 1H), 3.53 (s, 2H), 3.59-3.94 (m, 6H), 5.76 (d, J=2.49 Hz, 1H), and 5.78-5.88 (m, 1H).

Example 64

(1S,2R,3R,4aR,6aS,7R,8R,10aR,10bR,12aR)-3-(acetyloxy)-2-(2-amino-3-methoxypropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-60)

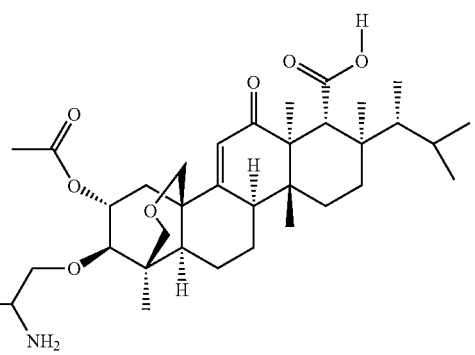

In a similar manner as described in Example 1(a), from Intermediate 3 (2.25 g; 3.7 mmol) and 3-chloro-2-chloromethyl propene (4.8 g) was obtained the desired chloromethyl compound, (1.37 g). This chloromethyl derivative (1.37 g) was dissolved in dimethylformamide (43 mL) and methanol (408 µL) was added. Sodium hydride (416 mg) was added and the reaction was stirred at room temperature for 1.5 hours. The reaction was judged complete by TLC analysis and ethyl acetate and water were slowly added until gas evolution ceased. Additional ethyl acetate and water were added; the organic phase was washed with water, dried over sodium sulfate, and concentrated. Material (1.36 g) was submitted to conditions outlined in Example 1 (b), (c) and (d) to yield an amino acid. The amino group was protected using benzyl chloroformate, oxidized and deprotected in a similar manner as described in Example 47 to yield the title compound as an acetate salt (66 mg). Calculated for $C_{36}H_{57}NO_8$: 631; observed: 632 (M+H)$^+$. $^1$H NMR (400 MHz, methanol-$d_4$) δ ppm 0.78 (d, J=7.22 Hz, 3H), 0.81 (s, 3H), 0.85-0.90 (m, 6H), 0.97 (d, J=6.69 Hz, 3H), 0.99-1.10 (m, 1H), 1.11 (s, 3H), 1.20-1.58 (m, 4H), 1.67-1.71 (m, 1H), 1.72 (s, 3H), 1.73-1.91 (m, 4H), 1.91 (s, 3H), 2.06 (s, 3H), 2.07-2.11 (m, 1H), 2.17-2.29 (m, 1H), 2.40-2.50 (m, 1H), 2.63-2.73 (m, 1H), 3.11 (s, 1H), 3.21 (d, J=8.79 Hz, 1H), 3.38 (s, 3H), 3.46-3.56 (m, 5H), 3.65-3.87 (m, 4H), 5.76 (d, J=2.54 Hz, 1H), and 5.78-5.87 (m, 1H).

Example 65

(1S,2R,3R,4aR,6aS,7R,8R,10aR,10bR,12aR)-3-(acetyloxy)-2-(2-dimethylamino-3-methoxypropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-41)

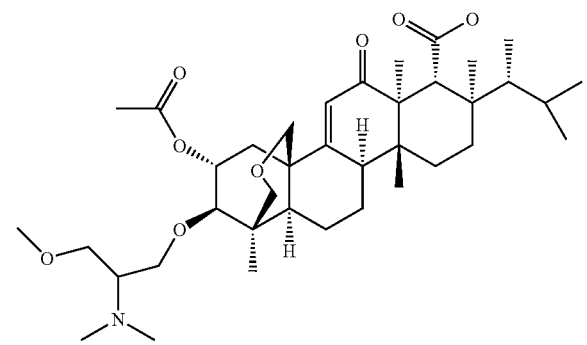

In a similar manner as described in Example 49, using the compound described in Example 64 was obtained the title compound, which was isolated as the acetate salt. Calculated for $C_{38}H_{61}NO_8$: 659; observed: 660 (M+H)$^+$. $^1$H NMR (400 MHz, methanol-$d_4$) δ ppm 0.79 (d, J=7.17 Hz, 3 H), 0.81 (s, 3H), 0.85-0.94 (m, 6H), 0.97 (d, J=6.74 Hz, 3H), 1.11 (s, 3H), 1.17-1.25 (m, 1H), 1.28-1.59 (m, 5H), 1.72 (s, 3H), 1.73-1.82 (m, 2H), 1.85-1.95 (m, 2H), 1.96 (s, 3H), 2.08 (s, 3H), 2.09-2.13 (m, 1H), 2.20-2.29 (m, 1H), 2.42-2.50 (m, 1H), 2.65-2.73 (m, 1H), 2.75-2.81 (m, 6H), 3.11 (s, 1H), 3.20-3.26 (m, 1H), 3.37-3.45 (m, 4H), 3.49-3.57 (m, 2H), 3.65 (d, J=5.32 Hz, 2H), 3.68-3.77 (m, 2H), 3.83-3.91 (m, 1H), 4.00-4.00 (m, 1H), 5.76 (d, J=2.64 Hz, 1H), and 5.78-5.88 (m, 1H).

Example 66

(1S,2R,3R,4aR,6aS,7R,8R,10aR,10bR,12aR)-3-(acetyloxy)-2-(2-amino-3-isopropoxypropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-44)

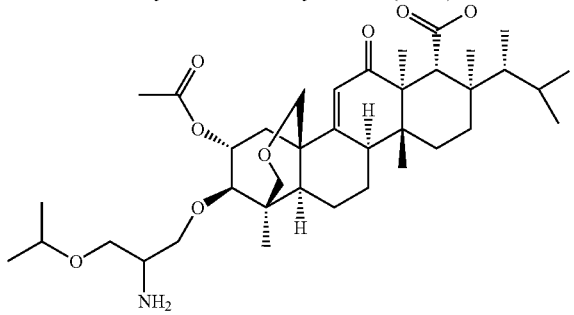

In a similar manner as described in Example 64, using isopropanol in place of methanol, was obtained the title compound, which was isolated as the acetate salt. Calculated for $C_{38}H_{61}NO_8$: 659; observed: 660 (M+H)$^+$. $^1$H NMR (400 MHz, methanol-$d_4$) δ ppm 0.78 (d, J=7.22 Hz, 3H), 0.81 (s, 3H), 0.87 (s, 3H), 0.89 (d, J=6.74 Hz, 3H), 0.97 (d, J=6.74 Hz, 3H), 1.11 (s, 3H), 1.15-1.19 (m, 6H), 1.20-1.35 (m, 3H), 1.36-1.58 (m, 4H), 1.72 (s, 3H), 1.74-1.90 (m, 4H), 1.91 (s, 3H), 2.06-2.08 (m, 4H), 2.21-2.29 (m, 1H), 2.42-2.49 (m, 1H), 2.65-2.72 (m, 1H), 3.10 (s, 1H), 3.21 (d, J=8.83 Hz, 1H), 3.39 (d, J=11.91 Hz, 1H), 3.47-3.55 (m, 3H), 3.55-3.71 (m, 3H), 3.71-3.87 (m, 3H), 5.76 (d, J=2.59 Hz, 1H), and 5.78-5.86 (m, 1H).

Example 67

(1S,2R,3R,4aR,6aS,7R,8R,10aR,10bR,12aR)-3-(acetyloxy)-2-(2-dimethylamino-3-isopropoxypropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-47)

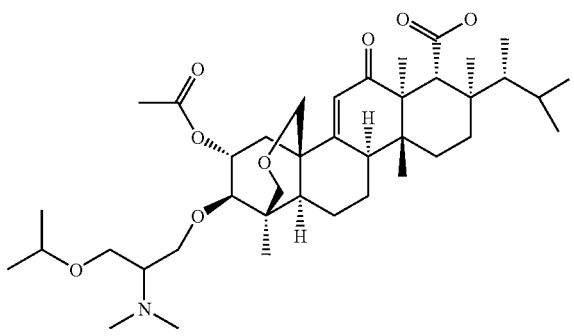

Prepared in a similar manner as described in Example 49 using the compound described in Example 66 and isolated as an acetate salt. Calculated for $C_{40}H_{65}NO_8$: 687; observed: 688 (M+H)$^+$. $^1$H NMR (400 MHz, methanol-$d_4$) δ ppm 0.78 (d, J=7.22 Hz, 3H), 0.81 (s, 3H), 0.86-0.93 (m, 6H), 0.97 (d, J=6.69 Hz, 3H), 1.11 (s, 3H), 1.17 (s, 3H), 1.19 (s, 3H), 1.20-1.35 (m, 5H), 1.36-1.58 (m, 3H), 1.72 (s, 3H), 1.73-1.93 (m, 3H), 1.94 (s, 3H), 2.08 (s, 3H), 2.09-2.13 (m, 1H), 2.19-2.28 (m, 1H), 2.40-2.52 (m, 1H), 2.73 (s, 3H), 2.76 (s, 3H), 3.11 (s, 1H), 3.16-3.27 (m, 1H), 3.41 (d, J=11.37 Hz, 1H), 3.51-3.55 (m, 2H), 3.59-3.77 (m, 5H), 3.80-3.92 (m, 1H), 3.98-4.06 (m, 1H), 5.76 (d, J=2.39 Hz, 1H), and 5.79-5.89 (m, 1H).

Example 68

(1S,2R,3R,4aR,6aS,7R,8R,10aR,10bR,12aR)-3-(acetyloxy)-2-(2-aminomethyl-3-dimethylaminopropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (E-1)

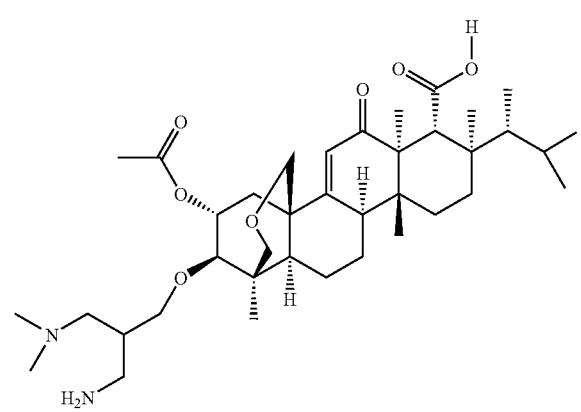

(a) To a solution of Intermediate 6 (1.26 g; 2.0 mmol) in dimethylformamide (70 mL) was added bromomethylacrilnitrile (2.19 g) and sodium hydride (1.12 g; 60% dispersion in mineral oil). The reaction solution stirred at room temperature for 11 minutes and was judged complete by TLC analysis. Dichloromethane (200 mL) was added to the reaction solution and the reaction solution was filtered over a pad of silica gel. The filtrate was washed with water; the aqueous phase was washed with ethyl acetate. The organic phases were combined, dried over magnesium sulfate, and concentrated. The residue was flash chromatographed (silica gel; 95:5 heptane:ethyl acetate) to yield the desired compound (840 mg).

(b) A portion of this material (0.23 g) was dissolved in ethyl acetate (6 mL) and methanol (6 mL). Dimethylamine (2.0 M in tetrahydrofuran; 4 mL) was added and the reaction solution stirred at room temperature for 1 hour. The reaction was judged complete by TLC analysis and the reaction contents were concentrated. The residue was flash chromatographed (silica cartridge (5 g); 100:0 to 97:3 dichloromethane:methanol) to give purified material (211 mg).

(c) A portion of this material (0.12 g) was submitted to conditions as in Example 1(e) to yield the title compound as the acetate salt (31 mg). Calculated for $C_{38}H_{62}NO_7$: 658; observed: 659 (M+H)$^+$. $^1$H NMR (400 MHz, methanol-$d_4$) δ ppm 0.74-0.85 (m, 9H), 0.89 (d, J=6.59 Hz, 3H), 0.97 (d, J=6.69 Hz, 3H), 1.11 (s, 3H), 1.16-1.58 (m, 6H), 1.72 (s, 3H), 1.73-1.81 (m, 2H), 1.83-1.92 (m, 3H), 1.95 (s, 6H), 2.04-2.10 (m, 3H), 2.19-2.28 (m, 1H), 2.32 (s, 6H), 2.33-2.52 (m, 2H), 2.57-2.72 (m, 1H), 2.98-3.18 (m, 5H), 3.35-3.43 (1H), 3.47-3.60 (m, 4H), 3.62-3.76 (m, 2H), 5.76-5.79 (m, 1H), and 5.79-5.88 (m, 1H).

Example 69

(1S,2R,3R,4aR,6aS,7R,8R,10aR,10bR,12aR)-3-(acetyloxy)-2-(3-amino-2-hydroxy-2-hydroxymethylpropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (B-1)

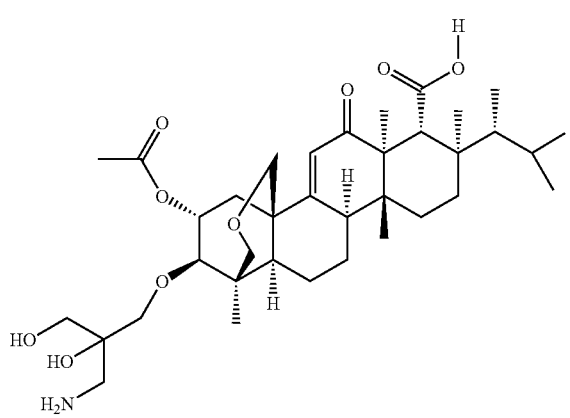

The compound described in Example 68 (a) (100 mg) was dissolved in tetrahydrofuran (8 mL) and water (2 mL). Osmium tetroxide (4%; 400 µL) and 4-methylmorpholine N-oxide (192 mg) were added and the reaction solution stirred for 14 hours. Additional osmium tetraoxide (4%; 200 µL) was added and the reaction solution stirred for 8 hours; the reaction was judged complete by TLC analysis. Ethyl acetate (50 mL) and saturated sodium sulfite solution (25 mL) were added. The aqueous phase was twice washed with ethyl acetate. The organic phases were combined, dried over magnesium sulfate, and concentrated. The residue was flash chromatographed (silica gel; 97:3 dichloromethane:methanol). Purified material (61 mg) was submitted to the hydrogenolysis conditions outlined in Example 1 (e) to yield the title compound as an acetate salt (32 mg). Calculated for $C_{36}H_{57}NO_9$: 648; observed: 649 (M+H)$^+$. $^1$H NMR (400 MHz, methanol-$d_4$) δ ppm 0.70 (d, J=7.22 Hz, 3H), 0.73 (s, 3H), 0.76-0.83 (m, 6H), 0.88 (d, J=6.69 Hz, 3H), 1.03 (s, 3H), 1.08-1.33 (m, 3H), 1.33-1.50 (m, 2H), 1.63 (s, 3H), 1.64-1.75 (m, 2H), 1.74-1.84 (m, 3H), 1.86 (s, 3H), 1.99 (s, 3H), 2.00-2.07 (m, 1H), 2.10-2.21 (m, 1H), 2.26-2.37 (m, 1H), 2.50-2.66 (m, 1H), 2.87-2.99 (m, 1H), 2.99-3.04 (m, 2H), 3.04-3.12 (m, 1H), 3.29-3.36 (m, 1H), 3.44 (m, 3H), 3.49-3.55 (m, 2H), 3.55-3.63 (m, 1H), 3.62-3.71 (m, 1H), 5.69 (d, J=2.54 Hz, 1H), and 5.72-5.83 (m, 1H).

The compounds in Table 1 were prepared using a general procedure involving alkylation of Intermediate 3 with an appropriate allyl halide; conversion to a ketone; reductive amination with an appropriate amine; exchange of methoxy to acetate; debenzylation of the acid protecting group; protection of the amino group; allylic oxidation and final deprotection. The final amino compounds can be optionally subjected to reductive alkylation conditions to afford alkylated amino derivatives. Said procedures are similar to those described in Examples 1 and Example 49.

TABLE 1

| Ex./Cpd | $R^{III}$ | $R^I$ | $R^{II}$ | Name | MS | $^1$H NMR (400 MHz, δ, ppm) |
|---|---|---|---|---|---|---|
| 70/D-12 | Me | | thieno[2,3-c] | (1S, 2R, 3R, 4aR, 6aS, 7R, 8R, 10aR, 10bR, 12aR)-3-(acetyloxy)-2-(2-thieno-[2,3-c]-pyrrol-5-ylpropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 708 (M + H)$^+$ | (chloroform-d) 0.71 (s, 3 H), 0.73 (s, 3 H), 0.79 (d, J = 6.64 Hz, 3 H), 0.88 (d, 3 H), 1.07 (s, 3 H), 1.19 (s, 5 H), 1.36-1.54 (m, 3 H), 1.51-1.61 (m, 2 H), 1.67-1.83 (m, 3 H), 1.89 (s, 3 H), 2.13 (s, 1 H), 2.27 (s, 3 H), 2.36-2.52 (m, 2 H), 2.94 (dd, 1 H), 3.11 (s, 1 H), 3.23 (d, 1 H), 3.37 (d, 1 H), 3.49 (d, 1 H), 3.69 (s, 3 H), 3.82 (s, 2 H), 4.20-4.36 (m, 1 H), 6.77 (d, J = 1.71 Hz, 1 H), 6.82 (s, 2 H), and 6.88-6.90 (m, 1 H). |

TABLE 1-continued

| Ex./Cpd | R<sup>III</sup> | R<sup>I</sup> | R<sup>II</sup> | Name | MS | $^1$H NMR (400 MHz, δ, ppm) |
|---|---|---|---|---|---|---|
| 71/ D-20 | Me | H | *-CH₂-(5-hydroxymethylfuran-2-yl) | (1S, 2R, 3R, 4aR, 6aS, 7R, 8R, 10aR, 10bR, 12aR)-3-(acetyloxy)-2-{2-[(5-hydroxymethyl furan-2-ylmethyl)-amino]-propoxy}-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy methano)chrysene-7-carboxylic acid | 711 (M + H)⁺ | (methanol-d₄) 0.81 (s, 3 H), 0.86 (s, 2 H), 0.89 (d, 3 H), 0.97 (d, 3 H), 1.11 (s, 3 H), 1.14 (d, 3 H), 1.31 (d, 5 H), 1.43-1.60 (m, 3 H), 1.62-1.79 (m, 5 H), 1.74-1.80 (m, 2 H), 1.84-1.92 (m, 3 H), 1.90-1.96 (m, 3 H), 1.99-2.10 (m, 3 H), 2.16-2.28 (m, 1 H), 2.37-2.52 (m, 2 H), 2.61-2.74 (m, 1 H), 2.72-2.86 (m, 1 H), 3.11 (s, 1 H), 3.13-3.21 (m, 1 H), 3.39 (d, 1 H), 3.52 (s, 2 H), 3.65-3.78 (m, 1 H), 3.79-3.93 (m, 2 H), 4.49 (s, 2 H), 5.75 (s, 1 H), 5.79-5.87 (m, 1 H), 6.15-6.24 (m, 1 H), and 6.26-6.36 (m, 1 H). |
| 72/ D-21 | Me | *-CH₂-(5-hydroxymethylfuran-2-yl) | *-CH₂-(5-hydroxymethylfuran-2-yl) | (1S, 2R, 3R, 4aR, 6aS, 7R, 8R, 10aR, 10bR, 12aR)-3-(acetyloxy)-2-{2-[bis-(5-hydroxy methylfuran-2-ylmethyl)-amino]-propoxy}-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy methano)chrysene-7-carboxylic acid | 822 (M + H)⁺ | (methanol-d₄) 0.81 (s, 3 H), 0.85 (s, 3 H), 0.89 (d, J = 6.64 Hz, 3 H), 0.97 (d, J = 6.69 Hz 3 H), 1.05-1.08 (m, J = 6.74 Hz, 3 H), 1.11 (s, 3 H), 1.25-1.39 (m, 5 H), 1.35-1.48 (m, 4 H), 1.47-1.60 (m, 3 H), 1.64-1.79 (m, 3 H), 1.72-1.79 (m, 3 H), 1.83-1.95 (m, 3 H), 2.01 (s, 3 H), 2.18-2.28 (m, 1 H), 2.37-2.49 (m, 1 H), 2.59-2.74 (m, 1 H), 3.11 (s, 1 H), 3.34-3.43 (m, 1 H), 3.42-3.59 (m, 3 H), 3.63-3.83 (m, 4 H), 4.47 (s, 4 H), 5.73-5.76 (m, 1 H), 5.77-5.84 (m, 1 H), 6.18-6.20 (m, 2 H), and 6.20-6.24 (m, 2 H). |
| 73/ D-1 | Me | H | *-CH₂-(1H-imidazol-2-yl) | (1S, 2R, 3R, 4aR, 6aS, 7R, 8R, 10aR, 10bR, 12aR)-3-(acetyloxy)-2-{2-[(1H-imidazol-2-ylmethyl)-amino]-propoxy}-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 682 (M + H)⁺ | (methanol-d₄) 0.78 (s, 3 H), 0.80 (s, 3 H), 0.87 (d, J = 6.44 Hz, 3 H), 0.95 (d, J = 6.64 Hz, 3 H), 1.09 (s, 3 H), 1.20 (s, 2 H), 1.25-1.36 (m, 2 H), 1.45-1.57 (m, 2 H), 1.70 (s, 3 H), 1.71-1.79 (m, 4 H), 1.84-1.93 (m, 3 H), 2.00-2.03 (m, 3 H), 2.03-2.09 (m, 1 H), 2.17-2.33 (m, 2 H), 2.36-2.47 (m, 1 H), 2.65 (s, 1 H), 2.77-2.95 (m, 1 H), 3.03-3.14 (m, 2 H), 3.33-3.42 (m, 1 H), 3.44-3.53 (m, 3 H), 3.53-3.62 (m, 2 H), 3.64-3.75 (m, 1 H), 3.84-3.94 (m, 1 H), 3.99-4.10 (m, 2 H), 5.74 (s, 1 H), 5.76-5.83 (m, 1 H), 7.02-7.06 (m, 1 H), and 7.21 (d, J = 1.76 Hz, 1 H). |
| 74/ D-4 | Me | Me | Me | (1S, 2R, 3R, 4aR, 6aS, 7R, 8R, 10aR, 10bR, 12aR)-3-(acetyloxy)-2-(2-dimethylamino propoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a- | 630 (M + H)⁺ | (chloroform-d) 0.73 (s, 3 H), 0.77 (s, 3 H), 0.79 (d, J = 6.74 Hz, 3 H), 0.88 (d, J = 6.59 Hz, 3 H), 1.02-1.11 (m, 6 H), 1.15-1.33 (m, 5 H), 1.33-1.53 (m, 2 H), 1.55-1.66 (m, 4 H), 1.73-1.84 (m, 3 H), 1.99 (s, 3 H), 2.00-2.06 (m, 1 H), 2.11-2.24 (m, 1 H), 2.33 (s, 6 H), 2.39-2.49 (m, 2 H), 2.86-3.04 (m, 2 H), 3.07 (s, 1 H), 3.24 (d, J = 12.01 Hz, |

TABLE 1-continued

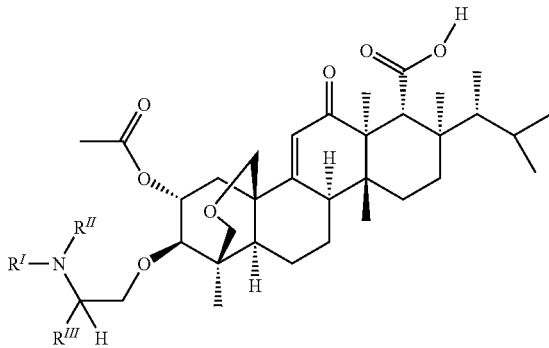

| Ex./Cpd | $R^{III}$ | $R^I$ | $R^{II}$ | Name | MS | $^1$H NMR (400 MHz, δ, ppm) |
|---|---|---|---|---|---|---|
| | | | | (methanooxymethano) chrysene-7-carboxylic acid | | 1 H), 3.35 (d, 1 H), 3.43-3.54 (m, J = 15.33 Hz, 3 H), 3.63 (s, 1 H), 3.69 (d, J = 11.81 Hz, 1 H), 3.77 (dd, J = 9.69, 5.30 Hz, 1 H), and 5.68-5.77 (m, 2 H). |
| 75/ D-8 | Me | Et | Et | (1S, 2R, 3R, 4aR, 6aS, 7R, 8R, 10aR, 10bR, 12aR)-3-(acetyloxy)-2-(2-diethylamino propoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 658 (M + H)⁺ | (methanol-d₄) 0.58 (none, 1 H), 0.78 (d, J = 7.22 Hz, 3 H), 0.81 (s, 3 H), 0.86-0.91 (m, 6 H), 0.97 (d, J = 6.69 Hz, 3 H), 1.11 (s, 3 H), 1.17-1.38 (m, 10 H), 1.36-1.59 (m, 3 H), 1.72 (s, 6 H), 1.92 (s, 6 H), 2.07 (s, 3 H), 2.13-2.33 (m, 1 H), 2.39-2.50 (m, 1 H), 2.67 (s, 2 H), 3.11 (s, 4 H), 3.21-3.28 (m, 1 H), 3.33-3.45 (m, 2 H), 3.53 (s, 2 H), 3.62-3.86 (m, 4 H), 3.87-4.02 (m, 1 H), 5.72-5.78 (m, 1 H), and 5.78-5.94 (m, 1 H). |
| 76/ D-45 | Me | H | cyclopropyl* | (1S, 2R, 3R, 4aR, 6aS, 7R, 8R, 10aR, 10bR, 12aR)-3-(acetyloxy)-2-(2-N-cyclopropylamino propoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 642 (M + H)⁺ | (chloroform-d) 0.42-0.52 (m, 4 H), 0.73 (d, J = 7.13 Hz, 3 H), 0.77 (s, 3 H), 0.80-0.84 (m, 7 H), 0.93 (d, J = 6.59 Hz, 3 H), 1.08 (s, 3 H), 1.13 (s, 3 H), 1.21-1.32 (m, 2 H), 1.50 (s, 2 H), 1.66 (s, 3 H), 1.82 (s, 3 H), 2.03 (s, 4 H), 2.06-2.30 (m, 3 H), 2.36-2.54 (m, 2 H), 2.58-2.81 (m, 1 H), 2.98-3.06 (m, 2 H), 3.08 (s, 1 H), 3.28 (d, J = 11.81 Hz, 1 H), 3.33-3.45 (m, 2 H), 3.51 (d, J = 12.93 Hz, 2 H), 3.59-3.67 (m, 2 H), 3.75 (d, J = 11.96 Hz, 1 H), and 5.61-5.86 (m, 2 H). |
| 77/ D-49 | Me | H | cyclobutyl* | (1S, 2R, 3R, 4aR, 6aS, 7R, 8R, 10aR, 10bR, 12aR)-3-(acetyloxy)-2-(2-N-cyclobutylaminopropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 656 (M + H)⁺ | (methanol-d₄) 0.81 (s, 3 H), 0.89 (d, 3 H), 0.97 (d, J = 6.74 Hz, 3 H), 1.11 (s, 3 H), 1.23 (s, 3 H), 1.27-1.32 (m, 4 H), 1.33-1.43 (m, 3 H), 1.46-1.59 (m, 3 H), 1.68-1.77 (m, 3 H), 1.74-1.82 (m, 2 H), 1.83-1.95 (m, 5 H), 2.07 (s, 3 H), 2.09 (s, 3 H), 2.11-2.26 (m, 3 H), 2.23-2.36 (m, 2 H), 2.40-2.55 (m, 1 H), 2.68 (d, J = 16.01 Hz, 1 H), 3.11 (s, 1 H), 3.21-3.30 (m, 2 H), 3.41 (d, J = 11.57 Hz, 1 H), 3.53 (s, 1 H), 3.61-3.68 (m, 1 H), 3.69-3.80 (m, 3 H), 3.81-3.92 (m, 1 H), 5.77 (s, 1 H), and 5.81-5.94 (m, 1 H). |
| 78/ D-10 | Et | H | H | (1S, 2R, 3R, 4aR, 6aS, 7R, 8R, 10aR, 10bR, 12aR)-3-(acetyloxy)-2-(2-aminobutoxy)-8-[(1R)-1,2-dimethyl propyl]-1,6a,8,10a-tetramethyl-6-oxo-1,3,4,6,6a,7,8,9,10,10a, | 616 (M + H)⁺ | (methanol-d₄) 0.77-0.80 (m, 3 H), 0.81 (s, 3 H), 0.87 (s, 3 H), 0.89 (d, J = 6.74 Hz, 3 H), 0.99-1.06 (m, 3 H), 1.11 (s, 3 H), 1.15-1.24 (m, 2 H), 1.27-1.38 (m, J = 11.81 Hz, 2 H), 1.41-1.50 (m, 2 H), 1.48-1.60 (m, 2 H), 1.69 (s, 3 H), 1.74-1.79 (m, 3 H), 1.83-1.98 (m, 4 H), 2.06 |

TABLE 1-continued

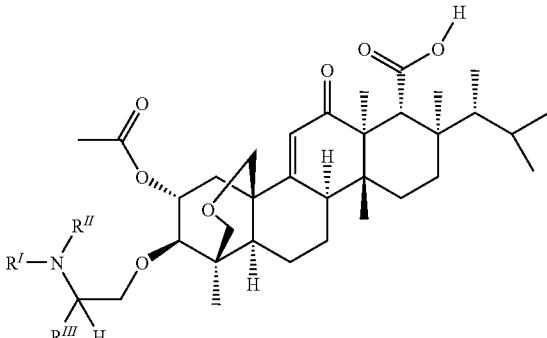

| Ex./Cpd | $R^{III}$ | $R^I$ | $R^{II}$ | Name | MS | $^1$H NMR (400 MHz, δ, ppm) |
|---|---|---|---|---|---|---|
| | | | | 10b,11,12,12a-tetra decahydro-2H-1,4a-(methanooxymethano)chrysene-7-carboxylic acid | | (s, 3 H), 2.18-2.27 (m, J = 25.19 Hz, 1 H), 2.35 (s, 1 H), 2.40-2.56 (m, 1 H), 2.61-2.71 (m, 1 H), 3.11 (s, 1 H), 3.18-3.30 (m, 3 H), 3.38-3.46 (m, 1 H), 3.53 (s, 1 H), 3.75-3.82 (m, 2 H), 3.91 (s, 1 H), 5.76 (s, 1 H), and 5.80-5.92 (m, 1 H). |
| 79/D-14 | Et | Me | Me | (1S, 2R, 3R, 4aR, 6aS, 7R, 8R, 10aR, 10bR, 12aR)-3-(acetyloxy)-2-(2-dimethylamino butoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 644 (M + H)$^+$ | (methanol-d$_4$) 0.79 (s, 3 H), 0.81 (s, 3 H), 0.87 (s, 6 H), 0.89 (s, 3 H), 0.93-1.00 (m, 3 H), 1.11 (s, 3 H), 1.25-1.35 (m, 2 H), 1.36-1.44 (m, 2 H), 1.48-1.58 (m, 3 H), 1.73 (s, 3 H), 1.74-1.81 (m, 2 H), 1.84-1.96 (m, 2 H), 2.06 (s, 3 H), 2.19-2.33 (m, 1 H), 2.47 (s, 6 H), 2.59-2.76 (m, 1 H), 3.10 (s, 1 H), 3.18 (d, J = 8.93 Hz, 1 H), 3.39 (d, J = 11.76 Hz, 1 H), 3.52 (s, 2 H), 3.61-3.80 (m, 2 H), 3.85-4.02 (m, 1 H), 5.75 (s, 1 H), and 5.77-5.86 (m, 1 H). |
| 80/D-17 | Et | Et | Et | (1S, 2R, 3R, 4aR, 6aS, 7R, 8R, 10aR, 10bR, 12aR)-3-(acetyloxy)-2-(2-diethylaminobutoxy)-8-[(1R)-1,2-dimethyl propyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid | 672 (M + H)$^+$ | (methanol-d$_4$) 0.79 (s, 3 H), 0.86 (s, 3 H), 0.88 (d, J = 6.78 Hz, 3 H), 0.97 (d, J = 6.54 Hz, 3 H), 0.97-1.00 (m, J = 1.56 Hz, 3 H), 1.11 (s, 3 H), 1.14 (s, 6 H), 1.24-1.36 (m, 1 H), 1.48-1.60 (m, 4 H), 1.72 (s, 3 H), 1.75 (s, 2 H), 1.83-1.96 (m, 3 H), 2.05 (s, 3 H), 2.17-2.32 (m, 1 H), 2.38-2.49 (m, 1 H), 2.67 (d, 1 H), 2.75-2.93 (m, 4 H), 3.10 (s, 1 H), 3.16 (d, J = 8.83 Hz, 1 H), 3.39 (d, J = 11.71 Hz, 1 H), 3.52 (s, 2 H), 3.59-3.66 (m, 1 H), 3.71 (s, 2 H), 3.79-3.87 (m, 1 H), 3.88-3.99 (m, 1 H), 5.75 (s, 1 H), and 5.77-5.85 (m, 1 H). |
| 81/D-29 | Et | Pr | Pr | (1S, 2R, 3R, 4aR, 6aS, 7R, 8R, 10aR, 10bR, 12aR)-3-(acetyloxy)-2-(2-dipropylamino butoxy)-8-[(1R)-1,2-dimethylpropyl]-1,6a,8,10a-tetramethyl-6-oxo-1,3,4,6,6a,7,8,9,10,10a,10b,11,12,12a-tetra decahydro-2H-1,4a-(methanooxymethano)chrysene-7-carboxylic acid | 700 (M + H)$^+$ | (methanol-d$_4$) 0.73 (s, 3 H), 0.80 (s, 3 H), 0.81 (s, 3 H), 0.86-0.90 (m, 3 H), 0.91 (s, 3 H), 0.93 (s, 3 H), 0.95-0.98 (m, 3 H), 1.02 (s, 3 H), 1.12 (s, 1 H), 1.16-1.32 (m, 2 H), 1.41 (s, 2 H), 1.40-1.53 (m, J = 24.11 Hz, 3 H), 1.63 (s, 3 H), 1.66-1.74 (m, 2 H), 1.73-1.91 (m, 2 H), 2.00 (s, 3 H), 2.13-2.24 (m, 1 H), 2.28-2.41 (m, 1 H), 2.54-2.67 (m, 1 H), 2.84-2.98 (m, 2 H), 3.02 (s, 1 H), 3.33 (s, 1 H), 3.45 (s, 2 H), 3.52-3.66 (m, 2 H), 3.68-3.79 (m, 1 H), 3.87-4.04 (m, 1 H), 4.23-4.39 (m, 1 H), 5.67 (s, 1 H), and 5.70-5.83 (m, 1 H). |

TABLE 1-continued

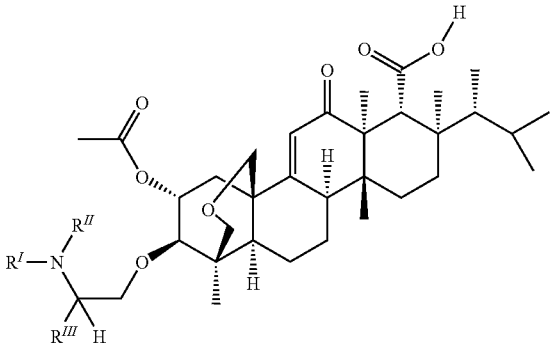

| Ex./Cpd | $R^{III}$ | $R^I$ | $R^{II}$ | Name | MS | $^1$H NMR (400 MHz, δ, ppm) |
|---|---|---|---|---|---|---|
| 82/ D-22 | Et | H | ![*](furan with CH2OH) | (1S, 2R, 3R, 4aR, 6aS, 7R, 8R, 10aR, 10bR, 12aR)-3-(acetyloxy)-2-{2-[(5-hydroxymethyl-furan-2-ylmethyl)-amino]-butoxy}-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 726 (M + H)$^+$ | (methanol-d$_4$) 0.81 (s, 3 H), 0.84 (s, 3 H), 0.89 (d, J = 6.64 Hz, 3 H), 0.91-0.94 (m, 3 H), 0.97 (d, J = 6.78 Hz, 3 H), 1.11 (s, 3 H), 1.27-1.35 (m, 2 H), 1.38-1.50 (m, 3 H), 1.51-1.59 (m, 2 H), 1.72 (s, 3 H), 1.73-1.81 (m, 3 H), 1.84-1.96 (m, 3 H), 2.03 (s, 3 H), 2.18-2.31 (m, 1 H), 2.37-2.51 (m, 1 H), 2.66 (d, 1 H), 2.75-2.83 (m, 1 H), 3.11 (s, 1 H), 3.18-3.24 (m, 1 H), 3.33-3.42 (m, 1 H), 3.53 (s, 2 H), 3.63-3.82 (m, 2 H), 3.85-3.96 (m, 2 H), 4.50 (s, 2 H), 5.74-5.78 (m, 1 H), 5.78-5.84 (m, 1 H), 6.25-6.27 (m, 1 H), and 6.28-6.32 (m, 1 H). |
| 83/ D-30 | Et | H | Bn | (1S, 2R, 3R, 4aR, 6aS, 7R, 8R, 10aR, 10bR, 12aR)-3-(acetyloxy)-2-(2-N-benzylamino butoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 706 (M + H)$^+$ | (methanol-d$_4$) 0.79 (s, 3 H), 0.80-0.82 (m, J = 3.03 Hz, 3 H), 0.87 (s, 3 H), 0.88-0.89 (m, 3 H), 0.91 (s, 3 H), 0.93 (s, 3 H), 0.96 (d, J = 6.69 Hz, 3 H), 1.11 (s, 3 H), 1.25-1.35 (m, 2 H), 1.41-1.57 (m, 3 H), 1.72 (s, 3 H), 1.72-1.78 (m, 3 H), 1.83-1.92 (m, 3 H), 2.00 (s, 3 H), 2.16-2.31 (m, 1 H), 2.37-2.51 (m, 1 H), 2.61-2.76 (m, 1 H), 3.11 (s, 1 H), 3.14-3.20 (m, 1 H), 3.48-3.56 (m, 2 H), 3.64-3.73 (m, 3 H), 3.80-3.88 (m, 1 H), 4.84 (s, 2 H), 5.75 (s, 1 H), 5.78-5.85 (m, 1 H), and 7.24-7.40 (m, 5 H). |
| 84/ D-51 | Et | H | Me | (1S, 2R, 3R, 4aR, 6aS, 7R, 8R, 10aR, 10bR, 12aR)-3-(acetyloxy)-2-(2-methylaminobutoxy)-8-[(1R)-1,2-dimethyl propyl]-1,6a,8,10a-tetramethyl-6-oxo-1,3,4,6,6a,7,8,9,10,10a,10b,11,12,12a-tetra decahydro-2H-1,4a-(methanooxymethano)chrysene-7-carboxylic acid | 630 (M + H)$^+$ | (methanol-d$_4$) 0.78 (d, J = 7.22 Hz, 3 H), 0.81 (s, 3 H), 0.84-0.93 (m, 9 H), 0.94-1.04 (m, 6 H), 1.11 (s, 3 H), 1.14-1.35 (m, 3 H), 1.43-1.58 (m, 3 H), 1.67-1.80 (m, 6 H), 1.86-1.94 (m, 3 H), 2.03-2.09 (m, 3 H), 2.19-2.29 (m, 1 H), 2.43-2.52 (m, 1 H), 2.60-2.65 (m, 5 H), 3.10 (s, 1 H), 3.37-3.43 (m, 1 H), 3.50-3.54 (m, 2 H), 3.63-3.68 (m, 1 H), 3.68-3.76 (m, 1 H), 3.80-3.86 (m, 1 H), 3.95 (dd, 1 H), 5.76 (d, J = 2.54 Hz, 1 H), and 5.77-5.88 (m, 1 H). |

TABLE 1-continued

| Ex./Cpd | $R^{III}$ | $R^I$ | $R^{II}$ | Name | MS | $^1$H NMR (400 MHz, δ, ppm) |
|---|---|---|---|---|---|---|
| 85/D-50 | Et | H | ⎡cyclobutyl⎤ | (1S, 2R, 3R, 4aR, 6aS, 7R, 8R, 10aR, 10bR, 12aR)-3-(acetyloxy)-2-(2-cyclobutylamino butoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 670 (M + H)$^+$ | (methanol-d$_4$) 0.78 (d, J = 7.22 Hz, 3 H), 0.81 (s, 3 H), 0.87 (d, J = 2.68 Hz, 3 H), 0.89 (d, J = 6.74 Hz, 3 H), 0.96 (dd, J = 7.20, 3.73 Hz, 6 H), 1.11 (s, 3 H), 1.17-1.39 (m, 4 H), 1.40-1.64 (m, 7 H), 1.72 (s, 3 H), 1.73-1.83 (m, 4 H), 1.93-2.03 (m, J = 12.50 Hz, 3 H), 2.07 (s, 3 H), 2.21-2.32 (m, 3 H), 2.41-2.50 (m, J = 5.95 Hz, 1 H), 2.65-2.72 (m, 1 H), 2.80-2.88 (m, 1 H), 3.11 (s, 1 H), 3.19-3.25 (m, 1 H), 3.37-3.44 (m, 1 H), 3.51-3.55 (m, 2 H), 3.55-3.65 (m, 2 H), 3.68 (d, J = 5.03 Hz, 1 H), 3.72-3.86 (m, 2 H), 5.76 (d, J = 2.54 Hz, 1 H), and 5.78-5.87 (m, 1 H). |
| 86/D-11 | i-Pr | H | H | (1S, 2R, 3R, 4aR, 6aS, 7R, 8R, 10aR, 10bR, 12aR)-3-(acetyloxy)-2-(2-amino-3-methyl butoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 630 (M + H)$^+$ | (methanol-d$_4$) 0.81 (s, 3 H), 0.87 (s, 3 H), 0.89 (d, J = 6.59 Hz, 3 H), 0.97 (d, J = 6.64 Hz, 3 H), 1.01 (d, J = 6.69 Hz, 3 H), 1.05 (d, J = 6.83 Hz, 3 H), 1.11 (s, 3 H), 1.16-1.24 (m, 2 H), 1.26-1.36 (m, 2 H), 1.39-1.50 (m, 2 H), 1.52-1.58 (m, 1 H), 1.72 (s, 3 H), 1.73-1.79 (m, 2 H), 1.84-1.94 (m, 3 H), 1.95-2.03 (m, 3 H), 2.06 (s, 3 H), 2.23-2.29 (m, 1 H), 2.43-2.54 (m, 1 H), 2.64-2.74 (m, 1 H), 3.04-3.09 (m, 1 H), 3.05-3.16 (m, 1 H), 3.22-3.27 (m, 1 H), 3.40 (d, J = 11.96 Hz, 1 H), 3.50-3.57 (m, 2 H), 3.62-3.86 (m, J = 15.08 Hz, 2 H), 3.87-3.98 (m, 1 H), 5.76 (s, 1 H), and 5.77-5.88 (m, 1 H). |
| 87/D-16 | i-Pr | Me | Me | (1S, 2R, 3R, 4aR, 6aS, 7R, 8R, 10aR, 10bR, 12aR)-3-(acetyloxy)-2-(2-dimethylamino-3-methylbutoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 658 (M + H)$^+$ | (methanol-d$_4$) 0.79 (s, 3 H), 0.81 (s, 3 H), 0.89 (d, J = 3.37 Hz, 3 H), 0.93 (d, J = 6.78 Hz, 3 H), 0.97 (d, J = 6.69 Hz, 3 H), 1.01 (d, J = 5.08 Hz, 3 H), 1.11 (s, 3 H), 1.21-1.34 (m, 1 H), 1.36-1.45 (m, 2 H), 1.43-1.61 (m, 3 H), 1.61-1.80 (m, 3 H), 1.73-1.81 (m, 2 H), 1.81-1.97 (m, 3 H), 2.06 (s, 3 H), 2.23 (s, 1 H), 2.45 (s, 6 H), 2.68 (d, J = 16.06 Hz, 1 H), 3.10 (s, 1 H), 3.16 (d, J = 8.83 Hz, 1 H), 3.38 (d, J = 11.96 Hz, 1 H), 3.52 (s, 2 H), 3.61-3.81 (m, 2 H), 3.87-4.01 (m, 1 H), 5.75 (s, 1 H), and 5.78-5.84 (m, 1 H). |
| 88/D-15 | i-Pr | Et | Et | (1S, 2R, 3R, 4aR, 6aS, 7R, 8R, 10aR, 10bR, 12aR)-3-(acetyloxy)-2-(2-diethylamino-3-methylbutoxy)-8-[(1R)-1,2-dimethylpropyl]- | 686 (M + H)$^+$ | (methanol-d$_4$) 0.79 (s, 3 H), 0.81 (s, 3 H), 0.86-0.90 (m, 6 H), 0.94-0.99 (m, J = 3.76 Hz, 6 H), 1.02 (d, J = 6.74 Hz, 3 H), 1.09-1.14 (m, J = 4.20 Hz, 6 H), 1.27-1.32 (m, 1 H), 1.32-1.41 (m, 2 H), 1.45-1.54 |

TABLE 1-continued

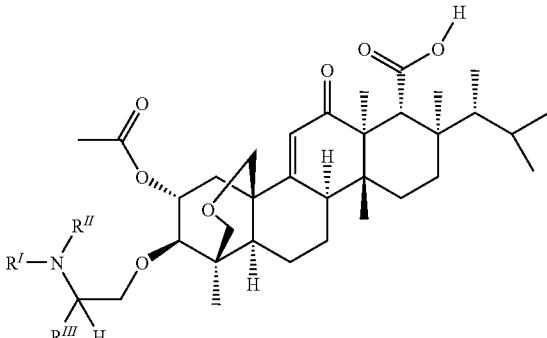

| Ex./Cpd | $R^{III}$ | $R^I$ | $R^{II}$ | Name | MS | $^1$H NMR (400 MHz, δ, ppm) |
|---|---|---|---|---|---|---|
| | | | | 1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | | (m, 2 H), 1.72 (s, 3 H), 1.73-1.79 (m, 2 H), 1.84-1.97 (m, 3 H), 2.05 (s, 3 H), 2.16-2.31 (m, 1 H), 2.38-2.50 (m, 1 H), 2.65-2.82 (m, 3 H), 2.85-2.96 (m, 2 H), 3.11 (s, 1 H), 3.13-3.19 (m, J = 13.52 Hz, 1 H), 3.39 (d, J = 11.76 Hz, 1 H), 3.52 (s, 2 H), 3.71 (d, J = 12.15 Hz, 2 H), 3.88-4.02 (m, 2 H), 5.69-5.82 (m, 1 H), and 5.76-5.87 (m, 1 H). |
| 89/D-19 | i-Pr | | | (1S, 2R, 3R, 4aR, 6aS, 7R, 8R, 10aR, 10bR, 12aR)-3-(acetyloxy)-2-(3-methyl-2-piperidin-1-ylbutoxy)-8-[(1R)-1,2-dimethylpropyl]-1,6a,8,10a-tetramethyl-6-oxo-1,3,4,6,6a,7,8,9,10,10a,10b,11,12,12a-tetra decahydro-2H-1,4a-(methanooxymethano)chrysene-7-carboxylic acid | 698 (M + H)$^+$ | methanol-d$_4$) 0.79 (s, 3 H), 0.81 (s, 3 H), 0.87 (d, J = 3.27 Hz, 3 H), 0.89 (d, J = 3.47 Hz, 3 H), 0.93 (d, J = 6.69 Hz, 3 H), 0.97 (d, J = 6.69 Hz, 3 H), 1.01 (d, J = 6.74 Hz, 3 H), 1.11 (s, 3 H), 1.27-1.38 (m, 2 H), 1.45-1.53 (m, 4 H), 1.58-1.67 (m, 4 H), 1.72 (s, 3 H), 1.73-1.80 (m, J = 10.93 Hz, 2 H), 1.84-1.98 (m, 3 H), 2.06 (s, 3 H), 2.20-2.28 (m, 1 H), 2.39-2.51 (m, 1 H), 2.61-2.75 (m, 2 H), 2.83-2.96 (m, 2 H), 3.11 (s, 1 H), 3.15 (d, J = 8.83 Hz, 1 H), 3.38 (d, J = 11.71 Hz, 1 H), 3.46-3.60 (m, 2 H), 3.65-3.80 (m, 2 H), 3.86-4.04 (m, 1 H), 5.70-5.81 (m, 1 H), and 5.78-5.85 (m, 1 H). |
| 90/D-7 | n-Pr | H | H | (1S, 2R, 3R, 4aR, 6aS, 7R, 8R, 10aR, 10bR, 12aR)-3-(acetyloxy)-2-(2-aminopentyloxy)-8-[(1R)-1,2-dimethyl propyl]-1,6a,8,10a-tetramethyl-6-oxo-1,3,4,6,6a,7,8,9,10,10a,10b,11,12,12a-tetra decahydro-2H-1,4a-(methanooxymethano)chrysene-7-carboxylic acid | 630 (M + H)$^+$ | (methanol-d$_4$) 0.78 (d, J = 7.17 Hz, 3 H), 0.81 (s, 3 H), 0.85-0.91 (m, 6 H), 0.94-1.00 (m, J = 6.37, 6.37 Hz, 6 H), 1.11 (s, 3 H), 1.15-1.71 (m, 10 H), 1.73 (s, 3 H), 1.74-1.88 (m, 4 H), 1.90 (s, 3 H), 2.06 (s, 3 H), 2.07-2.11 (m, 1 H), 2.18-2.32 (m, 1 H), 2.42-2.51 (m, 1 H), 2.64-2.72 (m, 1 H), 3.10 (s, 1 H), 3.17-3.27 (m, 2 H), 3.36-3.43 (m, 1 H), 3.53 (d, J = 27.38 Hz, 2 H), 3.70-3.76 (m, 2 H), 3.78-3.86 (m, 1 H), 5.76 (d, J = 2.29 Hz, 1 H), and 5.78-5.88 (m, 1 H). |
| 91/D-24 | n-Pr | Me | Me | (1S, 2R, 3R, 4aR, 6aS, 7R, 8R, 10aR, 10bR, 12aR)-3-(acetyloxy)-2-(2-dimethylamino pentyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 658 (M + H)$^+$ | (methanol-d$_4$) 0.78 (d, J = 7.13 Hz, 3 H), 0.81 (s, 3 H), 0.85-0.92 (m, 6 H), 0.94-1.02 (m, 6 H), 1.11 (s, 3 H), 1.15-1.59 (m, 8 H), 1.72 (s, 3 H), 1.73-1.92 (m, 6 H), 1.93 (s, 3 H), 2.03-2.12 (m, 4 H), 2.17-2.32 (m, 1 H), 2.46 (d, 1 H), 2.65-2.73 (m, 7 H), 3.11 (s, 1 H), 3.21-3.28 (m, 1 H), 3.41 (d, J = 14.40 Hz, 1 H), 3.47-3.58 (m, 2 H), 3.70-3.84 (m, 3 H), 3.87-4.03 (m, 1 H), 5.76 (d, J = 2.49 Hz, 1 H), and 5.78-5.90 (m, 1 H). |

TABLE 1-continued

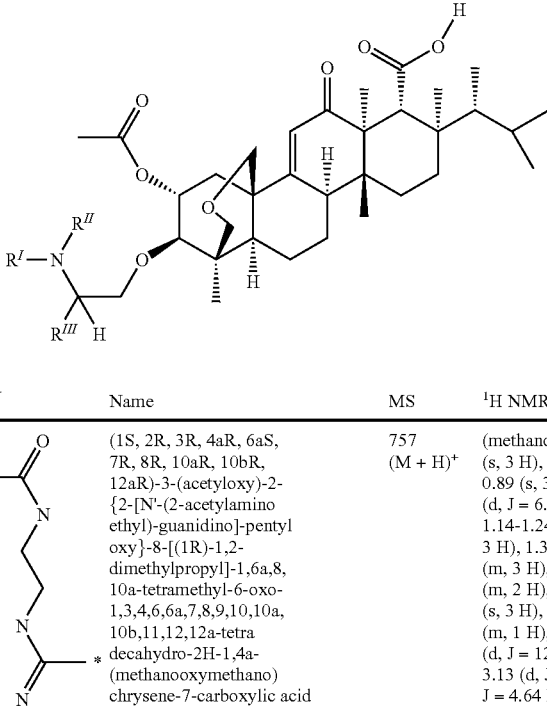

| Ex./Cpd | $R^{III}$ | $R^I$ | $R^{II}$ | Name | MS | $^1$H NMR (400 MHz, δ, ppm) |
|---|---|---|---|---|---|---|
| 92/D-48 | n-Pr | H | 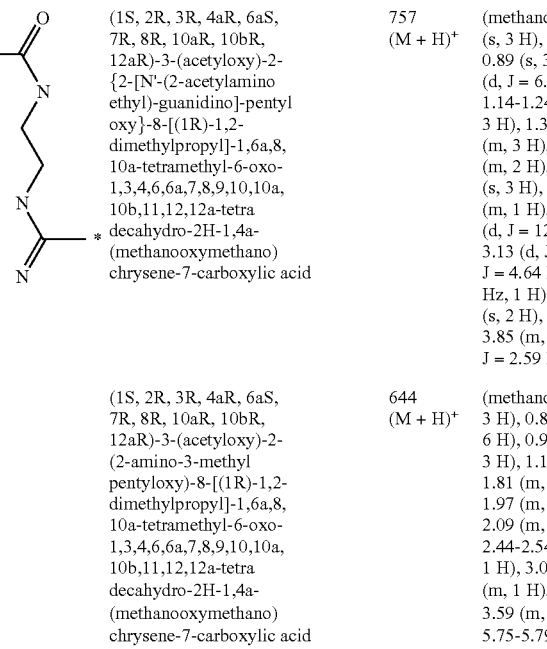 | (1S, 2R, 3R, 4aR, 6aS, 7R, 8R, 10aR, 10bR, 12aR)-3-(acetyloxy)-2-{2-[N'-(2-acetylamino ethyl)-guanidino]-pentyl oxy}-8-[(1R)-1,2-dimethylpropyl]-1,6a,8,10a-tetramethyl-6-oxo-1,3,4,6,6a,7,8,9,10,10a,10b,11,12,12a-tetra decahydro-2H-1,4a-(methanooxymethano) chrysene-7-carboxylic acid | 757 (M + H)+ | (methanol-d$_4$) 0.77 (s, 3 H), 0.79 (s, 3 H), 0.81 (s, 3 H), 0.87 (s, 3 H), 0.89 (s, 3 H), 0.93 (d, 2 H), 0.96 (d, J = 6.64 Hz, 3 H), 1.11 (s, 3 H), 1.14-1.24 (m, 5 H), 1.27-1.34 (m, 3 H), 1.36-1.45 (m, 3 H), 1.46-1.57 (m, 3 H), 1.72 (s, 3 H), 1.76-1.82 (m, 2 H), 1.85-1.92 (m, 2 H), 1.98 (s, 3 H), 2.05 (s, 3 H), 2.20-2.28 (m, 1 H), 2.34-2.44 (m, 1 H), 2.68 (d, J = 12.25 Hz, 1 H), 3.11 (s, 1 H), 3.13 (d, J = 5.56 Hz, 1 H), 3.21 (d, J = 4.64 Hz, 1 H), 3.24 (d, J = 4.59 Hz, 1 H), 3.33-3.39 (m, 2 H), 3.52 (s, 2 H), 3.57-3.70 (m, 2 H), 3.69-3.85 (m, 1 H), and 5.71-5.82 (m, J = 2.59 Hz, 2 H). |
| 93/D-35 | s-Bu | H | H | (1S, 2R, 3R, 4aR, 6aS, 7R, 8R, 10aR, 10bR, 12aR)-3-(acetyloxy)-2-(2-amino-3-methyl pentyloxy)-8-[(1R)-1,2-dimethylpropyl]-1,6a,8,10a-tetramethyl-6-oxo-1,3,4,6,6a,7,8,9,10,10a,10b,11,12,12a-tetra decahydro-2H-1,4a-(methanooxymethano) chrysene-7-carboxylic acid | 644 (M + H)+ | (methanol-d$_4$) 0.78 (d, J = 7.22 Hz, 3 H), 0.82 (s, 3 H), 0.85-0.91 (m, 6 H), 0.92-1.04 (m, 10 H), 1.11 (s, 3 H), 1.16-1.59 (m, 10 H), 1.66-1.81 (m, 2 H), 1.73 (s, 3 H), 1.85-1.97 (m, 1 H), 1.90 (s, 3 H), 2.03-2.09 (m, 3 H), 2.20-2.31 (m, 1 H), 2.44-2.54 (m, 1 H), 2.64-2.71 (m, 1 H), 3.08-3.17 (m, 2 H), 3.22-3.27 (m, 1 H), 3.36-3.43 (m, 1 H), 3.47-3.59 (m, 2 H), 3.64-3.91 (m, 3 H), 5.75-5.79 (m, 1 H), and 5.79-5.86 (m, 1 H). |
| 94/D-42 | s-Bu | Me | Me | (1S, 2R, 3R, 4aR, 6aS, 7R, 8R, 10aR, 10bR, 12aR)-3-(acetyloxy)-2-(2-dimethylamino-3-methylpentyloxy)-8-[(1R)-1,2-dimethyl propyl]-1,6a,8,10a-tetramethyl-6-oxo-1,3,4,6,6a,7,8,9,10,10a,10b,11,12,12a-tetradeca hydro-2H-1,4a-(methanooxy methano)chrysene-7-carboxylic acid | 672 (M + H)+ | (methanol-d$_4$) 0.78 (d, J = 7.22 Hz, 3 H), 0.81 (s, 3 H), 0.85-1.07 (m, 15 H), 1.09-1.14 (m, 4 H), 1.17-1.60 (m, 11 H), 1.72 (s, 3 H), 1.74-1.85 (m, 1 H), 1.84-1.97 (m, 2 H), 2.06-2.16 (m, 4 H), 2.19-2.30 (m, 1 H), 2.45-2.54 (m, 1 H), 2.65-2.75 (m, 1 H), 2.89-3.03 (m, 6 H), 3.07-3.13 (m, 1 H), 3.39-3.49 (m, 1 H), 3.50-3.58 (m, 2 H), 3.67-3.78 (m, 1 H), 3.81-3.93 (m, 1 H), 4.00-4.16 (m, 2 H), 5.76 (s, 1 H), and 5.80-5.88 (m, 1 H). |
| 95/D-43 | s-Bu | H | i-Pr | (1S, 2R, 3R, 4aR, 6aS, 7R, 8R, 10aR, 10bR, 12aR)-3-(acetyloxy)-2-(2-isopropylamino-3-methylpentyloxy)-8-[(1R)-1,2-dimethyl propyl]-1,6a,8,10a-tetramethyl-6-oxo-1,3,4,6,6a,7,8,9,10,10a,10b,11,12,12a-tetra decahydro-2H-1,4a-(methanooxymethano) chrysene-7-carboxylic acid | 686 (M + H)+ | (methanol-d$_4$) 0.78 (d, J = 7.22 Hz, 3 H), 0.81 (s, 3 H), 0.85-0.91 (m, 7 H), 0.93-1.05 (m, 10 H), 1.11 (s, 3 H), 1.22-1.59 (m, 15 H), 1.72 (s, 3 H), 1.74-1.80 (m, 3 H), 1.85-1.97 (m, 3 H), 2.04-2.11 (m, J = 4.30 Hz, 3 H), 2.21-2.29 (m, 1 H), 2.42-2.49 (m, 1 H), 2.65-2.72 (m, 1 H), 3.11 (s, 1 H), 3.22-3.28 (m, 1 H), 3.38-3.45 (m, 1 H), 3.51-3.55 (m, 1 H), 3.66-3.93 (m, 2 H), 5.74-5.77 (m, J = 2.39 Hz, 1 H), and 5.78-5.86 (m, 1 H). |

TABLE 1-continued

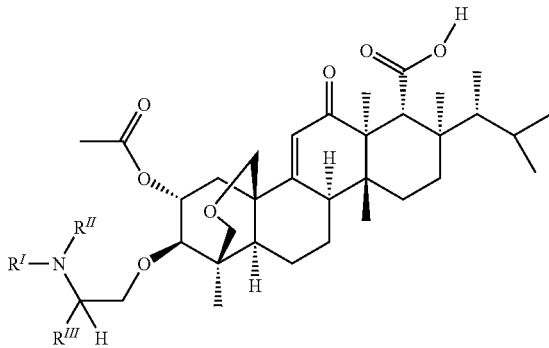

| Ex./Cpd | $R^{III}$ | $R^I$ | $R^{II}$ | Name | MS | $^1$H NMR (400 MHz, δ, ppm) |
|---|---|---|---|---|---|---|
| 96/D-52 | i-Bu | H | H | (1S, 2R, 3R, 4aR, 6aS, 7R, 8R, 10aR, 10bR, 12aR)-3-(acetyloxy)-2-(2-amino-4-methylpentyl oxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 644 (M + H)⁺ | (methanol-d₄) 0.78 (d, J = 7.22 Hz, 3 H), 0.81 (s, 3 H), 0.87 (s, 3 H), 0.89 (d, J = 6.78 Hz, 2 H), 0.90-0.95 (m, 1 H), 0.94-1.00 (m, J = 5.47 Hz, 9 H), 1.11 (s, 3 H), 1.21-1.59 (m, 9 H), 1.63-1.70 (m, 1 H), 1.72 (s, 3 H), 1.73-1.82 (m, 3 H), 1.85-1.93 (m, 2 H), 1.93 (s, 3 H), 2.06 (s, 3 H), 2.20-2.29 (m, 1 H), 2.43-2.53 (m, 1 H), 2.64-2.72 (m, 1 H), 3.11 (s, 1 H), 3.23-3.29 (m, 1 H), 3.29-3.37 (m, 1 H), 3.37-3.44 (m, 1 H), 3.52-3.56 (m, 2 H), 3.74-3.92 (m, 2 H), 5.76 (d, J = 2.44 Hz, 1 H), and 5.78-5.89 (m, 1 H). |
| 97/D-55 | i-Bu | Me | Me | (1S, 2R, 3R, 4aR, 6aS, 7R, 8R, 10aR, 10bR, 12aR)-3-(acetyloxy)-2-(2-dimethylamino-4-methylpentyloxy)-8-[(1R)-1,2-dimethylpropyl]-1,6a,8,10a-tetramethyl-6-oxo-1,3,4,6a,7,8,9,10,10a,10b,11,12,12a-tetra decahydro-2H-1,4a-(methanooxymethano)chrysene-7-carboxylic acid | 672 (M + H)⁺ | (methanol-d₄) 0.78 (d, J = 7.22 Hz, 3 H), 0.81 (s, 3 H), 0.86-0.91 (m, 9 H), 0.94-1.03 (m, 12 H), 1.11 (s, 3 H), 1.27-1.62 (m, 9 H), 1.72 (s, 3 H), 1.74-1.82 (m, 2 H), 1.86-1.94 (m, 2 H), 1.96 (s, 3 H), 2.08 (s, 3 H), 2.19-2.29 (m, 1 H), 2.79 (s, 6 H), 3.11 (s, 1 H), 3.39-3.48 (m, 1 H), 3.51-3.55 (m, 1 H), 3.73-3.87 (m, 1 H), 5.76 (d, J = 2.59 Hz, 1 H), and 5.80-5.90 (m, 1 H). |
| 98/D-34 | n-Bu | H | H | (1S, 2R, 3R, 4aR, 6aS, 7R, 8R, 10aR, 10bR, 12aR)-3-(acetyloxy)-2-(2-aminohexyloxy)-8-[(1R)-1,2-dimethyl propyl]-1,6a,8,10a-tetra methyl-6-oxo-1,3,4,6,6a,7,8,9,10,10a,10b,11,12,12a-tetradeca hydro-2H-1,4a-(methanooxy methano)chrysene-7-carboxylic acid | 644 (M + H)⁺ | (methanol-d₄) 0.78 (d, J = 7.22 Hz, 3 H), 0.81 (s, 3 H), 0.85-0.92 (m, 6 H), 0.92-0.99 (m, 8 H), 1.11 (s, 3 H), 1.17-1.46 (m, 7 H), 1.46-1.72 (m, 4 H), 1.72 (s, 3 H), 1.73-1.90 (m, 3 H), 1.90 (s, 3 H), 2.06 (s, 3 H), 2.07-2.10 (m, 1 H), 2.19-2.31 (m, 1 H), 2.43-2.51 (m, 1 H), 2.64-2.72 (m, 1 H), 3.10 (s, 1 H), 3.14-3.21 (m, 1 H), 3.24 (d, J = 9.96 Hz, 1 H), 3.36-3.43 (m, 1 H), 3.45-3.65 (m, 2 H), 3.74 (d, J = 4.93 Hz, 1 H), 3.77-3.87 (m, 2 H), 5.76 (d, J = 2.54 Hz, 1 H), and 5.78-5.87 (m, 1 H). |
| 99/D-40 | n-Bu | Me | Me | (1S, 2R, 3R, 4aR, 6aS, 7R, 8R, 10aR, 10bR, 12aR)-3-(acetyloxy)-2-(2-dimethylamino hexyloxy)-8-[(1R)-1,2-dimethylpropyl]-1,6a,8,10a-tetramethyl-6-oxo-1,3,4,6,6a,7,8,9,10,10a,10b,11,12,12a-tetra decahydro-2H-1,4a-(methanooxymethano)chrysene-7-carboxylic acid | 672 (M + H)⁺ | (methanol-d₄) 0.78 (d, J = 7.22 Hz, 3 H), 0.81 (s, 3 H), 0.84-0.9 1 (m, 6 H), 0.92-0.99 (m, 6 H), 0.99-1.10 (m, 1 H), 1.11 (s, 3 H), 1.16-1.29 (m, 3 H), 1.29-1.44 (m, 6 H), 1.44-1.71 (m, 5 H), 1.72 (s, 3 H), 1.73-1.91 (m, 3 H), 1.92 (s, 3 H), 2.03-2.12 (m, 3 H), 2.18-2.30 (m, 1 H), 2.40-2.54 (m, 1 H), 2.63-2.70 (m, 6 H), 3.11 (s, 1 H), 3.19-3.28 (m, 1 H), 3.37-3.45 (m, 1 H), 3.46-3.59 (m, 2 H), 3.72 (s, 3 H), |

TABLE 1-continued

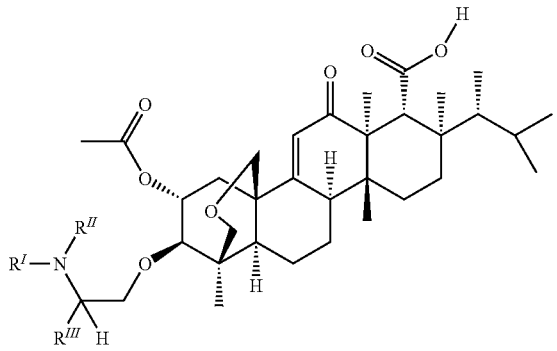

| Ex./Cpd | $R^{III}$ | $R^{I}$ | $R^{II}$ | Name | MS | $^1$H NMR (400 MHz, δ, ppm) |
|---|---|---|---|---|---|---|
| 100/D-33 | n-Pent | H | H | (1S, 2R, 3R, 4aR, 6aS, 7R, 8R, 10aR, 10bR, 12aR)-3-(acetyloxy)-2-(2-aminoheptyloxy)-8-[(1R)-1,2-dimethyl propyl]-1,6a,8,10a-tetramethyl-6-oxo-1,3,4,6,6a,7,8,9,10,10a,10b,11,12,12a-tetra decahydro-2H-1,4a-(methanooxymethano) chrysene-7-carboxylic acid | 658 (M + H)$^+$ | 3.88-4.00 (m, 1 H), 5.76 (d, J = 2.00 Hz, 1 H), and 5.78-5.89 (m, 1 H). (methanol-d$_4$) 0.78 (d, J = 7.22 Hz, 3 H), 0.81 (s, 3 H), 0.85-0.90 (m, 6 H), 0.93 (t, J = 6.52 Hz, 3 H), 0.97 (d, J = 6.69 Hz, 3 H), 1.11 (s, 3 H), 1.22-1.46 (m, 9 H), 1.46-1.70 (m, 5 H), 1.72 (s, 3 H), 1.73-1.90 (m, 4 H), 1.91 (s, 3 H), 2.06 (s, 3 H), 2.18-2.31 (m, 1 H), 2.41-2.54 (m, 1 H), 2.63-2.73 (m, 1 H), 3.10 (s, 1 H), 3.25 (d, J = 8.69 Hz, 2 H), 3.37-3.44 (m, 1 H), 3.48-3.58 (m, 2 H), 3.60-3.68 (m, 1 H), 3.74-3.89 (m, 3 H), 5.76 (d, J = 2.39 Hz, 1 H), and 5.78-5.88 (m, 1 H). |
| 101/D-28 | n-Hex | H | H | (1S, 2R, 3R, 4aR, 6aS, 7R, 8R, 10aR, 10bR, 12aR)-3-(acetyloxy)-2-(2-aminooctyloxy)-8-[(1R)-1,2-dimethyl propyl]-1,6a,8,10a-tetramethyl-6-oxo-1,3,4,6,6a,7,8,9,10,10a,10b,11,12,12a-tetra decahydro-2H-1,4a-(methanooxymethano) chrysene-7-carboxylic acid | 672 (M + H)$^+$ | (methanol-d$_4$) 0.77 (s, 3 H), 0.79 (s, 3 H), 0.81 (s, 3 H), 0.88 (s, 3 H), 0.89-0.92 (m, J = 8.88 Hz, 3 H), 0.97 (d, J = 6.69 Hz, 3 H), 1.11 (s, 3 H), 1.16-1.22 (m, 2 H), 1.27-1.41 (m, 10 H), 1.44-1.50 (m, 2 H), 1.52-1.58 (m, 2 H), 1.72 (s, 3 H), 1.74-1.85 (m, 3 H), 1.82-1.95 (m, J = 15.52 Hz, 3 H), 1.92 (s, 3 H), 2.05 (s, 3 H), 2.12-2.28 (m, 1 H), 2.39-2.51 (m, 1 H), 2.57-2.76 (m, 1 H), 3.11 (s, 1 H), 3.26 (d, J = 8.98 Hz, 1 H), 3.39 (d, J = 11.52 Hz, 1 H), 3.53 (s, 2 H), 3.65-3.74 (m, 1 H), 3.74-3.98 (m, 2 H), 5.76 (s, 1 H), and 5.79-5.90 (m, 1 H). |
| 102/D-27 | c-Pent | H | H | (1S, 2R, 3R, 4aR, 6aS, 7R, 8R, 10aR, 10bR, 12aR)-3-(acetyloxy)-2-(2-amino-2-cyclopentyl ethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 656 (M + H)$^+$ | (methanol-d$_4$) 0.78 (s, 3 H), 0.79 (s, 3 H), 0.81 (s, 3 H), 0.87-0.90 (m, J = 7.13 Hz, 6 H), 0.97 (d, J = 6.69 Hz, 3 H), 1.11 (s, 3 H), 1.18-1.26 (m, 2 H), 1.25-1.42 (m, 3 H), 1.43-1.57 (m, J = 30.31 Hz, 4 H), 1.57-1.67 (m, 3 H), 1.72 (s, 3 H), 1.74-1.79 (m, 2 H), 1.83-1.96 (m, 4 H), 2.02-2.10 (m, 3 H), 2.17-2.33 (m, 1 H), 2.41-2.56 (m, 1 H), 2.67 (s, 1 H), 3.11 (s, 1 H), 3.28 (d, J = 8.98 Hz, 1 H), 3.40 (d, J = 11.71 Hz, 1 H), 3.53 (s, 2 H), 3.67-3.80 (m, 1 H), 3.75-3.95 (m, 2 H), 5.77 (s, 1 H), and 5.78-5.88 (m, 1 H). |
| 103/D-36 | c-Pent | Me | Me | (1S, 2R, 3R, 4aR, 6aS, 7R, 8R, 10aR, 10bR, 12aR)-3-(acetyloxy)-2-(2-cyclopentyl-2-dimethylaminoethoxy)-8-[(1R)-1,2-dimethyl propyl]-1,6a,8,10a-tetramethyl-6-oxo-1,3,4,6,6a,7,8,9,10,10a, | 684 (M + H)$^+$ | (methanol-d$_4$) 0.79 (s, 3 H), 0.81 (s, 3 H), 0.88 (s, 3 H), 0.89 (s, 3 H), 0.97 (d, J = 6.69 Hz, 3 H), 1.11 (s, 3 H), 1.15-1.47 (m, 6 H), 1.46-1.61 (m, 5 H), 1.64-1.70 (m, 3 H), 1.66-1.80 (m, 3 H), 1.80-1.95 (m, 4 H), 2.06 (s, 3 H), 2.11-2.30 (m, 2 H), 2.36-2.50 (m, 1 H), 2.55 (s, 6 H), 2.63-2.71 (m, 1 H), 2.72- |

TABLE 1-continued

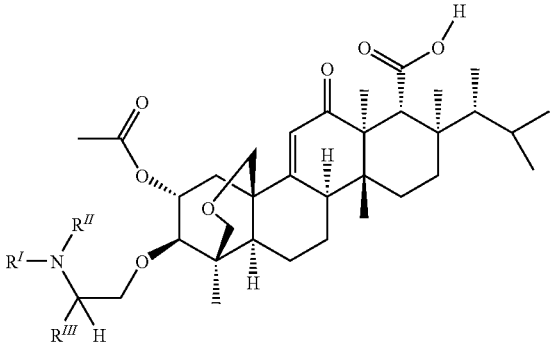

| Ex./ Cpd | $R^{III}$ | $R^{I}$ | $R^{II}$ | Name | MS | $^1$H NMR (400 MHz, δ, ppm) |
|---|---|---|---|---|---|---|
| | | | | 10b,11,12,12a-tetra decahydro-2 H-1,4a-(methanooxymethano) chrysene-7-carboxylic acid | | 2.86 (m, 1 H), 3.10 (s, 1 H), 3.17 (d, J = 8.88 Hz, 1 H), 3.39 (d, J = 11.91 Hz, 1 H), 3.52 (s, 2 H), 3.66-3.84 (m, 3 H), 3.94-4.08 (m, 1 H), 5.75 (s, 1 H), and 5.77-5.86 (m, 1 H). |
| 104/ D-37 | c-Hex | H | H | (1S, 2R, 3R, 4aR, 6aS, 7R, 8R, 10aR, 10bR, 12aR)-3-(acetyloxy)-2-(2-amino-2-cyclohexyl ethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 670 (M + H)$^+$ | (methanol-d$_4$) 0.79 (s, 3 H), 0.82 (s, 3 H), 0.87 (d, J = 2.34 Hz, 3 H), 0.88 (d, J = 5.32 Hz, 3 H), 0.97 (d, J = 6.69 Hz, 3 H), 1.02-1.10 (m, 2 H), 1.11 (s, 3 H), 1.14-1.27 (m, 4 H), 1.27-1.34 (m, 4 H), 1.34-1.45 (m, 2 H), 1.47-1.58 (m, 2 H), 1.73 (s, 3 H), 1.75-1.83 (m, 5 H), 1.85-1.98 (m, 3 H), 2.06 (s, 3 H), 2.26 (s, 1 H), 2.40-2.52 (m, J = 7.27 Hz, 1 H), 2.62-2.72 (m, 1 H), 3.01-3.06 (m, 1 H), 3.09 (s, 1 H), 3.26 (d, J = 8.83 Hz, 1 H), 3.39 (d, J = 11.81 Hz, 1 H), 3.53 (d, J = 5.22 Hz, 2 H), 3.71-3.79 (m, 1 H), 3.83 (d, J = 11.91 Hz, 1 H), 3.87-3.94 (m, 1 H), 5.77 (s, 1 H), and 5.79-5.84 (m, 1 H). |
| 105/ D-38 | c-Hex | Me | Me | (1S, 2R, 3R, 4aR, 6aS, 7R, 8R, 10aR, 10bR, 12aR)-3-(acetyloxy)-2-(2-cyclohexyl-2-dimethylaminoethoxy)-8-[(1R)-1,2-dimethyl propyl]-1,6a,8,10a-tetramethyl-6-oxo-1,3,4,6,6a,7,8,9,10,10a,10b,11,12,12a-tetra decahydro-2H-1,4a-(methanooxymethano) chrysene-7-carboxylic acid | 698 (M + H)$^+$ | (methanol-d$_4$) 0.77 (s, 3 H), 0.79 (s, 3 H), 0.81 (s, 3 H), 0.88 (s, 3 H), 0.89 (d, J = 3.90 Hz, 3 H), 0.98 (s, 3 H), 1.01-1.09 (m, J = 11.91 Hz, 2 H), 1.09-1.14 (m, 5 H), 1.19-1.35 (m, 5 H), 1.38-1.44 (m, 2 H), 1.47-1.59 (m, 2 H), 1.69-1.76 (m, 3 H), 1.74-1.83 (m, 6 H), 1.86-1.95 (m, 3 H), 2.06 (s, 3 H), 2.19-2.29 (m, 1 H), 2.42-2.51 (m, 1 H), 2.57 (s, 6 H), 2.63-2.75 (m, 1 H), 3.10 (s, 1 H), 3.19 (dd, J = 8.76, 3.73 Hz, 1 H), 3.40 (dd, J = 11.76, 4.39 Hz, 1 H), 3.52 (s, 2 H), 3.72 (d, J = 11.81 Hz, 1 H), 3.80 (dd, J = 16.08, 5.10 Hz, 1 H), 3.98 (dd, J = 10.84, 6.39 Hz, 1 H), 5.75 (s, 1 H), and 5.77-5.87 (m, 1 H). |
| 106/ D-32 | c-Pr | H | H | (1S, 2R, 3R, 4aR, 6aS, 7R, 8R, 10aR, 10bR, 12aR)-3-(acetyloxy)-2-(2-amino-2-cyclopropyl ethoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid | 628 (M + H)$^+$ | (methanol-d$_4$) 0.29-0.50 (m, 2 H), 0.56-0.73 (m, 2 H), 0.77 (d, J = 7.17 Hz, 3 H), 0.82 (s, 3 H), 0.87 (s, 3 H), 0.89 (d, J = 4.54 Hz, 3 H), 0.97 (d, J = 6.59 Hz, 3 H), 1.13 (s, 3 H), 1.22-1.61 (m, 5 H), 1.64-1.84 (m, 5 H), 2.03-2.10 (m, 3 H), 2.20-2.34 (m, 1 H), 2.3 8-2.53 (m, 2 H), 2.64-2.75 (m, 1 H), 3.45-3.62 (m, 2 H), 3.69-4.00 (m, 3 H), 5.73-5.78 (m, 1 H), and 5.78-5.95 (m, 1 H). |

Example 107

(1S,2R,3R,4aR,6aS,7R,8R,10aR,10bR,12aR)-3-(acetyloxy)-2-[2-amino-2-(4-trifluoromethoxy phenyl)-ethoxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-25)

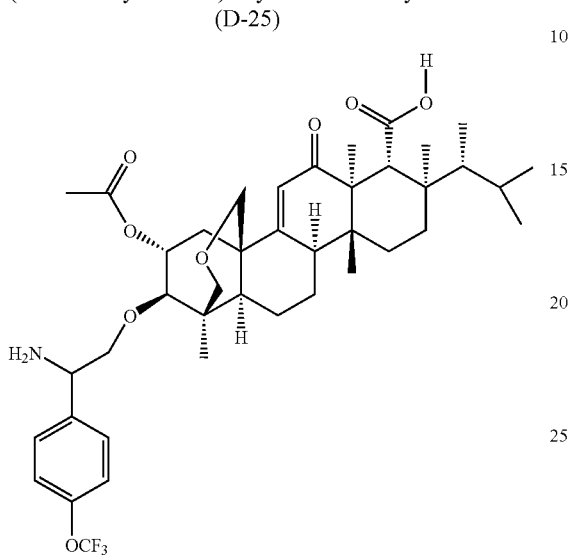

The title compound was prepared in a similar manner as described for Example 61, using iodo-4-(trifluoromethoxy)benzene. Calculated for $C_{41}H_{56}NO_8F_3$: 747; observed: 748 (M+H)$^+$. $^1$H NMR (400 MHz, chloroform-d) δ ppm 0.70-0.78 (m, 6H), 0.79 (s, 3H), 0.85 (d, J=6.59 Hz, 3H), 0.94 (d, J=6.69 Hz, 3H), 1.12 (s, 3H), 1.15-1.92 (m, 13H), 1.98-2.05 (m, 3H), 2.12-2.30 (m, 1H), 2.41-2.58 (m, 1H), 2.87-3.09 (m, 1H), 3.15 (s, 1H), 3.30 (d, J=11.62 Hz, 1H), 3.42 (d, J=11.57 Hz, 1H), 3.53-3.97 (m, 6H), 4.11-4.26 (m, 1H), 5.80 (s, 1H), 5.82-6.00 (m, 1H), 7.17 (d, J=7.66 Hz, 2H), and 7.41 (d, J=8.59 Hz, 2H).

Example 108

(1S,2R,3R,4aR,6aS,7R,8R,10aR,10bR,12aR)-3-(acetyloxy)-2-[2-amino-2-(4-fluorophenyl)-ethoxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (D-39)

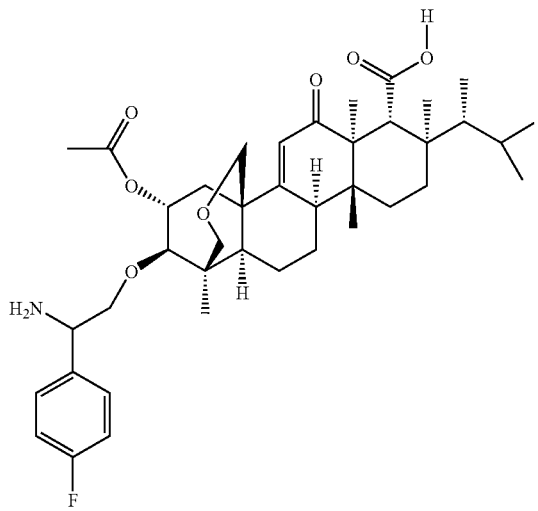

The title compound was prepared in a similar manner as described for Example 61, using p-fluoroiodobenzene. Calculated for $C_{40}H_{56}NO_7F$: 681; observed: 682 (M+H)$^+$. $^1$H NMR (400 MHz, methanol-d$_4$) δ ppm 0.68-0.73 (m, 3H), 0.77 (d, 3H), 0.80 (s, 3H), 0.88 (d, 3H), 0.96 (d, 3H), 1.10 (s, 3H), 1.18-1.57 (m, 8H), 1.64-2.07 (m, 11H), 2.18-2.31 (m, 1H), 2.43 (dd, 1H), 2.60-2.72 (m, 1H), 3.09 (s, 1H), 3.17 (d, 1H), 3.34 (d, 1H), 3.44-3.58 (m, 2H), 3.63-3.79 (m, 2H), 3.80-3.91 (m, 1H), 4.08-4.21 (m, 1H), 5.75 (s, 1H), 5.75-5.85 (m, 1H), 7.02-7.13 (m, 2H), and 7.33-7.48 (m, 2H).

The compounds in Table 2 were prepared from the compounds described in Examples 35 and 38 in a similar manner as described in Example 36 and 49.

TABLE 2

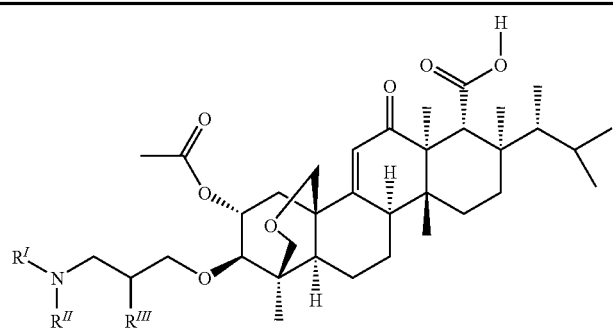

| Ex/Cpd | R$^{III}$ | R$^I$ | R$^{II}$ | Name | MS | $^1$H NMR (400 MHz, δ, ppm) |
|---|---|---|---|---|---|---|
| 109/E-3 | H | H | H | (1S, 2R, 3R, 4aR, 6aS, 7R, 8R, 10aR, 10bR, 12aR)-3-(acetyloxy)-2-(3-aminopropoxy)-8-[(1R)-1,2-dimethyl propyl]-1,6a,8,10a-tetramethyl-6- | 602 (M + H)$^+$ | (methanol-d$_4$) 0.71-0.86 (m, 9 H), 0.89 (d, J = 6.25 Hz, 3 H), 0.97 (d, J = 6.39 Hz, 3 H), 1.11 (s, 3 H), 1.22-1.56 (m, 7 H), 1.65-1.80 (m, 5 H), 1.81-1.94 (m, 4 H), 1.97 (s, 3 H), 2.08 |

TABLE 2-continued

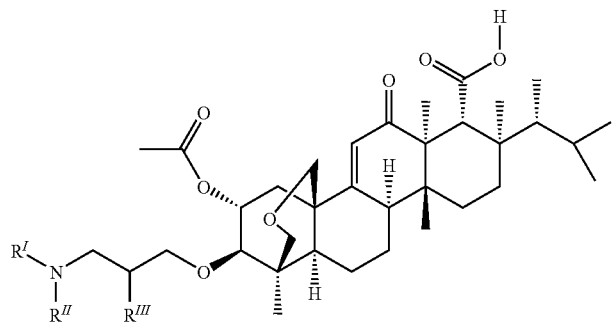

| Ex/Cpd | R$^{III}$ | R$^{I}$ | R$^{II}$ | Name | MS | $^1$H NMR (400 MHz, δ, ppm) |
|---|---|---|---|---|---|---|
| | | | | oxo-1,3,4,6,6a,7,8,9,10,10a,10b,11,12,12a-tetradeca hydro-2H-1,4a-(methano oxymethano)chrysene-7-carboxylic acid | | (s, 3 H), 2.15-2.30 (m, 1 H), 2.34-2.51 (m, 1 H), 2.63-2.76 (m, 1 H), 2.79-3.19 (m, 4 H), 3.37-3.92 (m, 6 H), and 5.69-5.99 (m, 2 H). |
| 110/E-4 | H | H | H$_2$N⤴NH (guanidino) | (1S, 2R, 3R, 4aR, 6aS, 7R, 8R, 10aR, 10bR, 12aR)-3-(acetyloxy)-2-(3-guanidino-propoxy)-8-[(1R)-1,2-dimethylpropyl]-1,6a,8,10a-tetramethyl-6-oxo-1,3,4,6,6a,7,8,9,10,10a,10b,11,12,12a-tetra-decahydro-2H-1,4a-(methanooxymethano)chrysene-7-carboxylic acid | 644 (M + H)$^+$ | (methanol-d$_4$) 0.78 (d, J = 7.17 Hz, 3 H), 0.81 (s, 3 H), 0.84 (s, 3 H), 0.88 (d, J = 6.64 Hz, 3 H), 0.90-0.95 (m, 2 H), 0.97 (d, J = 6.69 Hz, 3 H), 1.11 (s, 3 H), 1.23-1.35 (m, 4 H), 1.35-1.58 (m, 3 H), 1.72 (s, 3 H), 1.73-1.89 (m, 4 H), 1.91 (s, 9 H), 2.05 (s, 3 H), 2.18-2.28 (m, 1 H), 2.38-2.46 (m, 1 H), 2.65-2.72 (m, 1 H), 3.11 (s, 1 H), 3.12-3.17 (m, 2 H), 3.21-3.29 (m, 2 H), 3.39 (d, J = 12.30 Hz, 1 H), 3.50-3.54 (m, 2 H), 3.63-3.81 (m, 2 H), 5.76 (d, J = 2.54 Hz, 1 H), and 5.78-5.85 (m, 1 H). |
| 111/E-5 | Me | H | H | (1S, 2R, 3R, 4aR, 6aS, 7R, 8R, 10aR, 10bR, 12aR)-3-(acetyloxy)-2-(3-amino-2-methylpropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 616 (M + H)$^+$ | (methanol-d$_4$) 0.78 (d, J = 7.17 Hz, 3 H), 0.81 (s, 3 H), 0.85 (d, J = 2.49 Hz, 3 H), 0.89 (d, J = 6.59 Hz, 3 H), 0.97 (d, J = 6.78 Hz, 3 H), 1.06 (d, J = 6.98 Hz, 3 H), 1.11 (s, H), 1.16-1.43 (m, 3 H), 1.44-1.59(m, 4 H), 1.72 (s, 3 H), 1.73-1.81 (m, 5 H), 1.84-1.93 (m, 5 H), 2.07 (s, 3 H), 2.09 (s, 3 H), 2.19-2.28 (m, 1 H), 2.31-2.46 (m, 1 H), 2.32-2.44 (m, 1 H), 2.64-2.72 (m, 1 H), 2.80-3.09 (m, 2 H), 3.11 (s, 1 H), 3.12-3.18 (m, 1 H), 3.41 (d, J = 11.91 Hz, 1 H), 3.47-3.60 (m, 3 H), 3.62-3.74 (m, 2 H), 5.75-5.79 (m, 1 H), and 5.80-5.95 (m, 1 H). |
| 112/E-2 | Me | Et | Et | (1S, 2R, 3R, 4aR, 6aS, 7R, 8R, 10aR, 10bR, 12aR)-3-(acetyloxy)-2-(3-diethyl amino-2-methylpropoxy)-8-[(1R)-1,2-dimethyl propyl]-1,6a,8,10a-tetra methyl-6-oxo-1,3,4,6,6a,7,8,9,10,10a,10b,11,12,12a-tetradecahydro-2H-1,4a-(methanooxymethano)chrysene-7-carboxylic acid | 672 (M + H)$^+$ | (methanol-d$_4$) 0.79 (d, J = 7.22 Hz, 3 H), 0.81 (s, 3 H) 0.87 (s, 3 H), 0.89 (d, J = 6.69 Hz, 3 H), 0.97 (d, J = 6.69 Hz, 3 H), 1.00 (d, J = 6.83 Hz, 3 H), 1.08 (d, J = 6.78 Hz, 2 H), 1.11 (s, 3 H), 1.25-1.32 (m, 2 H), 1.34 (t, J = 7.27 Hz, 3 H), 1.45-1.59 (m, 3 H), 1.66-1.98 (m, 10 H), 2.07-2.09 (m, 1 H), 2.10-2.13 (m, 2 H), 2.20-2.29 (m, 1 H), 2.33-2.43 (m, 1 H), 2.66-2.72 (m, 1 H), 2.99-3.34 (m, 8 H), 3.39-3.72 (m, 8 H), 5.76-5.79 (m, 1 H), and 5.82-5.93 (m, 1 H). |

Example 113

(1S,2R,3R,4aR,6aS,7R,8R,10aR,10bR,12aR)-3-(acetyloxy)-2-(2-amino-2-methylpropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (J-1)

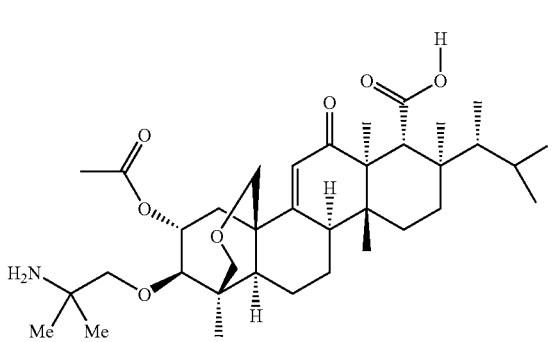

(a) To a solution of Intermediate 3 (1.5 g; 2.5 mmol) in dimethylformamide (30 mL) was added sodium hydride (1.0 g; 60% dispersion, 25.3 mmol) and 1-benzenesulfonyl-2,2-dimethyl-aziridine (2.67 g; 12.5 mmol). The reaction mixture was heated to 70° C. and stirred for 1 hour; the reaction was judged complete by TLC analysis. The reaction was cooled to room temperature and ethyl acetate (100 mL), methanol (10 mL) and water (50 mL) were added. The aqueous phase was twice washed with ethyl acetate. The organic phases were combined, dried over magnesium sulfate, and concentrated. The residue was flash chromatographed (silica gel; 90:10 heptane:ethyl acetate) to yield a white solid (1.75 g).

(b) A portion of this purified material (800 mg) was dissolved in dimethylformamide (20 mL) and the solution was chilled to −70° C. Ammonia (20 g) was added to the reaction solution and sodium metal (enough to sustain a blue color) was added over the course of 1.5 hours. The reaction solution was stirred at −60° C. for 2 hours and then warmed to ammonia reflux for 30 minutes. The reaction was judged complete and methanol (15 mL) was slowly added. The reaction was then warmed to 0° C. and water (50 mL) was added. The aqueous phase was thrice washed with ethyl acetate (75 mL); the organic phases were combined, dried over magnesium sulfate, and concentrated to give a white solid (1.14 g).

The resulting amino derivative was subjected to conditions similar to those described in Example 47 to afford the title compound. Calculated for $C_{36}H_{57}NO_7$: 675; observed: 676 (M+H)$^+$. $^1$H NMR (400 MHz, methanol-d$_4$) δ ppm 0.78 (d, 3H), 0.82 (s, 3H), 0.86-0.90 (m, 6H), 0.90-0.95 (m, 1H), 0.97 (d, 3H), 1.11 (s, 3H), 1.12-1.29 (m, 2H), 1.30 (s, 3H), 1.32 (s, 3H), 1.39-1.59 (m, 3H), 1.72 (s, 3H), 1.74-1.83 (m, 2H), 1.84-1.96 (m, 2H), 2.06 (s, 3H), 2.07-2.11 (m, 1H), 2.20-2.29 (m, 1H), 2.44-2.51 (m, 1H), 2.65-2.72 (m, 1H), 3.11 (s, 1H), 3.27 (d, 1H), 3.42 (d, J=12.18 Hz, 1H), 3.52-3.55 (m, 1H), 3.57-3.67 (m, 3H), 3.85 (d, 1H), 5.77 (d, 1H), and 5.82-5.90 (m, 1H).

Example 114

(1S,2R,3R,4aR,6aS,7R,8R,10aR,10bR,12aR)-3-(acetyloxy)-2-(2-diamino-2-methylpropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (J-2)

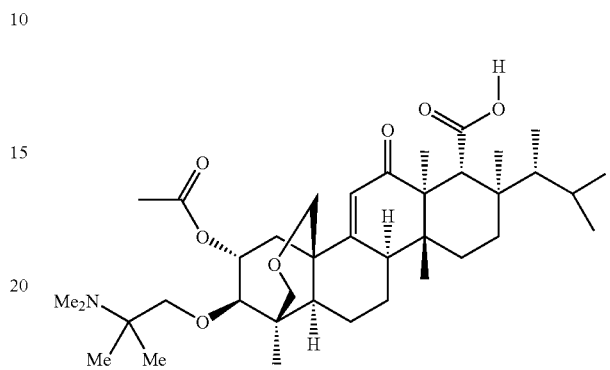

The title compound was prepared in a similar manner as described in Example 50 using the compound described in Example 112 and paraformaldehyde. Calculated for $C_{38}H_{61}NO_7$: 643; observed: 644 (M+H)$^+$. $^1$H NMR (400 MHz, methanol-d$_4$) δ ppm 0.76-0.83 (m, 6H), 0.84-0.95 (m, 6H), 0.95-0.99 (m, 3H), 1.11 (s, 3H), 1.14-1.23 (m, 1H), 1.23-1.32 (m, 2H), 1.33 (s, 3H), 1.34-1.42 (m, 1H), 1.43 (s, 3H), 1.46-1.59 (m, 2H), 1.72 (s, 3H), 1.73-1.93 (m, 2H), 2.07 (s, 3H), 2.08-2.13 (m, 1H), 2.19-2.29 (m, 1H), 2.44-2.54 (m, 1H), 2.64-2.73 (m, 1H), 2.80 (s, 6H), 3.11 (s, 1H), 3.38-3.49 (m, 1H), 3.50-3.58 (m, 1H), 3.68-3.77 (m, 1H), 3.78-3.91 (m, 3H), 4.20-4.42 (m, 1H), 5.76 (d, J=2.59 Hz, 1H), and 5.79-5.91 (m, 1H).

Example 113

Alternative (1S,2R,3R,4aR,6aS,7R,8R,10aR,10bR,12aR)-3-(acetyloxy)-2-(2-amino-2-methylpropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (J-1)

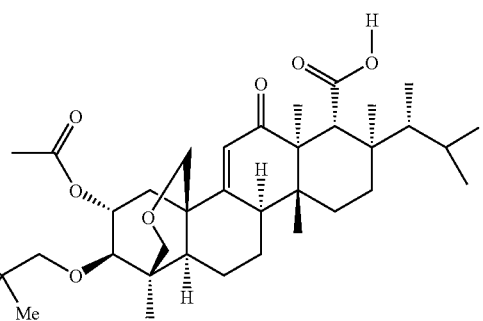

(a) To a solution of Intermediate 3 (1.5 g; 2.5 mmol) in dimethylformamide (30 mL) was added sodium hydride (1.0 g; 60% dispersion, 25.3 mmol) and 1-benzenesulfonyl-2,2- dimethyl-aziridine (2.67 g; 12.5 mmol). The reaction mixture was heated to 70° C. and stirred for 1 hour; the reaction was judged complete by TLC analysis. The reaction was cooled to room temperature and ethyl acetate (100 mL), methanol (10 mL) and water (50 mL) were added. The aqueous phase was twice washed with ethyl acetate. The organic phases were combined, dried over magnesium sulfate, and concentrated. The residue was flash chromatographed (silica gel; 90:10 heptane:ethyl acetate) to yield a white solid (1.75 g).

(b) A portion of this purified material (800 mg) was dissolved in dimethoxyethane (20 mL) and the solution was chilled to −70° C. Ammonia (20 g) was added to the reaction solution and sodium metal (enough to sustain a blue color) was added over the course of 1.5 hours. The reaction solution was stirred at −60° C. for 2 hours and then warmed to ammonia reflux for 30 minutes. The reaction was judged complete and methanol (15 mL) was slowly added. The reaction was then warmed to 0° C. and water (50 mL) was added. The aqueous phase was thrice washed with ethyl acetate (75 mL); the organic phases were combined, dried over magnesium sulfate, and concentrated to give a white solid.

(c) To a stirred solution of the white solid from Step (b) in acetic acid (100 mL) was added p-TsOH—$H_2O$ (0.93 g) and the reaction mixture was heated at 113° C. for 1.5 h. The reaction mixture was then allowed to cool to room temperature and the acetic acid was evaporated under reduced pressure. The residue was dissolved in EtOAc (200 mL) and washed with a saturated $NaHCO_3$ solution (100 mL) carefully. The aqueous phase was re-extracted with EtOAc (2×100 mL). The combined organic solutions were dried over anhydrous $MgSO_4$. After filtration and evaporation of the solvent the desired product was isolated as a white solid (0.87 g).

(d) To a stirred solution of the amine from Step (c) (0.81 g, 1.38 mmol) in acetone (24 mL) was added water (12 mL), MeOH (5 mL), $NaHCO_3$ (1.18 g, 14 mmol), and CBz-OSu (0.41 g, 1.65 mmol). The reaction mixture was stirred at room temperature overnight. The solvent was evaporated in vacuo and the residue was partitioned between EtOAc (80 mL) and water (40 mL). The aqueous phase was separated and extracted with EtOAc (2×30 mL). The combined organic solutions were dried over anhydrous $MgSO_4$, filtered and the solvent was removed by evaporation to afford the desired product as a pale yellow solid (1.14 g). This solid was purified by flash chromatography using MeOH/DCM (1-5%) as eluent to yield the desired product as a pale white solid (0.74 g).

(e) To a one-liter flask was added $CrO_3$ (9.63 g, 96 mmol) and dichloromethane (450 ml). The mixture was cooled to −40° C. (internal temperature) and 3,5-dimethylpyrazole (9.24 g, 96 mmol) was added in a single portion. The mixture was stirred at −20° C. for one hour. The CBz protected amine prepared as described in Step (d) above (1.60 g, 2.18 mmol) dissolved in dichloromethane (30 mL) was added in a single portion and the reaction was allowed to warm overnight. The reaction mixture was washed with a saturated $NaHCO_3$ solution. The organic layer was separated and the combined aqueous fractions were re-extracted with dichloromethane (2×200 mL). The combined organic fractions were dried over $MgSO_4$. The drying agent was removed by filtration and the solvent was carefully evaporated (water bath temp<25° C.), to leave a brown solid. This solid was immediately dissolved in dichloromethane and loaded on a flash column for purification. This solid was purified by flash chromatography using EtOAc/heptanes (10-30%) as eluent. After removal of solvent, the residue was dissolved in EtOAc (300 mL). The organic solution was washed with 1N HCl (2×150 mL). The organic solution was dried over $MgSO_4$, filtered to remove the drying agent and the solvent evaporated to yield the desired compound as a pale white solid (0.34 g).

(f) To a solution of 12-keto intermediate from Step (e) above (0.17 g, 0.23 mmol) in methanol (20 ml) was added HOAc (0.17 mL) and 20% wet $Pd(OH)_2/C$ (0.17 g). The solution was then degassed by passage of nitrogen for 5 minutes. The flask was purged with hydrogen and the reaction was subjected to hydrogenation under balloon pressure. After about 30 minutes the mixture was filtered through a thin layer of Celite. The solvent was evaporated and the residue was dissolved in small volume of dichloromethane and purified by a silica gel chromatography (5 g cartridge). The eluent was a gradient of 1% to 7.5% MeOH in dichloromethane. The desired amine was isolated as a light yellow solid (0.15 g). Calculated for $C_{36}H_{57}NO_7$: 675; observed: 676 (M+H)$^+$. $^1$H NMR (400 MHz, methanol-$d_4$) δ ppm 0.78 (d, 3H), 0.82 (s, 3H), 0.86-0.90 (m, 6H), 0.90-0.95 (m, 1H), 0.97 (d, 3H), 1.11 (s, 3H), 1.12-1.29 (m, 2H), 1.30 (s, 3H), 1.32 (s, 3H), 1.39-1.59 (m, 3H), 1.72 (s, 3H), 1.74-1.83 (m, 2H), 1.84-1.96 (m, 2H), 2.06 (s, 3H), 2.07-2.11 (m, 1H), 2.20-2.29 (m, 1H), 2.44-2.51 (m, 1H), 2.65-2.72 (m, 1H), 3.11 (s, 1H), 3.27 (d, 1H), 3.42 (d, J=12.18 Hz, 1H), 3.52-3.55 (m, 1H), 3.57-3.67 (m, 3H), 3.85 (d, 1H), 5.77 (d, 1H), and 5.82-5.90 (m, 1H).

Example 114

Alternative (1S,2R,3R,4aR,6aS,7R,8R,10aR,10bR,12aR)-3-(acetyloxy)-2-(2-diamino-2-methylpropoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (J-2)

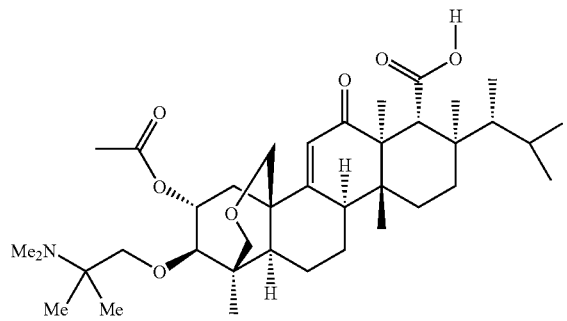

To a solution of the amino compound from Example 113 (60 mg, 0.089 mmol) in MeOH (4 mL), were added paraformaldehyde (9 mg) and $NaHCO_3$ (14 mg) and the mixture was heated at 60° C. for 1.5 h. The reaction mixture was then cooled to room temperature and acetic acid (0.06 mL) and $Pd(OH)_2$—C (20% wet, 60 mg) were added. The mixture was degassed and hydrogenated under balloon pressure at room temperature overnight. The mixture was filtered through a thin layer of Celite, the solvent was evaporated and the residue was purified by silica gel chromatography (5 g cartridge) eluting with MeOH in DCM (2.5-15%) to yield the desired product (40 mg) as a pale yellow solid. Calculated for $C_{38}H_{61}NO_7$: 643; observed: 644 (M+H)$^+$. $^1$H NMR (400 MHz, methanol-$d_4$) δ ppm 0.76-0.83 (m, 6H), 0.84-0.95 (m, 6H), 0.95-0.99 (m, 3H), 1.11 (s, 3H), 1.14-1.23 (m, 1H), 1.23-1.32 (m, 2H), 1.33 (s, 3H), 1.34-1.42 (m, 1H), 1.43 (s, 3H), 1.46-1.59 (m, 2H), 1.72 (s, 3H), 1.73-1.93 (m, 2H), 2.07

(s, 3H), 2.08-2.13 (m, 1H), 2.19-2.29 (m, 1H), 2.44-2.54 (m, 1H), 2.64-2.73 (m, 1H), 2.80 (s, 6H), 3.11 (s, 1H), 3.38-3.49 (m, 1H), 3.50-3.58 (m, 1H), 3.68-3.77 (m, 1H), 3.78-3.91 (m, 3H), 4.20-4.42 (m, 1H), 5.76 (d, J=2.59 Hz, 1H), and 5.79-5.91 (m, 1H).

The compounds described in Table 3 were prepared from Intermediate 3 and an appropriately substituted aziridine in a similar manner as described in Example 113. The resulting amino derivatives could be subjected to an alkylation procedure in a similar manner as described in example 114.

TABLE 3

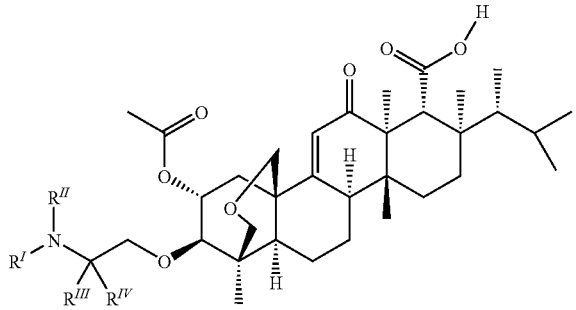

Numbers 115-123 are not used in this application to identify examples
The next example following "Example 114" is numbered "Example 124".

| Ex./cpd | $R^{III}$ | $R^{IV}$ | $R^I$ | $R^{II}$ | Name | MS | $^1$H NMR (400 MHz, methanol-d$_4$, δ, ppm) |
|---|---|---|---|---|---|---|---|
| 124/ J-3 | n-Pr | Me | H | H | (1S, 2R, 3R, 4aR, 6aS, 7R, 8R, 10aR, 10bR, 12aR)-3-(acetyloxy)-2-(2-amino-2-methyl pentyloxy)-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid | 644 (M + H)$^+$ | 0.75-0.83 (m, 6 H), 0.86-0.94 (m, 6 H), 0.95-1.00 (m, 6 H), 1.01-1.09 (m, 2 H), 1.11 (s, 3 H), 1.12-1.26 (m, 5 H), 1.28-1.32 (m, 5 H), 1.32-1.69 (m, 8 H), 1.72 (s, 3 H), 1.74-2.03 (m, 4 H), 2.06 (s, 3 H), 2.07-2.12 (m, 2 H), 2.19-2.32 (m, 2 H), 2.43-2.64 (m, 2 H), 2.65-2.73 (m, 1 H), 3.11 (s, 1 H), 3.34-3.44 (m, 1 H), 3.45-3.56 (m, 2 H), 3.56-3.63 (m, 1 H), 3.63-3.72 (m, 1 H), 3.72-3.79 (m, 1 H), 3.80-3.95 (m, 1 H), 5.75-5.78 (m, 1 H), and 5.78-5.89 (m, 1 H). |
| 125/ J-5 | n-Pr | Me | Me | Me | (1S, 2R, 3R, 4aR, 6aS, 7R, 8R, 10aR, 10bR, 12aR)-3-(acetyloxy)-2-(2-dimethylamino-2-methylpentyloxy)-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy methano)chrysene-7-carboxylic acid | Cal'ed for C$_{40}$H$_{65}$NO$_7$: 671; observed: 672 (M + H)$^+$ | 0.74-0.83 (m, 6 H), 0.85-0.91 (m, 6 H), 0.93-1.08 (m, 6 H), 1.11 (s, 3 H), 1.13-1.39 (m, 6 H), 1.41 (s, 3 H), 1.43-1.70 (m, 3 H), 1.71 (s, 3 H), 1.73-1.93 (m, 4 H), 1.95 (s, 3 H), 2.07 (s, 3 H), 2.08 (s, 1 H), 2.17-2.34 (m, 1 H), 2.46-2.56 (m, 1 H), 2.64-2.73 (m, 1 H), 2.82 (m, 7 H), 3.11 (s, 1 H), 3.44 (d, J = 11.96 Hz, 1 H), 3.48-3.58 (m, 2 H), 3.66-3.76 (m, 1 H), 3.78-3.88 (m, 2 H), 3.90-3.99 (m, 1 H), 5.74-5.78 (m, 1 H), and 5.78-5.93 (m, 1 H). |
| 126/ J-8 | n-Pr | Me | Et | Et | (1S, 2R, 3R, 4aR, 6aS, 7R, 8R, 10aR, 10bR, 12aR)-3-(acetyloxy)-2-(2-diethylamino-2-methylpentyloxy)-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy methano)chrysene-7-carboxylic acid | Cal'ed for C$_{42}$H$_{69}$NO$_7$: 700; observed: 701 (M + H)$^+$ | 0.76 (d, J = 7.22 Hz, 3 H), 0.80 (s, 3 H), 0.85 (s, 3 H), 0.87 (s, 3 H), 0.89-0.93 (m, 6 H), 0.96 (d, J = 6.64 Hz, 3 H), 1.10 (s, 3 H), 1.12-1.17 (m, 4 H), 1.19 (dd, J = 11.62, 2.64 Hz, 1 H), 1.23-1.42 (m, 7 H), 1.47-1.60 (m, 3 H), 1.72 (s, 3 H), 1.71-1.81 (m, 4 H), 1.80-1.94 (m, 3 H), 2.04 (s, 3 H), 2.20-2.34 (m, 1 H), 2.37-2.55 (m, 2 H), 2.66 (d, J = 13.67 Hz, 1 H), 2.78-2.93 (m, 2 H), 3.08 (s, 1 H), 3.09-3.22 (m, 1 H), 3.39 (d, J = 11.91 Hz, 1 H), 3.45-365 (m, 3 H), 3.67-3.81 (m, 2 H), 5.73 (s, 1 H), and 5.73-5.85 (m, 1 H). |
| 127/ J-9 | Et | Me | H | H | (1S, 2R, 3R, 4aR, 6aS, 7R, 8R, 10aR, 10bR, 12aR)-3-(acetyloxy)-2-(2-amino-2-methyl butyloxy)-8-[(1R)- | Cal'ed for C$_{37}$H$_{59}$NO$_7$: 629; observed: 630 | 0.78 (d, J = 7.22 Hz, 3 H), 0.81 (s, 3 H), 0.86-0.90 (m, 6 H), 0.96-0.98 (m, 6 H), 1.11 (s, 3 H), 1.17-1.23 (m, 1 H), 1.26 (d, J = 2.88 Hz, 3 H), 1.29-1.71 (m, 8 H), 1.72 (s, 3 H), 1.72-1.80 (m, 2 H), 1.86-1.91 (m, |

TABLE 3-continued

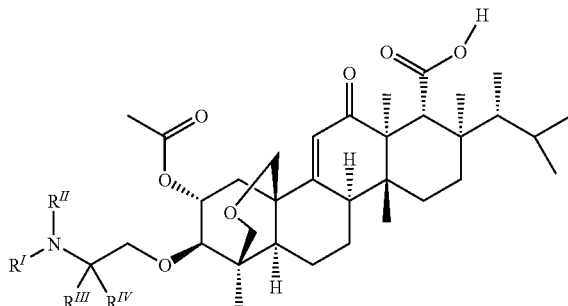

Numbers 115-123 are not used in this application to identify examples
The next example following "Example 114" is numbered "Example 124".

| Ex./cpd | $R^{III}$ | $R^{IV}$ | $R^{I}$ | $R^{II}$ | Name | MS | $^1$H NMR (400 MHz, methanol-$d_4$, δ, ppm) |
|---|---|---|---|---|---|---|---|
| | | | | | 1,2-dimethylpropyl]-1,6a,8,10a-tetra methyl-6-oxo-1,3,4, 6,6a,7,8,9,10,10a,10 b,11,12,12a-tetra decahydro-2H-1,4a-(methanooxymethano) chrysene-7-carboxylic acid | $(M + H)^+$ | 1 H), 1.92 (s, 3 H), 2.04-2.11 (m, 4 H), 2.19-2.28 (m, 1R), 2.48 (dd, J = 13.15, 7.15 Hz, 1 H), 2.68 (m, 1 H), 3.11 (s, 1 H), 3.41 (d, J = 11.81 Hz, 1 H), 3.51-3.59 (m, 3 H), 3.61-3.76 (m, 2 H), 3.85 (d, J = 11.91 Hz, 1 H), 5.76 (d, J = 2.29 Hz, 1 H), and 5.78-5.89 (m, 1 H). |
| 128/ J-10 | Et | Me | Me | Me | (1S, 2R, 3R, 4aR, 6aS, 7R, 8R, 10aR, 10bR, 12aR)-3-(acetyloxy)-2-(2-dimethylamino-2-methylbutyloxy)-8-[(1R)-1,2-dimethyl propyl]-1,6a,8,10a-tetramethyl-6-oxo-1,3,4,6,6a,7,8,9,10, 10a,10b,11,12,12a-tetradecahydro-2H-1,4a-(methanooxy methano)chrysene-7-carboxylic acid | Cal'ed for $C_{39}H_{63}NO_7$: 657; observed: 658 $(M + H)^+$ | 0.75-0.83 (m, 6 H), 0.84-1.05 (m, 12 H), 1.11 (s, 3 H), 1.12-1.35 (m, 6 H), 1.37 (s, 3 H), 1.39-1.70 (m, 3 H), 1.70-1.73 (m, 3 H), 1.73-1.92 (m, 4 H), 1.95 (s, 3 H), 2.04-2.12 (m, 3 H), 2.18-2.28 (m, 1 H), 2.45-2.72 (m, 2 H), 2.78-2.83 (m, 6 H), 3.11 (s, 1 H), 3.34-3.49 (m, 2 H), 3.49-3.60 (m, 1 H), 3.69-3.95 (m, 4 H), 5.76 (d, J = 2.64 Hz, 1 H), and 5.79-5.91 (m, 1 H). |
| 129/ J-7 | i-Pr | Me | H | H | (1S, 2R, 3R, 4aR, 6aS, 7R, 8R, 10aR, 10bR, 12aR)-3-(acetyloxy)-2-(2-amino-2,3-dimethyl butyloxy)-8-[(1R)-1,2-dimethyl propyl]-1,6a,8,10a-tetra methyl-6-oxo-1,3,4, 6,6a,7,8,9,10,10a, 10b,11,12,12a-tetra decahydro-2H-1,4a-(methanooxymethano) chrysene-7-carboxylic acid | Cal'ed for $C_{38}H_{61}NO_7$: 643; observed: 644 $(M + H)^+$ | 0.78 (d, J = 7.17 Hz, 3 H), 0.82 (s, 3 H), 0.87-0.90 (m, 6 H), 0.93-1.03 (m, 9 H), 1.11 (s, 3 H), 1.17 (d, J = 1.17 Hz, 3 H), 1.28-1.72 (m, 5 H), 1.73 (s, 3 H), 1.76-1.88 (m, 3 H), 1.90 (s, 3 H), 1.91-2.03 (m, 3 H), 2.05 (s, 3 H), 2.24-2.30 (m, 1 H), 2.51 (d, J = 24.75 Hz, 1 H), 2.65-2.71 (m, 1 H), 3.09 (s, 1 H), 3.24-3.30 (m, 1 H), 3.40 (m, 1 H), 3.48-3.60 (m, 3 H), 3.64-3.71 (m, 1 H), 3.78-3.91 (m, 1 H), 5.76-5.80 (m, 1 H) and 5.79-5.88 (m, 1 H). |
| 130/ J-11 | i-Pr | Me | Me | Me | (1S, 2R, 3R, 4aR, 6aS, 7R, 8R, 10aR, 10bR, 12aR)-3-(acetyloxy)-2-(2-dimethylamino-2,3-dimethylbutyl oxy)-8-[(1R)-1,2-dimethyl propyl]-1,6a,8,10a-tetra methyl-6-oxo-1,3,4,6,6a,7,8,9,10, 10a,10b,11,12,12a-tetradecahydro-2H-1,4a-(methanooxy methano)chrysene-7-carboxylic acid | Cal'ed for $C_{40}H_{65}NO_7$: 671; observed: 672 $(M + H)^+$ | 0.71 (d, J = 7.22 Hz, 3 H), 0.74 (s, 3 H), 0.78-0.85 (m, 6 H), 0.89 (d, J = 6.69 Hz, 3 H), 0.92-1.02 (m, 6 H), 1.03 (s, 3 H), 1.06-1.16 (m, 3 H), 1.19-1.63 (m, 5 H), 1.64 (s, 3 H), 1.65-1.83 (m, 4 H), 1.84 (s, 3 H), 2.00 (s, 3 H), 2.13-2.24 (m, 2 H), 2.28-2.48 (m, 2 H), 2.56-2.64 (m, 1 H), 2.70-2.76 (m, 7 H), 3.03 (s, 1 H), 3.20 (d, J = 3.71 Hz, 1 H), 3.36 (d, J = 11.96 Hz, 1 H), 3.40-3.51 (m, 2 H), 3.61-3.73 (m, 2 H), 3.81-3.91 (m, 1 H), 5.66-5.69 (m, 1 H), and 5.69-5.79 (m, 1 H). |
| 131/ J-6 | Me | Me | H | i-Pr | (1S, 2R, 3R, 4aR, 6aS, 7R, 8R, 10aR, 10bR, 12aR)-3-(acetyloxy)-2-(2- | Cal'ed for $C_{39}H_{63}NO_7$: 657; | 0.70 (d, J = 7.27 Hz, 3 H), 0.73 (s, 3 H), 0.78-0.82 (m, 6 H), 0.88 (d, J = 6.69 Hz, 3 H), 1.02 (s, 3 H), 1.18-1.28 (m, 9 H), 1.29 (s, 3 H), 1.31- |

TABLE 3-continued

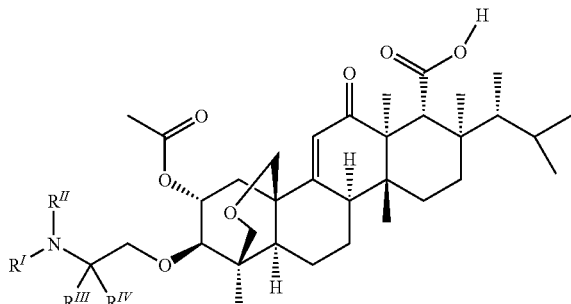

Numbers 115-123 are not used in this application to identify examples
The next example following "Example 114" is numbered "Example 124".

| Ex./cpd | $R^{III}$ | $R^{IV}$ | $R^{I}$ | $R^{II}$ | Name | MS | $^1$H NMR (400 MHz, methanol-d$_4$, δ, ppm) |
|---|---|---|---|---|---|---|---|
| | | | | | isopropylamino-2-methylpropyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | observed: 658 (M + H)$^+$ | 1.63 (m, 4 H), 1.63 (s, 3 H), 1.64-1.81 (m, 3 H), 1.82 (s, 3 H), 1.98 (s, 3 H), 1.99-2.04 (m, 1 H), 2.13-2.19 (m, 1 H), 2.37-2.44 (m, 1 H), 2.56-2.63 (m, 1 H), 3.02 (s, 1 H), 3.35 (d, J = 11.76 Hz, 1 H), 3.37-3.49 (m, 4 H), 3.55 (d, J = 10.20 Hz, 1 H), 3.69-3.76 (m, 2 H), 5.68 (d, J = 2.59 Hz, 1 H), and 5.73 (m, 1 H). |
| 132/J-4 | Me | Me | Et | Et | (1S, 2R, 3R, 4aR, 6aS, 7R, 8R, 10aR, 10bR, 12aR)-3-(acetyloxy)-2-(2-diethylamino-2-methylpropyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | Cal'ed for $C_{40}H_{65}NO_7$: 671; observed: 672 (M + H)$^+$ | 0.78 (d, J = 7.22 Hz, 3 H), 0.81 (s, 3 H), 0.89 (d, J = 6.78 Hz, 3 H), 0.90 (s, 3 H), 0.97 (s, J = 6.69 Hz, 3 H), 1.11 (s, 3 H), 1.14-1.35 (m, 2 H), 1.35-1.41 (m, 9 H), 1.42-1.48 (m, 1 H), 1.48 (s, 3 H), 1.49-1.71 (m, 2 H), 1.72 (s, 3 H), 1.72-1.83 (m, 2 H), 1.87-1.97 (m, 3 H), 2.09 (s, 3 H), 2.09-2.13 (m, 1 H), 2.20-2.28 (m, 1 H), 2.44-2.52 (m, 1 H), 2.65-2.72 (m, 1 H), 3.11 (s, 1 H), 3.31-3.38 (m, 4 H), 3.45 (d, J = 11.81 Hz, 1 H), 3.42-3.60 (m, 3 H), 3.72-3.82 (m, 2 H), 3.92 (d, J = 11.03 Hz, 1 H), 5.76 (d, J = 2.59 Hz, 1 H), and 5.81-5.89 (m, 1 H). |
| 133/J-12 | Me | Me | Me | H | (1S, 2R, 3R, 4aR, 6aS, 7R, 8R, 10aR, 10bR, 12aR)-3-(acetyloxy)-2-(2-methylamino-2-methylpropyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | Cal'ed for $C_{37}H_{59}NO_7$: 629; observed: 630 (M + H)$^+$ | 0.78 (d, J = 7.22 Hz, 3 H), 0.82 (s, 3 H), 0.86-0.89 (m, 6 H), 0.89-1.09 (m, 2 H), 1.11 (s, 3 H), 1.21 (s, 3 H), 1.23 (m, 1 H), 1.24-1.25 (s, 3 H), 1.25-1.71 (m, 6 H), 1.74 (s, 3 H), 1.76-1.88 (m, 1 H), 1.89 (s, 1 H), 2.05 (s, 3 H), 2.06-2.10 (m, 1 H), 2.21-2.32 (m, 1 H), 2.47 (s, 3 H), 2.48-2.52 (m, 1 H), 2.63-2.71 (m, 1 H), 3.08 (s, 1 H), 3.25 (d, J = 9.08 Hz, 1 H), 3.41 (d, J = 11.37 Hz, 1 H), 3.49-3.61 (m, 3 H), 3.66 (d, J = 9.57 Hz, 1 H), 3.82 (d, J = 11.76 Hz, 1 H), 5.77-5.79 (m, 1 H), and 5.79-5.89 (m, 1 H). |
| 134/J-13 | n-Pr | Me | CF$_3$-CH$_2$ | H | (1S, 2R, 3R, 4aR, 6aS, 7R, 8R, 10aR, 10bR, 12aR)-3-(acetyloxy)-2-(2-trifluoroethylamino-2-methylpentyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | Cal'ed for $C_{40}H_{62}F_3NO_7$: 725; observed: 726 (M + H)$^+$ | 0.70-0.86 (m, 6 H), 0.85-0.94 (m, 9 H), 0.93-1.00 (m, 6 H), 1.03-1.13 (m, 3 H), 1.16-1.33 (m, 8 H), 1.33-1.41 (m, 3 H), 1.42-1.65 (m, 2 H), 1.69 (s, 3 H), 1.72-1.97 (m, 3 H), 2.03-2.09 (m, 3 H), 2.09-2.25 (m, 1 H), 2.43-2.74 (m, 1 H), 3.13-3.28 (m, 2 H), 3.33-3.48 (m, 1 H), 3.49-3.59 (m, 1 H), 3.65 (d, J = 3.95 Hz, 1 H), 3.68-3.78 (m, 2 H), 3.85 (d, J = 12.59 Hz, 1 H), 4.46-4.60 (m, 2 H), 5.72-5.78 (m, 1 H), and 5.78-5.91 (m, 1 H). |

TABLE 3-continued

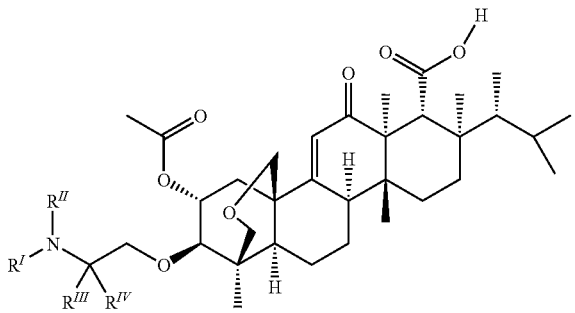

Numbers 115-123 are not used in this application to identify examples
The next example following "Example 114" is numbered "Example 124".

| Ex./ cpd | $R^{III}$ | $R^{IV}$ | $R^{I}$ | $R^{II}$ | Name | MS | $^1$H NMR (400 MHz, methanol-$d_4$, δ, ppm) |
|---|---|---|---|---|---|---|---|
| 135/ J-14 | i-Bu | Me | H | H | (1S, 2R, 3R, 4aR, 6aS, 7R, 8R, 10aR, 10bR, 12aR)-3-(acetyloxy)-2-(2-amino-2,4-dimethyl pentyloxy)-8-[(1R)-1,2-dimethylpropyl]-1,6a,8,10a-tetra methyl-6-oxo-1,3,4,6,6a,7,8,9,10,10a,10b,11,12,12a-tetra decahydro-2H-1,4a-(methanooxymethano) chrysene-7-carboxylic acid | Cal'ed for $C_{39}H_{63}NO_7$: 657; observed: 658 $(M + H)^+$ | 0.78 (d, J = 7.22 Hz, 3 H), 0.82 (s, 3 H), 0.86-0.90 (m, 6 H), 0.95-1.03 (m, 11 H), 1.11 (s, 3 H), 1.30 (d, J = 5.27 Hz, 3 H), 1.32-1.72 (m, 7 H), 1.72 (s, 3 H), 1.74-1.89 (m, 4 H), 1.90 (s, 3 H), 2.06 (2s, 3 H), 2.06-2.10 (m, 1 H), 2.21-2.29 (m, J = 26.50 Hz, 1 H), 2.49 (d, J = 25.48 Hz, 1 H), 2.63-2.71 (m, 1 H), 3.10 (s, 1 H), 3.28 (d, J = 10.15 Hz, 1 H), 3.41 (m, 1 H), 3.52-3.58 (m, 2 H), 3.60-3.69 (m, 1 H), 3.72-3.88 (m, 2H), 5.75-5.78 (m, 1 H), and 5.79-5.88 (m, 1 H). |
| 136/ J-15 | i-Bu | Me | Me | Me | (1S, 2R, 3R, 4aR, 6aS, 7R, 8R, 10aR, 10bR, 12aR)-3-(acetyloxy)-2-(2-dimethylamino-2,4-dimethylpentyloxy)-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy methano)chrysene-7-carboxylic acid | Cal'ed for $C_{41}H_{67}NO_7$: 685; observed: 686 $(M + H)^+$ | 0.78 (d, J = 7.22 Hz, 3 H), 0.81 (s, 3 H), 0.87-0.92 (m, 6 H), 0.97 (d, J = 6.69 Hz, 3 H), 0.99-1.06 (m, 6 H), 1.11 (s, 3 H), 1.28-1.35 (m, 3 H), 1.43 (s, 3 H), 1.44-1.71 (m, 5 H), 1.72 (s, 3 H), 1.74-1.89 (m, 4 H), 1.91 (s, 3 H), 2.07 (s, 3 H), 2.08-2.11 (m, 1 H), 2.21-2.29 (m, 1 H), 2.45-2.56 (m, 1 H), 2.67-2.71 (m, 8 H), 3.11 (s, 1 H), 3.33-3.36 (m, 1 H), 3.43 (d, J = 11.91 Hz, 1 H), 3.50-3.58 (m, 2 H), 3.66-3.98 (m, 3 H), 5.74-5.77 (m, 1 H), and 5.78-5.89 (m, 1 H). |
| 137/ J-16 | Et | Et | H | H | (1S, 2R, 3R, 4aR, 6aS, 7R, 8R, 10aR, 10bR, 12aR)-3-(acetyloxy)-2-(2-amino-2-ethylbutyl oxy)-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid | Cal'ed for $C_{38}H_{61}NO_7$: 643; observed: 644 $(M + H)^+$ | 0.69 (d, J = 7.17 Hz, 3 H), 0.73 (s, 3 H), 0.77-0.82 (m, 6 H), 0.81-0.93 (m, 5 H), 0.83-0.93 (m, 8 H), 1.03 (s, 3 H), 1.20 (s, 3 H), 1.23-1.51 (m, 6 H), 1.55-1.71 (m, 6 H), 1.64 (s, 3 H), 1.97 (s, 3 H), 2.13-2.22 (m, 1 H), 2.41 (dd, J = 13.15, 7.10 Hz, 1 H), 2.56-2.64 (m, 1 H), 3.01 (s, 1 H), 3.39-3.47 (m, J = 12.84 Hz, 1 H), 3.45 (s, 2 H), 3.52-3.58 (m, 1 H), 3.67 (d, J = 9.91 Hz, 1 H), 3.77 (d, J = 11.96 Hz, 1 H), 5.67 (d, J = 2.59 Hz, 1 H), and 5.70-5.78 (m, 1 H). |
| 138/ J-17 | Me | CH$_2$O$^i$Pr | H | H | (1S, 2R, 3R, 4aR, 6aS, 7R, 8R, 10aR, 10bR, 12aR)-3-(acetoxy)-2-(2-amino-3-isopropoxy-2-methylpropoxy)-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy | Cal'ed for $C_{39}H_{63}NO_8$: 673; observed: 674 $(M + H)^+$ | 0.79 (d, J = 7.22 Hz, 3 H), 0.81 (s, 3 H), 0.86-0.91 (m, 6 H), 0.91-0.95 (m, 1 H), 0.97 (d, J = 6.74 Hz, 3 H), 1.11 (s, 3 H), 1.17-1.22 (m, 6 H), 1.30 (d, J = 4.34 Hz, 3 H), 1.32-1.63 (m, 5 H), 1.72 (s, 3 H), 1.73-1.80 (m, 2 H), 1.86-1.95 (m, 2 H), 2.07 (2s, 3 H), 2.08-2.13 (m, 1 H), 2.19-2.29 (m, 1 H), 2.42-2.51 (m), 2.64-2.72 (m, 1 H), 3.11 (s, 1 H), 3.22-3.28 (m, 1 H), 3.35-3.49 (m, 2 H), 3.54 (m, 3 H), 3.60-3.70 (m, 2 H), 3.73 (d, J = 6.49 Hz, 1 H), 3.74-3.86 |

TABLE 3-continued

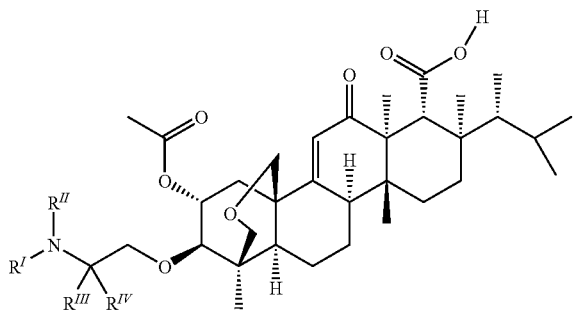

Numbers 115-123 are not used in this application to identify examples
The next example following "Example 114" is numbered "Example 124".

| Ex./cpd | $R^{III}$ | $R^{IV}$ | $R^{I}$ | $R^{II}$ | Name | MS | $^1$H NMR (400 MHz, methanol-$d_4$, δ, ppm) |
|---|---|---|---|---|---|---|---|
| | | | | | methano)chrysene-7-carboxylic acid | | (m, 1 H), 5.72-5.78 (m, 1 H), and 5.80-5.91 (m, 1 H). |
| 139/J-18 | Me | CH$_2$O$^i$Pr | Me | Me | (1S, 2R, 3R, 4aR, 6aS, 7R, 8R, 10aR, 10bR,12aR)-3-(acetoxy)-2-(2-dimethylamino-3-isopropoxy-2-methyl propoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | Cal'ed for C$_{41}$H$_{67}$NO$_8$: 701; observed; 702 (M + H)$^+$ | 0.78 (d, J = 7.22 Hz, 3 H), 0.81 (s, 3 H), 0.86-0.91 (m, 6 H), 0.91-0.94 (m, 1 H), 0.97 (d, J = 6.74 Hz, 3 H), 1.11 (s, 3 H), 1.17-1.21 (m, 9 H), 1.26 (s, 3 H), 1.32-1.34 (m, 3 H), 1.36-1.58 (m, 1 H), 1.72 (s, 3 H), 1.74-1.91 (m, 1 H), 1.92 (s, 3 H), 2.06-2.11 (m, 4 H), 2.20-2.28 (m, 1 H), 2.43-2.53 (m, 1 H), 2.65-2.72 (m, 1 H), 2.75-2.82 (m, 7 H), 3.11 (s, 1 H), 3.24-3.29 (m, 1 H), 3.40-3.73 (m, 6 H), 3.73-3.85 (m, 2 H), 3.88-4.03 (m, 1 H), 5.74-5.77 (m, 1 H), and 5.79-5.89 (m, 1 H). |
| 140/J-19 | Me | Et | Et | Et | (1S, 2R, 3R, 4aR, 6aS, 7R, 8R, 10aR, 10bR,12aR)-3-(acetoxy)-2-(2-diethylamino-2-methyl butoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | Cal'ed for C$_{41}$H$_{67}$NO$_7$: 685; observed: 686 (M + H)$^+$ | 0.78 (d, J = 7.22 Hz, 3 H), 0.81 (s, 3 H), 0.87 (s, 3 H), 0.88-0.93 (m, 6 H), 0.97 (d, J = 6.69 Hz, 3 H), 1.11 (s, 3 H), 1.13 (d, J = 2.54 Hz, 3 H), 1.15 (s, 3 H), 1.26-1.32 (m, 2 H), 1.36-1.47 (m, 2 H), 1.49-1.59 (m, 3 H), 1.59-1.72 (m, 3 H), 1.73 (s, 3 H), 1.75-1.80 (m, 2 H), 1.82-1.99 (m, 3 H), 2.05 (s, 3 H), 2.20-2.31 (m, 1 H), 2.39-2.50 (m, 1 H), 2.67 (d, J = 12.01 Hz, 1 H), 2.78-2.95 (m, 5 H), 3.09 (s, 1 H), 3.16 (d, J = 8.88 Hz, 1 H), 3.40 (d, J = 11.71 Hz, 1 H), 3.52 (s, 2 H), 3.57 (d, J = 9.76 Hz, 1 H), 3.75 (d, J = 9.81 Hz, 2 H), 5.74 (s, 1 H), and 5.77-5.85 (m, 1 H). |
| 141/J-20 | Me | Et | n-Pr | n-Pr | (1S, 2R, 3R, 4aR, 6aS, 7R, 8R, 10aR, 10bR,12aR)-3-(acetoxy)-2-(2-dipropylamino-2-methylbutoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | Cal'ed for C$_{43}$H$_{71}$NO$_7$: 714; observed: 715 (M + H)$^+$ | 0.78 (d, J = 7.22 Hz, 3 H), 0.81 (s, H), 0.86-0.91 (m, 6 H), 0.91-0.98 (m, 12 H), 1.00-1.05 (m, 2 H), 1.11 (s, 3 H), 1.17-1.27 (m, 2 H), 1.27-1.36 (m, 3 H), 1.38-1.58 (m, 6 H), 1.58-1.68 (m, 3 H), 1.72 (s, 3 H), 1.73-1.81 (m, 3 H), 1.84-1.95 (m, 3 H), 2.07 (s, 3 H), 2.17-2.29 (m, 1 H), 2.42-2.54 (m, 1 H), 2.68 (d, J = 12.64 Hz, 1 H), 2.85-3.04 (m, 2 H), 3.11 (s, 1 H), 3.43 (d, J = 11.86 Hz, 1 H), 3.53 (s, 2 H), 3.58-3.70 (m, 1 H), 3.69-3.96 (m, 2 H), 5.70-5.82 (m, 2 H), and 5.79-5.87 (m, 1 H). |

Example 142

(1S,2R,3R,4aR,6aS,7R,8R,10aR,10bR,12aR)-3-(N-methylcarbamate)-2-(2-aminoethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid
(K-39)

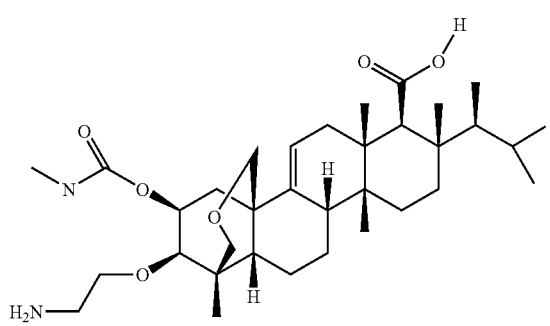

A solution of Intermediate 1 (300 mg; 0.45 mmol) was submitted to the conditions outlined in Example 1 (a). During the course of the reaction, the 2-OH byproduct was isolated (160 mg). Material was dissolved in tetrahydrofuran (4 mL) and pyridine (84 µL). Triphosgene (154 mg; 0.52 mmol) was added and the reaction solution stirred at room temperature for 30 minutes. Methylamine (2.0 M solution in tetrahydrofuran) was added portionwise until the reaction was judged complete by TLC analysis. Dichloromethane (10 mL) and water (10 mL) were added to the reaction solution. The aqueous phase was washed with dichloromethane and ethyl acetate. The organic phases were combined, washed with aqueous hydrochloric acid (1.0 M) and saturated NaCl solution, dried over sodium sulfate, and concentrated. The residue was flash chromatographed (87:13 heptane:ethyl acetate).

Purified material (110 mg) was submitted to the conditions outlined Example 1 (b) to yield the desired aldehyde. A portion of this material (60 mg) was dissolved in methanol (6 mL). Hydroxylamine hydrochloride (62 mg) and sodium bicarbonate (302 mg) were added and the reaction stirred at room temperature for 1 hour. The reaction was judged complete by TLC analysis and dichloromethane (6 mL) and water (6 mL) were added. The aqueous phase was twice washed with ethyl acetate. The organic phases were combined, washed with water and saturated NaCl solution, dried over sodium sulfate, and concentrated.

Material was subsequently submitted to the hydrogenolysis conditions outlined in Example 1 (e). A portion of this material (10 mg) was dissolved in methanol (1 mL). Raney nickel (100 µL slurry) and aqueous sodium hydroxide solution (5%; 50 µL) were added and the reaction stirred at room temperature for 3 hours. The reaction was judged to be nearly complete by TLC analysis and the reaction contents were filtered over a pad of Celite. The filtrate was concentrated and the residue was flash chromatographed ($C_{18}$ cartridge; 50:50 to 100:0 methanol:water) to yield the title compound as the acetate salt (3 mg). Calcuated for $C_{34}H_{56}N_2O_6$: 588; observed: 589 (M+H)$^+$. $^1$H NMR (400 MHz, methanol-$d_4$) δ ppm 0.76-0.78 (m, J=2.25 Hz, 6H), 0.81 (d, J=13.18 Hz, 3H), 0.87 (d, J=6.69 Hz, 3H), 0.91 (d, J=6.83 Hz, 3H), 1.17 (s, 3H), 1.22 (s, 3H), 1.24-1.52 (m, 6H), 1.53-1.68 (m, 3H), 1.72-1.89 (m, 3H), 1.94 (s, 3H), 2.04-2.14 (m, 1H), 2.17-2.27 (m, 1H), 2.37-2.49 (m, 1H), 2.71 (s, 3H), 2.85 (s, 1H), 3.01-3.18 (m, 3H), 3.36 (d, J=12.25 Hz, 1H), 3.40-3.52 (m, 2H), 3.73-3.82 (m, 2H), 3.84-3.93 (m, 1H), 5.49 (d, J=5.37 Hz, 1H), and 5.60-5.72 (m, 1H).

Example 143

(1S,2R,3R,4aR,6aS,7R,8R,10aR,10bR,12aR)-3-(acetamide)-2-(2-aminoethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid
(C-39)

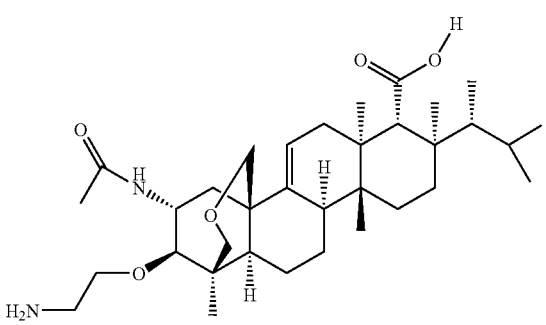

Material submitted to conditions outlined in Example 1 (a) (100 mg; 0.15 mmol) was dissolved in toluene (2 mL) and acetonitrile (3 mL) was added trifluoromethanosulfonic acid (12 uL). The reaction stirred at room temperature for 1 hour. Additional trifluoromethanolsulfonic acid (10 µL) was added and the reaction stirred at room temperature for 2 hours. The reaction was judged complete by TLC analysis and triethylamine (100 mL) was added. The reaction contents were concentrated and the residue was flash chromatographed (50:50 heptane:ethyl acetate). Purified material (100 mg) was submitted to the conditions outlined in Example 1 (b) to generate the desired aldehyde.

Purified material (70 mg) was dissolved in methanol (4 mL). Benzylamine (52 µL), acetic acid (150 µL), and sodium cyanoborohydride (25 mg) were added and the reaction stirred at room temperature for 72 hours. The reaction was judged complete by TLC analysis. Dichloromethane (6 mL) and water (6 mL) were added to the reaction solution. The organic phase was washed with saturated NaCl solution, dried over sodium sulfate, and concentrated. The residue was flash chromatographed (100:0 to 78:22 ethyl acetate:methanol).

Purified material (12 mg) was submitted to the hydrogenolysis conditions outlined in Example 1 (e) to yield the title compound as an acetate salt (6 mg). Calculated for $C_{34}H_{56}N_2O_5$: 572; observed: 573 (M+H)$^+$. $^1$H NMR (400 MHz, methanol-$d_4$) δ ppm 0.75-0.83 (m, 9H) m 0.87 (d, J=6.69 Hz, 3H), 0.91 (d, J=6.78 Hz, 3H), 1.18 (s, 3H), 1.22 (s, 3H), 1.24-1.69 (m, 8H), 1.71-1.92 (m, 4H), 1.93-1.96 (m, 1H), 1.97 (s, 3H), 2.05-2.14 (m, 1H), 2.15-2.26 (m, 2H), 2.86 (s, 1H), 2.98 (d, J=9.76 Hz, 1H), 3.01-3.15 (m, 2H), 3.38 (d, J=11.62 Hz, 1H), 3.43-3.56 (m, 2H), 3.74-3.85 (m, 2H), 4.92-5.02 (m, 1H), and 5.51 (s, 1H).

Example 144

(1S,2R,3R,4aR,6aS,7R,8R,10aR,10bR,12aR)-3-(acetyloxy)-2-(2-aminohexyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-2)

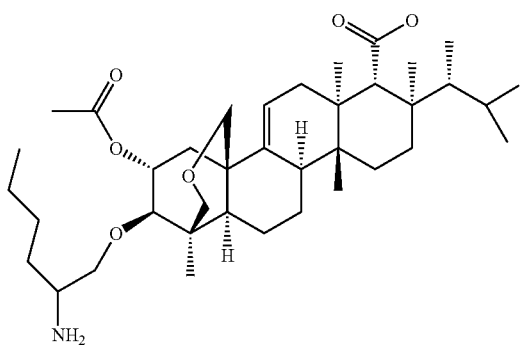

In a similar manner as described in Example 1(a), from Intermediate 3 and 2-bromomethylhex-1-ene was obtained the desired hexenyl derivative. This derivative was subjected to the conditions outlined in Example 1 (b-e) to yield the title compound which was converted to the acetate salt. Calculated for $C_{37}H_{61}NO_6$: 615; observed: 616 (M+H)$^+$. $^1$H NMR (400 MHz, methanol-$d_4$) δ ppm 0.77 (s, 3H), 0.78 (d, J=7.27 Hz, 3H), 0.83-0.85 (s, 3H), 0.87 (d, J=6.74 Hz, 3H), 0.89-0.98 (m, 6H), 1.18 (s, 3H), 1.23 (s, 3H), 1.24-1.52 (m, 10H), 1.52-1.70 (m, 4H), 1.71-1.92 (m, 4H), 1.93 (s, 3H), 1.94-2.01 (m, 1H), 2.06 (s, 3H), 2.07-2.14 (m, 1H), 2.17-2.26 (m, 1H), 2.41-2.49 (m, 1H), 2.85 (s, 1H), 3.22 (d, J=8.93 Hz, 1H), 3.35-3.41 (m, 1H), 3.41-3.51 (m, 2H), 3.64-3.90 (m, 4H), 5.48 (d, J=5.61 Hz, 1H), and 5.72-5.82 (m, 1H).

Example 145

(1S,2R,3R,4aR,6aS,7R,8R,10aR,10bR,12aR)-3-(acetyloxy)-2-(2-aminoheptyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-8)

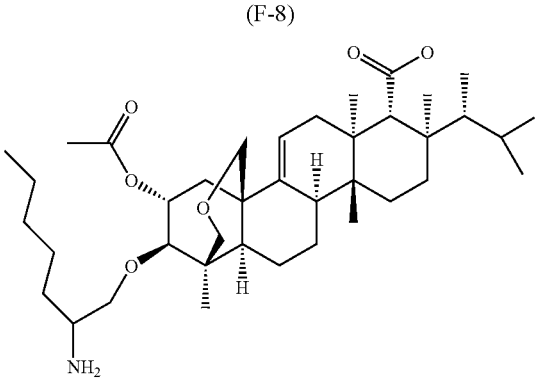

In a similar manner as described in Example 1(a), from Intermediate 3 and 2-bromomethylhept-1-ene was obtained the desired heptenyl derivative. This derivative was subjected to the conditions outlined in Example 1 (b-e) to yield the title compound which was converted to the acetate salt. Calculated for $C_{37}H_{61}NO_6$: 615; observed: 616 (M+H)$^+$. $^1$H NMR (400 MHz, methanol-$d_4$) δ ppm 0.72-0.79 (m, 6H), 0.80-0.83 (m, 3H), 0.85 (d, J=6.83 Hz, 3H), 0.88-0.94 (m, 6H), 1.17 (s, 3H), 1.22 (s, 3H), 1.40 (m, 9H), 1.43-1.68 (m, 7H), 1.68-1.86 (m, 4H), 1.89 (s, 2H), 1.91-2.01 (m, 1H), 2.04 (s, 3H), 2.05-2.14 (m, 1H), 2.16-2.27 (m, 1H), 2.38-2.49 (m, 1H), 2.81 (s, 1H), 3.16-3.23 (m, 2H), 3.35-3.49 (m, 3H), 3.70-3.78 (m, 2H), 5.43-5.49 (m, 1H), and 5.70-5.83 (m, 1H).

Example 146

(1S,2R,3R,4aR,6aS,7R,8R,10aR,10bR,12aR)-3-(acetyloxy)-2-(2-amino-2-cyclopentyl-ethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-4)

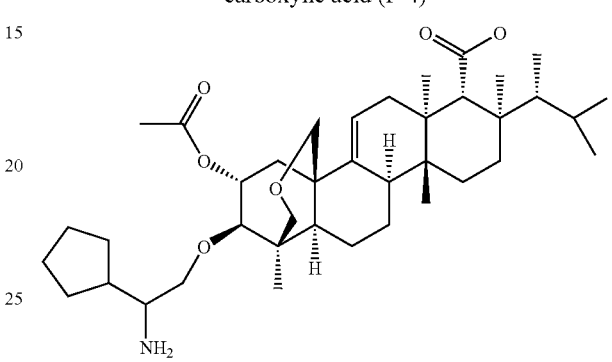

In a similar manner as described in Example 1(a), from Intermediate 3 and 1-bromomethylvinyl-cyclopentane was obtained the desired heptenyl derivative. This derivative was subjected to the conditions outlined in Example 1 (b-e) to yield the title compound which was converted to the acetate salt. $^1$H NMR (400 MHz, METHANOL-$d_4$) δ ppm 0.76 (d, J=2.73 Hz, 6H), 0.83 (s, 3H), 0.85 (d, J=6.64 Hz, 3H), 0.90 (d, J=6.83 Hz, 3H), 1.18 (s, 3H), 1.22 (s, 3H), 1.24-1.35 (m, 3H), 1.34-1.43 (m, 1H), 1.44-1.52 (m, 1H), 1.56-1.67 (m, 7H), 1.68-1.86 (m, 6H), 1.91-1.98 (m, 2H), 1.98-2.02 (m, 1H), 2.00-2.06 (m, 3H), 2.07-2.13 (m, 2H), 2.23 (s, 1H), 2.38-2.49 (m, 1H), 2.80 (s, 1H), 2.95-3.10 (m, 1H), 3.14-3.26 (m, J=8.59 Hz, 1H), 3.39-3.50 (m, 3H), 3.75 (s, 2H), 3.81-3.94 (m, 1H), 5.46 (d, J=5.47 Hz, 1H), and 5.61-5.91 (m, 1H).

Example 147

(1S,2R,3R,4aR,6aS,7R,8R,10aR,10bR,12aR)-3-(acetyloxy)-2-(2-amino-2-cyclohexyl-ethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (F-5)

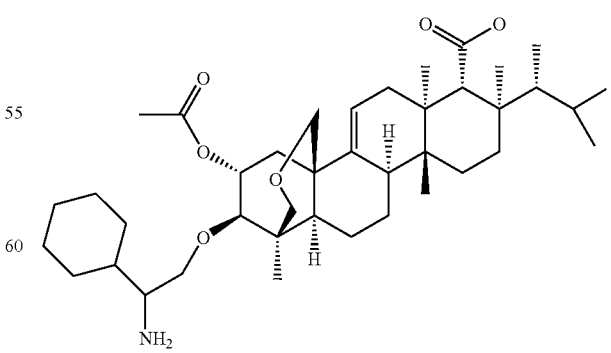

In a similar manner as described in Example 1(a), from Intermediate 3 and 1-bromomethylvinyl-cyclohexane was obtained the desired heptenyl derivative. This derivative was subjected to the conditions outlined in Example 1 (b-e) to yield the title compound which was converted to the acetate salt. $^1$H NMR (400 MHz, methanol-$d_4$) δ ppm 0.75-0.76 (m, J=2.93 Hz, 3H), 0.83 (d, J=4.49 Hz, 3H), 0.86 (d, J=6.64 Hz, 3H), 0.90 (d, J=6.83 Hz, 3H), 1.16 (s, 3H), 1.21 (s, 3H), 1.23-1.34 (m, 5H), 1.38-1.46 (m, 2H), 1.53-1.87 (m, 17H), 1.90-1.97 (m, 2H), 2.05 (s, 3H), 2.05-2.12 (m, 2H), 2.14-2.24 (m, 1H), 2.38-2.49 (m, 1H), 2.85 (s, 1H), 3.01-3.14 (m, 1H), 3.21 (d, J=8.98 Hz, 1H), 3.38-3.52 (m, 3H), 3.66-3.82 (m, 2H), 3.82-3.96 (m, 1H), 5.41-5.51 (m, 1H), and 5.68-5.86 (m, 1H).

Example 148

(1S,2R,3R,4aR,6aS,7R,8R,10aR,10bR,12aR)-3-(acetyloxy)-2-[(2S)-2-amino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid

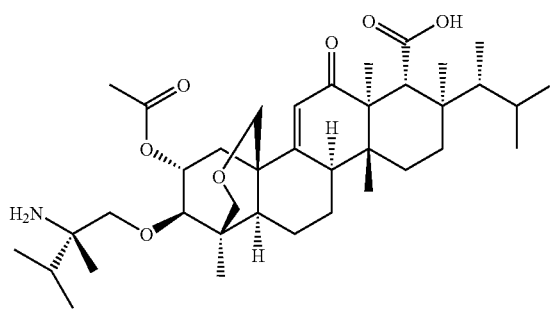

Step 1: Benzyl (1S,2R,3R,4aR,6aS,7R,8R,10aR, 10bR,12aR)-8-[(1R)-1,2-dimethylpropyl]-2-[[(2S)-2, 3-dimethyl-2-[(p-tolylsulfonyl)amino]butyl]oxy]-3-(methoxy)-1,6a,8,10a-tetramethyl-1,3,4,6,6a,7,8,9, 10,10a,10b,11,12,12a-tetradecahydro-2H-1,4a-(methanooxymethano)chrysene-7-carboxylate To a stirred solution of benzyl (1S,2R,3R,4aR,6aS,7R,8R, 10aR,10bR,12aR)-8-[(1R)-1,2-dimethylpropyl]-2-(hydroxyl)-3-(methoxy)-1,6a,8,10a-tetramethyl-1,3,4,6,6a,7,8, 9,10,10a,10b,11,12,12a-tetradecahydro-2H-1,4a-(methanooxymethano)chrysene-7-carboxylate (30.2 g, 51 mmol) dissolved in anhydrous dimethoxyethane (400 mL) was added 18-crown-6 (33.7 g, 127.5 mmol) and 2-isopropyl-2-methyl-1-[(4-methylphenyl)sulfonyl]aziridine (21.4 g, 84.6 mmol, 1.66 equiv). The mixture was stirred under nitrogen for 10 min until all solids were dissolved. Potassium hydride (30% in oil, 17.0 g, 127.5 mmol, 2.5 equiv) was added portionwise (ca. 1 g portions) over a period of about 30 minutes. After the completion of the addition, the resulting suspension was stirred at room temperature for about 3 h. The reaction was carefully quenched by the dropwise addition of methanol (40 mL). The reaction mixture was then diluted with water (300 mL) and extracted with EtOAc (300 mL). The organic solution was washed with water (2×200 mL) and dried over anhydrous MgSO$_4$. The drying agent was removed by filtration and the organic solvent was removed under reduced pressure to afford the desired compound (67.4 g) as a mixture of diastereomers. Separation of the diastereomers was accomplished by chromatography on silica gel (0-15% EtOAc/heptanes) to give the faster eluting isomer, benzyl (1S,2R,3R,4aR,6aS,7R,8R,10aR,10bR,12aR)-8-[(1R)-1,2-dimethylpropyl]-2-[[(2R)-2,3-dimethyl-2-[(p-tolylsulfonyl) amino]butyl]oxy]-3-(methoxy)-1,6a,8,10a-tetramethyl-1,3, 4,6,6a,7,8,9,10,10a,10b,11,12,12a-tetradecahydro-2H-1,4a-(methanooxymethano)chrysene-7-carboxylate, and the slower eluting isomer, benzyl (1S,2R,3R,4aR,6aS,7R,8R, 10aR,10bR,12aR)-8-[(1R)-1,2-dimethylpropyl]-2-[[(2S)-2, 3-dimethyl-2-[(p-tolylsulfonyl)amino]butyl]oxy]-3-(methoxy)-1,6a,8,10a-tetramethyl-1,3,4,6,6a,7,8,9,10,10a,10b,11, 12,12a-tetradecahydro-2H-1,4a-(methanooxymethano) chrysene-7-carboxylate.

Step 2: (1S,2R,3R,4aR,6aS,7R,8R,10aR,10bR, 12aR)-2-[[(2S)-2-amino-2,3-dimethylbutyl]oxy]-8-[(1R)-1,2-dimethylpropyl]-3-(methoxy)-1,6a,8,10a-tetramethyl-1,3,4,6,6a,7,8,9,10,10a,10b,11,12,12a-tetradecahydro-2H-1,4a-(methanooxymethano) chrysene-7-carboxylic acid A solution of benzyl (1S,2R,3R,4aR,6aS,7R,8R,10aR, 10bR,12aR)-8-[(1R)-1,2-dimethylpropyl]-2-[[(2S)-2,3-dimethyl-2-[(p-tolylsulfonyl)amino]butyl]oxy]-3-(methoxy)-1, 6a,8,10a-tetramethyl-1,3,4,6,6a,7,8,9,10,10a,10b,11,12, 12a-tetradecahydro-2H-1,4a-(methanooxymethano) chrysene-7-carboxylate (18.21 g, 21.60 mmol) in dimethoxyethane (300 mL) was added over about 20 minutes to liquid ammonia (approx. 400 mL) kept at −35 to −50° C. (bath temp). Sodium metal (4.0 g, in 0.2 g portions that were quickly washed with heptane prior to addition) was added to the ammonia solution over a period of 30 minutes ensuring that the reaction temperature was maintained at about −35° C. (bath temp). The deep blue reaction mixture was allowed to stir for 3 h. Analysis by TLC (50% EtOAc in Heptanes and 10% MeOH in DCM) indicated an incomplete reaction so additional sodium metal (1.0 g, divided into 0.5 g portions) was added over the course of about 10 minutes as described above. The reaction was stirred for an additional 2 h, whereupon the reaction was judged to be complete by TLC and LC-MS analysis. The reaction was quenched by the careful addition of isopropanol (10 mL, added dropwise over about 15 minutes), followed by 1:1 isopropanol-MeOH (80 mL over 30 minutes), and MeOH (40 mL over 30 minutes). The reaction mixture was stirred for 1 h and water (15 mL) was then added over 15 minutes. The ammonia was allowed to evaporate (several hours or overnight) and then water (300 mL) was added to the reaction. The mixture was extracted with EtOAc (3×350 mL). The organic solution was dried over anhydrous MgSO$_4$. Removal of the drying agent and evaporation of the solvent gave a white solid (7.96 g). The aqueous solution was treated with brine (400 mL) and re-extracted with dichloromethane (3×300 mL). The combined dichloromethane extracts were dried (MgSO$_4$), filtered and evaporated to afford additional white solid (4.53 g). The combined yield of (1S,2R,3R,4aR,6aS,7R,8R,10aR,10bR,12aR)-2-[[(2S)-2-amino-2,3-dimethylbutyl]oxy]-8-[(1R)-1,2-dimethylpropyl]-3-(methoxy)-1,6a,8,10a-tetramethyl-1,3,4,6, 6a,7,8,9,10,10a,10b,11,12,12a-tetradecahydro-2H-1,4a-(methanooxymethano)chrysene-7-carboxylic acid was 12.49 g, which was used directly in the next step.

Step 3: (1S,2R,3R,4aR,6aS,7R,8R,10aR,10bR, 12aR)-3-acetoxy-2-[[(2S)-2-amino-2,3-dimethylbutyl]oxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid To a stirred solution of (1S,2R,3R,4aR,6aS,7R,8R,10aR, 10bR,12aR)-2-[[(2S)-2-amino-2,3-dimethylbutyl]oxy]-8-[(1R)-1,2-dimethylpropyl]-3-(methoxy)-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (12.39 g, ~20.61 mmol) in acetic acid (970 mL) was added p-TsOH—H$_2$O (9.7 g) and the reaction mixture was heated at 110° C. (internal temperature) for 5 h. The reaction mixture was then allowed to cool to room temperature and the acetic acid was evaporated under reduced pressure. The residue was dissolved in EtOAc (400 mL) and washed with a saturated NaHCO$_3$ solution (400 mL) carefully. The aqueous phase was re-extracted with EtOAc (3×250 mL). The combined organic solutions were dried over anhydrous Na$_2$SO$_4$. After filtration and evaporation of the solvent the desired product was isolated as a pale yellow solid (5.61 g). The aqueous solution was re-extracted with 10% MeOH in DCM (4×250 ml) and these combined dichloromethane extracts were dried over Na$_2$SO$_4$, filtered and the solvent was evaporated to afford additional desired product (4.49 g). The combined (1S,2R,3R,4aR,6aS,7R,8R,10aR, 10bR,12aR)-3-acetoxy-2-[[(2S)-2-amino-2,3-dimethylbutyl]oxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid product (10.1 g) was used directly in the next step.

Step 4: (1S,2R,3R,4aR,6aS,7R,8R,10aR,10bR, 12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-1,3,4,6,6a,7,8,9,10, 10a,10b,11,12,12a-tetradecahydro-2H-1,4a-(methanooxymethano)chrysene-7-carboxylic acid To a stirred solution of (1S,2R,3R,4aR,6aS,7R,8R,10aR, 10bR,12aR)-3-acetoxy-2-[[(2S)-2-amino-2,3-dimethylbutyl]oxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid-(9.68 g, 15.4 mmol) in acetone (270 mL) was added water (55 mL), MeOH (130 mL), NaHCO$_3$ (12.9 g, 128 mmol), and CBz-OSu (5.06 g, 20.3 mmol). The reaction mixture was stirred at room temperature overnight. The solvent was evaporated in vacuo and the residue was partitioned between EtOAc (350 mL) and water (250 mL). The aqueous phase was separated and extracted with EtOAc (2×250 mL). The combined organic solutions were dried over anhydrous Na$_2$SO$_4$, filtered and the solvent was removed by evaporation to afford the desired product as a pale yellow solid (13.97 g). This solid was purified by flash chromatography using EtOAc/heptanes (10-25%) as eluent to yield (1S,2R,3R,4aR, 6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-1,3,4,6,6a,7,8,9, 10,10a,10b,11,12,12a-tetradecahydro-2H-1,4a-(methanooxymethano)chrysene-7-carboxylic acid as a white solid (8.61 g).

Step 5: (1S,2R,3R,4aR,6aS,7R,8R,10aR,10bR, 12aR)-3-acetoxy-2-[[(2S)-2-[(benzyloxy)carbonyl]amino-2,3-dimethylbutyl]oxy]-8-[(1R)-1,2-dimethylpropyl]-7-(oxomethylene)-1,6a,8,10a-tetramethyl-1, 3,4,6,6a,7,8,9,10,10a,10b,11,12,12a-tetradecahydro-2H-1,4a-(methanooxymethano)chrysene To a solution of (1S,2R,3R,4aR,6aS,7R,8R,10aR,10bR, 12aR)-3-acetoxy-2-[[(2S)-2-[(benzyloxy)carbonyl]amino-2, 3-dimethylbutyl]oxy]-8-[(1R)-1,2-dimethylpropyl]-1,6a,8, 10a-tetramethyl-1,3,4,6,6a,7,8,9,10,10a,10b,11,12,12a-tetradecahydro-2H-1,4a-(methanooxymethano)chrysene-7-carboxylic acid (8.41 g, 11 mmol) in dichloromethane (500 mL) was added N-Ethyl-N'-(3-dimethylaminopropyl)carbodiimide (17.0 g, 110 mmol) in a single portion. The reaction mixture was stirred at room temperature, under nitrogen, for 40 hours until all-starting material was consumed. The reaction mixture was washed with water (3×200 mL) and dried over anhydrous Na$_2$SO$_4$. The drying agent was removed by filtration and the solvent was evaporated to leave (1S,2R,3R, 4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-7-(oxomethylene)-1,6a,8,10a-tetramethyl-1,3,4,6,6a,7,8,9,10,10a,10b,11,12,12a-tetradecahydro-2H-1,4a-(methanooxymethano)chrysene as a light yellowish solid (8.15 g) that was used directly in the next step.

Step 6: (1S,2R,3R,4aR,6aS,7R,8R,10aR,10bR, 12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-1,3,4,6,6a,7,8,9,10, 10a,10b,11,12,12a-tetradecahydro-2H-1,4a-(methanooxymethano)chrysene-7-carboxamide To a 250 ml pressure reactor was added (1S,2R,3R,4aR,6 aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-7-(oxomethylene)-1,6a,8,10a-tetramethyl-1,3,4,6,6a,7,8,9,10,10a,10b,11,12,12a-tetradecahydro-2H-1, 4a-(methanooxymethano)chrysene (8.0 g, 10.7 mmol) and dichloromethane (85 mL). The reactor was cooled to about −60° C. and liquid ammonia (about 100 ml) was added. The reactor was sealed and the reaction was stirred at room temperature about 68 hours during which time the pressure increased to 98 psi. When the reaction was complete, the pressure was carefully released and the ammonia was allowed to evaporate over 2 h at room temperature. The reaction mixture was diluted with dichloromethane (400 mL), washed with water (3×150 mL), and dried over Na$_2$SO$_4$. The drying agent was removed by filtration and the solvent was evaporated to give (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxamide as a yellow solid (7.85 g). The product was used directly in the next step.

Step 7: (1S,2R,3R,4aR,6aS,7R,8R,10aR,10bR, 12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-6-oxo-1,3,4,6,6a,7,8, 9,10,10a,10b,11,12,12a-tetradecahydro-2H-1,4a-(methanooxymethano)chrysene-7-carboxamide To a one-liter flask was added CrO$_3$ (14.76 g, 148 mmol, 45 equiv, dried in a vacuum desiccator over P$_2$O$_5$ for 3 days) and dichloromethane (800 ml). The mixture was cooled to −20° C. (internal temperature) and 3,5-dimethylpyrazole (14.19 g, 148 mmol, 45 equiv) was added in a single portion. The mixture was stirred at −20° C. for one hour. A solution of (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxamide (2.50 g, 3.28 mmol) in dichloromethane (150 mL) was added in a single portion and the reaction was allowed to warm up overnight. After about 19 hour, the temperature of the acetone bath reached about 15° C. The reaction mixture was transferred to a 2-liter flask and quenched with a saturated NaHCO₃ solution (~400 mL). The organic layer was separated and washed with a saturated NaHCO₃ solution (2×300 mL). The combined aqueous fractions were re-extracted with dichloromethane (2×300 mL). The combined organic fractions were dried over Na₂SO₄. The drying agent was removed by filtration and the solvent was evaporated to leave a brown solid. This solid was immediately dissolved in dichloromethane (~2×15 mL) and quickly loaded on a silica gel flash column for purification. The gradient started from 5% EtOAc in heptane and the product eluted at 45% EtOAc in heptane. After removal of solvent, the residue was dissolved in EtOAc (500 mL). The organic solution was washed with 1N HCl (2×150 mL) and water (100 mL). The organic solution was dried over Na₂SO₄, filtered to remove the drying agent and the solvent evaporated to yield (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxamide as a pale yellow solid (2.36 g).

Step 8: (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid To a rapidly stirred solution of (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxamide (2.18, 2.68 mmol) in a solution of CH₃CN (90 mL)/KF (198 mg, 2.2 mg/ml)/H₂O (0.9 mL 1%) was added t-BuONO (1.59 mL, 13.4 mmol, 5 equiv). The mixture was stirred at room temperature for 1 hour. The solvent was removed in vacuo and the residue was purified by flash chromatography on silica gel (Eluent: EtOAc and heptane) to give (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid as a white solid (1.66 g).

Step 9: (1S,2R,3R,4aR,6aS,7R,8R,10aR,10bR,12aR)-3-acetoxy-2-[[(2S)-2-amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid To a solution of (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (1.06 g, 1.37 mmol) in methanol (50 ml) and EtOAc (50 mL) was added HOAc (0.50 mL) and 20% wet Pd(OH)₂/C (500 mg). The solution was then degassed by passage of nitrogen for 5 minutes. The flask was purged with hydrogen and the reaction was subjected to hydrogenation under balloon pressure. After about 25 minutes the mixture was filtered through a thin layer of Celite. The solvent was evaporated and the residue was dissolved in small volume of dichloromethane and purified by a silica gel chromatography (10 g cartridge; eluted with 2% to 10% MeOH in dichloromethane) to give a light yellow solid (0.83 g). A portion of the solid (0.76 g) was dissolved in dichloromethane (300 mL) and washed with a saturated NaHCO₃ solution (2×50 mL) and water (50 mL). Then the organic solution was dried over Na₂SO₄. After filtration and concentration, (1S,2R,3R,4aR,6aS,7R,8R,10aR,10bR,12aR)-3-acetoxy-2-[[(2S)-2-amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid was obtained as a light yellow solid (0.71 g).

Conversion to the Fumarate Salt:

To a solution of (1S,2R,3R,4aR,6aS,7R,8R,10aR,10bR,12aR)-3-acetoxy-2-[[(2S)-2-amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (0.71 g) in dichloromethane (50 mL) was added a solution of fumaric acid (63.8 mg) in MeOH (50 mL). The solution was stirred at room temperature for 1 hour, and then the solvent was removed in vacuo. The residue was dissolved in CH₃CN (6 mL) and H₂O (7 mL). After it was frozen in a dry ice-acetone bath, it was lyophilized overnight to give (1S,2R,3R,4aR,6aS,7R,8R,10aR,10bR,12aR)-3-acetoxy-2-[[(2S)-2-amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (fumaric acid salt) as a light yellow solid (0.75 g). $^1$H NMR (CD₃OD, 600 MHz, ppm) δ 0.77 (d, J=7.2 Hz, 3H), 0.80 (s, 3H), 0.87 (s, 3H), 0.87 (d, J=6.7 Hz, 3H), 0.94 (d, J=6.9 Hz, 3H), 0.95 (d, J=6.4 Hz, 3H), 0.99 (d, J=6.9 Hz, 3H), 1.09 (s, 3H), 1.18 (s, 3H), 1.26-1.56 (m, 5H), 1.65-1.80 (m, 3H), 1.70 (s, 3H), 1.83-1.95 (m, 3H), 2.04 (s, 3H), 2.05-2.11 (m, 1H), 2.18-2.27 (m, 1H), 2.48 (dd, J=13.2, 7.2 Hz, 1H), 2.64-2.70 (m, 1H), 3.09 (s, 1H), 3.27 (d, J=8.7 Hz, 1H), 3.39 (d, J=12 Hz, 1H), 3.50 (dd, J=12, 1.8 Hz, 1H), 3.53 (d, J=12 Hz, 1H), 3.55 (d, J=10 Hz, 1H), 3.84 (d, J=10 Hz, 1H), 3.84 (d, J=12 Hz, 1H), 5.74 (d, J=2.6 Hz, 1H), 5.76-5.82 (m, 1H), 6.64 (s, 1H).

Mass spectrum: (ESI) m/z=644.5 (M+H).

Example 149

(1S,2R,3R,4aR,6aS,7R,8R,10aR,10bR,12aR)-3-(acetyloxy)-2-[(2S)-2-methylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid

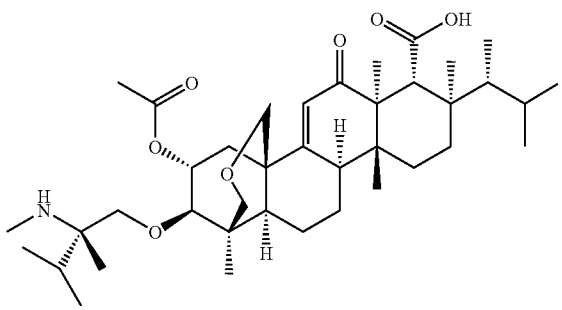

Step 1: (1S,2R,3R,4aR,6aS,7R,8R,10aR,10bR,12aR)-3-acetoxy-2-[[(2S)-2-[benzyl(methyl)amino]-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid To a solution of (1S,2R,3R,4aR,6aS,7R,8R,10aR,10bR,12aR)-3-acetoxy-2-[[(2S)-2-amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (2.00 g, 3.11 mmol) in MeOH (240 mL) was added HOAc (1.12 mL), benzaldehyde (14.5 mL) and NaCNBH$_3$ (3.60 g). The mixture was heated to 60° C. for 3 h and then stirred at room temperature for 5 hours. Additional NaCNBH$_3$ (1.80 g) and 37% formaldehyde in water (3.0 mL) were added and the mixture was stirred at room temperature overnight. The solvent was removed in vacuo and the residue was dissolved in EtOAc (400 ml). The solution was washed with a saturated NaHCO$_3$ solution (3×100 mL) and water (150 mL). The organic solution was dried over Na$_2$SO$_4$ and the drying agent was removed by filtration. After removal of solvent and benzaldehyde in vacuo, the residue was purified by chromatography on a small flash column (20 g silica gel cartridge; eluted with dichloromethane followed by 50% EtOAc in heptanes) to yield (1S,2R,3R,4aR,6aS,7R,8R,10aR,10bR,12aR)-3-acetoxy-2-[[(2S)-2-[benzyl(methyl)amino]-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (1.49 g).

Step 2: (1S,2R,3R,4aR,6aS,7R,8R,10aR,10bR,12aR)-3-acetoxy-2-[[(2S)-2-methylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid To a solution of (1S,2R,3R,4aR,6aS,7R,8R,10aR,10bR,12aR)-3-acetoxy-2-[[(2S)-2-[benzyl(methyl)amino]-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (1.29 g, 1.73 mmol) in methanol (120 ml) was added HOAc (5.4 mL) and 20% wet Pd(OH)$_2$/C (1.82 g). The solution was then degassed by passage of nitrogen for 5 minutes. The flask was purged with hydrogen and the reaction was subjected to hydrogenation under balloon pressure. After about 90 minutes the mixture was filtered through a thin layer of Celite. The solvent was evaporated and the residue was purified by a silica gel chromatography (10 g cartridge; elution with a gradient of 2% to 10% MeOH in dichloromethane) to give a light yellow solid. The solid was dissolved in dichloromethane (300 mL) and washed with a saturated NaHCO$_3$ solution (3×100 mL) and water (50 mL) and the organic solution was dried over Na$_2$SO$_4$. After filtration and concentration, (1S,2R,3R,4aR,6aS,7R,8R,10aR,10bR,12aR)-3-acetoxy-2-[[(2S)-2-methylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid was isolated as a light yellow solid (1.22 g).

Conversion to the Fumarate Salt:

To a solution of (1S,2R,3R,4aR,6aS,7R,8R,10aR,10bR,12aR)-3-acetoxy-2-[[(2S)-2-methylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (1.14 g) in methanol (20 mL) and dichloromethane (5 mL) was added fumaric acid (100 mg). The solution was stirred at room temperature for 1 hour, and then the solvent was removed in vacuo. The residue was dissolved in CH$_3$CN (7 mL) and H$_2$O (7 mL). After it was frozen in a dry ice-acetone bath, it was lyophilized overnight to give (1S,2R,3R,4aR,6aS,7R,8R,10aR,10bR,12aR)-3-acetoxy-2-[[(2S)-2-methylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (fumaric acid salt) as a white solid (1.24 g). $^1$H NMR (CD$_3$OD, 600 MHz, ppm) δ 0.77 (d, J=7.3 Hz, 3H), 0.80 (s, 3H), 0.87 (d, 3H, partially obscured), 0.88 (s, 3H), 0.95 (d, J=6.8 Hz, 3H), 0.97 (d, J=6.9 Hz, 3H), 1.00 (d, J=7.0 Hz, 3H), 1.09 (s, 3H), 1.21 (s, 3H), 1.27-1.56 (m, 5H), 1.70 (s, 3H), 1.65-1.80 (m, 3H), 1.84-1.95 (m, 3H), 2.05 (s, 3H), 2.08-2.16 (m, 1H), 2.18-2.28 (m, 1H), 2.51 (dd, J=13.2, 7.1 Hz, 1H), 2.59 (s, 3H), 2.64-2.69 (m, 1H), 3.09 (s, 1H), 3.32 (d, J=8.8 Hz, 1H), 3.41 (d, J=11.9 Hz, 1H), 3.50 (dd, J=12, 1.9 Hz, 1H), 3.53 (d, J=12 Hz, 1H), 3.66 (d, J=10.9 Hz, 1H), 3.83 (d, J=11.9 Hz, 1H), 3.86 (d, J=10.8 Hz, 1H), 5.75 (d, J=2.6 Hz, 1H), 5.76-5.82 (m, 1H) and 6.65 (s, 1H).

Mass spectrum: (ESI) m/z=657.6 (M+H).

Example 150

(1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid

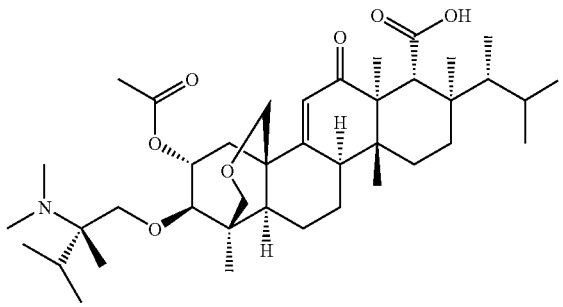

To a solution of (1S,2R,3R,4aR,6aS,7R,8R,10aR,10bR,12aR)-3-acetoxy-2-[[(2S)-2-amino-2,3-dimethylbutyl]oxy]-

8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (1.66 g) in MeOH (10 mL) and CH$_3$CN (50 mL) was added HOAc (0.64 mL), HCHO (37% in H$_2$O, 8.2 mL) and NaCNBH$_3$ (480 mg). The mixture was stirred at room temperature for 15 hours. LC-MS indicated the reaction was complete. Then the solvent was removed in vacuo and the residue was dissolved in dichloromethane (300 mL). The solution was washed with a saturated NaHCO$_3$ solution (3×100 mL) and water (100 mL). The organic solution was dried over Na$_2$SO$_4$. After filtration and concentration, the residue was purified by chromatography on a small silica gel flash column eluting with MeOH in dichloromethane (2-10%) to yield (1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (1.59 g).

Conversion to the Fumarate Salt:

To a solution of (1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (1.43 g, 2.22 mmol) in MeOH (100 mL) was added fumaric acid (0.10 g). The mixture was stirred at room temperature for 1 hour and then the solvent was removed in vacuo. The residue was dissolved in CH$_3$CN (7 mL) and H$_2$O (10 mL). After it was frozen in a dry ice-acetone bath, it was lyophilized overnight to give (1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano) chrysene-7-carboxylic acid (fumaric acid salt) as a pale-yellow solid (1.49 g). $^1$H NMR (CD$_3$OD, 600 MHz, ppm) δ 0.77 (d, J=7.2 Hz, 3H), 0.80 (s, 3H), 0.87 (d, J=6.7 Hz, 3H), 0.89 (s, 3H), 0.95 (d, J=6.8 Hz, 3H), 1.03 (d, J=7.0 Hz, 3H), 1.04 (d, J=7.0 Hz, 3H), 1.09 (s, 3H), 1.24 (s, 3H), 1.26-1.56 (m, 5H), 1.70 (s, 3H), 1.65-1.80 (m, 3H), 1.84-1.95 (m, 3H), 2.06 (s, 3H), 2.18-2.32 (m, 2H), 2.50 (dd, J=13.2, 7.2 Hz, 1H), 2.63-2.69 (m, 1H), 2.84 (s, 6H), 3.09 (s, 1H), 3.29-3.32 (d, 1H, partially obscured), 3.42 (d, J=11.9 Hz, 1H), 3.50 (dd, J=12, 1.9 Hz, 1H), 3.53 (d, J=12 Hz, 1H), 3.74 (d, J=11.6 Hz, 1H), 3.76 (d, J=11.6 Hz, 1H), 3.95 (d, J=11.7 Hz, 1H), 5.74 (d, J=2.6 Hz, 1H), 5.75-5.81 (m, 1H) and 6.65 (s, 1H).

Mass spectrum: (ESI) m/z=672.6 (M+H).

Examples 151-153

The following compounds were prepared using methods analogous to those described in the preceding examples:

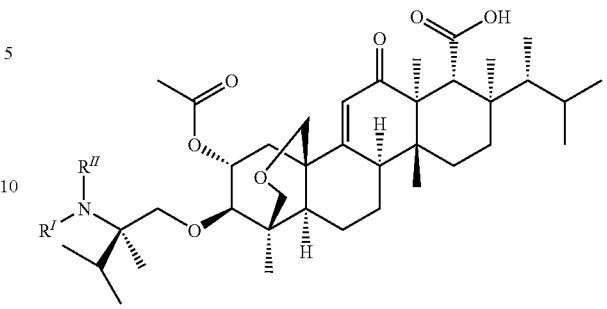

| | | |
|---|---|---|
| 151 | R$^I$ = H<br>R$^{II}$ = H | (1S,2R,3R,4aR,6aS,7R,8R,10aR,10bR,12aR)-3-acetoxy-2-[[(2R)-2-amino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (fumaric acid salt) |

$^1$H NMR (CD$_3$OD, 600 MHz, ppm) δ 0.77 (d, J = 7.3 Hz, 3 H), 0.80 (s, 3 H), 0.87 (d, J = 6.6 Hz, 3 H), 0.87 (s, 3 H), 0.95 (d, J = 6.8 Hz, 3 H), 0.96 (d, J = 7.0 Hz, 3 H), 1.09 (s, 3 H), 1.19 (s, 3 H), 1.26-1.56 (m, 5 H), 1.70 (s, 3 H), 1.65-1.80 (m, 3 H), 1.83-1.95 (m, 3 H), 1.98-2.07 (m, 1 H), 2.04 (s, 3 H), 2.18-2.27 (m, 1 H), 2.48 (dd, J = 13.2, 7.1 Hz, 1 H), 2.64-2.70 (m, 1 H), 3.09 (s, 1 H) 3.28 (d, 1 H, partially obscured), 3.39 (d, J = 12 Hz, 1 H), 3.50 (dd, J = 12, 2.0 Hz, 1 H), 3.53 (d, J = 12 Hz, 1 H), 3.69 (s, 2 H), 3.85 (d, J = 12 Hz, 1 H), 5.75 (d, J = 2.6 Hz, 1 H), 5.79-5.85 (m, 1 H), 6.64 (s, 1 H).
Mass spectrum: (ESI) m/z = 644.5 (M + H).

| | | |
|---|---|---|
| 152 | R$^I$ = Me<br>R$^{II}$ = H | (1S,2R,3R,4aR,6aS,7R,8R,10aR,10bR,12aR)-3-acetoxy-2-[[(2R)-2-methylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (fumaric acid salt) |

$^1$H NMR (CD$_3$OD, 500 MHz, ppm) δ 0.79 (d, J = 7.3 Hz, 3 H), 0.82 (s, 3 H), 0.89 (d, 3 H, partially obscured), 0.90 (s, 3 H), 0.97 (d, J = 6.8 Hz, 3 H), 1.01 (d, J = 6.9 Hz, 3 H), 1.03 (d, J = 6.8 Hz, 3 H), 1.12 (s, 3 H), 1.17 (s, 3 H), 1.28-1.59 (m, 5 H), 1.73 (s, 3 H), 1.67-1.83 (m, 3 H), 1.85-1.98 (m, 3 H), 2.07 (s, 3 H), 2.18-2.29 (m, 2 H), 2.52 (dd, J = 13.2, 7.1 Hz, 1 H), 2.62 (s, 3 H), 2.66-2.72 (m, 1 H), 3.11 (s, 1 H), 3.34 (d, J = 8.9 Hz, 1 H), 3.42 (d, J = 11.9 Hz, 1 H), 3.52 (dd, J = 11.5, 1.8 Hz, 1 H), 3.57 (d, J = 11.4 Hz, 1 H), 3.78 (s, 2 H), 3.85 (d, J = 11.9 Hz, 1 H), 5.80 (d, J = 2.5 Hz, 1 H), 5.81-5.89 (m, 1 H) and 6.67 (s, 1 H).
Mass spectrum: (ESI) m/z = 658.7 (M + H).

| | | |
|---|---|---|
| 153 | R$^I$ = Me<br>R$^{II}$ = Me | (1S,2R,3R,4aR,6aS,7R,8R,10aR,10bR,12aR)-3-acetoxy-2-[[(2R)-2-dimethylamino-2,3-dimethylbutyl]oxy]-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid (fumaric acid salt) |

$^1$H NMR (CD$_3$OD, 600 MHz, ppm) δ 0.77 (d, J = 7.2 Hz, 3 H), 0.80 (s, 3 H), 0.87 (d, J = 6.6 Hz, 3 H), 0.90 (s, 3 H), 0.95 (d, J = 6.8 Hz, 3 H), 1.04 (d, J = 6.7 Hz, 3 H), 1.06 (d, J = 6.8 Hz, 3 H), 1.09 (s, 3 H), 1.14 (s, 3 H), 1.27-1.56 (m, 5 H), 1.70 (s, 3 H), 1.65-1.80 (m, 3 H), 1.84-1.95 (m, 3 H), 2.06 (s, 3 H), 2.19-2.26 (m, 1 H), 2.36-2.44 (m, 1 H), 2.49 (dd, J = 13.2, 7.1 Hz, 1 H), 2.63-2.69 (m, 1 H), 2.80 (s, 6 H), 3.09 (s, 1 H), 3.27 (d, J = 8.9 Hz, 1 H), 3.42 (d, J = 11.8 Hz, 1 H), 3.46 (dd, J = 12, 1.8 Hz, 1 H), 3.53 (d, J = 12 Hz, 1 H), 3.70 (d, J = 11.9 Hz, 1 H), 3.77 (d, J = 11.6 Hz, 1 H), 3.90 (d, J = 11.7 Hz, 1 H), 5.74 (d, J = 2.6 Hz, 1 H), 5.77-5.83 (m, 1 H) and 6.65 (s, 1 H).
Mass spectrum: (ESI) m/z = 672.6 (M + H).

Examples 154-179

Examples 154-179, defined below, may be prepared according to procedures similar to the procedures described above, using the intermediates necessary to obtain the required substituents.

TABLE 3a

| Ex./cpd | $R^{III}$ | $R^{IV}$ | $R^I$ | $R^{II}$ | MS |
|---|---|---|---|---|---|
| 154 | Et | Et | Me | Me | 672 (M + H)+ |
| 155 | n-Bu | Me | Me | Me | 672 (M + H)+ |
| 156 | CH$_2$OMe | Me | Me | Me | 660 (M + H)+ |
| 157 | CH$_2$CH$_2$OMe | Me | H | H | 660 (M + H)+ |
| 158 | CH$_2$CH$_2$OMe | Me | Me | Me | 688 (M + H)+ |
| 159 | CH$_2$CH$_2$OEt | Me | H | H | 674 (M + H)+ |
| 160 | CH$_2$CH$_2$OEt | Me | Me | Me | MH+ = 716 |
| 161 | CH$_2$CH$_2$OEt | Me | Et | H | 688 (M + H)+ |
| 162 | Cyclohexyl |  | H | H | 656 (M + H)+ |
| 163 | (R) i-Pr | Me | Et | Et | 700 (M + H)+ |
| 164 | (R) i-Pr | Me | Et | H | 672 (M + H)+ |
| 165 | (R) i-Pr | Me | CH$_2$CH$_2$OMe | H | 702 (M + H)+ |
| 166 | (R) i-Pr | Me | (CH$_2$)$_3$OMe | H | 716 (M + H)+ |
| 167 | (R) i-Pr | Me | nPr | H | 686 (M + H)+ |
| 168 | (R) i-Pr | Me | cycloBu | H | 698 (M + H)+ |
| 169 | (S) i-Pr | Me | Et | H | 672 (M + H)+ |
| 170 | (S) i-Pr | Me | Et | Et | 700 (M + H)+ |
| 171 | (S) i-Pr | Me | nPr | H | 686 (M + H)+ |
| 172 | (S) i-Pr | Me | cPrCH$_2$ | H | 698 (M + H)+ |
| 173 | (S) i-Pr | Me | Et | Me | 672 (M + H)+ |
| 174 | (S) i-Pr | Me | iPr | H | 686 (M + H)+ |
| 175 | (S) i-Pr | Me | nBu | H | 700 (M + H)+ |
| 176 | (S) i-Pr | Me | iBu | H | 700 (M + H)+ |
| 177 | (S) i-Pr | Me | c-Butyl | H | 698 (M + H)+ |
| 178 | (S) i-Pr | Me | cPentyl | H | 712 (M + H)+ |
| 179 | (S) i-Pr | Me | cHexyl | H | 726 (M + H)+ |

Example No. 154

Name: (1S,2R,3R,4aR,6aS,7R,8R,10aR,10bR,12aR)-3-(acetyloxy)-2-(2-dimethylamino-2-ethylbutyl oxy)-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.76 (d, J=7.22 Hz, 3H) 0.80 (s, 3H) 0.87 (s, 3H) 0.88 (d, J=2.15 Hz, 3H) 0.90-0.93 (m, 3H) 0.96 (d, J=6.64 Hz, 3H) 1.07-1.13 (m, 3H) 1.22-1.33 (m, 4H) 1.34-1.44 (m, 3H) 1.49-1.63 (m, 4H) 1.64-1.70 (m, 3H) 1.73 (s, 3H) 1.81-1.93 (m, 3H) 2.05 (s, 3H) 2.20-2.31 (m, 1H) 2.44-2.48 (m, 2H) 2.50 (s, 3H) 2.52 (d, J=5.08 Hz, 1H) 2.61-2.68 (m, 1H) 3.07 (s, 1H) 3.16 (d, J=8.79 Hz, 1H) 3.39 (d, J=11.71 Hz, 1H) 3.46-3.55 (m, 2H) 3.59 (d, J=10.25 Hz, 1H) 3.73 (d, J=11.71 Hz, 1H) 3.82 (d, 1H) 5.73 (d, J=2.44 Hz, 1H) 5.75-5.81 (m, 1H)

Example No. 155

Name: (1S,2R,3R,4aR,6aS,7R,8R,10aR,10bR,12aR)-3-(acetyloxy)-2-(2-dimethylamino-2-methylhexyloxy)-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.74-0.84 (m, 6H) 0.84-0.92 (m, 6H) 0.92-1.01 (m, 6H) 1.11 (s, 3H) 1.16-1.59 (m, 10H) 1.62-1.83 (m, 6H) 1.70-1.74 (m, 3H) 1.83-1.99 (m, 6H) 2.07 (s, 3H) 2.18-2.30 (m, 1H) 2.45-2.56 (m, 1H) 2.68 (d, J=12.54 Hz, 1H) 2.75 (s, 3H) 2.77 (s, 3H) 3.11 (s, 1H) 3.44 (d, J=12.15 Hz, 1H) 3.49-3.58 (m, 2H) 3.63-3.98 (m, 3H) 5.75 (d, J=2.54 Hz, 1H) 5.77-5.93 (m, 1H)

Example No. 156

Name: (1S,2R,3R,4aR,6aS,7R,8R,10aR,10bR,12aR)-3-(acetyloxy)-2-[(±)-(2-dimethylamino-3-methoxy-2-methyl-propyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.78 (d, J=7.22 Hz, 3H) 0.81 (s, 3H) 0.84-0.93 (m, 6H) 0.97 (d, J=6.69 Hz, 3H) 1.11 (s, 3H) 1.18-1.60 (m, 10H) 1.62-1.82 (m, 6H) 1.85-1.92 (m, 6H) 1.93 (s, 3H) 2.07 (d, J=1.46 Hz, 3H) 2.17-2.32 (m, 1H) 2.47 (dd, J=13.15, 7.15 Hz, 1H) 2.64-2.69 (m, J=4.59 Hz, 1H) 2.71 (s, 3H) 2.72 (s, 3H) 3.11 (s, 1H) 3.25 (dd, J=9.18, 2.54 Hz, 2H) 3.38 (s, 3H) 3.43 (dd, J=11.84, 3.15 Hz, 1H) 3.47-3.67 (m, 4H) 3.75 (d, J=10.40 Hz, 1H) 3.85-4.02 (m, 1H) 5.76 (d, J=2.49 Hz, 1H) 5.78-5.89 (m, 1H)

Example No. 157

Name: (1S,2R,3R,4aR,6aS,7R,8R,10aR,10bR,12aR)-3-(acetyloxy)-2-[(±)-(2-amino-4-methoxy-2-methylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.78 (d, J=7.22 Hz, 3H) 0.81 (s, 3H) 0.86-0.90 (m, 6H) 0.97 (d, J=6.69 Hz, 3H) 1.11 (s, 3H) 1.25-1.60 (m, 12H) 1.64-2.02 (m, 12H) 2.05-2.08 (m, 3H) 2.13-2.31 (m, 1H) 2.40-2.54 (m, 1H) 2.68 (d, J=16.25 Hz, 1H) 3.11 (s, 1H) 3.28 (d, J=9.13 Hz, 1H) 3.41 (d, J=11.81 Hz, 1H) 3.50-3.80 (m, 7H) 3.84 (dd, J=11.93, 1.59 Hz, 1H) 5.76 (d, J=2.59 Hz, 1H) 5.79-5.90 (m, 1H)

Example No. 158

Name: (1S,2R,3R,4aR,6aS,7R,8R,10aR,10bR,12aR)-3-(acetyloxy)-2-[(±)-2-dimethylamino-4-ethoxy-2-methylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.78 (d, J=7.22 Hz, 3H) 0.81 (s, 3H) 0.84-1.00 (m, 2H) 1.01-1.16 (m, 2H) 1.11 (s, 3H) 1.22-1.60 (m, 10H) 1.63-2.13 (m, 10H) 1.72 (s, 3H) 1.93 (s, 3H) 2.06-2.08 (m, 3H) 2.16-2.34 (m, 1H) 2.44-2.55 (m, 1H) 2.72-2.84 (m, 2H) 2.75 (s, 6H) 3.11 (s, 1H) 3.33 (d, 3H) 3.44 (d, J=11.76 Hz, 1H) 3.50-3.60 (m, 4H) 3.74 (d, J=10.79 Hz, 1H) 3.80 (d, J=11.18 Hz, 1H) 3.85-3.90 (m, 1H) 3.94 (d, J=10.74 Hz, 1H) 5.75 (d, J=2.59 Hz, 1H) 5.78-5.94 (m, 1H)

Example No. 159

Name: (1S,2R,3R,4aR,6aS,7R,8R,10aR,10bR,12aR)-3-(acetyloxy)-2-(2-amino-4-ethoxy-2-methylbutyloxy)-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy $^1$H NMR (400 MHz, methanol-d$_4$, δ, ppm) 0.77 (d, J=7.16 Hz, 3H) 0.80 (s, 3H) 0.84-0.90 (m, 9H) 0.96 (d, J=6.63 Hz, 3H) 1.10 (s, 3H) 1.19 (t, J=7.01 Hz, 3H) 1.26-1.34 (m, 4H) 1.38-1.58 (m, 2H) 1.71 (s, 3H) 1.71-1.82 (m, 3H) 1.81-1.97 (m, 3H) 1.91 (s, 3H, HOAc) 2.04-2.08 (m, 4H) 2.19-2.27 (m, 1H) 2.42-2.51 (m, 1H) 2.63-2.71 (m, 1H) 3.10 (s, 1H) 3.11-3.14 (m, 1H) 3.26 (m, 1H) 3.41-3.54 (m, 4H) 3.57-3.63 (m, 3H) 3.63-3.75 (m, 1H) 3.82 (m, 1H) 5.75 (d, J=2.40 Hz, 1H) 5.78-5.88 (m, 1H)

Example No. 160

Name: (1S,2R,3R,4aR,6aS,7R,8R,10aR,10bR,12aR)-3-(acetyloxy)-2-(2-dimethylamino-4-ethoxy-2-methylbutyloxy)-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxy $^1$H NMR (400 MHz, methanol-d$_4$, δ, ppm) 0.77 (d, J=7.16 Hz, 3H) 0.80 (s, 3H) 0.85-0.90 (m, 6H) 0.95 (d, J=6.63 Hz, 4H) 1.10 (s, 3H) 1.14-1.21 (m, 6H) 1.28 (s, 3H) 1.29-1.57 (m, 5H) 1.67-1.83 (m, 2H) 1.70 (s, 3H) 1.82-2.02 (m, 3H) 1.89 (s, 3H, HOAc) 2.05 (s, 3H) 2.06-2.09 (m, 1H) 2.19-2.28 (m, 1H) 2.43-2.51 (m, 1H) 2.56 (s, 6H) 2.57-2.71 (m, 2H) 3.09 (s, 1H) 3.23 (d, J=8.88 Hz, 1H) 3.37-3.60 (m, 7H) 3.64-3.71 (m, 1H) 3.74-3.89 (m, 2H) 5.74 (d, J=2.40 Hz, 1H) 5.76-5.85 (m, 1H)

Example No. 161

Name: (1S,2R,3R,4aR,6aS,7R,8R,10aR,10bR,12aR)-3-(acetyloxy)-2-[(±)-2-N-ethylamino-4-ethoxy-2-methylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.78 (d, J=7.14 Hz, 3H) 0.81 (s, 3H) 0.84-0.91 (m, 6H) 0.97 (d, J=6.63 Hz, 3H) 1.11 (s, 3H) 1.11 (s, 3H) 1.21-1.27 (m, 3H) 1.27-1.60 (m, 8H) 1.62-2.04 (m, 8H) 1.72 (s, 3H) 1.90 (s, 3H) 2.07 (s, 3H) 2.15-2.34 (m, 1H) 2.41-2.56 (m, 1H) 2.65-2.74 (m, 1H) 2.83-3.04 (m, 2H) 3.10 (s, 1H) 3.25-3.29 (m, 1H) 3.33-3.36 (m, 3H) 3.43 (d, J=11.85 Hz, 1H) 3.46-3.71 (m, 4H) 3.76 (d, J=9.93 Hz, 1H) 3.78-3.83 (m, 1H) 5.75 (d, J=2.52 Hz, 1H) 5.77-5.89 (m, 1H)

Example No. 162

Name: (1S,2R,3R,4aR,6aS,7R,8R,10aR,10bR,12aR)-3-(acetyloxy)-2-[1-aminocyclohexylmethoxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.77 (d, J=7.22 Hz, 3H) 0.80 (s, 3H) 0.86-0.87 (m, 3H) 0.88 (s, 3H) 0.95 (d, J=6.64 Hz, 3H) 1.10 (s, 3H) 1.25-1.34 (m, 1H) 1.41-1.53 (m, 5H) 1.58-1.66 (m, 5H) 1.68-1.69 (m, 3H) 1.70 (s, 3H) 1.72-1.79 (m, 2H) 1.80-1.96 (m, 5H) 2.06 (s, 3H) 2.19-2.27 (m, 1H) 2.47 (dd, J=13.18, 7.13 Hz, 1H) 2.64-2.71 (m, 1H) 3.10 (s, 1H) 3.34 (s, 1H) 3.39 (d, J=11.91 Hz, 1H) 3.48-3.56 (m, 2H) 3.71 (d, J=10.05 Hz, 1H) 3.83 (s, 1H) 3.86 (d, J=1.85 Hz, 1H) 5.75 (d, J=2.54 Hz, 1H) 5.77-5.85 (m, 1H)

Example No. 163

Name: (1S,2R,3R,4aR,6aS,7R,8R,10aR,10bR,12aR)-3-(acetyloxy)-2-[(2R)-2-N,N-dimethylamino-2,3-dimethylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.78 (d, J=7.22 Hz, 3H) 0.81 (s, 3H) 0.86-0.90 (m, 3H) 0.89 (s, 3H) 0.97 (d, J=6.74 Hz, 3H) 1.02 (t, J=7.61 Hz, 6H) 1.06-1.59 (m, 14H) 1.11 (s, 3H) 1.62-1.98 (m, 7H) 1.71 (s, 3H) 2.07 (s, 3H) 2.15-2.29 (m, 1H) 2.47 (dd, J=13.23, 7.17 Hz, 1H) 2.68 (d, J=12.54 Hz, 1H) 3.11 (s, 1H) 3.24 (br. S., 4H) 3.24 (d, J=9.13 Hz, 1H) 3.42 (d, J=11.62 Hz, 1H) 3.49-3.58 (m, 2H) 3.66-3.78 (m, 2H) 3.83-3.91 (m, 1H) 5.75 (d, J=2.54 Hz, 1H) 5.76-5.85 (m, 1H) 6.68 (s, 1H)

Example No. 164

Name: (1S,2R,3R,4aR,6aS,7R,8R,10aR,10bR,12aR)-3-(acetyloxy)-2-[(2R)-2-N-ethylamino-2,3-dimethylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.78 (d, J=7.22 Hz, 3H) 0.81 (s, 3H) 0.89 (t, J=3.29 Hz, 6H) 0.94-1.00 (m, 6H) 1.02 (d, J=6.83 Hz, 3H) 1.11 (s, 3H) 1.17 (s, 3H) 1.31 (t, J=7.22 Hz, 3H) 1.33-1.60 (m, 6H) 1.62-2.01 (m, 6H) 1.72 (s, 3H) 2.08 (s, 3H) 2.15-2.33 (m, 2H) 2.49 (dd, J=13.13, 7.22 Hz, 1H) 2.68 (d, J=13.37 Hz, 1H) 2.96-3.09 (m, 2H) 3.11 (s, 1H) 3.33-3.36 (m, 1H) 3.43 (d, J=11.71 Hz, 1H) 3.49-3.59 (m, 2H) 3.78 (s, 2H) 5.76 (d, J=2.59 Hz, 1H) 5.78-5.90 (m, 1H) 6.68 (s, 1H)

Example No. 165

Name: (1S,2R,3R,4aR,6aS,7R,8R,10aR,10bR,12aR)-3-(acetyloxy)-2-[(2R)-2-N-(2-methoxyethyl)amino-2,3-dimethylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.77 (d, J=7.22 Hz, 3H) 0.80 (s, 3H) 0.86-0.89 (m, 6H) 0.91 (d, J=6.93 Hz, 3H) 0.95 (d, J=6.83 Hz, 6H) 1.06 (s, 3H) 1.10 (s, 3H) 1.26-1.35 (m, 3H) 1.43-1.56 (m, 2H) 1.71 (s, 3H) 1.71-1.78 (m, 3H) 1.83-1.87 (m, 1H) 1.89 (s, 3H) 1.99-2.02 (m, 1H) 2.04 (s, 3H) 2.16-2.28 (m, 1H) 2.42-2.50 (m, 1H) 2.63-2.70 (m, 1H) 2.87-2.94 (m, 1H) 3.09 (s, 1H) 3.23-3.27 (m, 1H) 3.36 (s, 3H) 3.36-3.40 (m, 1H) 3.50-3.58 (m, 5H) 3.66-3.70 (m, 2H) 3.80 (d, J=11.70 Hz, 1H) 5.74 (d, J=2.64 Hz, 1H) 5.75-5.84 (m, 1H)

Example No. 166

Name: (1S,2R,3R,4aR,6aS,7R,8R,10aR,10bR,12aR)-3-(acetyloxy)-2-[(2R)-2-N-(2-methoxypropyl)amino-2,3-dimethylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid ¹H NMR (400 MHz, methanol-d₄, δ, ppm) 0.77 (d, J=7.22 Hz, 3H) 0.80 (s, 3H) 0.86-0.88 (m, 6H) 0.94-0.99 (m, 9H) 1.10 (d, J=2.25 Hz, 6H) 1.24-1.41 (m, 4H) 1.53 (d, J=14.64 Hz, 4H) 1.71 (s, 3H) 1.72-1.78 (m, 3H) 1.88 (s, 3H) 1.89-1.95 (m, 2H) 2.05 (s, 3H) 2.06-2.13 (m, 1H) 2.17-2.28 (m, 1H) 2.43-2.51 (m, 1H) 2.63-2.71 (m, 1H) 2.85-3.01 (m, 2H) 3.09 (s, 1H) 3.35 (s, 3H) 3.41 (d, J=12.01 Hz, 1H) 3.48-3.55 (m, 3H) 3.71 (s, 2H) 3.77 (d, J=11.81 Hz, 1H) 5.74 (d, J=2.64 Hz, 1H) 5.76-5.85 (m, 1H)

Example No. 167

Name: (1S,2R,3R,4aR,6aS,7R,8R,10aR,10bR,12aR)-3-(acetyloxy)-2-[(2R)-2-N-propylamino-2,3-dimethylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid ¹H NMR (400 MHz, methanol-d₄, δ, ppm) 0.77 (d, J=7.22 Hz, 3H) 0.80 (s, 3H) 0.86-0.89 (m, 6H) 0.97 (t, J=7.17 Hz, 6H) 0.99-1.04 (m, 6H) 1.10 (s, 3H) 1.17 (s, 3H) 1.28-1.42 (m, 3H) 1.42-1.57 (m, 3H) 1.71 (s, 3H) 1.72-1.81 (m, 3H) 1.84-1.90 (m, 2H) 1.93 (s, 3H) 2.07 (s, 3H) 2.19-2.30 (m, 2H) 2.48 (dd, J=13.13, 7.17 Hz, 1H) 2.63-2.70 (m, 1H) 2.83-2.98 (m, 2H) 3.10 (s, 1H) 3.33 (d, J=9.18 Hz, 1H) 3.42 (d, J=11.91 Hz, 1H) 3.46-3.59 (m, 2H) 3.71-3.86 (m, 3H) 5.75 (d, J=2.54 Hz, 1H) 5.79-5.91 (m, 1H)

Example No. 168

Name: (1S,2R,3R,4aR,6aS,7R,8R,10aR,10bR,12aR)-3-(acetyloxy)-2-[(2R)-2-N-cyclobutylamino-2,3-dimethylbutyloxy]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid ¹H NMR (400 MHz, methanol-d₄, δ, ppm) ¹H NMR (400 MHz, CHLOROFORM-d) δ ppm 0.69 (d, J=7.60 Hz, 3H) 0.72 (s, 3H) 0.77 (s, 3H) 0.79 (s, 3H) 0.81 (d, J=7.03 Hz, 3H) 0.88 (dd, J=6.74, 4.98 Hz, 3H) 0.97 (s, 3H) 1.05 (s, 3H) 1.16-1.29 (m, 2H) 1.36-1.46 (m, 3H) 1.49-1.56 (m, 2H) 1.60 (s, 3H) 1.62-1.66 (m, 2H) 1.73-1.86 (m, 4H) 1.97 (s, 3H) 2.04-2.18 (m, 3H) 2.45 (dd, J=13.37, 6.93 Hz, 1H) 3.03 (d, J=8.59 Hz, 1H) 3.08 (s, 1H) 3.24 (d, J=12.10 Hz, 1H) 3.32-3.37 (m, 1H) 3.38-3.46 (m, 3H) 3.45-3.51 (m, 2H) 3.52-3.63 (m, 3H) 3.77 (d, J=11.91 Hz, 1H) 3.88-3.98 (m, 1H) 5.61-5.71 (m, 1H) 5.71-5.75 (m, 1H)

Example No. 169

Name: (1S,2R,3R,4aR,6aS,7R,8R,10aR,10bR,12aR)-3-(acetyloxy)-2-[(2S)-(2-ethylamino-2,3-dimethylbutyl oxy)]-8-[(1R)-1,2-dimethyl propyl]-1,6a,8,10a-tetra methyl-6-oxo-1,3,4,6,6a,7,8,9,10,10a,10b,11,12,12a-tetradecahydro-2H-1,4a-(methanooxy ¹H NMR (400 MHz, methanol-d₄, δ, ppm) 0.77 (d, J=7.17 Hz, 3H) 0.80 (s, 3H) 0.85-0.89 (m, 6H) 0.91 (d, 3H) 0.93-0.98 (m, 6H) 1.00 (d, J=6.81 Hz, 3H) 1.10 (s, 3H) 1.23 (s, 3H) 1.26-1.29 (m, 3H) 1.29-1.49 (m, 4H) 1.47-1.59 (m, 2H) 1.70 (s, 3H) 1.94 (d, J=12.10 Hz, 2H) 2.06 (s, 3H) 2.09-2.18 (m, 1H) 2.19-2.27 (m, 1H) 2.46-2.55 (m, 1H) 2.63-2.71 (m, 1H) 2.89-2.99 (m, 1H) 3.00-3.12 (m, 1H) 3.10 (s, 1H) 3.34 (d, J=4.34 Hz, 1H) 3.37-3.57 (m, 1H) 3.67 (d, 1H) 3.81-3.89 (m, 2H) 4.18-4.23 (m, 2H) 5.72-5.75 (m, 1H) 5.75-5.84 (m, 1H) 6.67 (s, 1H,)

Example No. 170

Name: (1S,2R,3R,4aR,6aS,7R,8R,10aR,10bR,12aR)-3-(acetyloxy)-2-[(2S)-(2-diethylamino-2,3-dimethylbutyl oxy)]-8-[(1R)-1,2-dimethyl propyl]-1,6a,8,10a-tetra methyl-6-oxo-1,3,4,6,6a,7,8,9,10,10a,10b,11,12,12a-tetradecahydro-2H-1,4a-(methanooxy ¹H NMR (400 MHz, methanol-d₄, δ, ppm) 0.77 (d, J=7.20 Hz, 3H) 0.80 (s, 3H) 0.85-0.90 (m, 9H) 0.93-1.05 (m, 9H) 1.09 (s, 3H) 1.13-1.57 (m, 9H) 1.70 (s, 3H) 1.71-1.79 (m, 4H) 1.82-1.97 (m, 3H) 2.07 (s, 4H) 2.18-2.28 (m, 2H) 2.49 (d, J=20.30 Hz, 1H) 2.62-2.71 (m, 1H) 3.10 (s, 1H) 3.11-3.35 (m, 6H) 3.37-3.56 (m, 3H) 3.75 (d, 1H) 3.93 (d, J=16.64 Hz, 1H) 5.69-5.83 (m, 2H)

Example No. 171

Name: (1S,2R,3R,4aR,6aS,7R,8R,10aR,10bR,12aR)-3-(acetyloxy)-2-[(2S)-(2-propylamino-2,3-dimethylbutyl oxy)]-8-[(1R)-1,2-dimethyl propyl]-1,6a,8,10a-tetra methyl-6-oxo-1,3,4,6,6a,7,8,9,10,10a,10b,11,12,12a-tetradecahydro-2H-1,4a-(methanooxy ¹H NMR (400 MHz, methanol-d₄, δ, ppm) 0.77 (d, J=7.22 Hz, 3H) 0.80 (s, 3H) 0.85-0.90 (m, 6H) 0.92-0.97 (m, 6H) 0.97-1.04 (m, 6H) 1.10 (s, 3H) 1.23 (s, 3H) 1.24-1.69 (m, 7H) 1.70 (s, 3H) 1.71-1.98 (m, 4H) 2.06 (s, 3H) 2.09-2.17 (m, 1H) 2.20-2.28 (m, 1H) 2.49 (dd, J=13.11, 7.15 Hz, 1H) 2.63-2.71 (m, 1H) 2.74-2.83 (m, 1H) 2.85-2.96 (m, 1H) 3.10 (s, 1H) 3.34 (b.s, 2H) 3.38-3.58 (m, 3H) 3.65 (d, J=10.49 Hz, 1H) 3.86 (t, J=11.08 Hz, 2H) 5.74 (d, 1H) 5.75-5.84 (m, 1H)

Example No. 172

Name: (1S,2R,3R,4aR,6aS,7R,8R,10aR,10bR,12aR)-3-(acetyloxy)-2-[(2S)-(2-cyclopropylmethylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid ¹H NMR (400 MHz, methanol-d₄, δ, ppm) 6.67 (s, 1H) 5.70-5.86 (m, 2H) 3.85 (dd, J=16.94, 11.13 Hz, 2H) 3.65 (d, J=10.49 Hz, 2H) 3.38-3.60 (m, 3H) 3.06-3.15 (m, 2H) 2.79 (dd, J=7.32, 3.32 Hz, 2H) 2.61-2.72 (m, 1H) 2.50 (dd, J=12.96, 7.10 Hz, 1H) 2.17-2.30 (m, 1H) 2.01-2.15 (m, 5H) 1.83-1.95 (m, 2H) 1.71-1.83 (m, 2H) 1.70 (s, 3H) 1.35-1.61 (m, 3H) 1.22-1.35 (m, 5H) 1.10 (s, 3H) 0.91-1.02 (m, 9H) 0.84-0.91 (m, 6H) 0.74-0.83 (m, 6H) 0.67-0.75 (m, 2H) 0.33-0.41 (m, 2H)

Example No. 173

Name: (1S,2R,3R,4aR,6aS,7R,8R,10aR,10bR,12aR)-3-(acetyloxy)-2-[(2S)-(2-N-methylethylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid ¹H NMR (400 MHz, methanol-d₄, δ, ppm) 6.67 (s, 1H) 5.68-5.82 (m, 1H) 5.41-5.53 (m, 1H) 3.96 (d, J=11.57 Hz, 1H) 3.65-3.83 (m, 2H) 3.36-3.55 (m, 3H) 2.80-2.91 (m, 4H) 2.47 (dd, J=13.35, 7.05 Hz, 1H) 2.28-2.41 (m, 1H) 2.14-2.27 (m, 1H) 2.02-2.14 (m, 4H) 1.93 (br. s., 1H) 1.71-1.89 (m, 3H)

1.37-1.72 (m, 3H) 1.34 (t, J=7.20 Hz, 4H) 1.24-1.31 (m, 4H) 1.21 (s, 3H) 1.16 (s, 3H) 1.03 (t, J=6.15 Hz, 6H) 0.82-0.95 (m, 9H) 0.71-0.81 (m, 6H)

Example No. 174

Name: (1S,2R,3R,4aR,6aS,7R,8R,10aR,10bR,12aR)-3-(acetyloxy)-2-[(2S)-(2-isopropylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 5.67-5.87 (m, 2H) 3.77-3.94 (m, 2H) 3.36-3.66 (m, 4H) 3.09 (s, 1H) 2.67 (d, J=11.96 Hz, 1H) 2.51 (dd, J=13.28, 7.13 Hz, 1H) 2.15-2.32 (m, 1H) 1.96-2.14 (m, 4H) 1.82-1.97 (m, 4H) 1.63-1.83 (m, 6H) 1.28-1.61 (m, 5H) 1.25 (t, J=6.81 Hz, 6H) 1.20 (s, 3H) 1.10 (s, 3H) 0.90-1.03 (m, 12H) 0.83-0.91 (m, 6H) 0.72-0.83 (m, 6H)

Example No. 175

Name: (1S,2R,3R,4aR,6aS,7R,8R,10aR,10bR,12aR)-3-(acetyloxy)-2-[(2S)-(2-butylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 5.70-5.85 (m, 2H) 3.77-3.90 (m, 2H) 3.62 (d, J=10.49 Hz, 1H) 3.45-3.58 (m, 2H) 3.42 (d, J=12.10 Hz, 1H) 3.05-3.16 (m, 2H) 2.82-2.93 (m, 1H) 2.71-2.82 (m, 1H) 2.67 (d, J=10.54 Hz, 1H) 2.49 (dd, J=12.74, 7.37 Hz, 1H) 2.18-2.30 (m, 1H) 2.06-2.17 (m, 1H) 2.06 (s, 3H) 1.89 (d, J=0.88 Hz, 4H) 1.72-1.83 (m, 2H) 1.71 (s, 3H) 1.53-1.64 (m, 3H) 1.44-1.53 (m, 2H) 1.35-1.44 (m, 4H) 1.31 (d, J=10.74 Hz, 2H) 1.18 (s, 3H) 1.10 (s, 3H) 0.91-1.02 (m, 12H) 0.87 (t, J=3.05 Hz, 6H) 0.74-0.82 (m, 6H)

Example No. 176

Name: (1S,2R,3R,4aR,6aS,7R,8R,10aR,10bR,12aR)-3-(acetyloxy)-2-[(2S)-(2-isobutylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 5.71-5.84 (m, 2H) 3.77-3.88 (m, 2H) 3.49-3.61 (m, 3H) 3.41 (d, J=11.67 Hz, 1H) 3.07-3.14 (m, 1H) 2.63-2.72 (m, 2H) 2.44-2.55 (m, 2H) 2.17-2.29 (m, 1H) 1.99-2.09 (m, 4H) 1.90 (s, 5H) 1.72-1.88 (m, 4H) 1.71 (s, 4H) 1.26-1.58 (m, 5H) 1.18 (s, 3H) 1.10 (s, 3H) 1.00 (d, J=6.64 Hz, 6H) 0.94-0.98 (m, 6H) 0.92 (d, J=6.83 Hz, 3H) 0.84-0.90 (m, 6H) 0.74-0.82 (m, 6H)

Example No. 177

Name: (1S,2R,3R,4aR,6aS,7R,8R,10aR,10bR,12aR)-3-(acetyloxy)-2-[(2S)-(2-cyclobutylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 0.77 (d, J=7.17 Hz, 3H) 0.80 (s, 3H) 0.85-0.89 (m, 6H) 0.90 (d, J=6.78 Hz, 3H) 0.93-0.99 (m, 6H) 1.10 (s, 6H) 1.24-1.58 (m, 5H) 1.71 (s, 3H) 1.72-1.91 (m, 8H) 1.89 (s, 3H, HOAc) 1.90-1.97 (m, 1H) 2.03-2.12 (m, 2H) 2.07 (s, 3H) 2.17-2.28 (m, 3H) 2.48 (dd, J=13.15, 7.20 Hz, 1H) 2.62-2.71 (m, 1H) 3.09 (s, 1H) 3.26 (bs, 1H) 3.40 (d, J=11.84 Hz, 1H) 3.46-3.57 (m, 3H) 3.60-3.70 (m, 1H) 3.79 (dd, 2H) 5.74 (d, J=2.24 Hz, 1H) 5.75-5.82 (m, 1H)

Example No. 178

Name: (1S,2R,3R,4aR,6aS,7R,8R,10aR,10bR,12aR)-3-(acetyloxy)-2-[(2S)-(2-cyclopentylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 5.68-5.85 (m, 2H) 3.88 (dd, J=15.25, 11.15 Hz, 2H) 3.62 (d, J=10.40 Hz, 1H) 3.44-3.59 (m, 3H) 3.32-3.45 (m, 2H) 3.10 (s, 1H) 2.67 (d, J=13.42 Hz, 1H) 2.51 (dd, J=13.28, 7.13 Hz, 1H) 2.17-2.36 (m, 1H) 2.00-2.16 (m, 6H) 1.83-1.99 (m, 6H) 1.72-1.83 (m, 4H) 1.71 (s, 3H) 1.56-1.68 (m, 4H) 1.27-1.57 (m, 6H) 1.22 (s, 3H) 1.10 (s, 3H) 0.91-1.05 (m, 8H) 0.82-0.91 (m, 6H) 0.71-0.83 (m, 6H)

Example No. 179

Name: (1S,2R,3R,4aR,6aS,7R,8R,10aR,10bR,12aR)-3-(acetyloxy)-2-[(2S)-(2-cyclohexylamino-2,3-dimethylbutyl oxy)]-8-[(1R)-1,2-dimethylpropyl]-1,6a,8,10a-tetra methyl-6-oxo-1,3,4,6,6a,7,8,9,10,10a,10b,11,12,12a-tetradecahydro-2H-1,4a-(methanooxy methano)chrysene-7-carboxylic acid $^1$H NMR (400 MHz, methanol-d$_4$, δ, ppm) 5.66-5.84 (m, 2H) 3.77-3.96 (m, 2H) 3.36-3.63 (m, 5H) 3.06-3.17 (m, 1H) 2.98 (br. s., 1H) 2.67 (d, J=12.45 Hz, 1H) 2.51 (dd, J=12.64, 6.74 Hz, 1H) 2.16-2.32 (m, 1H) 2.08 (s, 3H) 1.92-2.07 (m, 3H) 1.83-1.93 (m, 6H) 1.72-1.84 (m, 4H) 1.68-1.72 (m, 3H) 1.65 (d, J=12.93 Hz, 1H) 1.43-1.59 (m, 3H) 1.24-1.44 (m, 7H) 1.20 (s, 3H) 1.10 (s, 3H) 0.90-1.03 (m, 9H) 0.84-0.91 (m, 6H) 0.72-0.84 (m, 6H)

What is claimed is:

1. A compound of Formula I:

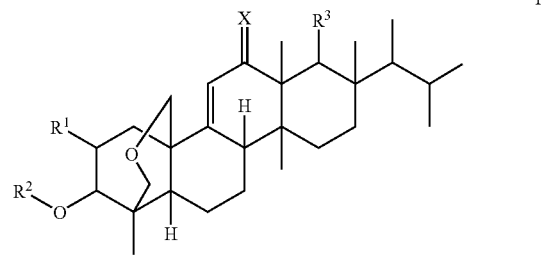

or a pharmaceutically acceptable salt thereof, wherein:
X is O or H,H;
$R^1$ is
  a) OH;
  b) OC(O)$C_1$-$C_{12}$-alkyl, unsubstituted or substituted with 1 or 2 substituents selected from OR$^o$, N(R$^o$)$_2$, and CO$_2$R$^o$;
  c) OC(O)$C_1$-$C_6$-haloalkyl;
  d) OC(O)$C_3$-$C_8$-cycloalkyl;
  e) O—$C_1$-$C_6$-alkyl, unsubstituted or substituted with 1 or 2 substituents selected from OR$^o$ and N(R$^o$)$_2$;
  f) OC(O)NH$C_1$-$C_6$-alkyl, unsubstituted or substituted with phenyl;
  g) OC(O)O$C_1$-$C_6$-alkyl;

201 h) NHC(O)$C_1$-$C_6$-alkyl, unsubstituted or substituted with phenyl; or
i) (O)$_n$CH$_2$C(O)$C_1$-$C_6$-alkyl;

n is 0 or 1;

$R^2$ is
a) CH$_2$$R^4$,
b) CH$_2$CHR$^5$(CH$_2$)$_m$NR$^6$R$^7$,
c) CH$_2$C(R$^8$)(R$^9$)(CH$_2$)$_m$NR$^6$R$^7$,
d) CH$_2$C(R$^{10}$)(R$^{11}$)R$^{12}$,
e) CH$_2$CH(OR$^0$)CH$_2$OR$^0$,
f) CHR$^{13}$CHR$^5$(CH$_2$)$_m$NR$^6$R$^7$,
g) (CH$_2$)$_p$C(R$^8$)(R$^9$)NR$^6$R$^7$, or,
h) CH$_2$CHR$^5$C(R$^8$)(R$^9$)NR$^6$R$^7$, m is 0, 1 or 2;
p is 2 to 6;

$R^1$ and $R^2$ are optionally taken together to form a methylenedioxy or ethylenedioxy, unsubstituted or substituted with 1 or 2 substituents selected from $C_1$-$C_6$-alkyl and $C_1$-$C_6$-alkoxy;

$R^3$ is
a) C(O)R$^{14}$;
b) CH$_2$OH; or
c) CH$_2$OC(O)$C_1$-$C_6$-alkyl;

$R^{14}$ is OH, OR$^{15}$, H, N(R$^0$)$_2$, or $C_1$-$C_6$-alkyl;

$R^{15}$ is $C_1$-$C_6$-alkyl, unsubstituted or substituted with 1 or 2 substituents selected from phenyl, OC(O)$C_1$-$C_6$-alkyl, C(O)OR$^0$, OR$^0$, C(O)N(R$^0$)$_2$, and C(O)NH$_2$(CH$_2$)$_{2-4}$NH$_2$ and wherein said phenyl is optionally substituted with 1 to 3 halo groups;

$R^4$ is
a) H;
b) (CH$_2$)$_{1-6}$—R$^{16}$;
c) OC$_1$-$C_6$-alkyl;
d) aryl, wherein aryl is phenyl or naphthyl and aryl is unsubstituted or substituted with 1 to 3 substituents selected from halo, N(R$^0$)$_2$, OR$^0$, $C_1$-$C_6$-alkyl, CF$_3$, OCF$_3$, CO$_2$R$^0$, and C(O)N(R$^0$)$_2$;
e) heterocyclyl, wherein heterocyclyl is a 5- or 6-membered, saturated or unsaturated non-aromatic ring having 1, 2 or 3 heteroatoms selected from N or S, at least one of which is N, attached through a carbon or nitrogen on the ring, and optionally substituted on a ring carbon or nitrogen that is not the point of attachment, with 1 to 2 substituents selected from oxo, N(R$^0$)$_2$, OR$^0$, CO$_2$R$^0$, CON(R$^0$)$_2$, and $C_1$-$C_6$-alkyl unsubstituted or substituted with 1 or 2 substituents selected from N(R$^0$)$_2$, NHC(=NH)NH$_2$, OC(O)$C_1$-$C_6$-alkyl and CO$_2$R$^0$; or
f) heteroaryl, wherein heteroaryl is a 5- or 6-membered aromatic ring having 1, 2 or 3 heteroatoms selected from N or S, at least one of which is N, attached through a ring carbon or nitrogen, and optionally substituted on a ring carbon or nitrogen that is not the point of attachment, with 1 or 2 substituents selected from N(R$^0$)$_2$, OR$^0$, CO$_2$R$^0$, CON(R$^0$)$_2$, and $C_1$-$C_6$ alkyl unsubstituted or substituted with 1 or 2 substituents selected from N(R$^0$)$_2$, NHC(=NH)NH$_2$, OC(O) $C_1$-$C_6$ alkyl and CO$_2$R$^0$;

$R^{16}$ is
a) H;
b) OH;
c) NH$_2$;
d) NHC(O)R$^{17}$;
e) NHSO$_2$R$^{17}$;
f) NHC(O)NHR$^0$;
g) NHC(O)CHR$^{18}$NH$_2$;

202 h) heterocyclyl, wherein heterocyclyl is a 5- or 6-membered, saturated or unsaturated non-aromatic ring having 1, 2 or 3 heteroatoms selected from N or S, at least one of which is N, attached through a carbon or nitrogen on the ring, and optionally substituted on a ring carbon or nitrogen that is not the point of attachment, with 1 to 2 substituents selected from N(R$^0$)$_2$, imino, oxo, OR$^0$, CO$_2$R$^0$, CON(R$^0$)$_2$, and $C_1$-$C_6$-alkyl unsubstituted or substituted with 1 or 2 substituents selected from N(R$^0$)$_2$, NHC(=NH)NH$_2$, OC(O) $C_1$-$C_6$-alkyl, OR$^0$, and CO$_2$R$^0$;
i) NH—N($C_1$-$C_6$-alkyl)$_2$;
j) NHC(=NH)NHC(=NH)NH$_2$;
k) NR$^a$(CH$_2$)$_p$NHR$^a$;
l) NR$^a$R$^b$;
m) N(R$^b$)$_2$;
n) NHC(=NR$^d$)NH$_2$;
o) NHC(=NR$^c$)NH—$C_1$-$C_6$-alkyl, wherein said alkyl is unsubstituted or substituted with phenyl, CF$_3$ or NHC(O)$C_1$-$C_6$-alkyl;
p) NHC(=NR$^d$)NH—$C_3$-$C_6$-cycloalkyl;
q) NHC(=NR$^d$)NH-phenyl, wherein said phenyl is unsubstituted or substituted with 1 or 2 substituents selected from halo and CF$_3$;
r) CO$_2$$C_1$-$C_6$-alkyl;
s) OCOC$_1$-$C_6$ alkyl;
t) heteroaryl, wherein heteroaryl is a 5- or 6-membered aromatic ring having 1, 2 or 3 heteroatoms selected from N or S, at least one of which is N, attached through a carbon or nitrogen on the ring, and optionally substituted on a ring carbon or nitrogen that is not the point of attachment, with 1 or 2 substituents selected from N(R$^0$)$_2$, OR$^0$, CO$_2$R$^0$, CON(R$^0$)$_2$, and $C_1$-$C_6$ alkyl unsubstituted or substituted with 1 or 2 substituents selected from N(R$^0$)$_2$, NHC(=NH)NH$_2$, OC(O)$C_1$-$C_6$ alkyl, OR$^0$, and CO$_2$R$^0$; or
u) CN;

p is 1, 2, 3 or 4;
$R^a$ is H or C(=NH)NH$_2$;
$R^b$ is $C_1$-$C_6$ alkyl, unsubstituted or substituted with 1 or 2 substituents selected from N(R$^0$)$_2$ and OR$^0$;
$R^c$ is H or CN;
$R^d$ is H or $C_3$-$C_6$-cycloalkyl;

$R^5$ is
a) $C_1$-$C_6$-alkyl, unsubstituted or substituted with 1 or 2 substituents selected from N(R$^0$)$_2$ and OR$^0$;
b) OH;
c) OC$_1$-$C_6$-alkyl, unsubstituted or substituted with phenyl;
d) OC(O)$C_1$-$C_6$-alkyl;
e) $C_3$-$C_6$-cycloalkyl;
f) aryl, wherein aryl is phenyl or naphthyl and aryl is unsubstituted or substituted with 1 to 3 substituents selected from halo, OCF$_3$, CF$_3$, N(R$^0$)$_2$ and OR$^0$;
g) heteroaryl, wherein heteroaryl is a 5- or 6-membered aromatic ring having 1, 2 or 3 heteroatoms selected from N or S, at least one of which is N, attached through a carbon or nitrogen on the ring, and optionally substituted on a ring carbon or nitrogen that is not the point of attachment, with 1 or 2 substituents selected from N(R$^0$)$_2$, OR$^0$, and $C_1$-$C_6$-alkyl; or
h) heterocyclyl, wherein heterocyclyl is a 5- or 6-membered, saturated or unsaturated non-aromatic ring having 1, 2 or 3 heteroatoms selected from N or S, at least one of which is N, attached through a ring carbon or nitrogen, and optionally substituted on a ring carbon or nitrogen that is not the point of attachment, with 1 to 2 substituents selected from $N(R^o)_2$, $OR^o$, and $C_1$-$C_6$-alkyl;

$R^6$ is H or $C_1$-$C_6$-alkyl, wherein said alkyl is unsubstituted or substituted with a 5- to 6-membered saturated, unsaturated or aromatic ring having 1, 2 or 3 heteroatoms selected from N, O or S, attached through a ring carbon or nitrogen, and optionally substituted on a ring carbon or nitrogen that is not the point of attachment, with 1 to 2 substituents selected from $N(R^o)_2$, $OR^o$, $CO_2R^o$, $CON(R^o)_2$ and $C_1$-$C_6$-alkyl unsubstituted or substituted with one or two substituents selected from $OR^o$, $N(R^o)_2$, $NHC(=NH)NH_2$, $OC(O)C_1$-$C_6$-alkyl, $CO_2R^o$, $C(O)N(R^o)_2$, and $NHC(O)R^o$;

$R^7$ is
- a) H;
- b) $C_1$-$C_6$-alkyl, unsubstituted or substituted with 1 or 2 substituents selected from $N(R^o)_2$, $OR^o$, $CO_2R^o$, $OC(O)C_1$-$C_6$-alkyl, $NHC(O)R^o$, $C(O)N(R^o)_2$, phenyl, heteroaryl, and heterocyclyl, wherein heteroaryl is as defined below in (k) and heterocyclyl is as defined below in (l);
- c) C(O)H;
- d) $C(O)C_1$-$C_6$-haloalkyl;
- e) $C(O)C_1$-$C_6$-alkyl, unsubstituted or substituted with 1 or 2 substituents selected from $CO_2R^o$, $OR^o$, $OCH_2CO_2R^o$, $N(R^o)_2$, $C(O)C_1$-$C_6$-alkyl, $O(CH_2)_2OC_1$-$C_6$-alkyl, $C(O)N(R^o)_2$, $OC(O)C_1$-$C_6$ alkyl, and $NHC(O)R^o$;
- f) $C(O)OC_1$-$C_6$-alkyl;
- g) $C(O)NH$—$C_1$-$C_6$-alkyl;
- h) $SO_2C_1$-$C_6$-alkyl;
- i) $C_3$-$C_6$-cycloalkyl;
- j) aryl, wherein aryl is phenyl or naphthyl and aryl is unsubstituted or substituted with 1 to 3 substituents selected from halo, $N(R^o)_2$, $OR^o$, $C_1$-$C_6$-alkyl, $CF_3$, $OCF_3$, $CO_2R^o$, and $C(O)N(R^o)_2$;
- k) heteroaryl, wherein heteroaryl is a 5- or 6-membered aromatic ring having 1, 2 or 3 heteroatoms selected from N or S, at least one of which is N, attached through a carbon or nitrogen on the ring, and optionally substituted on a ring carbon or nitrogen that is not the point of attachment, with 1 or 2 substituents selected from $N(R^o)_2$, $OR^o$, $CO_2R^o$, $OC(O)C_1$-$C_6$-alkyl, $CON(R^o)_2$, $NHC(O)R^o$, and $C_1$-$C_6$-alkyl unsubstituted or substituted with 1 or 2 substituents selected from $N(R^o)_2$, $NHC(=NH)NH_2$, $OC(O)C_1$-$C_6$ alkyl, $OR^o$, $CO_2R^o$, $C(O)N(R^o)_2$ and $NHC(O)R^o$;
- l) heterocyclyl, wherein heterocyclyl is a 5- or 6-membered, saturated or unsaturated non-aromatic ring having 1, 2 or 3 heteroatoms selected from N or S, at least one of which is N, attached through a carbon or nitrogen on the ring, and optionally substituted on a ring carbon or nitrogen that is not the point of attachment, with 1 to 2 substituents selected from $N(R^o)_2$, imino, oxo, $OR^o$, $CO_2R^o$, $OC(O)C_1$-$C_6$-alkyl, $CON(R^o)_2$, $NHC(O)R^o$, and $C_1$-$C_6$-alkyl unsubstituted or substituted with 1 or 2 substituents selected from $N(R^o)_2$, $NHC(=NH)NH_2$, $OC(O)C_1$-$C_6$-alkyl, $OR^o$, $CO_2R^o$, $C(O)N(R^o)_2$ and $NHC(O)R^o$;
- m) $C(=NH)C_1$-$C_6$-alkyl, wherein said alkyl is unsubstituted or substituted with 1 or 2 substituents selected from halo, $CF_3$, $N(R^o)_2$, $OR^o$, and $NHC(O)C_1$-$C_6$-alkyl;
- n) $C(=NR^d)NH_2$;
- o) $C(=NH)NH$—$C_1$-$C_6$-alkyl, wherein said alkyl is unsubstituted or substituted with 1 to 3 substituents selected from halo, $CF_3$, $N(R^o)_2$, $OR^o$, and $NHC(O)C_1$-$C_6$-alkyl;
- p) $C(=NH)NH$—$C_3$-$C_6$-cycloalkyl;
- q) $C(=NH)NH$-phenyl, wherein phenyl is unsubstituted or substituted with 1 to 3 substituents selected from halo and $CF_3$; or
- r) $C(=NH)NHC(=NH)NH_2$;

$R^6$ and $R^7$ are optionally taken together with the attached nitrogen atom to form a 3- to 6-membered saturated, unsaturated or aromatic ring having 0-2 additional heteroatoms selected from N, O and S, wherein said ring is optionally substituted on a ring carbon or nitrogen that is not the point of attachment, with 1 to 2 substituents selected from halo, $N(R^o)_2$, $OR^o$, $CO_2R^o$, $CON(R^o)_2$, and $C_1$-$C_6$ alkyl unsubstituted or substituted with 1 or 2 substituents selected from $OR^o$ and $N(R^o)_2$, and wherein two adjacent substituents of said ring are optionally taken together to form a fused 5- or 6-membered saturated, unsaturated, or aromatic ring having 0-2 heteroatoms selected from N, O and S; or $R^6$ and $R^9$ are optionally taken together, with the nitrogen atom $R^6$ is attached to, to form a pyrrolidinyl ring;

$R^8$ is selected from the group consisting of
- a) hydrogen,
- b) $C_1$-$C_6$-alkyl, unsubstituted or substituted with $OR^o$ or $SO_2R^o$,
- c) $C_3$-$C_6$-cycloalkyl, and
- d) aryl, wherein aryl is phenyl or naphthyl and aryl is unsubstituted or substituted with 1 to 3 substituents selected from halo, $OCF_3$, $CF_3$, $N(R^o)_2$ and $OR^o$;

$R^9$ is $C_1$-$C_6$-alkyl, unsubstituted or substituted with $OR^o$ or $SO_2R^o$;

$R^8$ and $R^9$ are optionally taken together to form a 3- to 6-membered saturated ring having 0-1 heteroatom selected from N, O or S;

$R^{10}$ is independently selected from the group consisting of
- a) $C_1$-$C_6$-alkyl unsubstituted or substituted with $OR^o$, $N(R^o)_2$, $OC(O)C_1$-$C_6$ alkyl or $CO_2R^o$, and
- b) $CO_2R^o$;

$R^{11}$ is $C_1$-$C_6$ alkyl unsubstituted or substituted with $OR^o$, $OC(O)C_1$-$C_6$ alkyl, $OC(O)$-phenyl, $CO_2R^o$, or $N(R^o)_2$;

$R^{12}$ is OH or $C_1$-$C_6$ alkyl, wherein said alkyl is unsubstituted or substituted with $OC(O)C_1$-$C_6$ alkyl or $OR^o$;

$R^{13}$ is $C_1$-$C_4$-alkyl;

$R^{17}$ is
- a) $C_1$-$C_6$-alkyl, unsubstituted or substituted with 1 to 2 substituents selected from $CO_2R^o$, $OR^o$, $N(R^o)_2$, and $OC(O)C_1$-$C_6$-alkyl;
- b) aryl, wherein aryl is phenyl or naphthyl and aryl is unsubstituted or substituted with 1 to 2 substituents selected from halo, $OR^o$ and $N(R^o)_2$; or
- c) $C_1$-$C_6$-haloalkyl;

$R^{18}$ is H or $C_1$-$C_6$-alkyl, wherein said alkyl is unsubstituted or substituted with 1 to 2 substituents selected from $OR^o$, $N(R^o)_2$, heteroaryl, heterocyclyl, $CO_2N(R^o)_2$, and $CO_2R^o$, wherein heteroaryl is as defined in $R^{16}$ (t) and heterocyclyl is as defined in $R^{16}$ (h); and each $R^o$ is independently H or $C_1$-$C_6$-alkyl.

2. The compound of claim 1, wherein $R^3$ is $C(O)R^{14}$.

3. The compound of claim 2, wherein $R^{14}$ is OH or $OR^{15}$.

4. The compound of claim 2, wherein the compound is of Formula II:

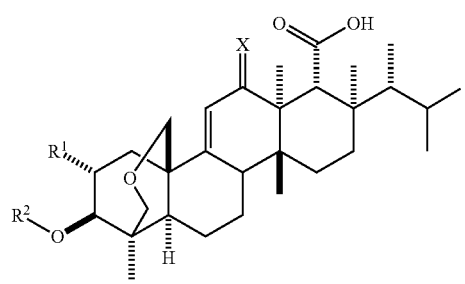

III-1

5. The compound of claim 1, wherein X is O.

6. The compound of claim 1, wherein X is $H_2$.

7. The compound of claim 1, wherein $R^1$ is $OC(O)C_1$-$C_{12}$ alkyl, unsubstituted or substituted with 1 or 2 substituents selected from $OR^0$, $N(R^0)_2$, and $CO_2R^0$.

8. The compound of claim 1, wherein $R^1$ is $OC(O)NHC_1$-$C_6$ alkyl, unsubstituted or substituted with phenyl.

9. The compound of claim 1, wherein $R^2$ is $CH_2CHR^5(CH_2)_mNR^6R^7$, $CH_2CR^8R^9(CH_2)_mNR^6R^7$, or $CHR^{13}CHR^5(CH_2)_mNR^6R^7$.

10. The compound of claim 9, wherein the compound is of Formula III-1, III-2, III-3 or III-4:

11. The compound of claim 9, wherein the compound is of Formula IV-1, IV-2, IV-3 or IV-4:

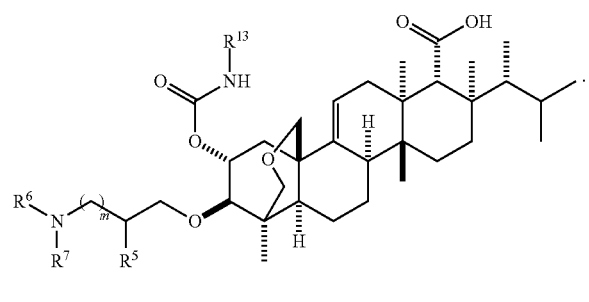

12. The compound of claim 9, wherein the compound is of Formula V-1 or Formula V-3:

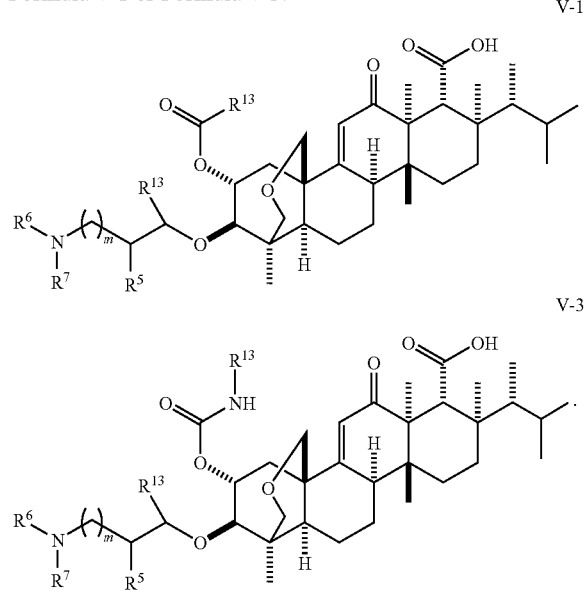

13. The compound of claim 11 having Formula IV-1 wherein $R^{13}$ is —$CH_3$;
   m is 0;
   $R^8$ is selected from the group consisting of —$CH_3$, $CH_2CH_3$, $CH_2OCH(CH_3)_2$, and $CH(CH_3)_2$;
   $R^9$ is selected from the group consisting of $CH_3$, $CH_2CH_3$, $CH_2CH_2CH_3$, $CH(CH_3)_2$, $CH(CH_3)(CH_2CH_3)$, $CH_2CH_2CH_2CH_3$, $CH_2OCH_3$, $CH_2CH_2OCH_3$, $CH_2CH_2OCH_2CH_3$, cyclohexyl, (R)$CH(CH_3)_2$, and (S)$CH(CH_3)_2$;
   $R^6$ is H, —$CH_3$, $CH_2CH_3$, $CH_2CF_3$, $CH_2CH_2CH_3$, $CH_2CH_2OCH_3$, cyclobutyl, $CH_2$-cyclopropyl, $CH(CH_3)_2$, $CH_2CH_2CH_2CH_3$, $CH(CH_3)(CH_2CH_3)$, cyclopentyl, and cyclohexyl; and
   $R^7$ is H, —$CH_3$, $CH_2CH_3$, $CH(CH_3)_2$, and $CH_2CH_2CH_3$.

14. The compound of claim 11 having Formula IV-1 wherein $R^{13}$ is —$CH_3$, m is 0, $R^8$ is —$CH_3$, and $R^9$ is —$CH(CH_3)_2$.

15. The compound of claim 14 wherein $R^6$ is H or —$CH_3$ and $R^7$ is H or —$CH_3$.

16. The compound of claim 15, wherein the compound is of Formula IV-1a:

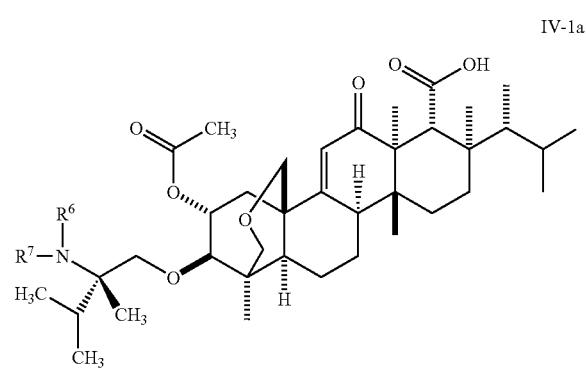

wherein $R^6$ is H or —$CH_3$, and $R^7$ is H or —$CH_3$.

17. The compound of claim 16 wherein $R^6$ is H or —$CH_3$, and $R^7$ is —$CH_3$.
18. The compound of claim 16 wherein $R^6$ is —$CH_3$, and $R^7$ is —$CH_3$.
19. The compound of claim 15, wherein the compound is of Formula IV-1b:

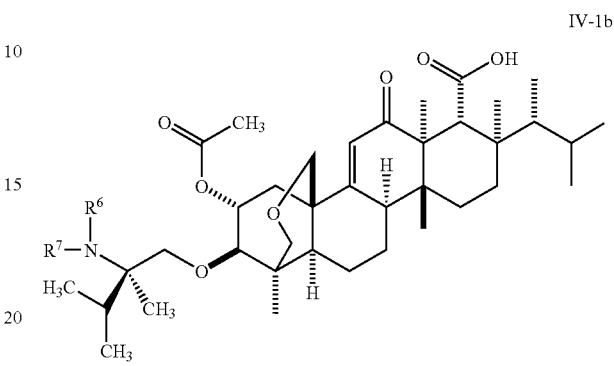

wherein $R^6$ is H or —$CH_3$, and $R^7$ is H or —$CH_3$.
20. The compound of claim 19 wherein $R^6$ is H or —$CH_3$, and $R^7$ is —$CH_3$.
21. The compound of claim 20 wherein $R^6$ is —$CH_3$, and $R^7$ is —$CH_3$.
22. The compound of claim 10, wherein m is 0.
23. The compound of claim 11, wherein m is 0.
24. The compound of any one of claims 10-12, wherein $R^{13}$ is methyl.
25. The compound of claim 23, wherein both $R^8$ and $R^9$ are $C_1$-$C_3$ alkyl; or $R^8$ and $R^9$ are taken together to form a 3- to 6-membered saturated ring having 0-1 heteroatom selected from N, O or S.
26. The compound of claim 25, wherein $R^8$ is methyl and $R^9$ is methyl, ethyl or propyl; or $R^8$ and $R^9$ are taken together to form a cyclobutyl.
27. The compound of claim 23 or 25, wherein both $R^6$ and $R^7$ are H.
28. The compound of claim 23 or 25, wherein $R^6$ and $R^7$ are independently unsubstituted $C_1$-$C_6$-alkyl.
29. The compound of claim 28, wherein $R^6$ and $R^7$ are independently methyl or ethyl, or $R^6$ is H and $R^7$ is propyl.
30. The compound of claim 10 or 12, wherein m is 1.
31. The compound of claim 11, wherein m is 1.
32. The compound of claim 1 selected from the group consisting of:
   (1S,2R,3R,4aR,6aS,7R,8R,10aR,10bR,12aR)-3-(acetyloxy)-2-[(2S)-2-amino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid,
   (1S,2R,3R,4aR,6aS,7R,8R,10aR,10bR,12aR)-3-(acetyloxy)-2-[(2S)-2-methylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid,
   (1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid, (1S,2R,3R,4aR,6aS,7R,8R,10aR,10bR,12aR)-3-acetoxy-
2-[[(2R)-2-amino-2,3-dimethylbutyl]oxy]-8-[(1R)-1,2-
dimethylpropyl]-1,6a,8,10a-tetramethyl-6-oxo-1,3,4,6,
6a,7,8,9,10,10a,10b,11,12,12a-tetradecahydro-2H-1,
4a-(methanooxymethano)chrysene-7-carboxylic acid, (1S,2R,3R,4aR,6aS,7R,8R,10aR,10bR,12aR)-3-acetoxy-
2-[[(2R)-2-methylamino-2,3-dimethylbutyl]oxy]-8-
[(1R)-1,2-dimethylpropyl]-1,6a,8,10a-tetramethyl-6-
oxo-1,3,4,6,6a,7,8,9,10,10a,10b,11,12,12a-
tetradecahydro-2H-1,4a-(methanooxymethano)
chrysene-7-carboxylic acid, and (1S,2R,3R,4aR,6aS,7R,8R,10aR,10bR,12aR)-3-acetoxy-
2-[[(2R)-2-dimethylamino-2,3-dimethylbutyl]oxy]-8-
[(1R)-1,2-dimethylpropyl]-1,6a,8,10a-tetramethyl-6-
oxo-1,3,4,6,6a,7,8,9,10,10a,10b,11,12,12a-
tetradecahydro-2H-1,4a-(methanooxymethano)
chrysene-7-carboxylic acid, and pharmaceutically acceptable salts thereof.

33. A compound of claim 32 which is:
(1S,2R,3R,4aR,6aS,7R,8R,10aR,10bR,12aR)-3-(acetyloxy)-2-[(2S)-2-dimethylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid or a pharmaceutically acceptable salt thereof.

34. The compound of claim 1, wherein the compound is selected from Tables A-H and J-M and 3a.

35. A composition comprising a compound of claim 1 and a carrier, adjuvant, or vehicle.

36. The method of treating a fungal infection in a mammal, comprising administering to said mammal an effective amount of a compound of claim 1.

37. The method of claim 36, wherein said fungal infection is caused by *Cryptococcus* spp., *Candida* spp, or *Aspergillus* spp, fungi.

38. A compound of claim 32 which is:
(1S,2R,3R,4aR,6aS,7R,8R,10aR,10bR,12aR)-3-(acetyloxy)-2-[(2S)-2-methylamino-2,3-dimethylbutyloxy]-8-[(1R)-1,2-dimethyl propyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid or a pharmaceutically acceptable salt thereof.

* * * * *